(12) United States Patent
Kim et al.

(10) Patent No.: US 12,012,598 B2
(45) Date of Patent: Jun. 18, 2024

(54) MANIPULATED IMMUNOREGULATORY ELEMENT AND IMMUNITY ALTERED THEREBY

(71) Applicant: TOOLGEN INCORPORATED, Seoul (KR)

(72) Inventors: Seok Joong Kim, Seoul (KR);
Yoon-Young Kim, Seoul (KR);
Ho-Sung Yu, Gyeonggi-do (KR);
In-Young Jung, Gyeonggi-do (KR);
Jung Min Lee, Seoul (KR)

(73) Assignee: TOOLGEN INCORPORATED, Seoul (KR)

( * ) Notice: Subject to any disclaimer, the term of this patent is extended or adjusted under 35 U.S.C. 154(b) by 961 days.

(21) Appl. No.: 16/324,955

(22) PCT Filed: Aug. 14, 2017

(86) PCT No.: PCT/KR2017/008835
§ 371 (c)(1),
(2) Date: Feb. 12, 2019

(87) PCT Pub. No.: WO2018/030874
PCT Pub. Date: Feb. 15, 2018

(65) Prior Publication Data
US 2019/0185860 A1  Jun. 20, 2019

Related U.S. Application Data

(60) Provisional application No. 62/502,822, filed on May 8, 2017.

(30) Foreign Application Priority Data

Aug. 12, 2016  (KR) ........................ 10-2016-0103308

(51) Int. Cl.
| | | |
|---|---|---|
| *C12N 15/113* | (2010.01) | |
| *A61K 35/14* | (2015.01) | |
| *C07K 1/00* | (2006.01) | |
| *C07K 14/705* | (2006.01) | |
| *C12N 5/0783* | (2010.01) | |
| *C12N 5/0784* | (2010.01) | |
| *C12N 15/10* | (2006.01) | |
| *C12N 15/52* | (2006.01) | |
| *C12N 15/63* | (2006.01) | |
| *C12N 15/85* | (2006.01) | |
| *A61K 31/70* | (2006.01) | |
| *C12N 9/22* | (2006.01) | |

(52) U.S. Cl.
CPC .......... *C12N 15/1132* (2013.01); *A61K 35/14* (2013.01); *C07K 14/70503* (2013.01); *C07K 14/70564* (2013.01); *C07K 14/70575* (2013.01); *C07K 14/70578* (2013.01); *C07K 14/70596* (2013.01); *C12N 5/0637* (2013.01); *C12N 5/0638* (2013.01); *C12N 5/064* (2013.01); *C12N 5/0646* (2013.01); *C12N 15/102* (2013.01); *C12N 15/1138* (2013.01); *C12N 15/52* (2013.01); *C12N 15/63* (2013.01); *C12N 15/85* (2013.01); *C12N 9/22* (2013.01); *C12N 2310/20* (2017.05); *C12N 2320/30* (2013.01); *Y02A 50/30* (2018.01)

(58) Field of Classification Search
CPC ...... C12N 15/113; C12N 15/85; C12N 15/52; C12N 9/22; C07K 1/00
See application file for complete search history.

(56) References Cited

U.S. PATENT DOCUMENTS

| | | | |
|---|---|---|---|
| 8,865,406 B2 * | 10/2014 | Zhang et al. | |
| 10,717,978 B2 | 7/2020 | Vakulskas et al. | |
| 10,876,120 B2 * | 12/2020 | Wucherpfennig | ........................... C07K 14/7051 |
| 2005/0221354 A1 * | 10/2005 | Mounts | ................ C12Q 1/6876 435/287.2 |
| 2005/0244851 A1 | 11/2005 | Blume et al. | |
| 2011/0166037 A1 | 7/2011 | Cao et al. | |
| 2013/0129668 A1 * | 5/2013 | Firestein | .............. C12Q 1/6883 424/85.1 |
| 2014/0120622 A1 | 5/2014 | Gregory et al. | |

(Continued)

FOREIGN PATENT DOCUMENTS

| | | |
|---|---|---|
| AU | 2013-359123 A1 | 7/2015 |
| AU | 2014 366047 A1 | 6/2016 |

(Continued)

OTHER PUBLICATIONS

Ding et al. Alternative splicing of the human diacylglycerol kinase gene in muscle. Proc. Natl. Acad. Sci. 94:5519-5524, (Year: 1997).*

(Continued)

*Primary Examiner* — Quang Nguyen
(74) *Attorney, Agent, or Firm* — Harness, Dickey & Pierce, P.L.C.

(57) ABSTRACT

The present invention relates to an artificially manipulated immune system having an improved immune effect. More particularly, the present invention relates to an immune system having functions artificially altered which comprises artificially manipulated immunoregulatory elements and cells containing the same. Contemplated according to a particular embodiment is an immune system comprising artificially manipulated immunoregulatory genes such as PD-1, CTLA-4, A20, DGKα, DGKζ, FAS, EGR2, PPP2R2D, PSGL-1, KDM6A, and TET2, and/or expression products thereof.

4 Claims, 26 Drawing Sheets

Specification includes a Sequence Listing.

(56) References Cited

U.S. PATENT DOCUMENTS

| | | | |
|---|---|---|---|
| 2015/0224142 | A1 | 8/2015 | Albelda et al. |
| 2016/0120906 | A1 | 5/2016 | Galetto et al. |
| 2016/0184362 | A1 | 6/2016 | Duchateau et al. |
| 2016/0272999 | A1 | 9/2016 | Duchateau et al. |
| 2017/0335281 | A1* | 11/2017 | Loew ............ A61K 39/001191 |
| 2018/0119140 | A1* | 5/2018 | Porteus ................. C12N 15/11 |
| 2019/0185860 | A1 | 6/2019 | Kim et al. |
| 2019/0388468 | A1 | 12/2019 | Lock et al. |
| 2020/0299686 | A1 | 9/2020 | Kwong et al. |
| 2021/0128616 | A1 | 5/2021 | Dave et al. |
| 2021/0147798 | A1 | 5/2021 | Kim et al. |
| 2021/0317406 | A1 | 10/2021 | Marson et al. |

FOREIGN PATENT DOCUMENTS

| | | |
|---|---|---|
| CN | 105121648 A | 12/2015 |
| EP | 3498846 A1 | 6/2019 |
| JP | 2017-500869 A | 1/2017 |
| JP | 2019-524140 A | 9/2019 |
| JP | 2019-533996 A | 11/2019 |
| KR | 10-2015-0016588 A | 2/2015 |
| KR | 10-2015-0105635 A | 9/2015 |
| KR | 10-2016-0018425 A | 2/2016 |
| KR | 10-2016-0138404 A | 12/2016 |
| KR | 10-2017-0032406 A | 3/2017 |
| WO | WO-2013/176772 A1 | 11/2013 |
| WO | WO-2014/039513 A2 | 3/2014 |
| WO | WO-2014/186585 A2 | 11/2014 |
| WO | WO-2015/090230 A1 | 6/2015 |
| WO | WO-2015/121454 A1 | 8/2015 |
| WO | WO-2016-021972 A1 | 2/2016 |
| WO | WO-2016/069283 A1 | 5/2016 |
| WO | WO-2016/080097 A1 | 5/2016 |
| WO | WO-2016/123578 A1 | 8/2016 |
| WO | WO-2018/030874 A1 | 2/2018 |

OTHER PUBLICATIONS

Fujikawa et al. Isolation and characterization of the human diacylglycerol kinase gene. Biochem. J. 294:443-449, (Year: 1993).*

Mout et al. In vivo delivery of CRISPR/Cas9 for therapeutic gene editing: Progress and Challenges. Bioconjugate Chem. 28:880-884, (Year: 2017).*

Su, S., et al.; "CRISPR-Cas9 mediated efficient PD-1 disruption on human primary T cells from cancer patients", Scientific Reports, 2016,6: 20070, pp. 1-14.

Kuklina E.M., Molecular Mechanisms of T Cell Anergy, Biokhimiya (Biochemistry), vol. 78, 144-156, 2013.

Fagerlun'd, Robert D. et al. (2015) "The Cpf1 CRISPR-Cas Protein Expands Genome-editing Tools.", *Genome Biology*, vol. 16, Thesis No. 251 (internal pp. 1-3).

Su, S., et al., "CRISPR-Cas9 mediated efficient PD-1 disruption on human primary T cells from cancer patients", Scientific Reports, vol. 6, Article 20070, pp. 1-13, Jan. 28, 2016.

Rupp, L., et al.; "CRISPR/Cas9-mediated PD-1 disruption enhances anti-tumor e chimeric antigen receptor T cells", The Journal of Immunology, vol. 196, Issue 1, Supplement, Immunology 2016 TM Meeting Abstract, 214.24, May 1, 2016.

Petra U. Prinz et al, "High DGK-[alpha] and Disabled MAPK Pathways Cause Dysfunction of Human Tumor-Infiltrating CD8 + T Cells That Is Reversible by Pharmacologic Intervention", The Journal of Immunology, (May 9, 2012), vol. 188, No. 12, doi: 10.4049/jimmunol.1103028, ISSN 0022-1767, pp. 5990-6000.

M. J. Riese et al, "Enhanced Effector Responses in Activated CD8+ T Cells Deficient in Diacylglycerol Kinases", Cancer Research, (Apr. 10, 2013), vol. 73, No. 12, doi:10.1158/0008-5472.CAN-12-3874, ISSN 0008-5472, pp. 3566-3577.

Regina Cencic et al, "Protospacer Adjacent Motif (PAM)-Distal Sequences Engage CRISPR Cas9 DNA Target Cleavage", PLOS One, (Oct. 2, 2014), vol. 9, No. 10, doi:10.1371/journal.pone.0109213, p. e109213.

In-Young Jung et al, "CRISPR/Cas9-Mediated Knockout of DGK Improves Antitumor Activities of Human T Cells", Cancer Research, US, (Jul. 2, 2018), vol. 78, No. 16, doi:10.1158/0008-5472.CAN-18-0030, ISSN 0008-5472, pp. 4692-4703.

Matthew J. Riese et al, "Diacylglycerol Kinases (DGKs): Novel Targets for Improving T Cell Activity in Cancer", Frontiers in Cell and Developmental Biology, (Oct. 17, 2016), vol. 4, doi:10.3389/fcell.2016.00108.

Yang et al, "Diacylglycerol Kinase z Is a Target to Enhance NK Cell Function", The Juornal of Immunology, vol. 197, No. 3, pp. 934-941, 2016.

Prinz et al, "NK?cell dysfunction in human renal carcinoma reveals diacylglycerol kinase as key regulator and target for therapeutic intervention" International Jornal of Cancer, vol. 135, No. 8, pp. 1832-1841, 2014.

Office Action from corresponding Japanese Patent Application No. 2019-561310, dated Dec. 17, 2021.

Park, J., et al.; "Cas-Designer: a web-based tool for choice of CRISPR-Cas9 target sites", Bioinformatics, 31(24), 2015, 4014-4016.

Notice of Allowance from corresponding Korean Patent Application No. 10-2019-0068999, dated Apr. 21, 2021.

Pennisi, E., "The CRISPR Craze", *Science*, 341 (6148), pp. 833-836, 2013.

Office Action from corresponding Canadian Patent Application No. 3,033,736, dated Aug. 26, 2022.

Office Action from corresponding U.S. Appl. No. 16/611,383, dated Mar. 9, 2023.

Chinese Office Action for application No. 201880045774.2, dated Nov. 24, 2022.

Office Action from corresponding Chinese Patent Application No. 201780063250.1, dated Mar. 31, 2023.

* cited by examiner

Y axis: $10^0$, $10^1$, $10^2$, $10^3$, $10^4$, $10^5$, $10^6$
X axis: 0.001, 500, 1000

MANIPULATED IMMUNOREGULATORY ELEMENT AND IMMUNITY ALTERED THEREBY

CROSS-REFERENCE TO RELATED APPLICATIONS

This application is a National Phase entry of PCT Application No. PCT/KR2017/008835, filed on Aug. 14, 2017, which claims the benefit and priority to Korean Patent Application No. 10-2016-0103308, filed on Aug. 12, 2016 and U.S. Provisional Application No. 62/502,822, filed on May 8, 2017. The entire disclosures of the applications identified in this paragraph are incorporated herein by references.

FIELD

The present invention relates to an artificially engineered immune system with improved immune efficacy. More specifically, the present invention relates to an artificially modified immune system comprising an artificially engineered immune manipulating elements and immune cell including thereof.

BACKGROUND

Cell therapeutic agents are pharmaceutical drugs that induce regeneration using live cells to restore damaged or diseased cells/tissues/entity and they are pharmaceutical drugs that are produced by physical, chemical, or biological manipulation, e.g., ex vivo cultivation, proliferation, selection, or the like of autologous, allogeneic, or heterologous cells.

Among them, immune regulatory cell therapeutic agents are pharmaceutical drugs that are used for the purpose of treating diseases by regulating immune responses in the body using immune cells (e.g., dendritic cells, natural killer cells, T cells, etc.).

Currently, immune regulatory cell therapeutic agents are being developed mainly targeting cancer treatment as an indication. Unlike the surgery therapy, anticancer agents, and radiation therapy which are conventionally used for cancer treatment, the immune regulatory cell therapeutic agents have therapeutic mechanisms and efficacies that acquire therapeutic effects by activating immune functions via direct administration of immune cells to patients; they are expected to occupy a major part of future new biologics.

The physical and chemical characteristics of the antigens introduced into cells vary with each other depending on the type of the immune regulatory cell therapeutic agents. When an exogenous gene is introduced into immune cells in the form of a viral vector, etc., these cells will be able to have both the characteristics of a cell therapeutic agent and a gene therapeutic agent.

The administration of immune regulatory cell therapeutic agents may be performed by activating various immune cells (e.g., peripheral blood mononuclear cells (PBMCs), T cells, NK cells, etc. isolated from patients through apheresis) with various antibodies and cytokines, then proliferating ex vivo, and injecting again into a patient; or injecting again into the patient immune cells, into which a gene (e.g., T-cell receptors (TCRs) or chimeric antigen receptors (CARs)) is introduced.

Adoptive immunotherapy, which involves the delivery of autologous antigen-specific immune cells (e.g., T cells) produced ex vivo, may become a promising strategy for treating various immune diseases as well as cancer.

Recently, it was reported that immune cell therapeutic agents can be used variously, for example, as an autoimmune inhibitor, etc. as well as exhibiting an anticancer function. Therefore, immune cell therapeutic agents can be used in various indications by modulating the immune responses. Accordingly, there is a great demand for improvement and development of therapeutic efficacy of manipulated immune cells used for adoptive immunotherapy.

SUMMARY

Technical Problem

As an exemplary embodiment, the present invention provides an artificially engineered immune system with improved immune effect.

As an exemplary embodiment, the present invention provides an artificially manipulated immune regulatory factor and a cell comprising thereof.

As an exemplary embodiment, the present invention provides a method for modifying (e.g., enhancing or inhibiting) the function of an immune cell.

As an exemplary embodiment, the present invention provides a therapeutic and/or prophylactic use of a disease accompanied by an immunological abnormality, which comprises an immune regulatory factor and/or an immune cell modified immune function as an effective components.

As an exemplary embodiment, the present invention provides an anticancer function by enhancing a proliferation, survival, cytotoxicity, infiltration, and cytokine-release of immune cells.

As an exemplary embodiment, the present invention provides an immune regulatory gene such as PD-1, CTLA-4, A20, DGKα, DGKζ, FAS, EGR2, PPP2R2D, PSGL-1, KDM6A, TET2, etc., and/or products expressed therefrom.

As an exemplary embodiment, the present invention provides a composition for editing genome of immune cell comprising a guide nucleic acid-editor protein complex applicable to the regulation of the activity of an immune regulatory gene, and a method of using thereof.

As an exemplary embodiment, the present invention provides a guide nucleic acid-editor protein complex which can be used for manipulating an immune regulatory gene such as PD-1, CTLA-4, A20, DGKα, DGKζ, FAS, EGR2, PPP2R2D, PSGL-1, KDM6A, TET2 etc.

Technical Solution

To solve these problems, the present invention provides an artificially engineered immune system with improved immune effect. More specifically, the present invention relates to an artificially engineered immune system comprising an artificially engineered immune regulatory factor and immune cell including thereof.

The present invention provides a genetically manipulated or modified immune regulating factor for a particular purpose.

The term "Immune regulatory factor" is substances that function in connection with the formation and performance of an immune response, including all of the various substances that may be non-natural, i.e., artificially engineered, having an immune response regulating function. For example, it may be a genetically engineered or modified gene or protein expressed in an immune cell.

The immune regulatory factor may function in an activation or inactivation of immune cells. The immune regulatory factor may function to promote an immune response (e.g. an immune cell growth regulatory factor, an immune cell death regulatory factor, an immune cell function loss factor, or a cytokine secretion element, etc.).

In an exemplary embodiment of the present invention, the immune regulatory factor may be, for example, a genetically engineered or modified a PD-1 gene, a CTLA-4 gene, a TNFAIP3 (A20) gene, a DGKA gene, a DGKZ gene, a FAS gene, an EGR2 gene, a PPP2R2D gene, a TET2 gene, a PSGL-1 gene, or a KDM6A gene.

In an exemplary embodiment of the present invention, the immune regulatory factor may be include two or more genetically manipulated or modified genes. For example, two or more genes selected from the group consisting of a PD-1 gene, a CTLA-4 gene, a TNFAIP3 (A20) gene, a DGKA gene, a DGKZ gene, a FAS gene, an EGR2 gene, a PPP2R2D gene, a TET2 gene, a PSGL-1 gene, or a KDM6A gene may be artificially manipulated or modified.

As a preferred example of the present invention, the immune regulatory factor may be a TNFAIP3 (A20) gene, a DGKA gene, a DGKZ gene, a FAS gene, an EGR2 gene, a PSGL-1 gene, or a KDM6A gene.

Therefore, in an exemplary embodiment of the present invention, one or more artificially manipulated immune regulatory factors selected from the group consisting of a PD-1 gene, a CTLA-4 gene, a TNFAIP3 (A20) gene, a DGKA gene, a DGKZ gene, a FAS gene, an EGR2 gene, a PPP2R2D gene, a TET2 gene, a PSGL-1 gene and a KDM6A gene, which have undergone modification in a nucleic acid sequence, are provided.

The modification in a nucleic acid sequence may be non-limitedly, artificially manipulated by a guide nucleic acid-editor protein complex.

The term "guide nucleic acid-editor protein complex" refers to a complex formed through the interaction between a guide nucleic acid and an editor protein, and the nucleic acid-protein complex includes the guide nucleic acid and the editor protein.

The guide nucleic acid-editor protein complex may serve to modify a subject. The subject may be a target nucleic acid, a gene, a chromosome or a protein.

For example, the gene may be an immune regulatory gene, artificially manipulated by a guide nucleic acid-editor protein complex, Wherein the immune regulatory gene artificially manipulated includes one or more modifications of nucleic acids which is at least one of a deletion or insertion of one or more nucleotides, a substitution with one or more nucleotides different from a wild-type gene, and an insertion of one or more foreign nucleotide, in a proto-spacer-adjacent motif (PAM) sequence in a nucleic acid sequence constituting the immune regulatory gene or in a continuous 1 bp to 50 bp the base sequence region adjacent to the 5' end and/or 3' end thereof, or a chemical modification of one or more nucleotides in a nucleic acid sequence constituting the immune regulatory gene.

The modification of nucleic acids may occur in a promoter region of the gene.

The modification of nucleic acids may occur in an exon region of the gene. In one exemplary embodiment, 50% of the modifications may occur in the upstream section of the coding regions of the gene.

The modification of nucleic acids may occur in an intron region of the gene.

The modification of nucleic acids may occur in an enhancer region of the gene.

The PAM sequence may be, for example, one or more of the following sequences (described in the 5' to 3' direction):

NGG (N is A, T, C or G);

NNNNRYAC (each of N is independently A, T, C or G, R is A or G, and Y is C or T);

NNAGAAW (each of N is independently A, T, C or G, and W is A or T);

NNNNGATT (each of N is independently A, T, C or G);

NNGRR(T) (each of N is independently A, T, C or G, R is A or G and Y is C or T); and TTN (N is A, T, C or G).

In addition, in another embodiment, the present invention provides a guide nucleic acid, which is capable of forming a complementary bond to each of target sequences of SEQ ID NOS: 1 to 289 in the nucleic acid sequences of at least one gene selected from the group consisting PD-1, CTLA-4, A20, Dgkα, Dgkζ, Fas, EGR2, PPP2R2D, PSGL-1, KDM6A and Tet2.

For example, the present invention may provide one or more guide nucleic acids selected from the group as described below:

a guide nucleic acid capable of forming a complementary bond to each of the target sequences of SEQ ID NOS: 6 and 11 in the nucleic acid sequence of the A20 gene;

a guide nucleic acid capable of forming a complementary bond to each of the target sequence of SEQ ID NO: 19, 20, 21, and 23, in the nucleic acid sequence of the Dgkα gene;

a guide nucleic acid capable of forming a complementary bond to the target sequence of SEQ ID NO: 25 in the nucleic acid sequence of the EGR2 gene;

a guide nucleic acid capable of forming a complementary bond to the target sequence of SEQ ID NO: 64 in the nucleic acid sequence of the PPP2R2D gene;

a guide nucleic acid capable of forming a complementary bond to each of the target sequence of SEQ ID NO: 87 and 89, in the nucleic acid sequence of the PD-1 gene;

a guide nucleic acid capable of forming a complementary bond to each of the target sequence of SEQ ID NO: 109, 110, 111, 112 and 113, in the nucleic acid sequence of the Dgkζ gene;

a guide nucleic acid capable of forming a complementary bond to each of the target sequence of SEQ ID NOS: 126, 128 and 129, in the nucleic acid sequence of the Tet-2 gene;

a guide nucleic acid capable of forming a complementary bond to the target sequence of SEQ ID NO: 182 in the nucleic acid sequence of the PSGL-1 gene;

a guide nucleic acid capable of forming a complementary bond to each of the target sequence of SEQ ID NOS: 252, 254, 257 and 264, in the nucleic acid sequence of the FAS gene; and a guide nucleic acid capable of forming a complementary bond to the target sequence of SEQ ID NO: 285 in the nucleic acid sequence of the KDM6A gene.

The guide nucleic acid may be non-limitedly 18 to 25 bp, 18 to 24 bp, 18 to 23 bp, 19 to 23 bp, or 20 to 23 bp nucleotides.

In addition, the present invention provides an artificially manipulated immune cell which comprises one or more artificially engineered immune regulatory genes and products expressed therefrom.

The cell is non-limitedly an immune cell and a stem cell. Immune cells are cells involved in an immune response, including all cells involving directly or indirectly involved in the immune response, and their differentiating cells.

The stem cells may be an embryonic stem cells, an adult stem cells, induced pluripotent stem cells (iPS cells) or cells derived from induced pluripotent stem cells (e.g., an iPS cell generated from a subject, manipulated to alter (e.g., induce a mutation in), which has self-replication and differentiation ability.

The immune cell may be a CD3 positive cell. For example, it may be a T cell or a CAR-T cell.

The immune cell may be a CD56 positive cell. For example, it may be a NK cell, such as a NK92 primary NK cell.

In an embodiment, the immune cell may be a CD3 and a CD56 double positive cell (CD3/CD56 double positive cell). For example, it may be a Natural killer T (NKT) cell or a Cytokine Induced Killer Cell (CIK).

Specifically, for example, the cell is at least one species selected from the group of consisting T cells such as CD8+T cells (e.g., a CD8+naïve T cell, a CD8+effector T cell, a central memory T cell, or an effector memory T cell), a CD4+T cell, a natural killer T cell (NKT cell), a regulatory T cell, a stem cell memory T cell, a lymphoid progenitor cell, a hematopoietic stem cell, a natural killer cell (NK cell), a dendritic cell, a cytokine induced cell (CIK), a Peripheral blood mononuclear cell (PBMC), a monocyte, a macrophage, a Natural Killer T (NKT) cell, and the like. Preferably, the immune cell may be a T cell, a CAR-T cell, a NK cell or a NKT cell.

The immune cell can be artificially manipulated to be suppressed or inactivated the activity of the immune regulatory gene.

The immune cell may further comprise a chimeric antigen receptor (CAR)

As an example, the T cell further comprises a chimeric antigen receptor (CAR) or an engineered TCR (T-cell receptor).

The immune cell further comprises a guide nucleic acid-editor protein complex or a nucleic acid sequence encoding the same.

The editor protein is at least one selected form the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein, and a Cpf1 protein. As an example, it may be *Streptococcus pyogenes*-derived Cas9 protein or a *Campylobacter jejuni*-derived Cas9 protein.

The guide nucleic acid may form a complementary bond with a part of nucleic acid sequences of one or more genes selected from the group consisting of a PD-1, CTLA-4, A20, DGKα, DGKζ, FAS, EGR2, PPP2R2D, PSGL-1, KDM6A, and TET2. It may create 0 to 5, 0 to 4, 0 to 3, or 0 to 2 mismatches. As a preferred example, the guide nucleic acid may be a nucleotide which forms a complementary bond with one or more of the target sequences of SEQ ID NOs: 1 to 289 of Table 1.

As an exemplary example, the guide nucleic acid may be nucleotides forming a complementary bond with one or more of the target sequence of SEQ ID NOs: 6 to 11 (A20), SEQ ID NOs: 19, 20, 21 and 23 (DGKa), SEQ ID NOs: 25 (EGR2), SEQ ID NOs: 64 (PPP2R2D), SEQ ID NOs: 87 and 89 (PD-1), SEQ ID NOs: 109, 110, 111, 112 and 113 (DGKζ), SEQ ID NOs: 126, 128 and 129 (TET-2), SEQ ID NOs: 182 (PSGL-1), SEQ ID NOs: 252, 254, 257 and 264 (FAS), and SEQ ID NOs: 285 (KDM6A), respectively.

In an exemplary embodiment of the present invention, the immune cell comprises at least one artificially engineered gene selected from DGKα gene and DGKζ gene which has undergone modification in a nucleic acid sequence.

In another exemplary embodiment of the present invention, the immune cell comprises the artificially engineered DGKα gene and DGKζ gene which have undergone modification in a nucleic acid sequence.

In an exemplary embodiment, the present invention provides a composition for causing the desired immune response. It may be referred to as a pharmaceutical composition or a therapeutic composition.

In an exemplary embodiment, the present invention provides a composition for gene manipulation comprising a guide nucleic acid capable of forming a complementary bond to each of the target sequences of SEQ ID NOS: 1 to 289 in a nucleic acid sequence of one or more genes selected from PD-1, CTLA-4, A20, Dgkα, Dgkζ, Fas, EGR2, PPP2R2D, PSGL-1, KDM6A and Tet2; and an editor protein or nucleic acid encoding the same.

The description of the relevant configuration is the same as described above.

In an exemplary embodiment, the present invention provides a method for artificially manipulating an immune cell comprising contacting an immune cell isolated from the human body at least one selected from:

(a) a guide nucleic acid capable of forming a complementary bond to each of the target sequences of SEQ ID NOS: 1 to 289 in the nucleic acid sequence of at least one gene selected from the group consisting of PD-1, CTLA-4, A20, Dgkα, Dgkζ, Fas, EGR2, PPP2R2D, PSGL-1, KDM6A and Tet2; and (b) an editor protein which is at least one selected from the group consisting of *Streptococcus pyogenes*-derived Cas9 protein, a *Campylobacter jejuni*-derved Cas9 protein, a *Streptococcus thermophilus*-derived Cas9 protein, a *Staphylococcus aureus*-derived Cas9 protein, a *Neisseria meningitidis*-derived Cas9 protein, and Cpf1 protein.

The guide nucleic acid and the editor protein may be present in one or more vectors each in the form of a nucleic acid sequence or may be present by forming a complex by binding of a guide nucleic acid and an editor protein.

The step of contacting is performed in vivo or ex vivo.

The step of contacting is carried out by one or more methods selected from electroporation, liposome, plasmid, viral vectors, nanoparticle and protein translocation domain fusion protein method.

The viral vector is at least one selected from the group of a retrovirus, a lentivirus, an adenovirus, an adeno-associated virus (AAV), a vaccinia virus, a poxvirus, and a herpes simplex virus.

In an exemplary embodiment, the present invention provides a method for providing information on a sequence of an immune cell target position in a subject, by sequencing at least one gene selected from the group of PD-1, CTLA-4, A20, Dgkα, Dgkζ, Fas, EGR2, PPP2R2D, PSGL-1, KDM6A, and Tet2.

In addition, the present invention provides a method for constructing a library using the information provide through the method.

In an exemplary embodiment, the present invention provides a kit for gene manipulation, which includes the following components:

(a) a guide nucleic acid capable of forming a complementary bond to each of the target sequences of SEQ ID NOS: 1 to 289 in the nucleic acid sequence of at least one gene selected from the group consisting of PD-1, CTLA-4, A20, Dgkα, Dgkζ, Fas, EGR2, PPP2R2D, PSGL-1, KDM6A, and Tet2; and (b) an editor protein which includes one or more proteins selected form the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein, and a Cpf1 protein.

These kits can be used to artificially manipulate the desired gene.

In one exemplary embodiment, the present invention provides all aspects of therapeutic use of a disease using an immune therapeutic approach comprising an administration of an artificially manipulated immune cell such as a genetically engineered immune cell or stem cell, to a subject. It is particularly useful for adoptive immunotherapy.

Targets for treatment may be mammals including primates (e.g. humans, monkeys, etc.), rodents (e.g. mice, rats, etc.).

Advantageous Effects

An effective immune cell therapy product can be obtained by an immune system in which the functions are artificially manipulated by artificially manipulated immune regulatory factors and cells containing the same.

For example, when the immune regulatory factors are artificially controlled by the method or composition of the present invention, the immune efficacies involved in survival, proliferation, persistency, cytotoxicity, cytokine-release and/or infiltration, etc. of immune cells may be improved.

BRIEF DESCRIPTIONS OF THE DRAWINGS

Figure 5:
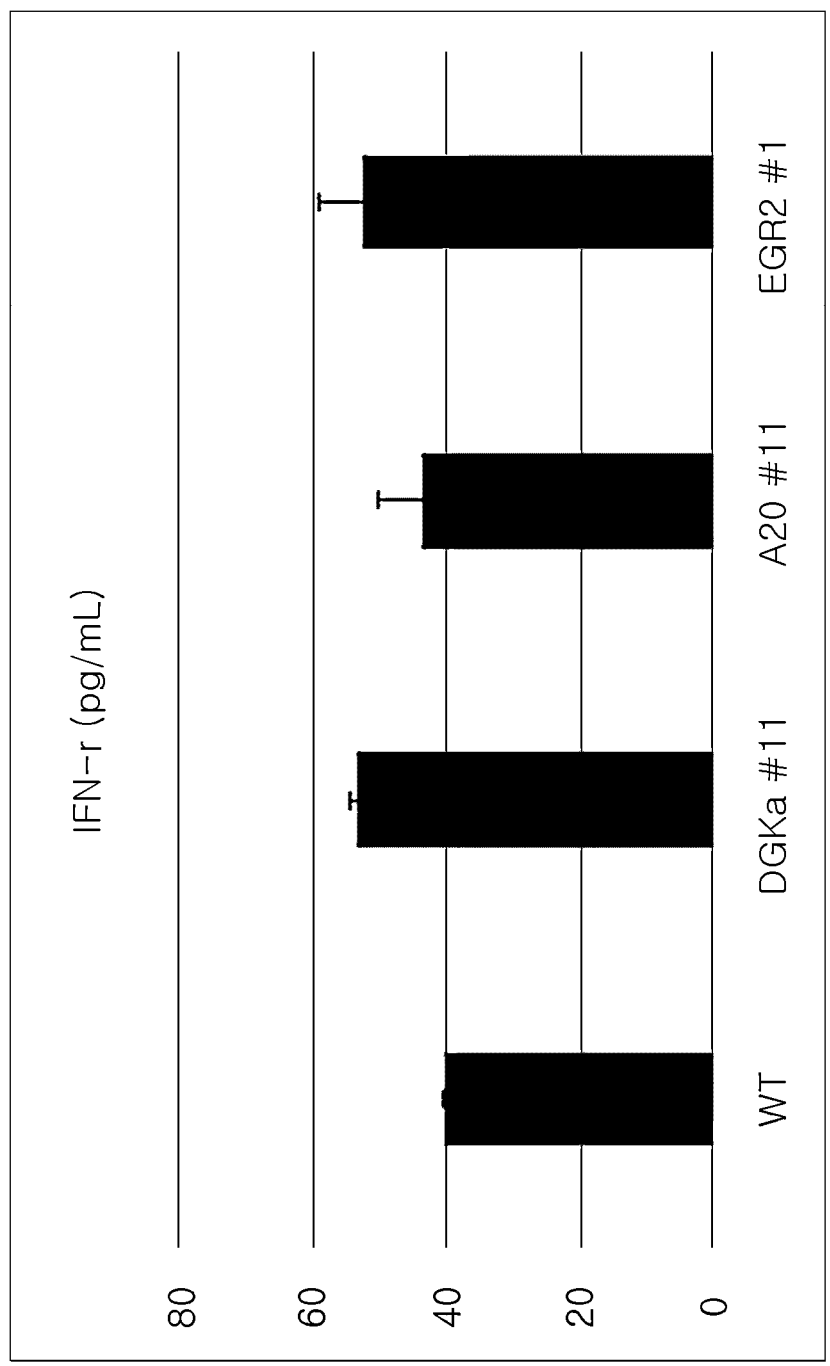

FIG. 5 is a graph showing the IFN-gamma level in a culture medium in cells, where DGK-alpha gene is knocked out, using sgRNA (#11; indicated as DGK-alpha #11) for DGKalpha; in cells, where A20 gene is knocked out, using sgRNA (#11; indicated as A20 #11) for A20; and in cells, where EGR2 gene is knocked out, using sgRNA (#1; indicated as EGR2 #1) for EGR2, respectively (unit of IFN-gamma level: pg/mL).

Figure 6:
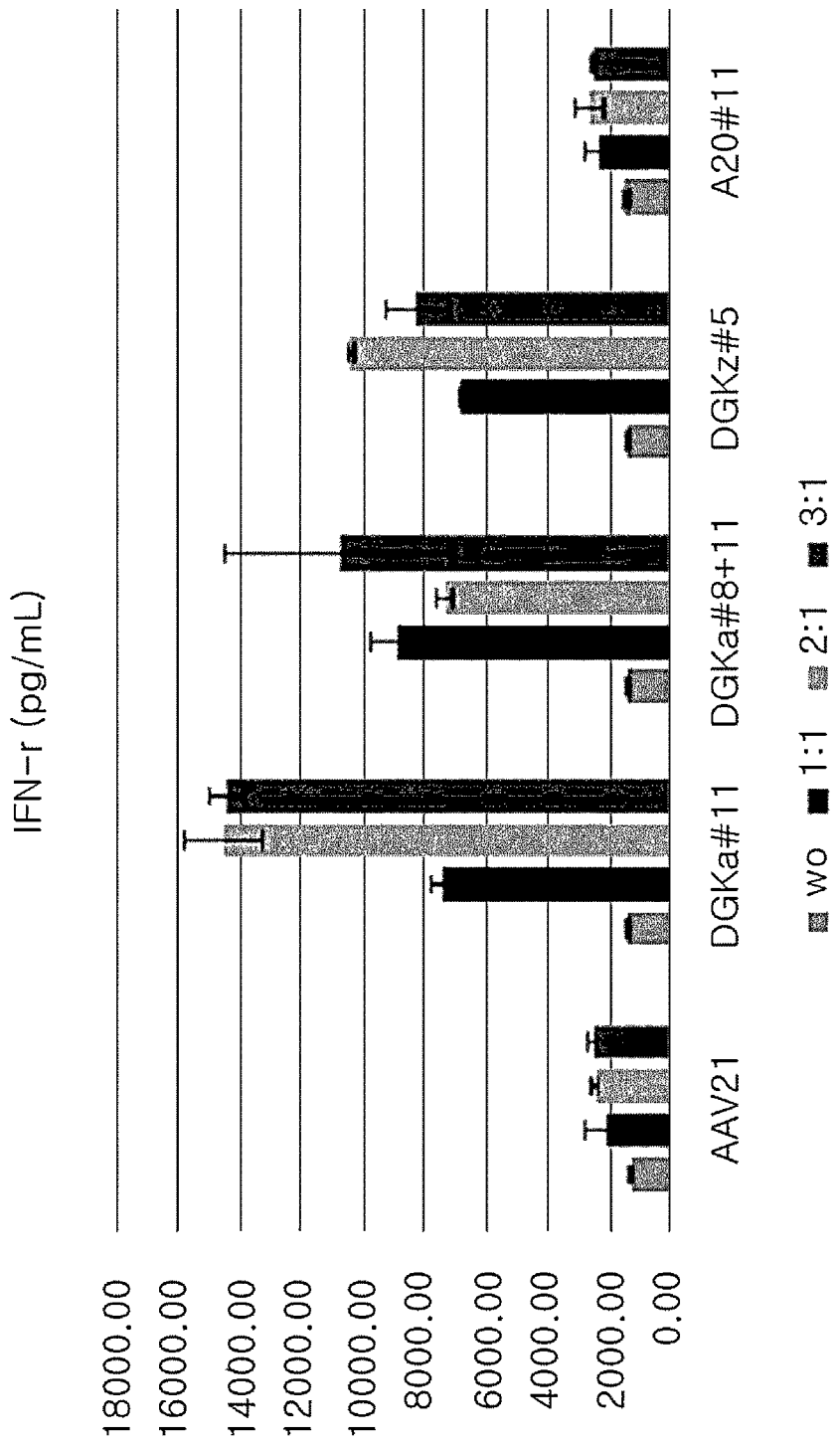

FIG. 6 is a graph showing the IFN-gamma level in a culture medium in cells, where DGKalpha gene is knocked out, using sgRNA (#11; indicated as DGK-alpha #11) for DGKalpha; in cells, where DGK-alpha gene is knocked out, using sgRNA (a combined use of #8 and #11; indicated as DGK-alpha #8+11) for DGKalpha; in cells, where DGK-zeta gene is knocked out, using sgRNA (#5; indicated as DGK-zeta #5) for DGK-zeta; and in cells, where A20 gene is knocked out, using sgRNA (#11; indicated as A20 #11) for A20, respectively (unit of IFN-gamma level: pg/mL).

Figure 7:
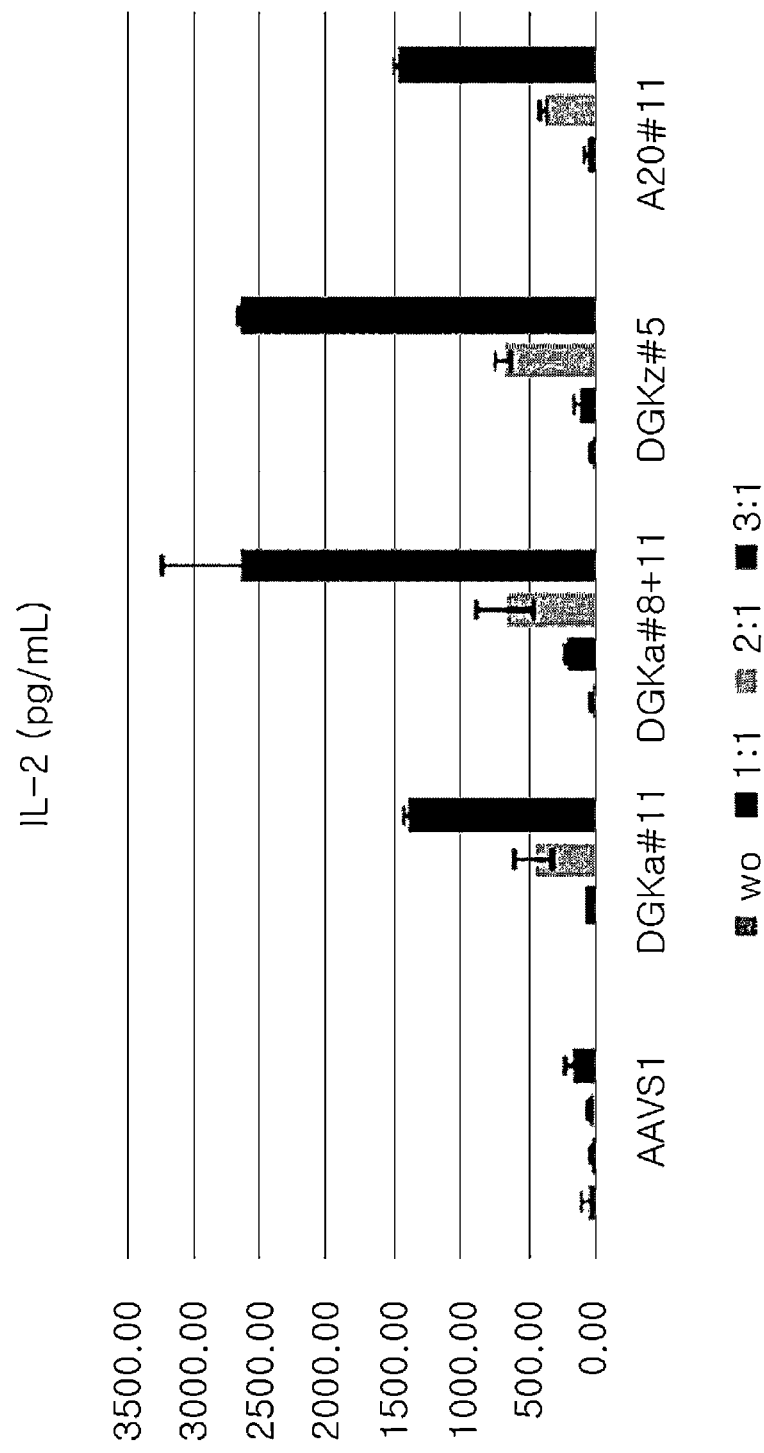

FIG. 7 is a graph showing the IL-2 level in a culture medium in cells, where DGK-alpha gene is knocked out using DGK-alpha #11; in cells, where DGK-alpha gene is knocked out using DGK-alpha #8+11; in cells, where DGK-zeta gene is knocked out, using DGKzeta #5; and in cells, where A20 gene is knocked out using A20 #11, respectively (unit of IL-2 level: pg/mL).

Figure 8A:
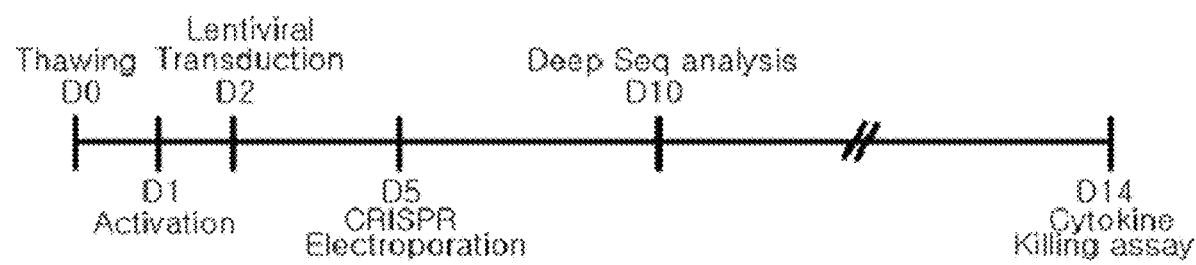
Figure 8A:
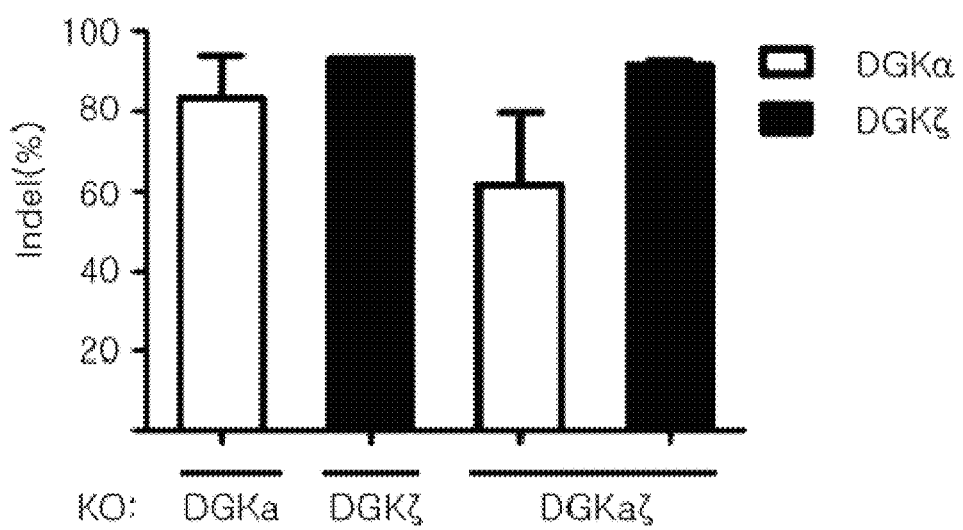
Figure 8B:
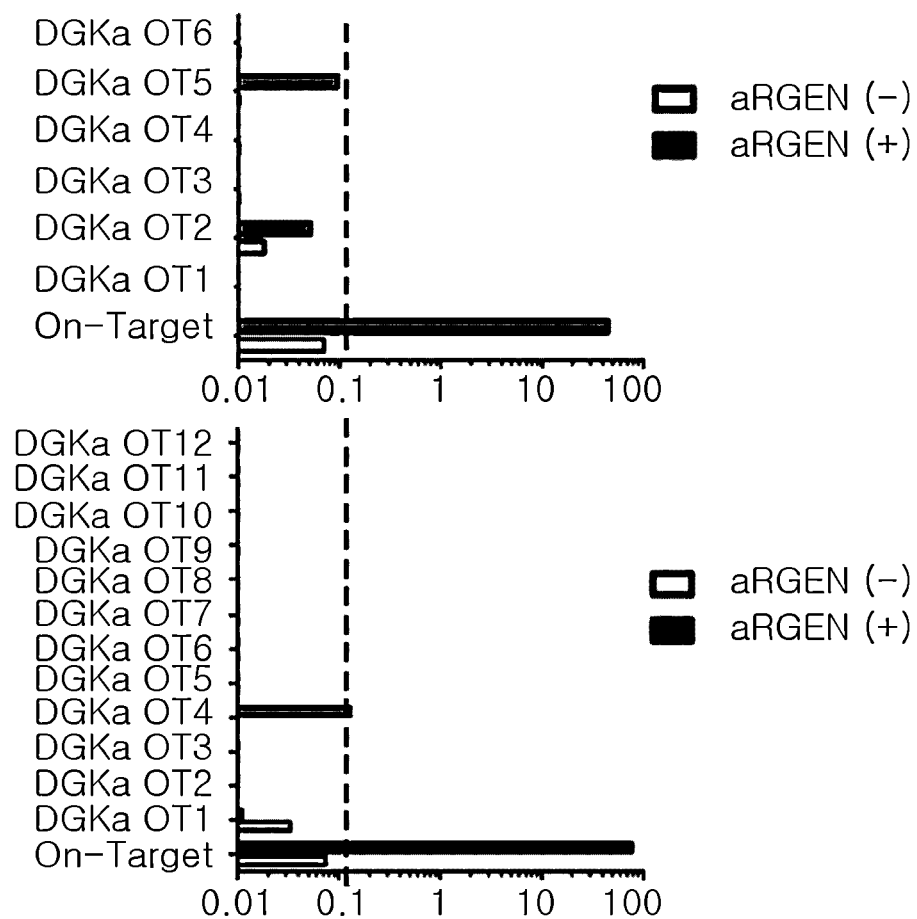

FIG. 8(a) shows the knockout results of CRISPR/Cas9-mediated DGK gene in human primary T cells, in which FIG. 8(a)(a) confirms the gene knockout timeline in human primary T cells (cell activation by CD3/CD28 beads, lentiviral delivery of 139 CAR, and knockout of DGK gene using electroporation d) and FIG. 8(a)(b) confirms the indel efficiencies for DGKα and DGKζ using the Mi-seq system; and FIG. 8(b) shows graphs illustrating the results of off-target analysis.

Figure 9A:
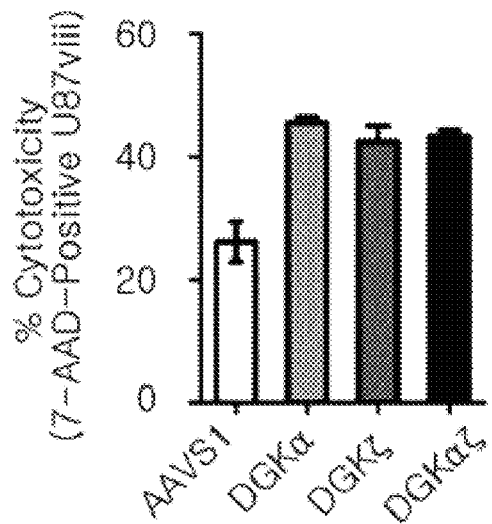
Figure 9A:
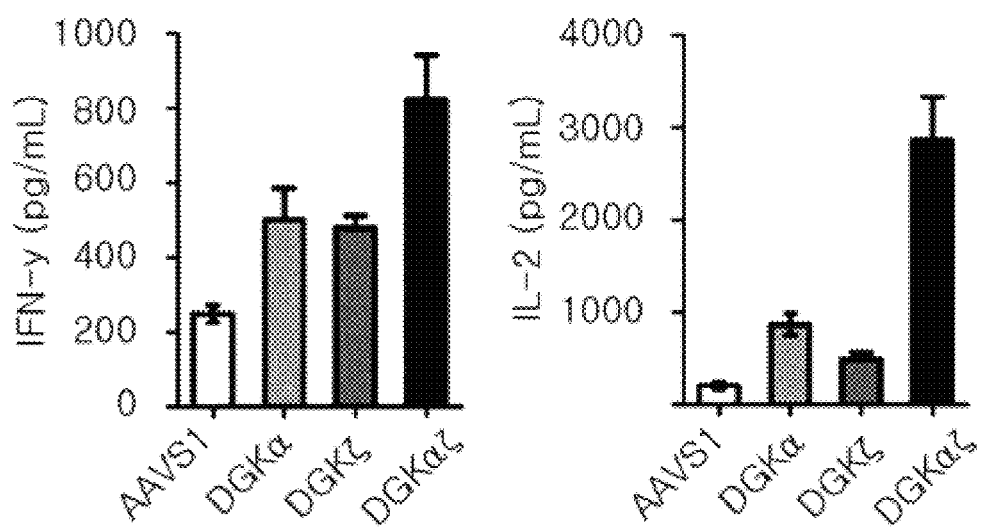
Figure 9B:
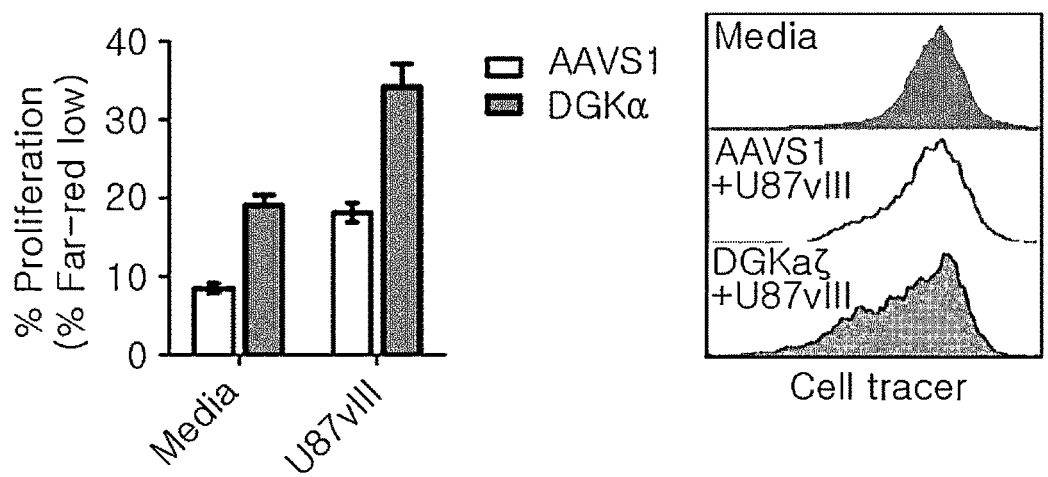

FIG. 9(a) shows graphs illustrating the effects of improving the effector and proliferation of CAR-T cells by knockout of DGK gene, in which FIG. 9(a)(a) the evaluation results of killing activity of 139 CAR-T cells by measuring 7-AAD positive U87vIII cells using flow cytometry, and FIG. 9(a)(a) the results of cytokine secretion ability assay by ELISA (IFN-γ, IL-2 kit, Biolegend) are shown; and FIG. 9(b) shows graphs illustrating the evaluation results of the proliferation ability of 139 CAR T-cells using flow cytometry.

Figure 10A:
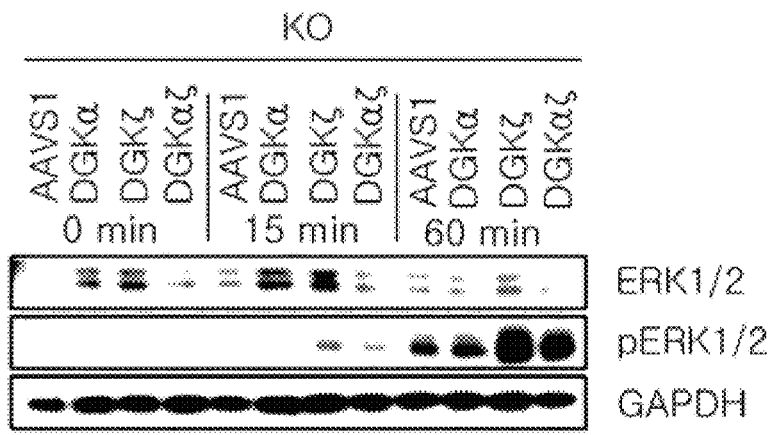
Figure 10B:
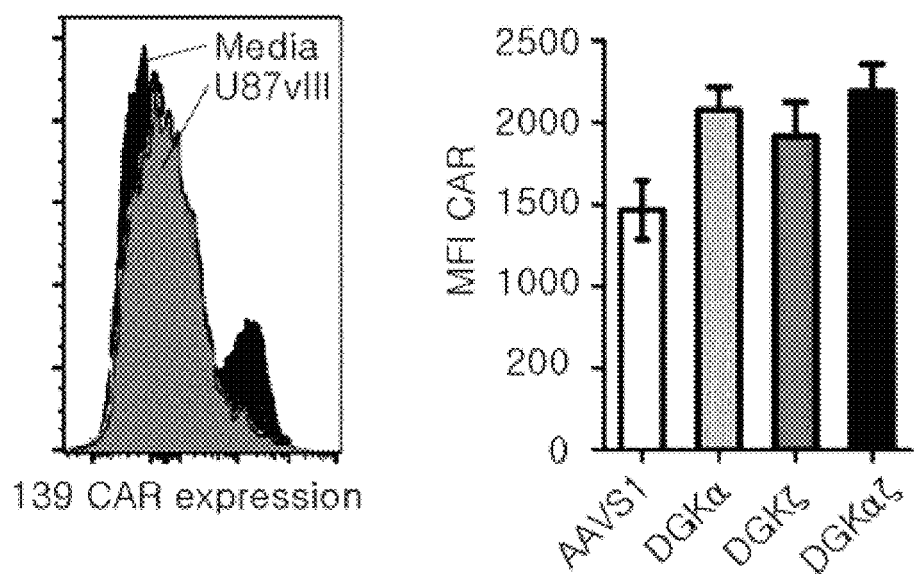

FIG. 10 shows the results of enhancing the 139 CAR expression and amplifying the signaling at CD3 terminus after DGKs knockout exposes antigens, in which FIG. 10(a) shows the western blot results on phosphorylated ERK signals of 139 CAR-T cells stimulated with CD3/CD28 beads, and FIG. 10(b) shows the results of the 139 CAR expression using flow cytometry (left: CAR expression depending on the presence of exposure of antigens; and right: comparison of CAR expression 3 days after the exposure of antigens).

Figure 11A:
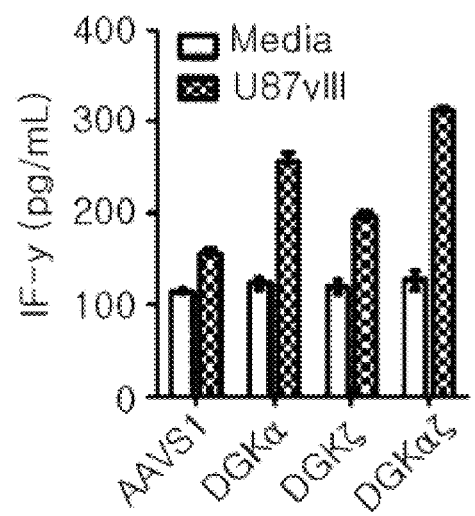
Figure 11B:
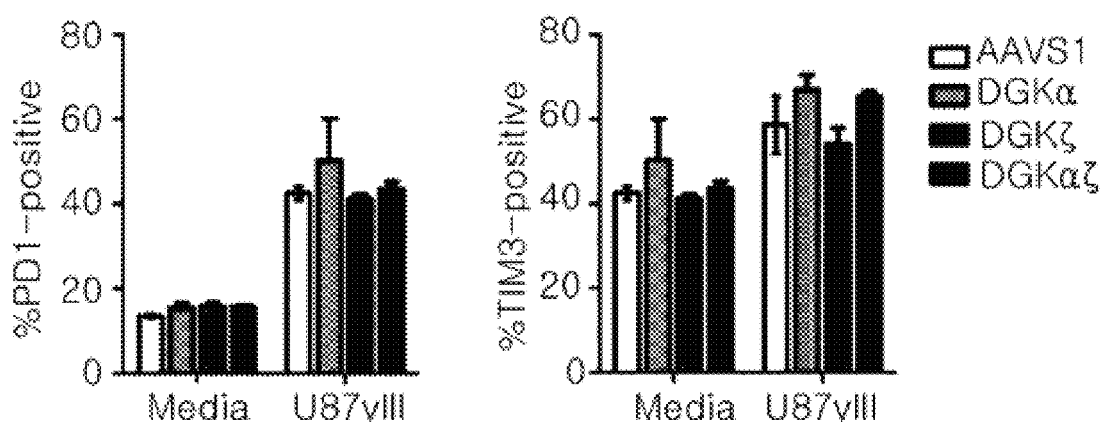

FIG. 11 shows graphs illustrating the results where DGKs knockout do not induce tonic activation and T-cell exhaustion, in which FIG. 11(a) shows the evaluation of IFN-γ secretion ability by ELISA, and FIG. 11(b) shows the analysis results of exhaustion markers in CAR-positive T-cells (i.e., PD-1 (left) and TIM-3 (right)).

Figure 12A:
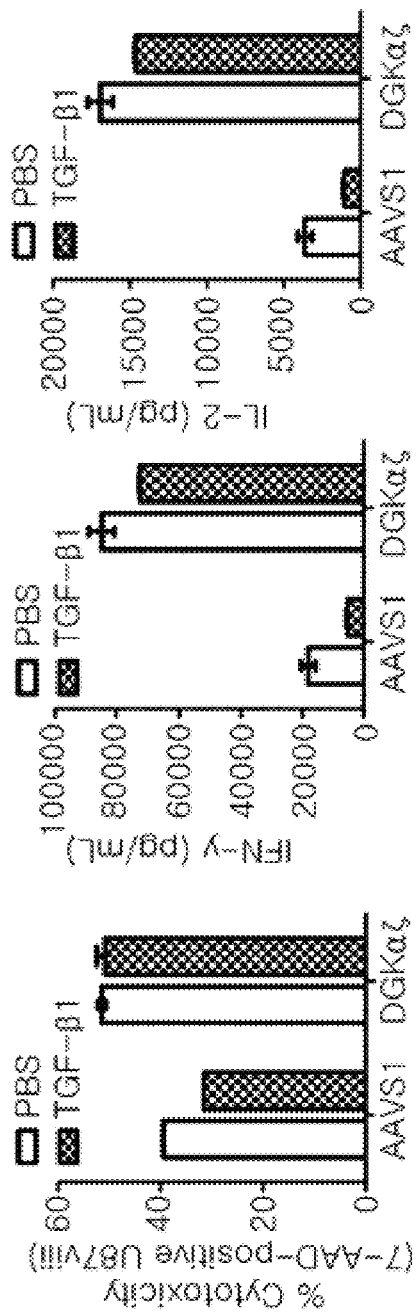
Figure 12B:
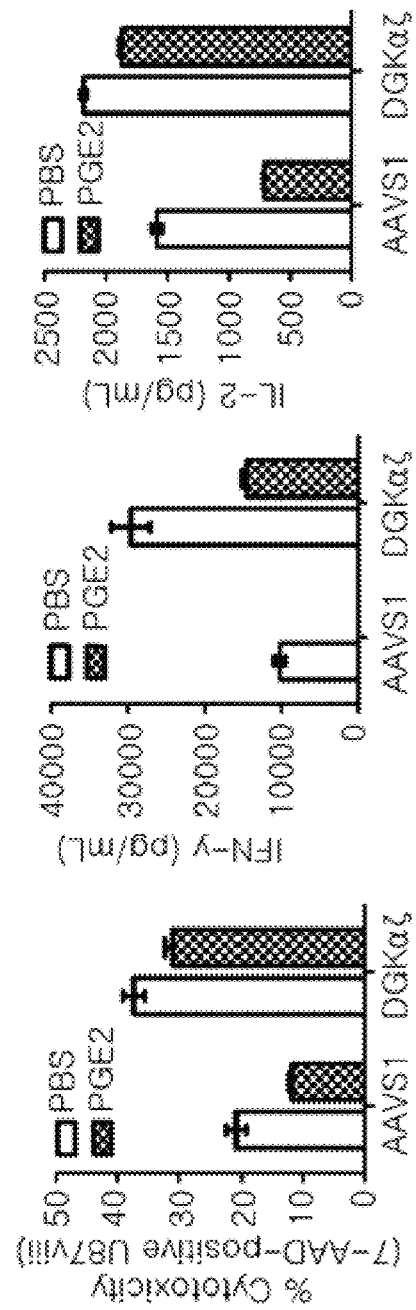

FIG. 12 shows graphs illustrating the results where DGK-knockout T-cells avoid immunosuppressive effects of TGF-β and PGE2, in which FIG. 12(a) shows the evaluation of killing activity, IFN-γ secretion ability, and IL-2 secretion ability of 139 CAR-T cells and 139 DGKαζ CAR-T cells, depending on the presence of TGF-β (10 ng/mL), and FIG. 12(b) shows the evaluation of killing activity, IFN-γ secretion ability, and IL-2 secretion ability of 139 CAR-T cells and 139 DGKαζ CAR-T cells, depending on the presence of PGE2 (0.5 μg/mL).

Figure 13A:
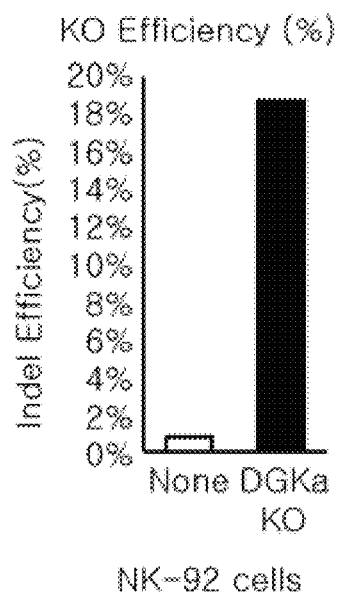
Figure 13B:
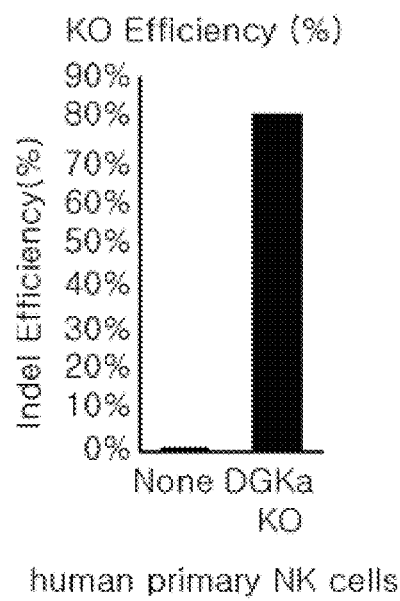
Figure 13C:
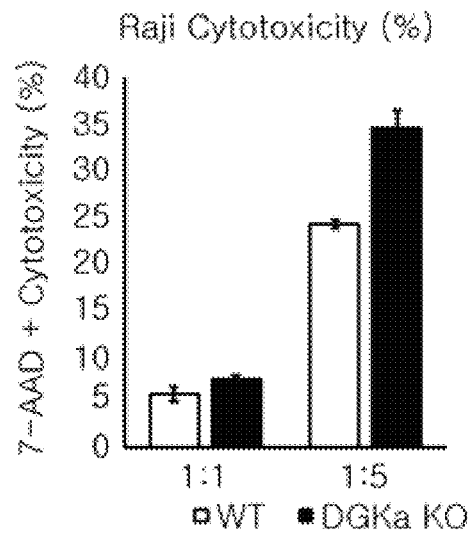

FIG. 13 shows graphs illustrating the results of the CRISPR/Cas9-mediated knockout efficiency of DGKα and the effect on effector functions in human NK cells, in which FIG. 13(a) and FIG. 13(b) show graphs illustrating knockout efficiency analysis in NK-92 cells and human primary NK cells using the Mi-seq system, and FIG. 13(c) shows a graph illustrating the killing activity of NK-92 by measurement of 7-AAD-positive Raji cells.

Figure 14A:
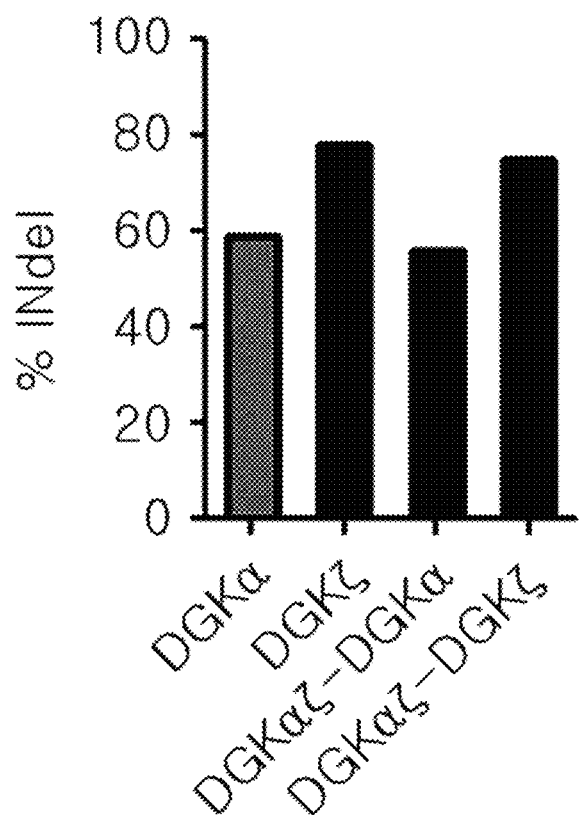
Figure 14B:
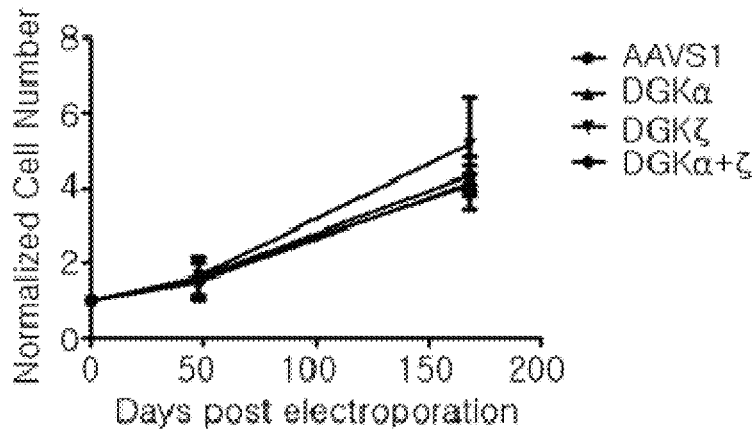
Figure 14C:
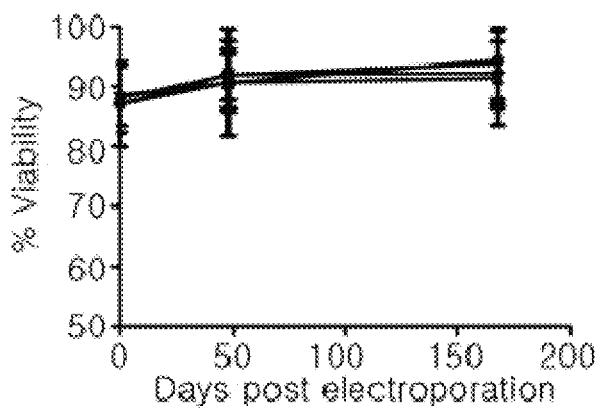
Figure 14D:

FIG. 14 shows the results of the CRISPR/Cas9-mediated knockout efficiencies of DGKα and DGKζ in human NKT cells, in which FIG. 14(a) shows the evaluation results of indel efficiency, FIG. 14 (b) shows the evaluation results of cell growth, FIG. 14 (c) shows the evaluation results of cell survival ability, and FIG. 14 (d) shows the western blot experimental results to identify the presence of expression at protein level.

Figure 15A:
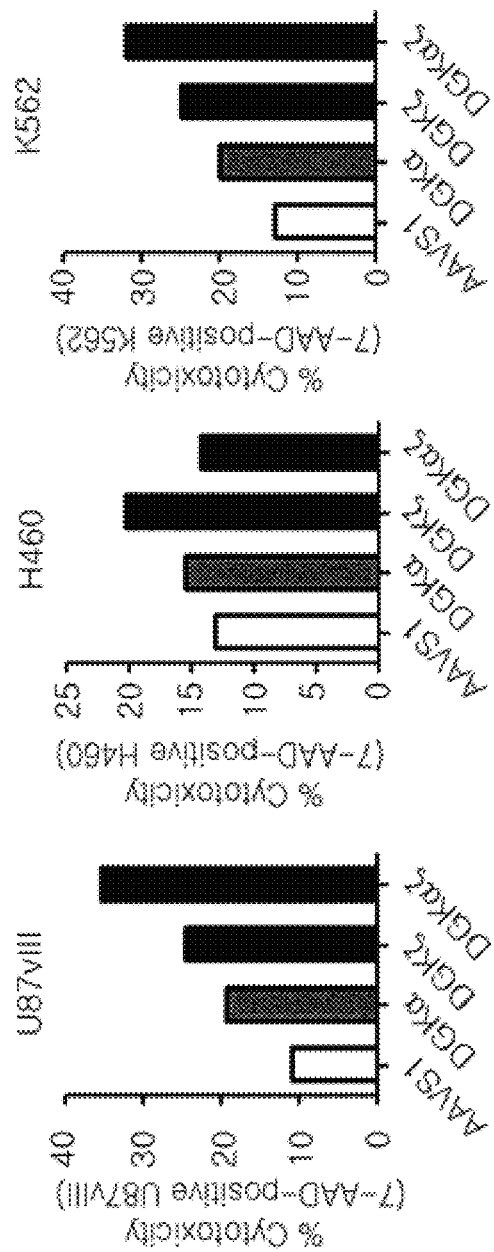
Figure 15B:
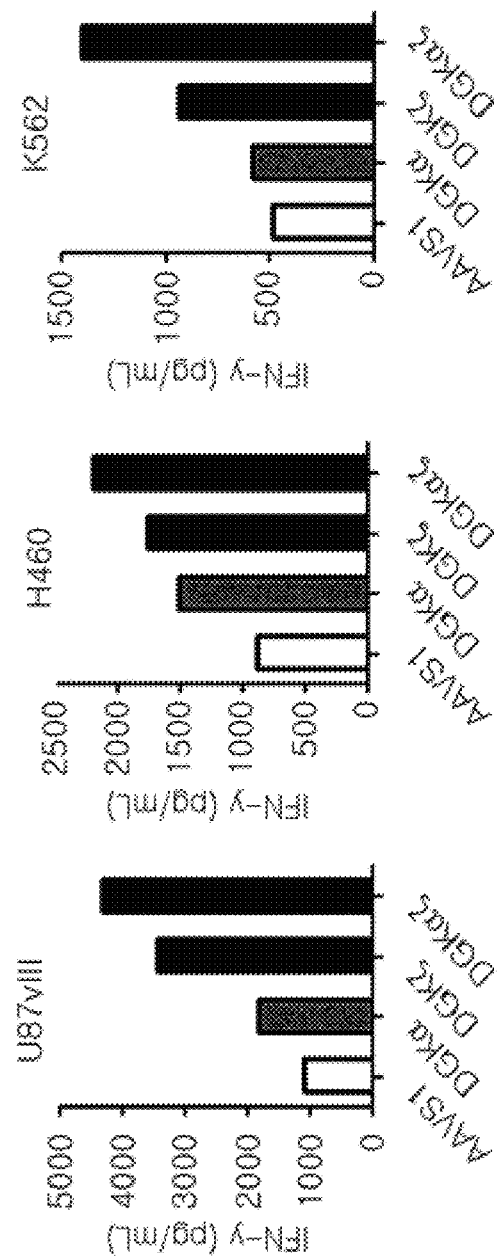

FIG. 15 shows graphs illustrating the effects of DGKα and DGKζ on effector functions in human NKT cells, in which the effect of respective knockout and simultaneous knockout of DGKα and DGKζ on FIG. 15(a) killing activity and FIG. 15(b) IFN-γ secretion ability by ELISA (IFN-kit, Biolegend) were confirmed.

Figure 16A:
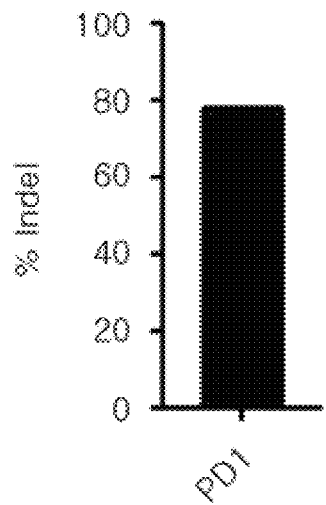
Figure 16B:
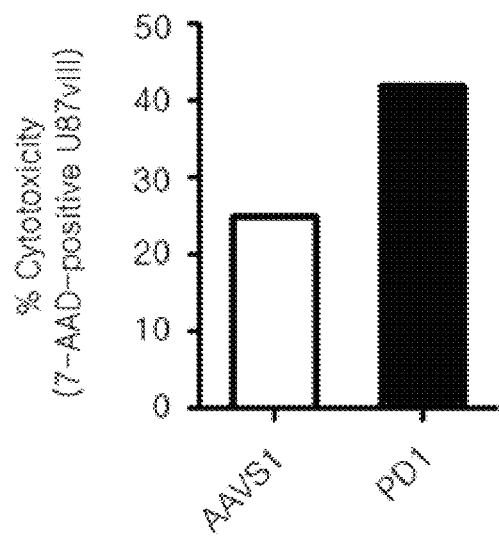

FIG. 16 shows graphs illustrating FIG. 16(a) the indel efficiency and FIG. 16(b) improvement of cytotoxicity (i.e, improvement of killing activity), after PA-1 is knocked out in NKT cells, for the functional evaluation of knockout of DGKα and DGKζ in human NKT cells.

Figure 17A:
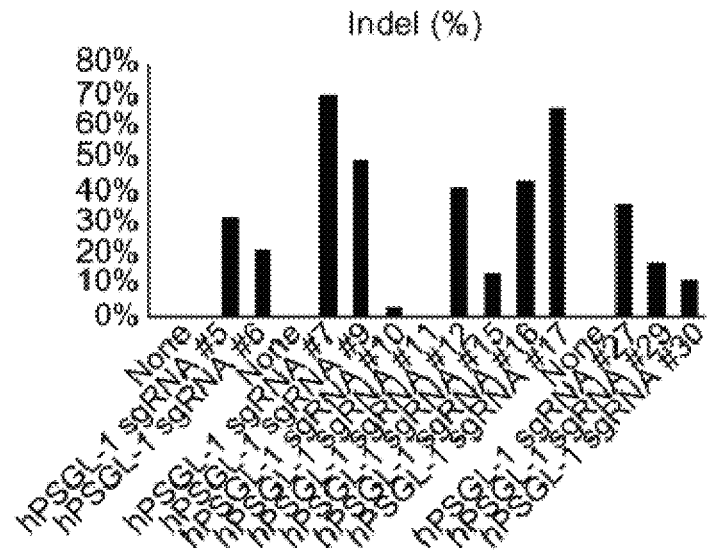
Figure 17A:
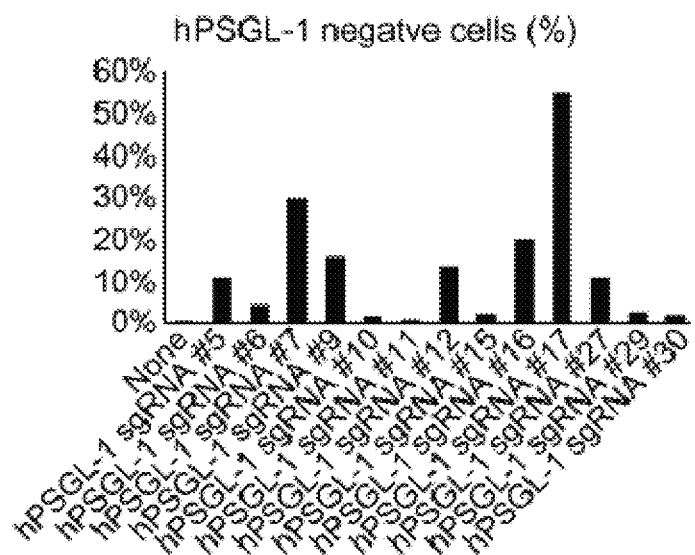
Figure 17B:
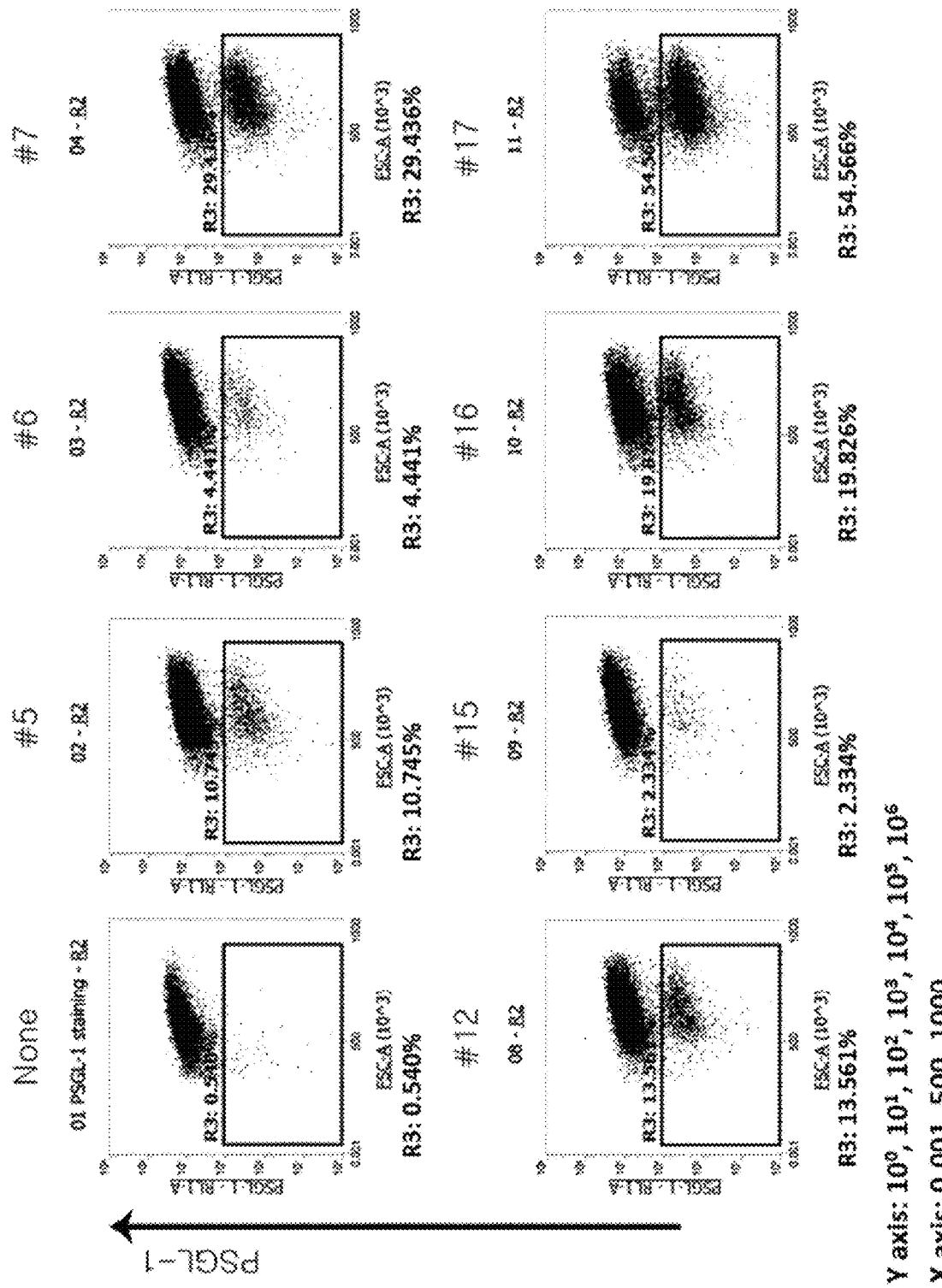
Figure 17C:
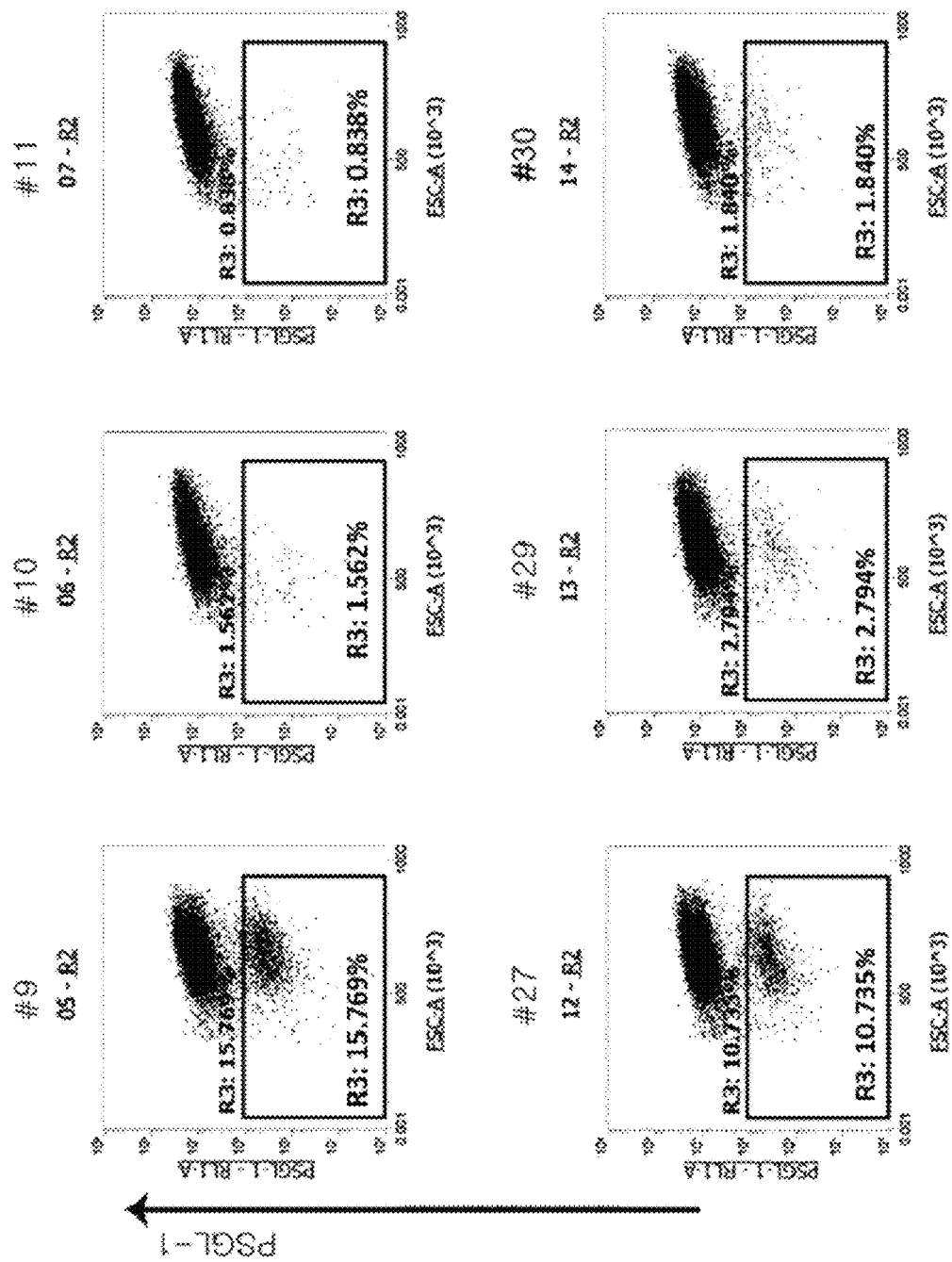

FIGS. 17(a), 17(b) and 17(c) shows graphs illustrating the analysis results for the screening of hPSGL-1 sgRNA in Jurkat cells, in which FIG. 17(a) shows the indel efficiency and the degree of Jurkat cells where PSGL-1 is not expressed after knockout, and FIGS. 17(b) and 17(c) show the degree of PSGL-1 expression expressed on the surface of Jurkat cells after knockout.

Figure 18A:
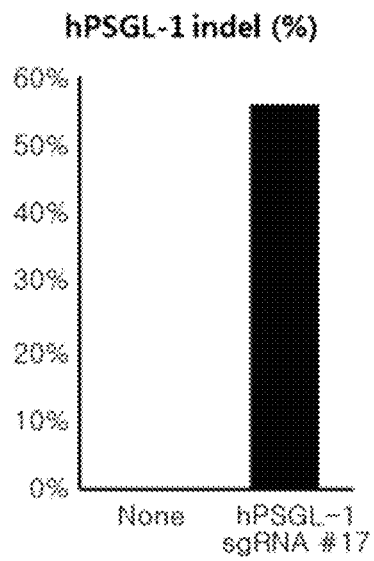
Figure 18B:
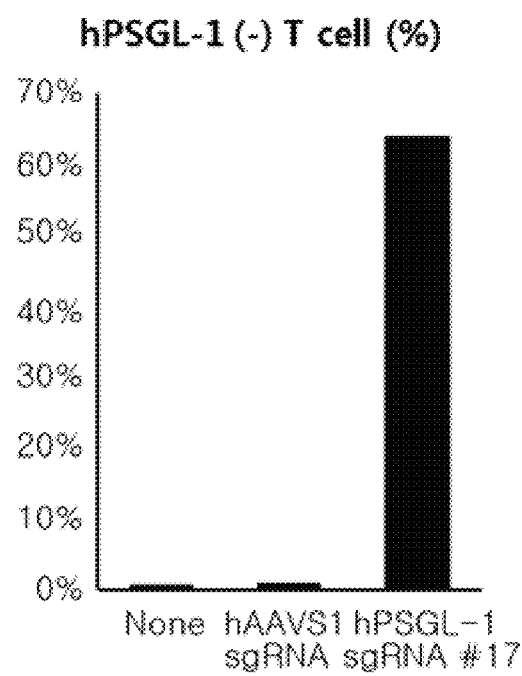
Figure 18C:
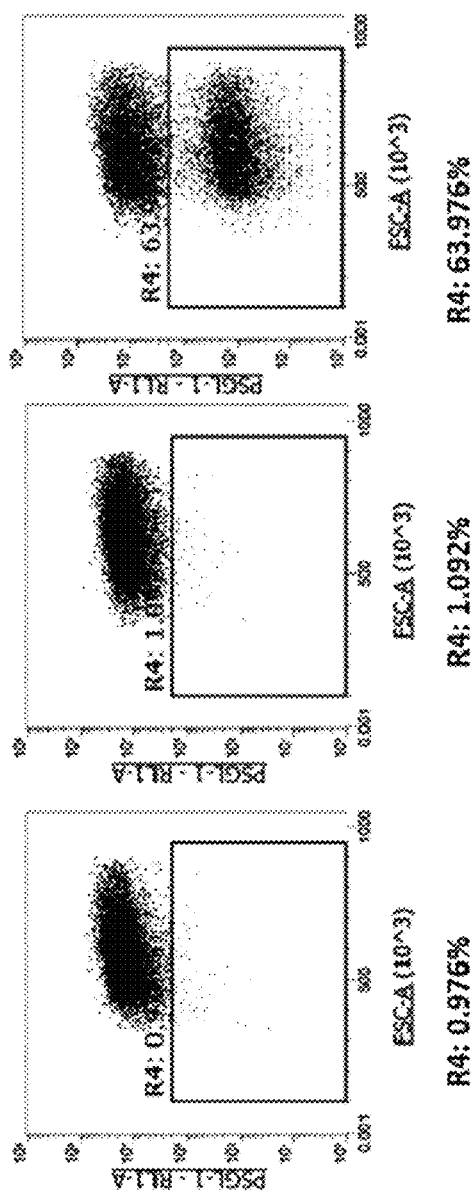

FIG. 18 shows graphs illustrating the results of hPSGL-1 knockout (KO) experiment in human primary T cells, in which FIG. 18(a) shows indel efficiency, FIG. 18(b) shows the degree of T cells where PSGL-1 is not expressed after knockout, and FIG. 18(c) shows the degree of PSGL-1 expression expressed on the surface of T cells after knockout.

DETAILED DESCRIPTION

Unless defined otherwise, all technical and scientific terms used herein have the same meaning as commonly understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, materials, methods and examples are merely illustrative, and not intended to be limited.

The present invention relates to an artificially manipulated immune system with improved immune efficacy. More specifically, it relates to an artificially modified immune system comprising an artificially manipulated immune regulatory factor and cells comprising the same.

[Immune Regulatory Factor]

Immune Regulatory Factor

The term "immune regulatory factor" is a material that functions in connection with the formation and performance of an immune response, including all of the various materials that may be non-natural, i.e., artificially manipulated, and capable of regulating immune responses. For example, the immune regulatory factor may be genetically manipulated or modified gene or protein, which is expressed in immune cells.

The term "artificially manipulated" means a state in which an artificial modification is applied, not a state of being as it is that occurs in a natural state.

The term "genetically manipulated" means a case where an operation of artificial application of genetic modification is performed to a biological or non-biological material referred to in the present invention, for example, it may be a gene and/or gene product (e.g., polypeptides, proteins, etc.) in which genome has been artificially modified under a particular purpose.

As a preferred example, the present invention provides a genetically manipulated or modified immune regulatory factor for a particular purpose.

The following listed elements are only examples of immune regulatory factors and thus do not limit the types of immune regulatory factors encompassed by the present invention. The genes or proteins listed below may not have only one type of immune regulatory function but may have multiple types of functions. In addition, two or more immune regulatory factors may be provided, if necessary.

[Immune Cell Activity Regulating Elements]

The term "immune cell activity regulating element" is an element that functions to regulate the degree or activity of an immune response, for example, it may be a genetically manipulated or modified gene or protein that functions to regulate the degree or activity of the immune response.

The immune cell activity regulating element can perform functions associated with activation or deactivation of immune cells.

The immune cell activity regulating element can function to stimulate or improve the immune response.

The immune cell activity regulating element can function to suppress the immune response.

The immune cell activity regulating element can bind to the channel proteins of the cell membrane and the receptors and thereby perform functions associated with signal transduction that regulates immune responses and functions associated with synthesis and decomposition of proteins.

For example, the immune cell activity regulating element may be Programmed cell death protein (PD-1).

The PD-1 gene (also referred to as the PDCD1 gene; hereinafter, the PD-1 gene and the PDCD1 gene are used to mean the same gene) refers to a gene (full-length DNA, cDNA or mRNA) that encodes the protein PD-1 which is also referred to as cluster of differentiation 279 (CD279). In an embodiment, the PD-1 gene may be, but is not limited to, one or more selected from the group consisting of the following genes: genes encoding human PD-1 (e.g., NCBI Accession No. NP_005009.2, etc.), for example PD-1 genes expressed as NCBI Accession No. NM_005018.2, NG_012110.1, etc.

The immune cell activity regulating element may be cytotoxic T-lymphocyte-associated protein 4 (CTLA-4).

CTLA-4 gene refers to a gene (full-length DNA, cDNA or mRNA) that encodes the protein CTLA-4, which is also referred to as cluster of differentiation 152 (CD152). In an embodiment, the CTLA-4 gene may be, but is not limited to, one or more selected from the group consisting of the following genes: genes encoding human CTLA-4 (e.g., NCBI Accession No. NP_001032720.1, NP_005205.2, etc.), for example CTLA-4 genes expressed as NCBI Accession No. NM_001037631.2, NM_005214.4, NG_011502.1, etc.

The immune cell activity regulating element may be CBLB.

The immune cell activity regulating element may be PSGL-1.

The immune cell activity regulating element may be ILT2.

The immune cell activity regulating element may be KIR2DL4.

The immune cell activity regulating element may be SHP-1.

The above genes may be derived from mammals including primates (e.g. humans, monkeys, etc.), rodents (e.g. rats, mice, etc.).

In one embodiment, the immune cell activity regulating element may function to stimulate the immune response.

The immune cell activity regulating element may be an immune cell growth regulating element.

The term "immune cell growth regulating element" refers to an element that functions to regulate the growth of immune cells by regulating protein synthesis, etc. in immune cells, for example, a gene or protein expressed in immune cells.

The immune cell growth regulating element may function in DNA transcription, RNA translation, and cell differentiation.

Examples of the immune cell growth regulating element may be genes or proteins involved in the expression pathways of NFAT, IκB/NF-κB, AP-1, 4E-BP1, eIF4E, and S6.

For example, the immune cell growth regulating element may be DGK-alpha.

The DGKA (Dgk-alpha) gene refers to a gene (full-length DNA, cDNA or mRNA) that encodes the protein diacylglycerol kinase alpha (DGKA). In an embodiment, the DGKA gene may be, but is not limited to, one or more selected from the group consisting of the following genes: genes encoding human DGKA (e.g., NCBI Accession No. NP_001336.2, NP_958852.1, NP_958853.1, NP_963848.1, etc.), for example DGKA genes expressed as NCBI Accession No. NM_001345.4, NM_201444.2, NM_201445.1, NM_201554.1, NC_000012.12, etc.

The immune cell growth regulating element may be DGK-zeta.

The DGKZ (Dgk-zeta) gene refers to a gene (full-length DNA, cDNA or mRNA) that encodes the protein diacylglycerol kinase zeta (DGKZ). In an embodiment, the DGKZ gene may be, but is not limited to, one or more selected from the group consisting of of the following genes: genes encoding human DGKZ (e.g., NCBI Accession No. NP_001099010.1, NP_001186195.1, NP_001186196.1, NP_001186197.1, NP_003637.2, NP_963290.1, NP_963291.2, etc.), for example DGKZ gene expressed as NCBI Accession No. NM_001105540.1, NM_001199266.1, NM_001199267.1, NM_001199268.1, NM_003646.3, NM_201532.2, NM_201533.3, NG_047092.1, etc.

The immune cell growth regulating element may be EGR2.

The EGR2 gene refers to a gene (full-length DNA, cDNA or mRNA) that encodes early growth response protein 2 (EGR2). In an embodiment, the EGR2 gene, may be, but is not limited to, one or more selected from the group consisting of the followings.

The immune cell growth regulating element may be EGR3.

The immune cell growth regulating element may be PPP2R2D.

The immune cell growth regulating element may be A20 (TNFAIP3).

The immune cell growth regulating element may be PSGL-1.

The above genes may be derived from mammals including primates (e.g. humans, monkeys, etc.), rodents (e.g. rats, mice, etc.).

The immune cell activity regulating element may be an immune cell death regulating element.

The term "immune cell death regulating element" refers to an element that functions relating to the death of immune cells, and it may be a gene or protein expressed in immune cells performing such a function.

The immune cell death regulating element can perform functions associated with apoptosis or necrosis of immune cells.

In one embodiment, the immune cell death regulating element may be a caspase cascade-associated protein or gene.

The immune cell death regulating element may be Fas. When referring to the protein or the gene hereinafter, it is apparent to those of ordinary skill in the art that a receptor or a binding region on which the protein or the gene acts can be manipulated.

In another embodiment, the immune cell death regulating element may be a death domain-associated protein or gene. In particular, the immune cell death regulating element may be Daxx.

The immune cell death regulating element may be a Bcl-2 family protein.

The immune cell death regulating element may be a BH3-only family protein.

The immune cell death regulating element may be Bim.

The immune cell death regulating element may be Bid.

The immune cell death regulating element may be BAD.

The immune cell death regulating element may be a ligand or a receptor located in the immune extracellular membrane.

In particular, the immune cell death regulating element may be PD-1.

Additionally, the immune cell death regulating element may be CTLA-4.

The immune cell activity regulating element may be an immune cell exhaustion regulating element.

The term "immune cell exhaustion regulating element" is an element performing functions associated with the progressive loss of functions of immune cells, and it may be a gene or protein expressed in immune cells performing such a function.

The immune cell exhaustion regulating element can function to help transcription or translation of genes involved in inactivation of immune cells.

In particular, the function of assisting transcription may be a function of demethylating the corresponding genes.

In addition, the genes involved in inactivation of immune cells include the gene of the immune cell activity regulating element.

In particular, the immune cell exhaustion regulating element may be TET2.

Genes encoding human (e.g., NCBI Accession No. NP_001120680.1, NP_060098.3, etc.), for example, TET2 gene expressed as NCBI Accession NM_001127208.2, No. NM_017628.4, NG_028191.1, etc.

The immune cell exhaustion regulating element can function to participate in the excessive growth of immune cells. Immune cells that undergo excessive growth and do not regenerate will lose their functions.

In particular, the immune cell exhaustion regulating element may be Wnt. Hereinafter, when a protein or gene is referred to, it is apparent to those of ordinary skill in the art that the protein or the gene in the signal transduction pathway in which the protein is included and the receptor on which the gene acts, and the binding region can be manipulated.

In addition, the immune cell exhaustion regulating element may be Akt. Hereinafter, when a protein or gene is referred to, it is apparent to those of ordinary skill in the art that the protein or the gene in the signal transduction pathway in which the protein is included and the receptor on which the gene acts, and the binding region can be manipulated.

The immune cell activity regulating element may be a cytokine production regulating element.

The term "cytokine production regulating element" is a gene or protein involved in the secretion of cytokines of immune cells and it may be a gene or protein expressed in immune cells performing such a function.

Cytokine is a collective term referring to a protein which is secreted by immune cells, and is a signal protein that plays an important role in vivo. Cytokines are involved in infection, immunity, inflammation, trauma, corruption, cancer, etc. Cytokines can be secreted from cells and then affect other cells or the cells which secreted themselves. For example, they can induce the proliferation of macrophages or promote the differentiation of the secretory cells themselves. However, when cytokines are secreted in an excessive amount, they may cause problems such as attacking normal cells, and thus proper secretion of cytokines is also important in immune responses.

The cytokine production regulating element may be, for example, preferably a gene or protein in the pathways of TTNFα, IFN-γ, TGF-β, IL-2, IL-4, IL-10, IL-13, IL-1, IL-6, IL-12, IL-7, IL-15, IL-17, and IFN-α.

Alternatively, the cytokines may function to deliver a signal to other immune cells to induce the immune cells to kill the recognized antigen-bearing cells or to assist in differentiation. In particular, the cytokine production regulating element may be, preferably, a gene or protein in the gene pathway relating to IL-2 secretion.

In an embodiment, the immune regulatory factor may refer to a group of molecules that are expressed in immune cells. These molecules can effectively work to downregulate/upregulate or inhibit/promote the immune responses.

For example, as a group of molecules which T cells express, "immune checkpoint" may be, but is not limited to, Programmed Death1 (PD-1. PDCD1 or CD279, Accession No.: NM_005018) cytotoxic T lymphocyte antigen 4 (CTLA-4 or CD152, GenBank Accession No.: AF414120.1), LAG3 (CD223, Accession No.: NM_002286.5), Tim3 (HAVCR2, GenBank Accession No.: JX049979.1), BTLA (CD272, Accession No.: NM_181780.3), BY55 (CD160, GenBank Accession No.: CR541888.1), TIGIT (IVSTM3, Accession No.: NM_173799), LAIR1 (CD305, GenBank Accession No.: CR542051.1), SIGLEC10 (GeneBank Accession No.: AY358337.1), 2B4 (CD244, Accession No.: NM_001166664.1), PPP2CA, PPP2CB, PTPN6, PTPN22, CD96, CRTAM, SIGLEC7, SIGLEC9, TNFRSF10B, TNFRSF10A, CASPB, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3, which directly inhibit immune cells.

In an embodiment of the present invention, the immune regulatory factor may be, for example, genetically manipulated or modified, PD-1 gene, CTLA-4 gene, TNFAIP3 (A20) gene, DGKA gene, DGKZ gene, FAS gene, EGR2 gene, PPP2R2D gene, TET2 gene, PSGL-1 gene, and KDM6A gene.

In an embodiment of the present invention, the immune regulatory factor may include two or more genetically manipulated or modified genes. For example, two or more genes selected from the group consisting of PD-1 gene, CTLA-4 gene, TNFAIP3 (A20) gene, DGKA gene, DGKZ gene, FAS gene, EGR2 gene, PPP2R2D gene, TET2 gene, PSGL-1 gene, and KDM6A gene may be manipulated or modified.

Preferred examples of these genes of the present invention may include, genetically manipulated or modified, TNFAIP3, DGKA, DGKZ, FAS, EGR2, PSGL-1, and KDM6A genes.

The genetic manipulation or modification may be obtained by inducing artificial insertion, deletion, substitution, and inversion mutation in all or partial regions of the genomic sequence of wild-type genes. In addition, the genetic manipulation or modification may also be obtained by a fusion of genetic manipulation or modification of two or more genes.

For example, these genes may be inactivated by such genetic manipulation or modification, and as a result, the proteins encoded by these genes are prevented from being expressed in the form of proteins having their original functions.

For example, these genes may be further activated by such genetic manipulation or modification such that the proteins encoded by these genes are expressed in the form of proteins having more improved functions compared to their original functions. In one example, when the function of a protein encoded by a particular gene is A, the function of the protein expressed by the manipulated gene may be entirely different from A, or it may have an additional function (A+B) including A.

For example, the gene manipulation or modification may be such that two or more proteins are expressed in a fused form by using two or more genes having functions that are different from each other or complementary to each other.

For example, the gene manipulation or modification may be such that two or more proteins are expressed in a separate independent form in a cell by using two or more genes having functions that are different from each other or complementary to each other.

Genetic information can be obtained from the known database such as GenBank of National Center for Biotechnology Information (NCBI).

In an embodiment, the manipulation or modification of a gene may be induced by one or more of the followings:
  deletion of all or part of the gene to be modified (hereinafter, "target gene"), for example, deletion of nucleotides of 1 bp or more of a target gene (e.g., 1 to 30 nucleotides, 1 to 27 nucleotides, 1 to 25 nucleotides, 1 to 23 nucleotides, 1 to 20 nucleotides, 1 to 15 nucleotides, 1 to 10 nucleotides, 1 to 5 nucleotides, 1 to 3 nucleotides, or 1 nucleotide); and
  substitution of nucleotides of 1 bp or more of a target gene (e.g., 1 to 30 nucleotides, 1 to 27 nucleotides, 1 to 25 nucleotides, 1 to 23 nucleotides, 1 to 20 nucleotides, 1 to 15 nucleotides, 1 to 10 nucleotides, 1 to 5 nucleotides, 1 to 3 nucleotides, or 1 nucleotide different from those of the original (wild-type)), and insertion of one or more nucleotides (e.g., 1 to 30 nucleotides, 1 to 27 nucleotides, 1 to 25 nucleotides, 1 to 23 nucleotides, 1 to 20 nucleotides, 1 to 15 nucleotides, 1 to 10 nucleotides, 1 to 5 nucleotides, 1 to 3 nucleotides, or 1 nucleotide) to any location of a target gene.

A part of the target gene to be modified ("target region") may be a continuous nucleotide sequence region in the gene of 1 bp or more, 3 bp or more, 5 bp or more, 7 bp or more, 10 bp or more, 12 bp or more, 15 bp or more, 17 bp or more, 20 bp or more (e.g., 1 bp to 30 bp, 3 bp to 30 bp, 5 bp to 30 bp, 7 bp to 30 bp, 10 bp to 30 bp, 12 bp to 30 bp, 15 bp to 30 bp, 17 bp to 30 bp, 20 bp to 30 bp, 1 bp to 27 bp, 3 bp to 27 bp, 5 bp to 27 bp, 7 bp to 27 bp, 10 bp to 27 bp, 12 bp to 27 bp, 15 bp to 27 bp, 17 bp to 27 bp, 20 bp to 27 bp, 1 bp to 25 bp, 3 bp to 25 bp, 5 bp to 25 bp, 7 bp to 25 bp, 10 bp to 25 bp, 12 bp to 25 bp, 15 bp to 25 bp, 17 bp to 25 bp, 20 bp to 25 bp, 1 bp to 23 bp, 3 bp to 23 bp, 5 bp to 23 bp, 7 bp to 23 bp, 10 bp to 23 bp, 12 bp to 23 bp, 15 bp to 23 bp, 17 bp to 23 bp, 20 bp to 23 bp, 1 bp to 20 bp, 3 bp to 20 bp, 5 bp to 20 bp, 7 bp to 20 bp, 10 bp to 20 bp, 12 bp to 20 bp, 15 bp to 20 bp, 17 bp to 20 bp, 21 bp to 25 bp, 18 bp to 22 bp, or 21 bp to 23 bp.

[Immune Regulatory Factor-Containing Cells]

An aspect of the present invention relate to cells including the artificially manipulated immune regulatory factor.

The cells are, but are not limited to, immune cells and stem cells.

The "immune cell" of the present invention is a cell involved in immune responses, and it includes all cells that are directly or indirectly involved in the immune response and the pre-differentiation cells thereof.

Immune cells may have the function of cytokine secretion, differentiation into other immune cells, and cytotoxicity. Immune cells also include cells that have undergone mutations from the natural state.

The immune cells differentiate from hematopoietic stem cells in the bone marrow and they largely include lymphoid progenitor cells and myeloid progenitor cells; and also include all of T cells and B cells in which lymphoid progenitor cells differentiate and are responsible for acquired immunity; and macrophages, eosinophils, neutrophils, basophils, megakaryocytes, erythrocytes, etc. differentiated from myeloid progenitor cells.

Specifically, the cells may be at least one selected from the group consisting of T cells, for example, CD8+ T cells (e.g., CD8+ naive T cells, CD8+ effector T cells, central memory T cells, or effector memory T cells), CD4+ T cells, natural killer T cells (NKT cells), regulatory T cells (Treg), stem cell memory T cells, lymphoid progenitor cells, hematopoietic stem cells, natural killer cells (NK cells), dendritic cells, cytokine induced killer cells (CIK), peripheral blood mononuclear cells (PBMC), monocytes, macrophages, natural killer T (NKT) cells, etc. Macrophages and dendritic cells may be referred to antigen presenting cells (APCs), which are specialized cells capable of activating T cells, when the major histocompatibility complex (MHC) receptors on the cell surface thereof interact with the TCR on the T cell surface. Alternatively, any hematopoietic stem cell or immune system cell can be converted to APC by introducing an antigen-expressing nucleic acid molecule, recognized by TCR or other antigen binding protein (e.g., CAR).

In an embodiment, the immune cell may be a cell which is used as immune therapy by inactivation or exchange of the gene that synthesizes the protein associated with MHC recognition and/or immune functions (e.g., immune checkpoint protein).

In an embodiment, the immune cell may further include polynucleotides encoding short-chain and multi-subunit receptors (e.g., CAR, TCR, etc.) for specific cell recognition.

In an embodiment, the immune cell of the present invention may be those derived from blood (e.g., peripheral blood), stem cells (e.g., embryonic stem cells, induced pluripotent stem cells, etc.), cord blood, bone marrow, etc. of a healthy donor or a patient, or may be those manipulated ex vivo.

In an embodiment, the immune cell may be a CD3 positive cell, for example, a T cell or CAR-T cell. CD3 is a receptor in which TCR and various proteins are present as a complex on the T cell surface. Five kinds of proteins, which are called. γ, δ, ε, ζ, and η chains, constitute the CD3, and these are present as a TCR/CD3 complex in a state of αβ:γδεζζ or αβ:γδεζη along with TCR. They are known to have the function of signal transduction into the cells during antigen recognition of T cells.

In an embodiment, the immune cell may be a CD56 positive cell, for example, an NK cell (e.g., NK92 cell and primary NK cell).

NK cells have the third largest number of immune cells, and about 10% of peripheral blood immunocytes are NK cells. NK cells have CD56 and CD16 and mature in the liver or bone marrow. NK cells attack viruses-infected cells or tumor cells. When NK cells recognize abnormal cells, they spray perforin on the cell membrane to dissolve the cell membrane to be punctured, spray granzyme inside of the cell membrane to dissemble the cytoplasm to cause apoptosis, and inject water and saline into the cells to cause necrosis. NK cells have the ability to kill various kinds of cancer cells. In particular, NK cells are well known as cells into which exogenous genetic materials are not easily introduced.

In an embodiment, the NK cell may be a double positive cell, for example, a natural killer T (NKT) cell or cytokine-induced killer (CIK) cell.

The natural killer T (NKT) cell or cytokine-induced killer (CIK) cell is an immune cell that simultaneously expresses CD3 (i.e., a T cell marker) and CD56 (i.e., a natural killer cell (NK cell) marker) molecules. The NKT cells or CIK cells kill tumor cells regardless of the primary histocompatibility complex (MHC) because these cells are derived from T cells and have both the characteristics and functions of NK cells. In particular, the NKT cells are cells that express T cell receptors (TCRs) and NK cell-specific surface marker NK1.1 or NKR-P1A (CD161).

In one example, NKT cells can recognize glycolipids presented by CD1d, a monomorphic protein with a structure similar to MHC class I. NKT cells secrete a wide variety of cytokines (e.g., IL-4, IL-13, IL-10, and IFN-γ) when activated by ligands, such as α-GalCer. In addition, the NKT cells have anti-tumor activity.

In another example, CIK cells are a kind of immune cells that proliferate when blood collected is treated with interleukin 2 and CD3 antibody and cultured for 2-3 weeks ex vivo, and they are CD3 and CD56 positive cells. CIK cells produce large amounts of IFN-γ and TNF-α.

In an embodiment, the cell may be an embryonic stem cell, an adult stem cell, an induced pluripotent stem cell (iPS cell), or a cell derived from the induced pluripotent stem cell (e.g., iPS cell derived cell) with self-replication and differentiation abilities.

As preferred embodiments of the present invention, the cell may include manipulated or modified genes which are immune regulatory factors.

The cell may include all or part of the manipulated or modified gene; or an expression product thereof.

For example, the cell may be one in which the protein encoded by the gene is not expressed in the form of a protein having the original function thereof by inactivating the corresponding gene via genetic manipulation or modification.

For example, the cell may be one in which the protein encoded by the gene is expressed in the form of a protein having an improved function compared to the original function thereof by further activating the corresponding gene via such genetic manipulation or modification.

For example, the cell may be one in which the protein encoded by the gene is expressed in the form of a protein exhibiting the original function thereof and/or additional function via such genetic manipulation or modification.

For example, the cell may be one in which two or more proteins are expressed in a modified form using two or more genes having different from each other or complementary to each other via such genetic manipulation or modification.

For example, the cell may be an immune cell with high cytokine production or secretion ability of three kinds of cytokines (e.g., IL-2, TNF-α, and IFN-γ) via such genetic manipulation or modification.

In one example, the cell of the present invention may further include the following constitutions.

Receptors

The cell of the present invention may include "immune receptor".

The term "immune receptor", which is a receptor present on the surface of an artificially manipulated or modified immune cell, refers to a material involved in immune responses, for example, a functional entity that recognizes antigens and performs a specific function.

The receptor may be in a wild-type or artificially manipulated state.

The receptor may have affinity for antigens.

The receptor may have recognition ability for the structures formed by the MHC structural proteins and the antigens disclosed in the structural proteins.

The receptor may produce an immune response signal.

The term "immune response signal" refers to any signal that occurs in the immune response process.

The immune response signal may be a signal associated with the growth and differentiation of immune cells.

The immune response signal may be a signal associated with the death of immune cells.

The immune response signal may be a signal associated with the activity of immune cells.

The immune response signal may be a signal associated with the aid of immune cells.

The immune response signal may be a signal that regulates the expression of the gene of interest.

The immune response signal may be one that promotes or inhibits the synthesis of cytokines.

The immune response signal may be one that promotes or inhibits the secretion of cytokines.

The immune response signal may be a signal that aids in the growth or differentiation of other immune cells.

The immune response signal may be a signal that regulates the activity of other immune cells.

The immune response signal may be a signal that attracts other immune cells to a position where the signal occurs.

In an embodiment, the receptor may be a T cell receptor (TCR).

In an embodiment, the cell may be one which is modified such that the cell can include a particular T cell receptor (TCR) gene (e.g., TRAC or TRBC gene). In another embodiment, the TCR may be one which has binding specificity for tumor associated antigen (e.g., melanoma antigen recognized by T cells 1 (MART1), melanoma-associated antigen3 (MAGEA3), NY-ESOI, NYESOI, carcinoembryonic antigen (CEA), GP100, etc.).

In an embodiment, the receptor may be a Toll like receptor (TLR).

The receptor may be CD4 and CD8, which are co-receptors involved in MHC-restricted T cell activation.

The receptor may be CTLA-4 (CD152).

The receptor may be CD28.

The receptor may be CD137 and 4-1BB which are receptors that amplify the response of T cells.

The receptor may be CD3ζ which is a signal transduction element of T cell antigen receptors.

The receptor may be chimeric antigen receptor (CAR).

In an embodiment of the present invention, the receptor may be an artificially manipulated artificial receptor.

The term "artificial receptor" refers to a functional entity which is artificially prepared, not a wild-type receptor and which has specific ability to recognize antigens and performs a specific function.

Such an artificial receptor can produce immune response signals with improved or enhanced recognition for specific antigens and thus can contribute to the improvement of immune responses.

The artificial receptor may have the following constitutions, as one example.

(i) Antigen Recognition Part

An artificial receptor includes an antigen recognition part.

The term "antigen recognition part", which is a part of artificial receptor, refers to a region that recognizes an antigen.

The antigen recognition part may be one which has improved recognition of specific antigens compared to wild-type receptors. In particular, the specific antigen may be an antigen of cancer cell. In addition, the specific antigen may be an antigen of common cells in the body.

The antigen recognition part may have a binding affinity for antigens.

The antigen recognition part may generate a signal while binding to the antigen. The signal may be an electrical signal. The signal may be a chemical signal.

The antigen recognition part may include a signal sequence.

The signal sequence refers to a peptide sequence that allows a protein to be delivered to a specific site during the process of protein synthesis.

The signal sequence may be located close to the N-terminus of the antigen recognition part. In particular, the distance from the N-terminus may be about 100 amino acids. The signal sequence may be located close to the C-terminus of the antigen recognition part. In particular, the distance from the C-terminus may be about 100 amino acids.

The antigen recognition part may have an organic functional relationship with a first signal generating part.

The antigen recognition part may be homologous to a fragment antigen binding (Fab) domain of an antibody.

The antigen recognition part may be a single-chain variable fragment (scFv).

The antigen recognition part may recognize antigens by itself or by forming an antigen recognition structure.

The antigen recognition structure can recognize antigens by establishing a specific structure, and the monomeric units constituting the specific structure and the binding of the monomeric units can be easily understood by those of ordinary skill in the art. In addition, the antigen recognition structure may consist of one or two or more monomeric units.

The antigen recognition structure may be a structure in which the monomeric units are connected in series or may be a structure in which the monomeric units are connected in parallel.

The structure connected in series refers to a structure in which two or more monomeric units are continuously connected in one direction, whereas the structure connected in parallel refers to a structure in which each of two or more monomeric units is concurrently connected at the distal end of one monomeric unit, for example, in different directions.

For example, the monomeric unit may be an inorganic material.

The monomeric unit may be a biochemical ligand.

The monomeric unit may be homologous to an antigen recognition part of a wild-type receptor.

The monomeric unit may be homologous to an antibody protein.

The monomeric unit may be a heavy chain of an immunoglobulin or may be homologous thereto.

The monomeric unit may a light chain of an immunoglobulin or may be homologous thereto.

The monomeric unit may include a signal sequence.

Meanwhile, the monomeric unit may be linked by a chemical bond or may be bonded through a specific combining part.

The term "antigen recognition unit combining part" is a region where antigen recognition units are connected to each other, and it may be an optional constitution which is present when an antigen recognition structure consisting of two or more antigen recognition units is present.

The antigen recognition unit combining part may be a peptide. In particular, the combining part may have high proportions of serine and threonine.

The antigen recognition unit combining part may be a chemical binding.

The antigen recognition unit combining part can aid in the expression of the three-dimensional structure of the antigen recognition unit by having a specific length.

The antigen recognition unit combining part can aid the function of the antigen recognition structure by having a specific positional relationship between the antigen recognition units.

(ii) Receptor Body

The artificial receptor includes a receptor body.

The term "receptor body" is a region where the connection between the antigen recognition part and the signal generating part are mediated, and the antigen recognition part and the signal generating part may be physically connected.

The function of the receptor body may be to deliver the signal produced in the antigen recognition part or the signal generating part.

The structure of the receptor body may have the function of the signal generating part at the same time depending on cases.

The function of the receptor body may be to allow that the artificial receptor to be immobilized on the immune cells.

The receptor body may include an amino acid helical structure.

The structure of the receptor body may include a part which is homologous to a part of the common receptor protein present in the body. The homology may be in a range of 50% to 100%.

The structure of the receptor body may include a part which is homologous to the proteins on immune cells. The homology may be in a range of 50% to 100%.

For example, the receptor body may be a CD8 transmembrane domain.

The receptor body may be a CD28 transmembrane domain. In particular, when a second signal generating part is CD28, CD28 can perform the functions of the second signal generating part and the receptor body.

(iii) Signal Generating Part

The artificial receptor may include a signal generating part.

The term "first signal generating part", which is a part of the artificial receptor, refers to a part that produces an immune response signal.

The term "second signal generating part", which is a part of the artificial receptor, refers to a part that produces an immune response signal by interacting with the first signal generating part or independently.

The artificial receptor may include the first signal generating part and/or the second signal generating part.

The artificial receptor may include two or more of the first and/or second signal generating part, respectively.

The first and/or second signal generating part may include a specific sequence motif.

The sequence motif may be homologous to the motifs of cluster of designation (CD) proteins.

In particular, the CD proteins may be CD3, CD247, and CD79.

The sequence motif may be an amino acid sequence of YxxL/I.

The sequence motif may be multiple in the first and/or second signal generating part.

In particular, a first sequence motif may be located at a distance of 1 to 200 amino acids from the start position of the first signal generating part. A second sequence motif may be located at a distance of 1 to 200 amino acids from the start position of the second signal generating part.

In addition, the distance between each sequence motif may be 1 to 15 amino acids.

In particular, the preferred distance between each sequence motif is 6 to 8 amino acids.

For example, the first and/or second signal generating part may be CD3 ζ.

The first and/or second signal generating part may be FcεRIγ.

The first and/or second signal generating part may be those which produce an immune response only when a specific condition is met.

The specific condition may be that the antigen recognition part recognizes antigens.

The specific condition may be that the antigen recognition part forms a binding with an antigen.

The specific condition may be that the signal generated is delivered when the antigen recognition part forms a binding with the antigen.

The specific condition may be that the antigen recognition part recognizes an antigen or the antigen recognition part is separated from an antigen while binding with the antigen.

The immune response signal may be a signal associated with the growth and differentiation of immune cells.

The immune response signal may be a signal associated with the death of immune cells.

The immune response signal may be a signal associated with the activity of immune cells.

The immune response signal may be a signal associated with the aid of immune cells.

The immune response signal may be activated to be specific for the signal produced in the antigen recognition part.

The immune response signal may be a signal that regulates the expression of a gene of interest.

The immune response signal may be a signal that suppresses immune responses.

In an embodiment, the signal generating part may include an additional signal generating part.

The term "additional signal generating part", which is a part of an artificial receptor, refers to a region that produces an additional immune response signal with regard to the immune response signal produced by the first and/or second signal generating parts.

Hereinafter, the additional signal generating part is referred to as the n$^{th}$ signal generating part (n≠1) according to the order.

The artificial receptor may include an additional signal generating part, in addition to the first signal generating part.

Two or more additional signal generating parts can be included in an artificial receptor.

The additional signal generating part may be a structure in which immune response signals of 4-1BB, CD27, CD28, ICOS, and OX40, or other signals thereof may be produced.

The conditions that the additional signal generating part produces an immune response signal and the characteristics of the immune response signals produced thereof include the details that correspond to the immune response signals of the first and/or second signal generating parts.

The immune response signal may be one which promotes the synthesis of cytokines. The immune response signal may be one which promotes or inhibits the secretion of cytokines. In particular, the cytokine may be, preferably, IL-2, TNFα or IFN-γ.

The immune response signal may be a signal that helps the growth or differentiation of other immune cells.

The immune response signal may be a signal that regulates the activity of other immune cells.

The immune response signal may be a signal that attracts other immune cells to a location where the signal occurs.

The present invention includes all possible binding relationships of artificial receptors. Accordingly, the aspects of the artificial receptors of the present invention are not limited to those described herein.

The artificial receptor may consist of an antigen recognition part-a receptor body-a first signal generating part. The receptor body may be optionally included.

The artificial receptor may consist of an antigen recognition part-a receptor body-a second signal generating part-a first signal generating part. The receptor body may be optionally included. In particular, the positions of the first signal generating part and the second signal generating part may be changed.

The artificial receptor may consist of antigen recognition part-a receptor body-a second signal generating part-a third signal generating part-a first signal generating part. The receptor body may be optionally included. In particular, the positions of from the first signal generating part to the third signal generating part may be changed.

In the artificial receptor, the number of signal generating parts is not limited to 1 to 3, but it may be included to have more than three.

In addition to the above embodiment, the artificial receptor may have the structure of an antigen recognition part-signal generating part-a receptor body. The structure may be advantageous at the time when an immune response signal that acts out of a cell which has the artificial receptor, must be produced.

The artificial receptor may function in a manner corresponding to the wild-type receptor.

The artificial receptor may function to form a specific positional relationship by forming a binding with a specific antigen.

The artificial receptor may function to recognize an antigen and produce an immune response signal that promotes an immune response against the specific antigen.

The artificial receptor may function to recognize the antigens of a general cell in the body and inhibit an immune response against the cell in the body.

(iv) Signal Sequence

In an embodiment, the artificial receptor may optionally include a signal sequence.

When the artificial receptor includes a signal sequence of a specific protein, this may aid the artificial receptor in being easily located on the membrane of an immune cell. Preferably, when the artificial receptor includes a signal sequence of a transmembrane protein, this may aid the artificial receptor in penetrating through the membrane of the immune cell to be located on the external membrane of the immune cell.

The artificial receptor may include one or more signal sequences.

The signal sequence may include many positively charged amino acids.

The signal sequence may include a positively charged amino acid at a location close to the N- or C-terminus.

The signal sequence may be a signal sequence of the transmembrane protein.

The signal sequence may be a signal sequence of a protein located on the external membrane of an immune cell.

The signal sequence may be included in the structure that the artificial receptor possesses, that is, an antigen recognition part, a receptor body, a first signal generating part, and additional signal generating part.

In particular, the signal sequence may be located at a position close to the N- or C-terminus of each structure.

In particular, the distance of the signal sequence from the N- or C-terminus may be about 100 amino acids.

In an embodiment, the cell may be one which is modified so that a specific T cell receptor (TCR) gene is included.

In another embodiment, the TCR may be one which has binding specificity for tumor associated antigen (e.g., melanoma antigen recognized by T cells 1 (MART1), melanoma-associated antigen3 (MAGEA3), NY-ESOI, carcinoembryonic antigen (CEA), NY-ES-OI (GP100, etc.), melanoma).

In still another embodiment, the cell may be one which is modified so that a specific chimeric antigen receptor (CAR) is included. In an embodiment, the CAR may be one which has binding specificity for tumor associated antigen (e.g., CD19, CD20, carbonic anhydrase IX (CAIX), CD171, CEA, ERBB2, GD2, alpha-folate receptor, Lewis Y antigen, prostate specific membrane antigen (PSMA), or tumor associated glycoprotein 72 (TAG72)).

In still another embodiment, the cell may be, for example, one which is modified so that the cell can be bound to one or more of the following tumor antigens by TCR or CAR The tumor antigens may include, but are not limited to, AD034, AKT1, BRAP, CAGE, CDX2, CLP, CT-7, CT8/HOM-TES-85, cTAGE-1, EGFR, EGFRvIII, Fibulin-1, HAGE, HCA587/MAGE-C2, hCAP-G, HCE661, HER2/neu, HLA-Cw, HOM-HD-21/Galectin9, HOM-MEEL-40/SSX2, HOM-RCC-3.1.3/CAXII, HOXA7, HOXB6, Hu, HUB 1, KM-HN-3, KM-KN-1, KOC1, KOC2, KOC3, KOC3, LAGE-1, MAGE-1, MAGE-4a, MPPI 1, MSLN, NNP-1, NY-BR-1, NY-BR-62, NY-BR-85, NY-CO-37, NY-CO-38, NY-ESO-1, NY-ESO-5, NY-LU-12, NY-REN-10, NY-REN-19/LKB/STK1 1, NY-REN-21, NY-REN-26/BCR, NY-REN-3/NY-CO-38, NY-REN-33/SNC6, NY-REN-43, NY-REN-65, NY-REN-9, NY-SAR-35, OGFr, PSMA, PSCA PLU-1, Rab38, RBPJkappa, RHAMM, SCP1, SCP-1, SSX3, SSX4, SSX5, TOP2A, TOP2B, and tyrosinase.

Antigen Binding Regulating Element

The cells of the present invention may further include an "antigen binding regulating element".

The "antigen binding regulating element", which is an element enabling the binding between a receptor and an antigen, may be a gene or protein performing such a function.

An immune response may be regulated using such an antigen binding regulating element. For example, when treatment is performed by adding cells which underwent external manipulation into the living body, and when HVGD (host HVGD (graft disease; graft-versus-host disease, and HostGraft) in which the immune response with regard to the cells which underwent external manipulation is activated and thus the effectiveness of treatment is eliminated becomes a problem, the problem may be solved by suppressing the antigen binding ability of the immune cell receptor.

The antigen binding regulating element may be a protein or gene associated with the structure of a receptor.

The antigen binding regulating element may be a protein or gene which is homologous to the structure of the receptor.

For example, the antigen binding regulating element may be dCK.

The antigen binding regulating element may be CD52.

The antigen binding regulating element may be B2M.

The antigen binding regulating element may be a protein or gene associated with the structures that a receptor recognizes.

For example, the antigen binding regulating element may be an MHC protein.

In an embodiment, the present invention relates to an immune cell which includes artificially manipulated immune regulatory genes or the proteins expressed by these genes.

In another embodiment, the present invention relates to an immune cell which includes artificially manipulated immune regulatory genes or the proteins expressed by these genes; and a receptor.

In still another embodiment, the present invention relates to an immune cell which includes artificially manipulated immune regulatory genes or the proteins expressed by these genes; a receptor; and an antigen binding regulating element.

The representing example of the cell of the present invention is an immune cell.

In some exemplary embodiments of the present invention, the immune cell may be at least one selected from the group consisting of peripheral blood mononuclear cells (PBMC), natural killer cells (NK cells), monocytes, T cells, CAR-T cells, macrophages, natural killer T cells (NKT cells), etc., and preferably, T cells, CAR-T cells, natural killer cells (NK cells), or natural killer T cells (NKT cells).

The factors that limit the efficacies of genetically manipulated immune cells (e.g., T cells, NK cells, and NKT cells) include:

(1) immune cell proliferation (e.g., limited propagation of immune cells after adoptive transfer);
(2) immune cell survival (e.g., induction of apoptosis of immune cells by factors in tumor environment); and
(3) immune cell function (e.g., inhibition of cytotoxic immune cell function by inhibitory factors secreted by host immune cells and cancer cells).

For this purpose, the above limiting factors are regulated through the immune cells, in which one or more genes expressed in immune cells (for example, one or more genes selected from the group consisting of PD-1, CTLA-4, TNFAIP3, DGKA, DGKZ, Fas, EGR2, PPP2R2D, PSGL-1, KDM6A, and TET2) are inactivated.

In one example, one or more genes expressed in immune cells (for example, one or more genes selected from the group consisting of PD-1, CTLA-4, TNFAIP3, DGKA, DGKZ, Fas, EGR2, PPP2R2D, PSGL-1, KDM6A and/or TET2 genes) may be targeted and manipulated to be each independently knocked out, knocked down, or knocked in, so as to affect the proliferation, survival, and function of one or more immune cells.

In one example, in an immune cell, two or more genes selected from the group consisting of PD-1, CTLA-4, TNFAIP3, DGKA, DGKZ, Fas, EGR2, PPP2R2D, PSGL-1, KDM6A and/or TET2 genes may be targeted and manipulated to be simultaneously knocked out, knocked down, or knocked in. In an embodiment, DGKA and DGKZ were simultaneously knocked out.

In one example, one or more genes that express immune cells (for example, one or more genes selected from the group consisting of PD-1, CTLA-4, TNFAIP3, DGKA, DGKZ, Fas, EGR2, PPP2R2D, PSGL-1, KDM6A and/or TET2 genes) may be targeted and manipulated to be each independently knocked out, knocked down, or knocked in, so as to affect the proliferation, survival, and function of one or more immune cells, by targeting a non-coding region or coding region (e.g., promoter region, enhancer, 3'UTR, and/or polyadenylation signal sequence, or transcription sequence (e.g., intron or exon sequence)).

In one example, one or more genes expressed in immune cells (for example, one or more genes selected from the group consisting of PD-1, CTLA-4, TNFAIP3, DGKA, DGKZ, Fas, EGR2, PPP2R2D, PSGL-1, KDM6A and/or TET2 genes) may be targeted and manipulated to be each independently knocked out, knocked down, or knocked in, so as to affect the proliferation, survival, and function of one or more immune cells, by induction of alterations including deletion, substitution, insertion or mutation at one or more regions of the sequences.

In particular, it is apparent that the immune regulatory genes that are not disclosed herein can be combined and targeted.

[Immune System]

Additionally, another aspect of the present invention provides an immune system that forms an immune response mechanism in which the artificially manipulated immune regulatory factor; and/or the cells including the same are involved.

The "immune system" of the present invention is a term including all phenomena that affects in vivo immune responses by the changes in the function of the manipulated immune regulatory factor (i.e., being involved in mechanism exhibiting new immune efficacies), and it includes all materials, compositions, methods, and uses which are directly or indirectly involved in such an immune system. For example, it includes all the genes, immune cells, and immune organs/tissues involved in innate immunity, adaptive immunity, cellular immunity, humoral immunity, active immunity, and passive immune response.

The elements that constitute such an immune system are often collectively referred to as the "immune system factor".

The immune system of the present invention includes manipulated immune cells.

The manipulated immune cell means an immune cell that has been subjected to an artificial manipulation, not in a natural state. Recently, techniques for enhancing immunity by extracting immune cells from the body and applying artificial manipulation have been actively studied. Such manipulated immune cell has been shown to be a new therapeutic method because of the excellent immune efficacy against certain diseases. In particular, studies on manipulated immune cells have been actively performed in connection with cancer treatment.

The manipulated immune cell may be a functionally manipulated immune cell or an artificial structure supplemented immune cell.

Functionally Manipulated Immune Cell

The "functionally manipulated immune cell" of the present invention refers to an immune cell, in which the wild-type receptor or immune regulatory factor has been manipulated in nature.

Hereinafter, manipulation refers to all kinds of manipulation including cleaving, ligating, removing, inserting, and modifying genes; or removing, adding, or modifying proteins, which those of ordinary skill in the art can utilize so as to manipulate proteins and genes. Hereinafter, immune cells include not only differentiated immune cells but also pre-differentiation cells (e.g., stem cells).

Functionally manipulated immune cells may be immune cells in which wild-type receptors are manipulated. In particular, the wild-type receptor may be TCR.

The functionally manipulated immune cells may be those in which the wild-type receptors are absent or present at a lower rate on the surface.

The functionally manipulated immune cells may be those in which the wild-type receptors are present at a greater proportion on the surface.

The functionally manipulated immune cells may be those in which wild-type receptors have enhanced recognition ability for specific antigens.

The functionally manipulated immune cells may be immune cells in which immune regulatory factors are manipulated.

The functionally manipulated immune cells may be those in which immune cell activity regulating elements are manipulated.

In particular, the functionally manipulated immune cells may be immune cells in which one or more selected from the group consisting of SHP-1, PD-1, CTLA-4, CBLB, ILT-2, KIR2DL4, and PSGL-1 are inactivated.

The functionally manipulated immune cells may be those in which immune cell growth regulating elements are manipulated.

In particular, the functionally manipulated immune cells may be immune cells in which one or more selected from the group consisting of DGK-alpha, DGK-zeta, Fas, EGR2, Egr3, PPP2R2D, and A20 are inactivated. In a preferred embodiment, one or more selected from the group consisting of DGK-alpha, DGK-zeta, EGR2, PPP2R2D, and A20 are inactivated.

The functionally manipulated immune cells may be those in which immune cell death regulating elements are manipulated.

In particular, the functionally manipulated immune cells may be immune cells in which one or more selected from the group consisting of Daxx, Bim, Bid, BAD, PD-1, and CTLA-4 are inactivated.

Additionally, the functionally manipulated immune cells may be immune cells in which elements that induce the death of self are inserted.

The functionally manipulated immune cells may be those in which immune cell exhaustion regulating elements are manipulated.

In particular, the functionally manipulated immune cells may be immune cells in which one or more selected from the group consisting of TET2, Wnt and Akt are inactivated.

The functionally manipulated immune cells may be those in which cytokine production regulating elements are manipulated.

The functionally manipulated immune cells may be those in which antigen binding regulating elements are manipulated.

In particular, the functionally manipulated immune cells may be immune cells in which one or more selected from the group consisting of dCK, CD52, B2M, and MHC are inactivated.

The functionally manipulated immune cells may be those in which an immune regulatory factor different from those mentioned above is manipulated.

The functionally manipulated immune cells may be those in which one or more immune regulatory factors are simultaneously manipulated. In particular, one or more kinds of immune regulatory factors may be manipulated.

The functionally manipulated immune cells may have new immunological efficacies by manipulating wild-type receptors and immune regulatory factors.

In particular, when manipulating one immune regulatory factor, it does not necessarily mean that a new immune regulatory effect must be exhibited. The manipulation of one immune regulatory factor may cause or inhibit a variety of new immune efficacy.

The new immune efficacy may be one in which the ability to recognize a specific antigen is regulated.

The new immune efficacy may be one in which the ability to recognize a specific antigen is improved.

In particular, the specific antigen may be an antigen of disease, for example, an antigen of cancer cells.

The new immune efficacy may be one in which the ability to recognize a specific antigen is deteriorated.

The new immune efficacy may be one in which the new immune efficacy is improved.

The new immune efficacy may be one in which the growth of immune cells is regulated. In particular, the immune efficacy may be one in which the growth and differentiation are promoted or delayed.

The new immune efficacy may be one in which the death of immune cells is regulated. In particular, the immune efficacy may be to prevent the death of immune cells. Additionally, the immune efficacy may be to cause the immune cells to kill themselves when appropriate time has elapsed.

The new immune efficacy may be one in which the loss of functions of immune cells is alleviated.

The new immune efficacy may be one in which the cytokine secretion of immune cells is regulated. In particular, the immune efficacy may be to promote or inhibit the secretion of cytokines.

The new immune efficacy may be to regulate the antigen binding ability of wild-type receptors in an immune cell. In particular, the immune efficacy may be to improve the specificity of wild-type receptors for specific antigens.

Artificial Structure Supplemented Immune Cell

The term "artificial structure supplemented immune cell" means one in which an artificial structure is supplemented in an immune cell.

For example, the artificial structure supplemented immune cell may be an immune cell in which an artificial receptor is supplemented.

The artificial receptor may be one which has the ability to recognize certain antigens. In one example, the artificial structure supplemented immune cell may be a CAR-T cell.

Additionally, the artificial receptor may be one in which artificial receptors, which have the ability to recognize each of two or more antigens caused by a specific disease, are supplemented. In particular, each of the artificial receptors may be one which is expressed in a time-dependent manner according to conditions.

For example, in the case of a manipulated immune cell for cancer treatment, a first artificial receptor may produce an immune response signal that initiated the expression of a second artificial receptor gene, and then a second artificial receptor may be expressed. The second artificial receptor may produce an immune response signal that induces an immune response against cancer cells. In this case, the ability of the manipulated immune cell to attack cancer cells may be improved.

The artificial receptor may be one which has the ability to recognize the manipulated immune cell.

The artificial receptor may be one which has the ability to recognize the general cells in the body. In one example, the artificial structure supplemented immune cell may be an iCAR-T cell.

The artificial receptor may be one which has the ability to recognize a third material. In particular, the third material may have a binding ability to antigens of a specific disease.

In particular, the third material may be able to bind to the artificial receptor, and simultaneously, bind to the antigens of a specific disease. For example, the third material may have the ability to simultaneously bind to the artificial receptor and antigen related to cancer cell.

In another example, the artificial structure supplemented immune cell may be an immune cell in which an artificial structure having a specific function is supplemented, in addition to the artificial receptors.

In the case where an artificial structure, which is different from a native state, is supplemented to an immune cell, the artificial structure supplemented immune cell may have a new immune efficacy.

For example, the new immune efficacy may be one in which an immune cell binds to a specific antigen such that the immune cell is in a specific positional relationship with the antigen.

The new immune efficacy may be a function to recognize and promote an immune response against the specific antigen.

The new immune efficacy may be a function to inhibit an excessive immune response.

The new immune efficacy may be a function to regulate the signal transduction pathway of an immune response.

The new immune efficacy may be a function that an immune cell forms a binding with a third material and confirms a specific disease. In particular, the third material may be a biomarker for a specific disease.

One preferred example of the above-mentioned specific antigen may be an antigen of cancer cells.

The antigens of cancer cells may include, but are not limited to, AD034, AKT1, BRAP, CAGE, CDX2, CLP, CT-7, CT8/HOM-TES-85, cTAGE-1, EGFR, EGFRvIII, Fibulin-1, HAGE, HCA587/MAGE-C2, hCAP-G, HCE661, HER2/neu, HLA-Cw, HOM-HD-21/Galectin9, HOM-MEEL-40/SSX2, HOM-RCC-3.1.3/CAXII, HOXA7, HOXB6, Hu, HUB 1, KM-HN-3, KM-KN-1, KOC1, KOC2, KOC3, KOC3, LAGE-1, MAGE-1, MAGE-4a, MPPI 1, MSLN, NNP-1, NY-BR-1, NY-BR-62, NY-BR-85, NY-CO-37, NY-CO-38, NY-ESO-1, NY-ESO-5, NY-LU-12, NY-REN-10, NY-REN-19/LKB/STK1 1, NY-REN-21, NY-REN-26/BCR, NY-REN-3/NY-CO-38, NY-REN-33/SNC6, NY-REN-43, NY-REN-65, NY-REN-9, NY-SAR-35, OGFr, PLU-1, PSMA, PSCA, Rab38, RBPJkappa, RHAMM, SCP1, SCP-1, SSX3, SSX4, SSX5, TOP2A, TOP2B, ROR-1, and tyrosinase.

Hybrid Manipulated Immune Cell

The term "hybrid manipulated immune cell" refers to an immune cell in which both manipulation of an immune regulatory factor and supplementation of an artificial structure are achieved.

In a hybrid manipulated immune cell, the manipulation of an immune regulatory factor is the same as descried above in the functionally manipulated immune cell. Additionally, the supplementation of an artificial structure is the same as descried above in the artificial structure supplemented immune cell.

When the manipulation of the function of an immune cell is a genetic manipulation, the location where the artificial structure is supplemented may be the same as the position of the gene where the manipulation of the function occurred.

The new immune efficacy of a hybrid manipulated immune cell may be one which includes the new immune efficacies of the functionally manipulated immune cell and the artificial structure supplemented immune cell, and exhibits more improved immune efficacy by the interaction between these cells.

The improved immune efficacy may be that the specificity and immune response for a particular disease is improved. In a preferred example, a hybrid manipulated immune cell may be one which has improvement in both cancer specificity and immune response.

The immune system of the present invention includes a desired immune response and a disease treatment mechanism therethrough, which is achieved by a manipulated immune regulatory factor and/or a manipulated immune cell.

In an embodiment, the immune regulatory factor and/or the manipulated immune cell, in which the gene that inhibits the proliferation of immune cells is inactivated, may be used to affect the proliferation of immune cells.

In an embodiment, the immune regulatory factor and/or the manipulated immune cell, in which the gene that mediates the death of immune cells is inactivated, may be used to affect the survival of immune cells.

In an embodiment, the immune regulatory factor and/or the manipulated immune cell, in which the gene that encodes a signal transduction factor for suppressing and inhibiting immunity is inactivated, may be used to affect the function of immune cells.

The methods and compositions described herein may be used as an individual or a combination thereof to have an affect on one or more of the factors that limit the efficacy of a genetically manipulated immune cell as a therapeutic treatment for a specific disease (e.g., immune cell proliferation, immune cell survival, immune cell function, or any combination thereof).

Meanwhile, the term "immune-regulating therapy" refers to the treatment of disease by regulating the immune response in the body using a manipulated immune regulatory factor and/or a manipulated immune cell.

For example, immune cells (e.g., dendritic cells, natural killer cells, T cells, etc.) may be used to treat diseases by activating or inactivating the immune response in the body.

Such an immune-regulating therapy has been developed primarily as indications for cancer therapy, and the immune-regulating therapy is a treatment mechanism differentiated from surgery therapy, anticancer agents or radiation therapy used for existing cancer treatment, because the immune function is activated by administering the immune cells directly to the patient and thereby eliciting a therapeutic effect.

In an embodiment of the immune-regulating therapy, according to the characteristics of the immune cells used and the genes introduced into the cells in the manufacturing process, the immune-regulating therapy includes dendritic immune regulatory cell therapeutic agents, lymphokine activated killer (LAK), tumor-infiltrating T lymphocytes (TIL), T cell receptor-modified T cells (TCR-T), chimeric antigen receptor-modified T cells (CAR-T), etc.

[Genetic Manipulation or Modification]

The manipulation or modification of materials involved in the immune regulatory factor, immune cell and immune system of the present invention may be preferably achieved by genetic manipulation.

In an aspect, the composition and the method for genetic manipulation may be provided by targeting all or part of the noncoding and coding regions of immune regulatory genes that affect the proliferation, survival and/or function of immune cells.

In an embodiment, the composition and the method, in order to form a desired immune system, can manipulate or modify one or more immune regulatory genes that are involved in the immune system. This may be achieved by modification of a nucleic acid that constitutes the gene. As a result of the manipulation, all in the form of knock down, knock out, and knock in are included.

In an embodiment, a promoter region, or transcription sequence (e.g., intron sequence, exon sequence) may be targeted. The coding sequence (e.g., a coding region and an initial coding region) can be targeted for alteration and knockout of the expression.

In an embodiment, the alteration of a nucleic acid may be, for example, substitution, deletion, and/or insertion of nucleotides in the range of 1 bp to 30 bp, 1 bp to 27 bp, 1 bp to 25 bp, 1 bp to 23 bp, 1 bp to 20 bp, 1 bp to 15 bp, 1 bp to 10 bp, 1 bp to 5 bp, 1 bp to 3 bp, or 1 bp.

In an embodiment, for the knockout of one or more genes, or removal of one or more expressions, or for the knockout of one or more of one allele or two alleles among the immune regulatory gene, the genes may be targeted such that deletion or mutation may be included in one or more of the immune regulatory genes.

In an embodiment, gene knock down may be used to reduce the expression of unwanted alleles or transcripts.

In an embodiment, targeting the promoter, enhancer, intron, 3'UTR, and/or non-coding sequence of polyadenylation signal may be used to alter the immune regulatory gene that affect the function of immune cells.

In an embodiment, the regulation of activity (e.g, activation, inactivation) of the immune regulatory gene may be induced by the alteration of the nucleic acid of the gene.

In an embodiment, the alteration of the nucleic acid of the gene may be to inactivate the targeted gene by cleavage of the single strands or double strands in the specific region of the targeted gene via a guide nucleic acid-editor protein complex, that is, by catalyzing the breaks of the nucleic acid strands.

In an embodiment, the breaks of the nucleic acid strands may be repaired via mechanisms (e.g, homologous recombination, nonhomologous end joining (NHEJ), etc.).

In this case, when the NHEJ mechanism occurs, an alteration of a DNA sequence is induced in the cleavage site, and the gene may be inactivated by the same. The repair via NHEJ may cause substitutions, insertions or deletions of short gene fragments and may be used to induce corresponding gene knockouts.

In another aspect, the present invention may provide the position for the above genetic manipulation.

In an embodiment, when the alteration is achieved by the NHEJ-mediated alteration, the position for the genetic manipulation refers to a position in the gene that results in the reduction or removal of the expression of the immune regulatory gene product.

For example, the position in the gene may be in the initial coding region, in the 50% upstream coding region, promoter sequence, specific intron sequence, and specific exon sequence.

The position may be at a specific position in the gene that affects the proliferation, survival and/or function of an immune cell.

The position may be at a specific position in the gene that affects the function of the proteins involved in the immune response.

The position may be at a specific position in the gene that affects the recognition ability for a specific antigen.

The position may be at a specific position in the gene that affects the function of regulating cytokine secretion in an immune cell.

The position may be at a specific position in the gene that affects the function of regulating antigen binding ability of receptors in an immune cell.

The gene manipulation may be performed considering the regulatory process of gene expression.

In an embodiment, the gene manipulation may be performed in steps of transcriptional regulation, RNA processing regulation, RNA transport regulation, RNA degradation regulation, translation regulation or protein modification regulation, by selecting a manipulation method suitable for each step.

In an embodiment, the expression of genetic information may be controlled by preventing or deteriorating the stability of mRNA by small RNA (sRNAs) using RNA interference (RNAi) or RNA silencing, and in some cases, by destroying so as to prevent the delivery of the information of protein synthesis during the intermediate step.

In an embodiment, a wild-type or variant enzyme capable of catalyzing the hydrolysis (cleavage) of DNA or RNA molecules, preferably bonds between nucleic acids in a DNA molecule, may be used. A guide nucleic acid-editor protein complex may be used.

For example, the expression of genetic information may be controlled by manipulating genes using one or more selected from the group consisting of meganuclease, zinc finger nuclease, CRISPR/Cas9 (Cas9 protein), CRISPR-Cpf1 (Cpf1 protein) and TALE-nuclease.

In a preferred example, without limitation, genetic manipulation may be mediated by non-homologous end joining (NHEJ) or homology-directed repair (HDR) using a guide nucleic acid-editor protein complex (e.g., CRISPR/Cas system).

In an embodiment, examples of the immune regulatory gene that affect the proliferation, survival and/or function of immune cells may include PD-1 gene, CTLA-4 gene, TNFAIP3 gene, DGKA gene, DGKZ gene, Fas gene, EGR2 gene, PPP2R2D gene, TET2 gene, PSGL-1 gene, or KDM6A gene.

The target sequence regions of the above genes (i.e., the sites at which the nucleic acid modification may occur) are summarized in Table 1 below (the target sequence part shown in Table 1 is described as containing the PAM sequence 5'-NGG-3' at the 3' end).

The target sequence may target two or more kinds simultaneously.

The gene may target two or more kinds simultaneously.

Two or more target sequences in a homologous gene or two or more target sequences in a heterologous gene may be targeted simultaneously.

In an exemplary embodiment, DGKa or DGKz may be targeted, respectively.

In an exemplary embodiment, DGKa and DGKz may be targeted simultaneously.

TABLE 1

Target sequence

| Target gene | DNA Target Sequence | ID SEQ NO |
|---|---|---|
| A20 | CTTGTGGCGCTGAAAACGAACGG | ID SEQ NO 1 |
| | ATGCCACTTCTCAGTACATGTGG | ID SEQ NO 2 |
| | GCCACTTCTCAGTACATGTGGGG | ID SEQ NO 3 |
| | GCCCCACATGTACTGAGAAGTGG | ID SEQ NO 4 |
| | TCAGTACATGTGGGGCGTTCAGG | ID SEQ NO 5 |
| | GGGCGTTCAGGACACAGACTTGG | ID SEQ NO 6 |
| | CACAGACTTGGTACTGAGGAAGG | ID SEQ NO 7 |
| | GGCGCTGTTCAGCACGCTCAAGG | ID SEQ NO 8 |
| | CACGCAACTTTAAATTCCGCTGG | ID SEQ NO 9 |
| | CGGGGCTTTGCTATGATACTCGG | ID SEQ NO 10 |
| | GGCTTCCACAGACACACCCATGG | ID SEQ NO 11 |
| | TGAAGTCCACTTCGGGCCATGGG | ID SEQ NO 12 |
| DGKα | CTGTACGACACGGACAGAAATGG | ID SEQ NO 13 |
| | TGTACGACACGGACAGAAATGGG | ID SEQ NO 14 |
| | CACGGACAGAAATGGGATCCTGG | ID SEQ NO 15 |
| | GATGCGAGTGGCTGAATACCTGG | ID SEQ NO 16 |
| | GAGTGGCTGAATACCTGGATTGG | ID SEQ NO 17 |
| | AGTGGCTGAATACCTGGATTGGG | ID SEQ NO 18 |
| | ATTGGGATGTGTCTGAGCTGAGG | ID SEQ NO 19 |
| | ATGAAAGAGATTGACTATGATGG | ID SEQ NO 20 |
| | CTCTGTCTCTCAAGCTGAGTGGG | ID SEQ NO 21 |
| | TCTCTCAAGCTGAGTGGGTCCGG | ID SEQ NO 22 |
| | CTCTCAAGCTGAGTGGGTCCGGG | ID SEQ NO 23 |
| | CAAGCTGAGTGGGTCCGGGCTGG | ID SEQ NO 24 |
| EGR2 | TTGACATGACTGGAGAGAAGAGG | ID SEQ NO 25 |
| | GACTGGAGAGAAGAGGTCGTTGG | ID SEQ NO 26 |
| | GAGACGGGAGCAAAGCTGCTGGG | ID SEQ NO 27 |
| | AGAGACGGGAGCAAAGCTGCTGG | SEQ ID NO 28 |
| | TGGTTTCTAGGTGCAGAGACGGG | SEQ ID NO 29 |
| | TAAGTGAAGGTCTGGTTTCTAGG | SEQ ID NO 30 |
| | TGCCCATGTAAGTGAAGGTCTGG | SEQ ID NO 31 |
| | GAACTTGCCCATGTAAGTGAAGG | SEQ ID NO 32 |
| | TCCATTGACCCTCAGTACCTTGG | SEQ ID NO 33 |
| | TATGCCTTCTGGGTAGCAGCTGG | SEQ ID NO 34 |
| | TGAGTGCAGGCATCTTGCAAGGG | SEQ ID NO 35 |
| | GAGTGCAGGCATCTTGCAAGGGG | SEQ ID NO 36 |
| | GATGAGGCTGTGGTTGAAGCTGG | SEQ ID NO 37 |
| | CCACTGGCCACAGGACCCCTGGG | SEQ ID NO 38 |
| | GGGACATGGTGCACACACCCAGG | SEQ ID NO 39 |
| | GAGTACAGGTGGTCCAGGTCAGG | SEQ ID NO 40 |
| | GCGGAGAGTACAGGTGGTCCAGG | SEQ ID NO 41 |
| | GCGGTGGCGGAGAGTACAGGTGG | SEQ ID NO 42 |
| | TCTCCTGCACAGCCAGAATAAGG | SEQ ID NO 43 |
| | ACGCAGAAGGGTCCTGGTAGAGG | SEQ ID NO 44 |
| | AGGTGGTGGGTAGGCCAGAGAGG | SEQ ID NO 45 |
| | CCCAAGCCAGCCACGGACCCAGG | SEQ ID NO 46 |
| | ACCTGGGTCCGTGGCTGGCTTGG | SEQ ID NO 47 |
| | AAGAGACCTGGGTCCGTGGCTGG | SEQ ID NO 48 |
| | GGATCATTGGGAAGAGACCTGGG | SEQ ID NO 49 |
| | GGGATCATTGGGAAGAGACCTGG | SEQ ID NO 50 |
| | CAGGATAGTCTGGGATCATTGGG | SEQ ID NO 51 |
| | GGAAAGAATCCAGGATAGTCTGG | SEQ ID NO 52 |
| | CAGTGCCAGAGAGACCTACATGG | SEQ ID NO 53 |
| | CTGTACCATGTAGGTCTCTCTGG | SEQ ID NO 54 |

TABLE 1-continued

Target sequence

| Target gene | DNA Target Sequence | ID SEQ NO |
|---|---|---|
| | AGAGACCTACATGGTACAGCTGG | SEQ ID NO 55 |
| | CTGGGCCAGCTGTACCATGTAGG | SEQ ID NO 56 |
| | AGGGAAAGGGCTTACGGTCTGGG | SEQ ID NO 57 |
| | CAGGGAAAGGGCTTACGGTCTGG | ID SEQ NO 58 |
| PPP2R2D | TCTGGAGATCTTCTTGCAACAGG | ID SEQ NO 59 |
| | CTCCGGTTCATGACTTTGAAAGG | ID SEQ NO 60 |
| | GTCTTCCATCTTCGTCTTTCAGG | ID SEQ NO 61 |
| | GAAGACTTCGAGACCCATTTAGG | ID SEQ NO 62 |
| | TCGAGACCCATTTAGGATCACGG | ID SEQ NO 63 |
| | GTAGCGCCGTGATCCTAAATGGG | ID SEQ NO 64 |
| | CGTAGCGCCGTGATCCTAAATGG | ID SEQ NO 65 |
| | CATTTAGGATCACGGCGCTACGG | ID SEQ NO 66 |
| | GGTCCCAATATTGAAGCCCATGG | ID SEQ NO 67 |
| | GATCCATGGGCTTCAATATTGGG | ID SEQ NO 68 |
| | AGATCCATGGGCTTCAATATTGG | ID SEQ NO 69 |
| | GCTTCTACCATAAGATCCATGGG | ID SEQ NO 70 |
| | CGCTTCTACCATAAGATCCATGG | ID SEQ NO 71 |
| | GCATTTGCAAAAATTCGCCGTGG | ID SEQ NO 72 |
| | ATGACCTGAGAATTAATTTATGG | ID SEQ NO 73 |
| | CCATGCACTCCCAGACATCGTGG | ID SEQ NO 74 |
| | GCACTGGTGCGGGTGGAACTCGG | ID SEQ NO 75 |
| | ACACGTTGCACTGGTGCGGGTGG | ID SEQ NO 76 |
| | CGAACACGTTGCACTGGTGCGGG | ID SEQ NO 77 |
| | ACGAACACGTTGCACTGGTGCGG | ID SEQ NO 78 |
| | TGTAGACGAACACGTTGCACTGG | ID SEQ NO 79 |
| | GCGCATGTCACACAGGCGGATGG | ID SEQ NO 80 |
| | AGGAGCGCATGTCACACAGGCGG | ID SEQ NO 81 |
| | CCGAGGAGCGCATGTCACACAGG | ID SEQ NO 82 |
| | CCTGTGTGACATGCGCTCCTCGG | ID SEQ NO 83 |
| PD-1 | CGACTGGCCAGGGCGCCTGTGGG | ID SEQ NO 84 |
| | ACCGCCCAGACGACTGGCCAGGG | ID SEQ NO 85 |
| | CACCGCCCAGACGACTGGCCAGG | SEQ ID NO 86 |
| | GTCTGGGCGGTGCTACAACTGGG | SEQ ID NO 87 |
| | CTACAACTGGGCTGGCGGCCAGG | SEQ ID NO 88 |
| | CACCTACCTAAGAACCATCCTGG | SEQ ID NO 89 |
| | CGGTCACCACGAGCAGGGCTGGG | SEQ ID NO 90 |
| | GCCCTGCTCGTGGTGACCGAAGG | SEQ ID NO 91 |
| | CGGAGAGCTTCGTGCTAAACTGG | SEQ ID NO 92 |
| | CAGCTTGTCCGTCTGGTTGCTGG | SEQ ID NO 93 |
| | AGGCGGCCAGCTTGTCCGTCTGG | SEQ ID NO 94 |
| | CCGGGCTGGCTGCGGTCCTCGGG | SEQ ID NO 95 |
| | CGTTGGGCAGTTGTGTGACACGG | SEQ ID NO 96 |
| CTLA-4 | CATAAAGCCATGGCTTGCCTTGG | SEQ ID NO 97 |
| | CCTTGGATTTCAGCGGCACAAGG | SEQ ID NO 98 |
| | CCTTGTGCCGCTGAAATCCAAGG | SEQ ID NO 99 |
| | CACTCACCTTTGCAGAAGACAGG | SEQ ID NO 100 |
| | TTCCATGCTAGCAATGCACGTGG | SEQ ID NO 101 |
| | GGCCACGTGCATTGCTAGCATGG | SEQ ID NO 102 |
| | GGCCCAGCCTGCTGTGGTACTGG | SEQ ID NO 103 |
| | AGGTCCGGGTGACAGTGCTTCGG | SEQ ID NO 104 |
| | CCGGGTGACAGTGCTTCGGCAGG | SEQ ID NO 105 |
| | CTGTGCGGCAACCTACATGATGG | SEQ ID NO 106 |
| | CAACTCATTCCCCATCATGTAGG | SEQ ID NO 107 |
| | CTAGATGATTCCATCTGCACGGG | SEQ ID NO 108 |
| DGKζ | GGCTAGGAGTCAGCGACATATGG | SEQ ID NO 109 |
| | GCTAGGAGTCAGCGACATATGGG | SEQ ID NO 110 |
| | CTAGGAGTCAGCGACATATGGGG | SEQ ID NO 111 |
| | GTACTGTGTAGCCAGGATGCTGG | SEQ ID NO 112 |
| | ACGAGCACTCACCAGCATCCTGG | SEQ ID NO 113 |
| | AGGCTCCAGGAATGTCCGCGAGG | SEQ ID NO 114 |
| | ACTTACCTCGCGGACATTCCTGG | SEQ ID NO 115 |
| | CACCCTGGGCACTTACCTCGCGG | SEQ ID NO 116 |
| | GTGCCGTACAAAGGTTGGCTGGG | SEQ ID NO 117 |
| | GGTGCCGTACAAAGGTTGGCTGG | SEQ ID NO 118 |
| | CTCTCCTCAGTACCACAGCAAGG | SEQ ID NO 119 |
| | CCTGGGGCCTCCGGGCCTGGTGG | SEQ ID NO 120 |
| | AGTACTCACCTGGGGCCTCCGGG | SEQ ID NO 121 |
| | AGGGTCTCCAGCGGCCCTCCTGG | SEQ ID NO 122 |
| | GCAAGTACTTACGCCTCCTTGGG | SEQ ID NO 123 |
| | TTGCGGTACATCTCCAGCCTGGG | SEQ ID NO 124 |
| | TTTGCGGTACATCTCCAGCCTGG | SEQ ID NO 125 |

TABLE 1-continued

| Target gene | DNA Target Sequence | ID SEQ NO |
|---|---|---|
| Tet2 | GCAAAACCTGTCCACTCTTATGG | SEQ ID NO 126 |
| | TTGGTGCCATAAGAGTGGACAGG | SEQ ID NO 127 |
| | GGTGCAAGTTTCTTATATGTTGG | SEQ ID NO 128 |
| | ACCTGATGCATATAATAATCAGG | SEQ ID NO 129 |
| | ACCTGATTATTATATGCATCAGG | SEQ ID NO 130 |
| | CAGAGCACCAGAGTGCCGTCTGG | SEQ ID NO 131 |
| | AGAGTGCCGTCTGGGTCTGAAGG | SEQ ID NO 132 |
| | AGAGTGCCGTCTGGGTCTGAAGG | SEQ ID NO 133 |
| | AGGAAGGCCGTCCATTCTCAGG | SEQ ID NO 134 |
| | GGATAGAACCAACCATGTTGAGG | SEQ ID NO 135 |
| | TCTGTTGCCCTCAACATGGTTGG | SEQ ID NO 136 |
| | TTAGTCTGTTGCCCTCAACATGG | SEQ ID NO 137 |
| | GTCTGGCAAATGGGAGGTGATGG | SEQ ID NO 138 |
| | CAGAGGTTCTGTCTGGCAAATGG | SEQ ID NO 139 |
| | TTGTAGCCAGAGGTTCTGTCTGG | SEQ ID NO 140 |
| | ACTTCTGGATGAGCTCTCTCAGG | SEQ ID NO 141 |
| | AGAGCTCATCCAGAAGTAAATGG | SEQ ID NO 142 |
| | TTGGTGTCTCCATTTACTTCTGG | SEQ ID NO 143 |
| | TTCTGGCTTCCCTTCATACAGGG | SEQ ID NO 144 |
| | CAGGACTCACACGACTATTCTGG | SEQ ID NO 145 |
| | CTACTTTCTTGTGTAAAGTCAGG | SEQ ID NO 146 |
| | GACTTTACACAAGAAAGTAGAGG | SEQ ID NO 147 |
| | GTCTTTCTCCATTAGCCTTTTGG | SEQ ID NO 148 |
| | AATGGAGAAAGACGTAACTTCGG | SEQ ID NO 149 |
| | ATGGAGAAAGACGTAACTTCGGG | SEQ ID NO 150 |
| | TGGAGAAAGACGTAACTTCGGGG | SEQ ID NO 151 |
| | TTTGGTTGACTGCTTTCACCTGG | SEQ ID NO 152 |
| | TCACTCAAATCGGAGACATTTGG | SEQ ID NO 153 |
| | ATCTGAAGCTCTGGATTTTCAGG | SEQ ID NO 154 |
| | GCTTCAGATTCTGAATGAGCAGG | SEQ ID NO 155 |
| | CAGATTCTGAATGAGCAGGAGGG | SEQ ID NO 156 |
| | AAGGCAGTGCTAATGCCTAATGG | SEQ ID NO 157 |
| | GCAGAAACTGTAGCACCATTAGG | SEQ ID NO 158 |
| | ACCGCAATGGAAACACAATCTGG | SEQ ID NO 159 |
| | TGTGGTTTTCTGCACCGCAATGG | SEQ ID NO 160 |
| | CATAAATGCCATTAACAGTCAGG | SEQ ID NO 161 |
| | ATTAGTAGCCTGACTGTTAATGG | SEQ ID NO 162 |
| | CGATGGGTGAGTGATCTCACAGG | SEQ ID NO 163 |
| | ACTCACCCATCGCATACCTCAGG | SEQ ID NO 164 |
| | CTCACCCATCGCATACCTCAGGG | SEQ ID NO 165 |
| PSGL-1 | AGCAACAGGAGGAGTTGCAGAGG | SEQ ID NO 166 |
| | CCAGTAGGATCAGCAACAGGAGG | SEQ ID NO 167 |
| | CTCCTGTTGCTGATCCTACTGGG | SEQ IQ NO 168 |
| | GGCCCAGTAGGATCAGCAACAGG | SEQ ID NO 169 |
| | TTGCTGATCCTACTGGGCCCTGG | SEQ ID NO 170 |
| | TGGCAACAGCTTGCAGCTGTGGG | SEQ ID NO 171 |
| | CTTGGGTCCCCTGCTTGCCCGGG | SEQ ID NO 172 |
| | GTCCCCTGCTTGCCCGGGACCGG | SEQ ID NO 173 |
| | CTCCGGTCCCGGGCAAGCAGGG | SEQ ID NO 174 |
| | TCTCCGGTCCCGGGCAAGCAGG | SEQ ID NO 175 |
| | GTCTCCGGTCCCGGGCAAGCAGG | SEQ ID NO 176 |
| | GCTTGCCCGGGACCGGAGACAGG | SEQ ID NO 177 |
| | GGTGGCCTGTCTCCGGTCCCTGG | SEQ ID NO 178 |
| | CGGTGGCCTGTCTCCGGTCCCGG | SEQ ID NO 179 |
| | CATATTCGGTGGCCTGTCTCCGG | SEQ ID NO 180 |
| | ATCTAGGTACTCATATTCGGTGG | SEQ ID NO 181 |
| | ATAATCTAGGTACTCATATTCGG | SEQ ID NO 182 |
| | TTATGATTTCCTGCCAGAAACGG | SEQ ID NO 183 |
| | ATTTCTGGAGGCTCCGTTTCTGG | SEQ ID NO 184 |
| | ACTGACACCACTCCTCTGACTGG | SEQ ID NO 185 |
| | CTGACACCACTCCTCTGACTGGG | SEQ ID NO 186 |
| | ACCACTCCTCTGACTGGGCCTGG | SEQ ID NO 187 |
| | AACCCCTGAGTCTACCACTGTGG | SEQ ID NO 188 |
| | CTCCACAGTGGTAGACTCAGGGG | SEQ ID NO 189 |
| | GCTCCACAGTGGTAGACTCAGGG | SEQ ID NO 190 |
| | GGCTCCACAGTGGTAGACTCAGG | SEQ ID NO 191 |
| | CCTGCTGCAAGGCGTTCTACTGG | SEQ ID NO 192 |
| | CCAGTAGAACGCCTTGCAGCAGG | SEQ ID NO 193 |
| | CGTTCTACTGGCTGGATGGAGG | SEQ ID NO 194 |
| | TCTACTGGCTGGATGCAGGAGG | SEQ ID NO 195 |
| | CCACGGAGCTGGCCAACATGGGG | SEQ ID NO 196 |
| | CGTGGACAGGTTCCCCATGTTGG | SEQ ID NO 197 |
| | GTCCACGGATTCAGCAGCTATGG | SEQ ID NO 198 |
| | GACCACTCAACCAGTGCCCACGG | SEQ ID NO 199 |
| | GGAGTGGTCTGTGCCTCCGTGGG | SEQ ID NO 200 |
| | GGCACAGACAACTCGACTGACGG | SEQ ID NO 201 |
| | GACAACTCGACTGACGGCCACGG | SEQ ID NO 202 |
| | AACTCGACTGACGGCCACGGAGG | SEQ ID NO 203 |
| | CACAGAACCCAGTGCCACAGAGG | SEQ ID NO 204 |
| | GGTAGTAGGTTCCATGGACAGGG | SEQ ID NO 205 |
| | TGGTAGTAGGTTCCATGGACAGG | SEQ ID NO 206 |
| | TCTTTTGGTAGTAGGTTCCATGG | SEQ ID NO 207 |
| | ATGGAACCTACTACCAAAAGAGG | SEQ ID No 208 |
| | AACAGACCTCTTTTGGTAGTAGG | SEQ ID NO 209 |
| | GGGTATGAACAGACCTCTTTTGG | SED ID NO 210 |
| | TGTGTCCTCTGTTACTCACAAGG | SEQ ID NO 211 |
| | GTGTCCTCTGTTACTCACAAGGG | SEQ ID NO 212 |
| | GTAGTTGACGGACAAATTGCTGG | SEQ ID NO 213 |
| | TTTGTCCGTCAACTACCCAGTGG | SEQ ID NO 214 |
| | TTGTCCGTCAACTACCCAGTGGG | SEQ ID NO 215 |
| | TGTCCGTCAACTACCCAGTGGGG | SEQ ID NO 216 |
| | GTCCGTCAACTACCCAGTGGGGG | SEQ ID NO 217 |
| | CTCTGTGAAGCAGTGCCTGCTGG | SEQ ID NO 218 |
| | CCTGCTGGCCATCCTAATCTTGG | SEQ ID NO 219 |
| | CCAAGATTAGGATGGCCAGCAGG | SEQ ID NO 220 |
| | GGCCATCCTAATCTTGGCGCTGG | SEQ ID NO 221 |
| | CACCAGCGCCAAGATTAGGATGG | SEQ ID NO 222 |
| | AGTGCACACGAAGAAGATAGTGG | SEQ ID NO 223 |
| | TATCTTCTTCGTGTGCACTGTGG | SEQ ID NO 224 |
| | CTTCGTGTGCACTGTGGTGCTGG | SEQ ID NO 225 |
| | GGCGGTCCGCCTCTCCCGCAAGG | SEQ ID NO 226 |
| | GCGGTCCGCCTCTCCCGCAAGGG | SEQ ID NO 227 |
| | AATTACGCACGGGTACATGTGG | SEQ ID NO 228 |
| | TGGGGGAGTAATTACGCACGGGG | SEQ ID NO 229 |
| | GTGGGGGAGTAATTACGCACGGG | SEQ ID NO 230 |
| | GGTGGGGGAGTAATTACGCACGG | SEQ ID NO 231 |
| | TAATTACTCCCCCACCGAGATGG | SEQ ID NO 232 |
| | AGATGCAGACCATCTCGGTGGGG | SEQ ID NO 233 |
| | GAGATGCAGACCATCTCGGTGGG | SEQ ID NO 234 |
| | TGAGATGCAGACCATCTCGGTGG | SEQ ID NO 235 |
| | GGATGAGATGCAGACCATCTCGG | SEQ ID NO 236 |
| | ATCTCATCCCTGTTGCCTGATGG | SEQ ID NO 237 |
| | TCATCCCTGTTGCCTGATGGGGG | SEQ ID NO 238 |
| | CTCACCCCCATCAGGCAACAGGG | SEQ ID NO 239 |
| | GAGGGCCCCTCACCCCCATCAGG | SEQ ID NO 240 |
| | GGGCCCTCTGCCACAGCCAATGG | SEQ ID NO 241 |
| | CCCTCTGCCACAGCCAATGGGGG | SEQ ID NO 242 |
| | CCCCCATTGGCTGTGGCAGAGGG | SEQ ID NO 243 |
| | GCCCCCATTGGCTGTGGCAGAGG | SEQ ID NO 244 |
| | GGACAGGCCCCCATTGGCTGTGG | SEQ ID NO 245 |
| | CCGGGCTCTTGGCCTTGGACAGG | SEQ ID NO 246 |
| | CTGTCCAAGGCCAAGAGCCCGGG | SEQ ID NO 247 |
| | TGGCGTCAGGCCCGGGCTCTTGG | SEQ ID NO 248 |
| | CGGGGCCTGACGCCAGAGCCCAGG | SEQ ID NO 249 |
| FAS | CAACAACCATGCTGGGCATCTGG | SEQ ID NO 250 |
| | GAGGGTCCAGATGCCCAGCATGG | SEQ ID NO 251 |
| | CATCTGGACCCTCCTACCTCTGG | SEQ ID NO 252 |
| | AGGGCTCACCAGAGGTAGGAGGG | SEQ ID NO 253 |
| | GGAGTTGATGTCAGTCACTTGGG | SEQ ID NO 254 |
| | TGGAGTTGATGTCAGTCACTTGG | SEQ ID NO 255 |
| | AGTGACTGACATCAACTCCAAGG | SEQ ID NO 256 |
| | GTGACTGACATCAACTCCAAGGG | SEQ ID NO 257 |
| | ACTCCAAGGGATTGGAATTGAGG | SEQ ID NO 258 |
| | CTTCCTCAATTCCAATCCCTTGG | SEQ ID NO 259 |
| | TACAGTTGAGACTCAGAACTTGG | SEQ ID NO 260 |
| | TTGGAAGGCCTGCATCATGATGG | SEQ ID NO 261 |
| | AGAATTGGCCATCATGATGCAGG | SEQ ID NO 262 |
| | GACAGGGCTTATGGCAGAATTGG | SEQ ID NO 263 |
| | TGTAACATACCTGGAGGACAGG | SEQ ID NO 264 |
| | GTGTAACATACCTGGAGGACAGG | SEQ ID NO 265 |
| KDM6A | CGTACCTGTGCAACTCCTGTTGG | SEQ ID NO 266 |
| | GATCTACTGAATTCCTAATGGG | SEQ ID NO 267 |
| | GAGTCAGCTGTTGGCCCATTAGG | SEQ ID NO 268 |
| | CTGCCTACAAACTCAGTCTCTGG | SEQ ID NO 269 |
| | GGGCAGGCAGGACGGACTCCAGG | SEQ ID NO 270 |
| | GGAGTCCGTCCTGCCTGCCCTGG | SEQ ID NO 271 |
| | GAGTCCGTCCTGCCTGCCCTGGG | SEQ ID NO 272 |

TABLE 1-continued

Target sequence

| Target gene | DNA Target Sequence | ID SEQ NO |
|---|---|---|
| | GAAAAGGGTCCATTGGCCAAAGG | SEQ ID NO 273 |
| | GCCTGCAGAAAAGGGTCCATTGG | SEQ ID NO 274 |
| | TTGATGTGCTACAGGGAACATGG | SEQ ID NO 275 |
| | AGCGTTCTTGATGTGCTACAGGG | SEQ ID NO 276 |
| | CAGCGTTCTTGATGTGCTACAGG | SEQ ID NO 277 |
| | CTGTAGCACATCAAGAACGCTGG | SEQ ID NO 278 |
| | TGTAGCACATCAAGAACGCTGGG | SEQ ID NO 279 |
| | ATAGGCAATAATCATATAACAGG | SEQ ID NO 280 |
| | AGTGCGTTTCGCTGCAGGTAAGG | SEQ ID NO 281 |
| | GAGTGAGTGCGTTTCGCTGCAGG | SEQ ID NO 282 |
| | GTCAGGTTTGTGCGGTTATGAGG | SEQ ID NO 283 |
| | CGCTGCTGGTCAGGTTTGTGCGG | SEQ ID NO 284 |
| | AAACCTGACCAGCAGCGCAGAGG | SEQ ID NO 285 |
| | CCAGCAGCGCAGAGGAGCCGTGG | SEQ ID NO 286 |
| | CCACGGCTCCTCTGCGCTGCTGG | SEQ ID NO 287 |
| | CCAACTATCTAACTCCACTCAGG | SEQ ID NO 288 |
| | CCTGAGTGGAGTTAGATAGTTGG | SEQ ID NO 289 |

[Genetic Scissors (Engineered Nuclease) System]

The genetic manipulation or modification of materials involved in the immune regulatory factors, immune cells, and the immune system of the present invention may be achieved using the "a guide nucleic acid-editor protein complex".

Guide Nucleic Acid-Editor Protein Complex

The term "guide nucleic acid-editor protein complex" is referred to as a complex which are formed by interacting between guide nucleic acid and editor protein, and a nucleic acid-protein complex comprises a guide nucleic acid and an editor protein.

The term "guide nucleic acid" is configured to recognize a nucleic acid, gene, chromosome or protein targeted by the guide nucleic acid-protein complex.

The guide nucleic acid may be present in the form of DNA, RNA or a DNA/RNA mixture, and have a 5 to 150-nucleic acid sequence.

The guide nucleic acid may include one or more domains.

The domains may be, but are not limited to, a guide domain, a first complementary domain, a linker domain, a second complementary domain, a proximal domain, or a tail domain.

The guide nucleic acid may include two or more domains, which may be the same domain repeats, or different domains.

The guide nucleic acid may be one continuous nucleic acid sequence.

For example, the one continuous nucleic acid sequence may be (N)m, where N is A, T, C or G, or A, U, C or G, and m is an integer of 1 to 150.

The guide nucleic acid may be two or more continuous nucleic acid sequences.

For example, the two or more continuous nucleic acid sequences may be (N)m and (N)o, where N represents A, T, C or G, or A, U, C or G, m and o are an integer of 1 to 150, and may be the same as or different from each other.

The term "editor protein" refers to a peptide, polypeptide or protein which is able to directly bind to or interact with, without direct binding to, a nucleic acid. The editor protein may also be conceptually referred to as "gene scissors" or RNA-Guided Endonuclease (RGEN).

The editor protein may be an enzyme.

The editor protein may be a fusion protein.

Here, the "fusion protein" refers to a protein that is produced by fusing an enzyme with an additional domain, peptide, polypeptide or protein.

The term "enzyme" refers to a protein that contains a domain capable of cleaving a nucleic acid, gene, chromosome or protein.

The additional domain, peptide, polypeptide or protein may be a functional domain, peptide, polypeptide or protein, which has a function the same as or different from the enzyme.

The fusion protein may include an additional domain, peptide, polypeptide or protein at one or more regions of the amino terminus (N-terminus) of the enzyme or the vicinity thereof; the carboxyl terminus (C-terminus) or the vicinity thereof; the middle part of the enzyme; and a combination thereof.

The fusion protein may include a functional domain, peptide, polypeptide or protein at one or more regions of the N-terminus of the enzyme or the vicinity thereof; the C-terminus or the vicinity thereof; the middle part of the enzyme; and a combination thereof.

The guide nucleic acid-editor protein complex may serve to modify a subject.

The subject may be a target nucleic acid, gene, chromosome or protein.

For example, the guide nucleic acid-editor protein complex may result in final regulation (e.g., inhibition, suppression, reduction, increase or promotion) of the expression of a protein of interest, removal of the protein, or expression of a new protein.

Here, the guide nucleic acid-editor protein complex may act at a DNA, RNA, gene or chromosome level.

The guide nucleic acid-editor protein complex may act in gene transcription and translation stages.

The guide nucleic acid-editor protein complex may act at a protein level.

1. Guide Nucleic Acids

The guide nucleic acid is a nucleic acid that is capable of recognizing a target nucleic acid, gene, chromosome or protein, and forms a guide nucleic acid-protein complex.

Here, the guide nucleic acid is configured to recognize or target a nucleic acid, gene, chromosome or protein targeted by the guide nucleic acid-protein complex.

The guide nucleic acid may be present in the form of DNA, RNA or a DNA/RNA mixture, and have a 5 to 150-nucleic acid sequence.

The guide nucleic acid may be present in a linear or circular shape.

The guide nucleic acid may be one continuous nucleic acid sequence.

For example, the one continuous nucleic acid sequence may be $(N)_m$, where N is A, T, C or G, or A, U, C or G, and m is an integer of 1 to 150.

The guide nucleic acid may be two or more continuous nucleic acid sequences.

For example, the two or more continuous nucleic acid sequences may be $(N)_m$ and $(N)_o$, where N represents A, T, C or G, or A, U, C or G, m and o are an integer of 1 to 150, and may be the same as or different from each other.

The guide nucleic acid may include one or more domains.

Here, the domains may be, but are not limited to, a guide domain, a first complementary domain, a linker domain, a second complementary domain, a proximal domain, or a tail domain.

The guide nucleic acid may include two or more domains, which may be the same domain repeats, or different domains.

The domains will be described below.

i) Guide Domain

The term "guide domain" is a domain having a complementary guide sequence which is able to form a complementary bond with a target sequence on a target gene or nucleic acid, and serves to specifically interact with the target gene or nucleic acid.

The guide sequence is a nucleic acid sequence complementary to the target sequence on a target gene or nucleic acid, which has, for example, at least 50% or more, 55%, 60%, 65%, 70%, 75%, 80%, 85%, 90% or 95% complementarity or complete complementarity.

The guide domain may be a sequence of 5 to 50 bases.

In an example, the guide domain may be a sequence of 5 to 50, 10 to 50, 15 to 50, 20 to 50, 25 to 50, 30 to 50, 35 to 50, 40 to 50 or 45 to 50 bases.

In another example, the guide domain may be a sequence of 1 to 5, 5 to 10, 10 to 15, 15 to 20, 20 to 25, 25 to 30, 30 to 35, 35 to 40, 40 to 45, or 45 to 50 bases.

The guide domain may have a guide sequence.

The guide sequence may be a complementary base sequence which is able to form a complementary bond with the target sequence on the target gene or nucleic acid.

The guide sequence may be a nucleic acid sequence complementary to the target sequence on the target gene or nucleic acid, which has, for example, at least 70%, 75%, 80%, 85%, 90% or 95% or more complementarity or complete complementarity.

The guide sequence may be a 5 to 50-base sequence.

In an example, the guide domain may be a 5 to 50, 10 to 50, 15 to 50, 20 to 50, 25 to 50, 30 to 50, 35 to 50, 40 to 50, or 45 to 50-base sequence.

In another example, the guide sequence may be a 1 to 5, 5 to 10, 10 to 15, 15 to 20, 20 to 25, 25 to 30, 30 to 35, 35 to 40, 40 to 45, or 45 to 50-base sequence.

In addition, the guide domain may include a guide sequence and an additional base sequence.

The additional base sequence may be utilized to improve or degrade the function of the guide domain.

The additional base sequence may be utilized to improve or degrade the function of the guide sequence.

The additional base sequence may be a 1 to 35-base sequence.

In one example, the additional base sequence may be a 5 to 35, 10 to 35, 15 to 35, 20 to 35, 25 to 35 or 30 to 35-base sequence.

In another example, the additional base sequence may be a 1 to 5, 5 to 10, 10 to 15, 15 to 20, 20 to 25, 25 to 30 or 30 to 35-base sequence.

The additional base sequence may be located at the 5' end of the guide sequence.

The additional base sequence may be located at the 3' end of the guide sequence.

ii) First Complementary Domain

The term "first complementary domain" is a nucleic acid sequence including a nucleic acid sequence complementary to a second complementary domain, and has enough complementarity so as to form a double strand with the second complementary domain.

The first complementary domain may be a 5 to 35-base sequence.

In an example, the first complementary domain may be a 5 to 35, 10 to 35, 15 to 35, 20 to 35, 25 to 35, or 30 to 35-base sequence.

In another example, the first complementary domain may be a 1 to 5, 5 to 10, 10 to 15, 15 to 20, 20 to 25, 25 to 30 or 30 to 35-base sequence.

iii) Linker Domain

The term "linker domain" is a nucleic acid sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a 1 to 30-base sequence.

In one example, the linker domain may be a 1 to 5, 5 to 10, 10 to 15, 15 to 20, 20 to 25, or 25 to 30-base sequence.

In another example, the linker domain may be a 1 to 30, 5 to 30, 10 to 30, 15 to 30, 20 to 30, or 25 to 30-base sequence.

iv) Second Complementary Domain

The term "second complementary domain" is a nucleic acid sequence including a nucleic acid sequence complementary to the first complementary domain, and has enough complementarity so as to form a double strand with the first complementary domain.

The second complementary domain may have a base sequence complementary to the first complementary domain, and a base sequence having no complementarity to the first complementary domain, for example, a base sequence not forming a double strand with the first complementary domain, and may have a longer base sequence than the first complementary domain.

The second complementary domain may have a 5 to 35-base sequence.

In an example, the second complementary domain may be a 1 to 35, 5 to 35, 10 to 35, 15 to 35, 20 to 35, 25 to 35, or 30 to 35-base sequence.

In another example, the second complementary domain may be a 1 to 5, 5 to 10, 10 to 15, 15 to 20, 20 to 25, 25 to 30, or 30 to 35-base sequence.

v) Proximal Domain

The term "proximal domain" is a nucleic acid sequence located adjacent to the second complementary domain.

The proximal domain may have a complementary base sequence therein, and may be formed in a double strand due to a complementary base sequence.

The proximal domain may be a 1 to 20-base sequence.

In one example, the proximal domain may be a 1 to 20, 5 to 20, 10 to 20 or 15 to 20-base sequence.

In another example, the proximal domain may the proximal domain may be a 1 to 20, 5 to 20, 10 to 20 or 15 to 20-base sequence. be a 1 to 5, 5 to 10, 10 to 15 or 15 to 20-base sequence.

vi) Tail Domain

The term "tail domain" is a nucleic acid sequence located at one or more ends of the both ends of the guide nucleic acid.

The tail domain may have a complementary base sequence therein, and may be formed in a double strand due to a complementary base sequence.

The tail domain may be a 1 to 50-base sequence.

In an example, the tail domain may be a 5 to 50, 10 to 50, 15 to 50, 20 to 50, 25 to 50, 30 to 50, 35 to 50, 40 to 50, or 45 to 50-base sequence.

In another example, the tail domain may be a 1 to 5, 5 to 10, 10 to 15, 15 to 20, 20 to 25, 25 to 30, 30 to 35, 35 to 40, 40 to 45, or 45 to 50-base sequence.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3'phosphorothioate (MS) or 2'-O-methyl 3'thioPACE (MSP).

The guide nucleic acid includes one or more domains.

The guide nucleic acid may include a guide domain.

The guide nucleic acid may include a first complementary domain.

The guide nucleic acid may include a linker domain.

The guide nucleic acid may include a second complementary domain.

The guide nucleic acid may include a proximal domain.

The guide nucleic acid may include a tail domain.

Here, there may be 1, 2, 3, 4, 5, 6 or more domains.

The guide nucleic acid may include 1, 2, 3, 4, 5, 6 or more guide domains.

The guide nucleic acid may include 1, 2, 3, 4, 5, 6 or more first complementary domains.

The guide nucleic acid may include 1, 2, 3, 4, 5, 6 or more linker domains.

The guide nucleic acid may include 1, 2, 3, 4, 5, 6 or more second complementary domains.

The guide nucleic acid may include 1, 2, 3, 4, 5, 6 or more proximal domains.

The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleic acid sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

As a specific example of the guide nucleic acid in the present specification, the guide nucleic acid is described below.

gRNA

The term "gRNA" refers to a nucleic acid capable of specifically targeting a gRNA-CRISPR enzyme complex, that is, a CRISPR complex, with respect to a target gene or nucleic acid. In addition, the gRNA is a nucleic acid-specific RNA which may bind to a CRISPR enzyme and guide the CRISPR enzyme to the target gene or nucleic acid.

The gRNA may include multiple domains. Due to each domain, interactions may occur in a three-dimensional structure or active form of a gRNA strand, or between these strands.

The gRNA may be called single-stranded gRNA (single RNA molecule); or double-stranded gRNA (including more than one, generally, two discrete RNA molecules).

In one exemplary embodiment, the single-stranded gRNA may include a guide domain, that is, a domain including a guide sequence capable of forming a complementary bond with a target gene or nucleic acid; a first complementary domain; a linker domain; a second complementary domain, a domain having a sequence complementary to the first complementary domain sequence, thereby forming a double-stranded nucleic acid with the first complementary domain; a proximal domain; and optionally a tail domain in the 5' to 3' direction.

In another embodiment, the double-stranded gRNA may include a first strand which includes a guide domain, that is, a domain including a guide sequence capable of forming a complementary bond with a target gene or nucleic acid and a first complementary domain; and a second strand which includes a second complementary domain, a domain having a sequence complementary to the first complementary domain sequence, thereby forming a double-stranded nucleic acid with the first complementary domain, a proximal domain; and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a target gene or nucleic acid; a first complementary domain; a second complementary domain, and a domain having a sequence complementary to the first complementary domain sequence, thereby forming a double-stranded nucleic acid with the first complementary domain in the 3' to 5' direction.

Guide Domain

The guide domain includes a complementary guide sequence capable of forming a complementary bond with a target sequence on a target gene or nucleic acid. The guide sequence may be a nucleic acid sequence having complementarity to the target sequence on the target gene or nucleic acid, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

The guide domain may be a 5 to 50-base sequence.

As an exemplary embodiment, the guide domain may be a 16, 17, 18, 19, 20, 21, 22, 23, 24 or 25-base sequence.

As an exemplary embodiment, the guide domain may include a 16, 17, 18, 19, 20, 21, 22, 23, 24 or 25-base sequence.

Here, the guide domain may include a guide sequence.

The guide sequence may be a complementary base sequence capable of forming a complementary bond with a target sequence on a target gene or nucleic acid.

The guide sequence may be a nucleic acid sequence complementary to the target sequence on the target gene or nucleic acid, which has, for example, at least 70%, 75%, 80%, 85%, 90% or 95% or more complementarity or complete complementarity.

The guide sequence may be a 5 to 50-base sequence.

In an exemplary embodiment, the guide sequence may be a 16, 17, 18, 19, 20, 21, 22, 23, 24 or 25-base sequence.

In one exemplary embodiment, the guide sequence may include a 16, 17, 18, 19, 20, 21, 22, 23, 24 or 25-base sequence.

Here, the guide domain may include a guide sequence and an additional base sequence.

The additional base sequence may be a 1 to 35-base sequence.

In one exemplary embodiment, the additional base sequence may be a 1, 2, 3, 4, 5, 6, 7, 8, 9 or 10-base sequence.

For example, the additional base sequence may be a single base sequence, guanine (G), or a sequence of two bases, GG.

The additional base sequence may be located at the 5' end of the guide sequence.

The additional base sequence may be located at the 3' end of the guide sequence.

Selectively, a part or all of the base sequence of the guide domain may include a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

First Complementary Domain

The first complementary domain includes a nucleic acid sequence complementary to a second complementary domain, and has enough complementarity such that it is able to form a double strand with the second complementary domain.

Here, the first complementary domain may be a 5 to 35-base sequence. The first complementary domain may include a 5 to 35-base sequence.

In one exemplary embodiment, the first complementary domain may be a 5, 6, 7, 8, 9, 10, 11, 12, 13, 14, 15, 16, 17, 18, 19, 20, 21, 22, 23, 24, or 25-base sequence.

In another embodiment, the first complementary domain may include a 5, 6, 7, 8, 9, 10, 11, 12, 13, 14, 15, 16, 17, 18, 19, 20, 21, 22, 23, 24, or 25-base sequence.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of Streptococcus pyogenes, Campylobacter jejuni, Streptococcus thermophilus, Staphylococcus aureus or Neisseria meningitides, or a first complementary domain derived therefrom.

For example, when the first complementary domain is the first complementary domain of Streptococcus pyogenes or a first complementary domain derived therefrom, the first complementary domain may be 5'-GUUUUAGAGCUA-3' (SEQ ID NO: 290) or a base sequence having partial, that is, at least 50% or more, or complete homology with 5'-GUUUUAGAGCUA-3' (SEQ ID NO: 290). Here, the first complementary domain may further include $(X)_n$, resulting in 5'-GUUUUAGAGCUA(X)n-3' (SEQ ID NO: 291). The X may be selected from the group consisting of bases A, T, U and G, and the n may represent the number of bases, which is an integer of 5 to 15. Here, the $(X)_n$ may be n repeats of the same base, or a mixture of n bases of A, T, U and G.

In another embodiment, when the first complementary domain is the first complementary domain of Campylobacter jejuni or a first complementary domain derived therefrom, the first complementary domain may be 5'-GUUUUAGUCCCUUUUUAAAUUUCUU-3' (SEQ ID NO: 292), or a base sequence having partial, that is, at least 50% or more, or complete homology with 5'-GUUUUA-GUCCCUUUUUAAAUUUCUU-3' (SEQ ID NO: 292). Here, the first complementary domain may further include (X)n, resulting in 5'-GUUUUAGUCCC-UUUUUAAAUUUCUU(X)n-3' (SEQ ID NO: 293). The X may be selected from the group consisting of bases A, T, U and G, and the n may represent the number of bases, which is an integer of 5 to 15. Here, the $(X)_n$ may represent n repeats of the same base, or a mixture of n bases of A, T, U and G.

In another embodiment, the first complementary domain may have partial, that is, at least 50% or more, or complete homology with a first complementary domain of Parcubacteria bacterium (GWC2011_GWC2_44_17), Lachnospiraceae bacterium (MC2017), Butyrivibrio proteoclasiicus, Peregrinibacteria bacterium (GW2011_GWA_33_10), Acidaminococcus sp. (BV3L6), Porphyromonas macacae, Lachnospiraceae bacterium (ND2006), Porphyromonas crevioricanis, Prevotella disiens, Moraxella bovoculi (237), Smiihella sp. (SC_KO8D17), Leptospira inadai, Lachnospiraceae bacterium (MA2020), Francisella novicida (U112), Candidatus Methanoplasma termitum or Eubacterium eligens, or a first complementary domain derived therefrom.

For example, when the first complementary domain is the first complementary domain of Parcubacteria bacterium or a first complementary domain derived therefrom, the first complementary domain may be 5'-UUUGUAGAU-3', or a base sequence having partial, that is, at least 50% or more homology with 5'-UUUGUAGAU-3'. Here, the first complementary domain may further include $(X)_n$, resulting in 5'-(X)nUUUGUAGAU-3' (SEQ ID NO: 294). The X may be selected from the group consisting of bases A, T, U and G, and the n may represent the number of bases, which is an integer of 1 to 5. Here, the $(X)_n$ may represent n repeats of the same base, or a mixture of n bases of A, T, U and G.

Selectively, a part or all of the base sequence of the first complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Linker Domain

The linker domain is a nucleic acid sequence connecting two or more domains, and connects two or more identical or different domains. The linker domain may be connected with two or more domains, or may connect two or more domains by covalent or non-covalent bonding.

The linker domain may be a nucleic acid sequence connecting a first complementary domain with a second complementary domain to produce single-stranded gRNA.

The linker domain may be connected with the first complementary domain and the second complementary domain by covalent or non-covalent bonding.

The linker domain may connect the first complementary domain with the second complementary domain by covalent or non-covalent bonding The linker domain may be a 1 to 30-base sequence. The linker domain may include a 1 to 30-base sequence.

In an exemplary embodiment, the linker domain may be a 1 to 5, 5 to 10, 10 to 15, 15 to 20, 20 to 25 or 25 to 30-base sequence.

In an exemplary embodiment, the linker domain may include a 1 to 5, 5 to 10, 10 to 15, 15 to 20, 20 to 25, or 25 to 30-base sequence.

The linker domain is suitable to be used in a single-stranded gRNA molecule, and may be used to produce single-stranded gRNA by being connected with a first strand and a second strand of double-stranded gRNA or connecting the first strand with the second strand by covalent or non-covalent bonding. The linker domain may be used to produce single-stranded gRNA by being connected with crRNA and tracrRNA of double-stranded gRNA or connecting the crRNA with the tracrRNA by covalent or non-covalent bonding.

The linker domain may have homology with a natural sequence, for example, a partial sequence of tracrRNA, or may be derived therefrom.

Selectively, a part or all of the base sequence of the linker domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Second Complementary Domain

The second complementary domain includes a nucleic acid sequence complementary to the first complementary domain, and has enough complementarity so as to form a double strand with the first complementary domain. The second complementary domain may include a base sequence complementary to the first complementary domain, and a base sequence having no complementarity with the first complementary domain, for example, a base sequence not forming a double strand with the first complementary domain, and may have a longer base sequence than the first complementary domain.

Here, the second complementary domain may be a 5 to 35-base sequence. The first complementary domain may include a 5 to 35-base sequence.

In an exemplary embodiment, the second complementary domain may be a 5, 6, 7, 8, 9, 10, 11, 12, 13, 14, 15, 16, 17, 18, 19, 20, 21, 22, 23, 24 or 25-base sequence.

In an exemplary embodiment, the second complementary domain may include a 5, 6, 7, 8, 9, 10, 11, 12, 13, 14, 15, 16, 17, 18, 19, 20, 21, 22, 23, 24 or 25-base sequence.

In addition, the second complementary domain may have homology with a natural second complementary domain, or may be derived from the natural second complementary domain. In addition, the second complementary domain may have a difference in base sequence of a second complementary domain according to a species existing in nature, and may be derived from a second complementary domain contained in the species existing in nature, or may have partial or complete homology with the second complementary domain contained in the species existing in nature.

In an exemplary embodiment, the second complementary domain may have partial, that is, at least 50% or more, or complete homology with a second complementary domain of *Streptococcus pyogenes, Campylobacter jejuni, Streptococcus thermophilus, Staphylococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-UAGCAAGUUAAAAU-3' (SEQ ID NO: 295), or a base sequence having partial, that is, at least 50% or more homology with 5'-UAGCAAGUUAAAAU-3' (SEQ ID NO: 295) (a base sequence forming a double strand with the first complementary domain is underlined). Here, the second complementary domain may further include $(X)_n$ and/or $(X)_m$, resulting in 5'-$(X)_n$ UAGCAAGUUAAAAU$(X)_m$-3' (SEQ ID NO: 296). The X may be selected from the group consisting of bases A, T, U and G, and each of the n and m may represent the number of bases, in which the n may be an integer of 1 to 15, and the m may be an integer of 1 to 6. Here, the $(X)_n$ may represent n repeats of the same base, or a mixture of n bases of A, T, U and G. In addition, $(X)_m$ may represent m repeats of the same base, or a mixture of m bases of A, T, U and G.

In another example, when the second complementary domain is the second complementary domain of *Campylobacter jejuni* or a second complementary domain derived therefrom, the second complementary domain may be 5'-AAGAAAUUUAAAAAGGGACUAAAAU-3' (SEQ ID NO: 297), or a base sequence having partial, that is, at least 50% or more homology with 5'-AAGAAAUUUAAAAAGGGACUAAAAU-3' (SEQ ID NO: 297) (a base sequence forming a double strand with the first complementary domain is underlined). Here, the second complementary domain may further include $(X)_n$ and/or $(X)_m$, resulting in 5'-$(X)_n$AAGAAAUUUAAAAAGGGACUAAAAU$(X)_m$-3' (SEQ ID NO: 298). The X may be selected from the group consisting of bases A, T, U and G, and each of the n and m may represent the number of bases, in which the n may be an integer of 1 to 15, and the m may be an integer of 1 to 6. Here, $(X)_n$ may represent n repeats of the same base, or a mixture of n bases of A, T, U and G. In addition, $(X)_m$ may represent m repeats of the same base, or a mixture of m bases of A, T, U and G.

In another embodiment, the second complementary domain may have partial, that is, at least 50% or more, or complete homology with a first complementary domain of Parcubacteria *bacterium* (GWC2011_GWC2_44_17), Lachnospirameae *bacterium* (MC2017), *Butyrivibrio proteoclasiicus*, Peregrinibacteria *bacterium* (GW2011_GWA_33_10), *Acidaminococcus* sp. (BV3L6), *Porphyromonas macacae*, Lachnospirameae *bacterium* (ND2006), *Porphyromonas crevioricanis, Prevotella disiens, Moraxella bovoculi* (237), Smiihella sp. (SC_KO8D17), *Leptospira inadai*, Lachnospirameae *bacterium* (MA2020), *Francisella novicida* (0112), *Candidatus* Methanoplasma *termitum* or *Eubacterium eligens*, or a second complementary domain derived therefrom.

For example, when the second complementary domain is a second complementary domain of Parcubacteria *bacterium* or a second complementary domain derived therefrom, the second complementary domain may be 5'-AAAUUUC-UACU-3' (SEQ ID NO: 299), or a base sequence having partial, that is, at least 50% or more homology with 5'-AAAUUUCUACU-3' (SEQ ID NO: 299) (a base sequence forming a double strand with the first complementary domain is underlined). Here, the second complementary domain may further include $(X)_n$ and/or $(X)_m$, resulting in 5'-$(X)_n$AAAUUUCUACU$(X)_m$-3' (SEQ ID NO: 300). The X may be selected from the group consisting of bases A, T, U and G, and each of the n and m may represent the number of bases, in which the n may be an integer of 1 to 10, and the m may be an integer of 1 to 6. Here, the $(X)_n$ may represent n repeats of the same base, or a mixture of n bases of A, T, U and G. In addition, the $(X)_m$ may represent m repeats of the same base, or a mixture of m bases of A, T, U and G.

Selectively, a part or all of the base sequence of the second complementary domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Proximal Domain

The proximal domain is a sequence of 1 to 20 bases located adjacent to the second complementary domain, and a domain located at the 3' end direction of the second complementary domain. Here, the proximal domain may be used to form a double strand between complementary base sequences therein.

In one exemplary embodiment, the proximal domain may be a 5, 6, 7, 8, 9, 10, 11, 12, 13, 14 or 15-base sequence.

In another embodiment, the proximal domain may include a 5, 6, 7, 8, 9, 10, 11, 12, 13, 14 or 15-base sequence.

In addition, the proximal domain may have homology with a natural proximal domain, or may be derived from the natural proximal domain. In addition, the proximal domain may have a difference in base sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes, Campylobacter jejuni, Streptococcus thermophilus, Staphylococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGC-UAGUCCG-3' (SEQ ID NO: 301), or a base sequence having partial, that is, at least 50% or more homology with 5'-AAGGCUAGUCCG-3' (SEQ ID NO: 301). Here, the proximal domain may further include $(X)_n$, resulting in 5'-AAGGCUAGUCCG$(X)_n$-3' (SEQ ID NO: 302). The X may be selected from the group consisting of bases A, T, U and G, and the n may represent the number of bases, which is an integer of 1 to 15. Here, the $(X)_n$ may represent n repeats of the same base, or a mixture of n bases of A, T, U and G.

In yet another example, when the proximal domain is a proximal domain of *Campylobacter jejuni* or a proximal domain derived therefrom, the proximal domain may be 5'-AAAGAGUUUGC-3' (SEQ ID NO: 303), or a base sequence having at least 50% or more homology with 5'-AAAGAGUUUGC-3' (SEQ ID NO: 303). Here, the proximal domain may further include $(X)_n$, resulting in 5'-AAAGAGUUUGC$(X)_n$-3' (SEQ ID NO: 304). The X may be selected from the group consisting of bases A, T, U and G, and the n may represent the number of bases, which is an integer of 1 to 40. Here, the $(X)_n$ may represent n repeats of the same base, or a mixture of n bases of A, T, U and G.

Selectively, a part or all of the base sequence of the proximal domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Tail Domain

The tail domain is a domain which is able to be selectively added to the 3' end of single-stranded gRNA or double-stranded gRNA. The tail domain may be a 1 to 50-base sequence, or include a 1 to 50-base sequence. Here, the tail domain may be used to form a double strand between complementary base sequences therein.

In an exemplary embodiment, the tail domain may be a 1 to 5, 5 to 10, 10 to 15, 15 to 20, 20 to 25, 25 to 30, 30 to 35, 35 to 40, 40 to 45, or 45 to 50-base sequence.

In an exemplary embodiment, the tail domain may include a 1 to 5, 5 to 10, 10 to 15, 15 to 20, 20 to 25, 25 to 30, 30 to 35, 35 to 40, 40 to 45, or 45 to 50-base sequence.

In addition, the tail domain may have homology with a natural tail domain, or may be derived from the natural tail domain. In addition, the tail domain may have a difference in base sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes, Campylobacter jejuni, Streptococcus thermophilus, Staphylococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAAC-UUGAAAAAGUGGCACCGAGUCGGUGC-3' (SEQ ID NO: 305), or a base sequence having partial, that is, at least 50% or more homology with 5'-UUAUCAAC-UUGAAAAAGUGGCACCGAGUCGGUGC-3' (SEQ ID NO: 305). Here, the tail domain may further include $(X)_n$, resulting in 5'-UUAUCAAC-UUGAAAAAGUGGCACCGAGUCGGUGC$(X)_n$-3' (SEQ ID NO: 306). The X may be selected from the group consisting of bases A, T, U and G, and the n may represent the number of bases, which is an integer of 1 to 15. Here, the $(X)_n$ may represent n repeats of the same base, or a mixture of n bases such as A, T, U and G.

In another example, when the tail domain is a tail domain of *Campylobacter jejuni* or a tail domain derived therefrom, the tail domain may be 5'-GGGACUCUGCGGGGUUA-CAAUCCCCUAAAACCGCUUUU-3' (SEQ ID NO: 307), or a base sequence having partial, that is, at least 50% or more homology with 5'-GGGACUCUGCGGGGUUA-CAAUCCCCUAAAACCGCUUUU-3' (SEQ ID NO: 307). Here, the tail domain may further include $(X)_n$, resulting in 5'-GGGACUCUGCGGGGUUACAAUCCCC-UAAAACCGCUUUU(X)$_n$-3' (SEQ ID NO: 308). The X may be selected from the group consisting of bases A, T, U and G, and the n may represent the number of bases, which is an integer of 1 to 15. Here, the (X)$_n$ may represent n repeats of the same base, or a mixture of n bases of A, T, U and G.

In another embodiment, the tail domain may include a 1 to 10-base sequence at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

Selectively, a part or all of the base sequence of the tail domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

The gRNA may include a plurality of domains as described above, and therefore, the length of the nucleic acid sequence may be regulated according to a domain contained in the gRNA, and interactions may occur in strands in a three-dimensional structure or active form of gRNA or between theses strands due to each domain.

The gRNA may be referred to as single-stranded gRNA (single RNA molecule); or double-stranded gRNA (including more than one, generally two discrete RNA molecules).

Double-Stranded gRNA

The double-stranded gRNA consists of a first strand and a second strand.

Here, the first strand may consist of
5'-[guide domain]-[first complementary domain]-3', and the second strand may consist of
5'-[second complementary domain]-[proximal domain]-3' or
5'-[second complementary domain]-[proximal domain]-[tail domain]-3'.

Here, the first strand may be referred to as crRNA, and the second strand may be referred to as tracrRNA.

First Strand

[Guide Domain]

In the first strand, the guide domain includes a complementary guide sequence which is able to form a complementary bond with a target sequence on a target gene or nucleic acid. The guide sequence is a nucleic acid sequence complementary to the target sequence on the target gene or nucleic acid, which has, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

Here, the guide domain may be a 5 to 50-base sequence, or includes a 5 to 50-base sequence. For example, the guide domain may be or include a 16, 17, 18, 19, 20, 21, 22, 23, 24 or 25-base sequence.

In addition, the guide domain may include a guide sequence.

Here, the guide sequence may be a complementary base sequence which is able to form a complementary bond with a target sequence on a target gene or nucleic acid, which has, for example, at least 70%, 75%, 80%, 85%, 90% or 95% or more complementarity or complete complementarity.

Here, the guide sequence may be a 5 to 50-base sequence or include a 5 to 50-base sequence. For example, the guide sequence may be or include a 16, 17, 18, 19, 20, 21, 22, 23, 24 or 25-base sequence.

Selectively, the guide domain may include a guide sequence and an additional base sequence.

Here, the additional base sequence may be a 1 to 35-base sequence. For example, the additional base sequence may be a 1, 2, 3, 4, 5, 6, 7, 8, 9 or 10-base sequence.

In one exemplary embodiment, the additional base sequence may include one base, guanine (G), or two bases, GG.

Here, the additional base sequence may be located at the 5' end of the guide domain, or at the 5' end of the guide sequence.

The additional base sequence may be located at the 3' end of the guide domain, or at the 3' end of the guide sequence.

[First Complementary Domain]

The first complementary domain includes a nucleic acid sequence complementary to a second complementary domain of the second strand, and is a domain having enough complementarity so as to form a double strand with the second complementary domain.

Here, the first complementary domain may be or include a 5 to 35-base sequence. For example, the first complementary domain may be or include a 5, 6, 7, 8, 9, 10, 11, 12, 13, 14, 15, 16, 17, 18, 19, 20, 21, 22, 23, 24 or 25-base sequence.

The first complementary domain may have homology with a natural first complementary domain, or may be derived from a natural first complementary domain. In addition, the first complementary domain may have a difference in base sequence according to a species existing in nature, may be derived from the first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes*, *Campylobacter jejuni*, *Streptococcus thermophilus*, *Staphylococcus aureus* or *Neisseria meningitides*, or a first complementary domain derived therefrom.

Selectively, the first complementary domain may include an additional base sequence which does not undergo complementary bonding with the second complementary domain of the second strand.

Here, the additional base sequence may be a sequence of 1 to 15 bases. For example, the additional base sequence may be a sequence of 1 to 5, 5 to 10, or 10 to 15 bases.

Selectively, a part or all of the base sequence of the guide domain and/or first complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Therefore, the first strand may consist of 5'-[guide domain]-[first complementary domain]-3' as described above.

In addition, the first strand may optionally include an additional base sequence.

In one example, the first strand may be
5'-(N$_{target}$)-(Q)$_m$-3'; or
5'-(X)$_a$-(N$_{target}$)-(X)$_b$-(Q)$_m$-(X)$_c$-3'.

Here, the $N_{target}$ is a base sequence capable of forming a complementary bond with a target sequence on a target gene or nucleic acid, and a base sequence region which may be changed according to a target sequence on a target gene or nucleic acid.

Here, the $(Q)_m$ is a base sequence including the first complementary domain, which is able to form a complementary bond with the second complementary domain of the second strand. The $(Q)_m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a *Streptococcus pyogenes*-derived first complementary domain, the $(Q)_m$ may be 5'-GUUUUAGAGCUA-3' (SEQ ID NO: 290), or a base sequence having at least 50% or more homology with 5'-GUUUUAGAGCUA-3' (SEQ ID NO: 290).

In another example, when the first complementary domain has partial or complete homology with a first complementary domain of *Campylobacter jejuni* or a *Campylobacter jejuni*-derived first complementary domain, the $(Q)_m$ may be 5'-GUUUUAGUCCC-UUUUUAAAUUUCUU-3' (SEQ ID NO: 292), or a base sequence having at least 50% or more homology with 5'-GUUUUAGUCCCUUUUUAAAUUUCUU-3' (SEQ ID NO: 292).

In still another example, when the first complementary domain has partial or complete homology with a first complementary domain of *Streptococcus thermophilus* or a *Streptococcus thermophilus*-derived first complementary domain, the $(Q)_m$ may be 5'-GUUUUAGAGCUGUGUU-GUUUCG-3', (SEQ ID NO: 309) or a base sequence having at least 50% or more homology with 5'-GUUUUAGAGCU-GUGUUGUUUCG-3' (SEQ ID NO: 309).

In addition, each of the $(X)_a$, $(X)_b$ and $(X)_c$ is selectively an additional base sequence, where the X may be each independently selected from the group consisting of A, U, C and G, and each of the a, b and c may be the number of bases, which is 0 or an integer of 1 to 20.

Second Strand

The second strand may consist of a second complementary domain and a proximal domain, and selectively include a tail domain.

[Second Complementary Domain]

In the second strand, the second complementary domain includes a nucleic acid sequence complementary to the first complementary domain of the first strand, and has enough complementarity so as to form a double strand with the first complementary domain. The second complementary domain may include a base sequence complementary to the first complementary domain and a base sequence not complementary to the first complementary domain, for example, a base sequence not forming a double strand with the first complementary domain, and may have a longer base sequence than the first complementary domain.

Here, the second complementary domain may be a 5 to 35-base sequence, or include a 5 to 35-base sequence. For example, the second complementary domain may be or include a 5, 6, 7, 8, 9, 10, 11, 12, 13, 14, 15, 16, 17, 18, 19, 20, 21, 22, 23, 24 or 25-base sequence, but the present invention is not limited thereto.

The second complementary domain may have homology with a natural second complementary domain, or may be derived from a natural second complementary domain. In addition, the second complementary domain may have a difference in base sequence thereof according to a species existing in nature, may be derived from a second complementary domain contained in the species existing in nature, or may have partial or complete homology with the second complementary domain contained in the species existing in nature.

In one exemplary embodiment, the second complementary domain may have partial, that is, at least 50% or more, or complete homology with a second complementary domain of *Streptococcus pyogenes, Campylobacter jejuni, Streptococcus thermophilus, Staphylococcus aureus* or *Neisseria meningitides*, or a second complementary domain derived therefrom.

Selectively, the second complementary domain may further include an additional base sequence which does not undergo complementary bonding with the first complementary domain of the first strand.

Here, the additional base sequence may be a 1 to 25-base sequence. For example, the additional base sequence may be a 1 to 5, 5 to 10, 10 to 15, 15 to 20 or 20 to 25-base sequence.

[Proximal Domain]

In the second strand, the proximal domain is a sequence of 1 to 20 bases, and a domain located at the 3' end direction of the second complementary domain. For example, the proximal domain may be or include a sequence of 5, 6, 7, 8, 9, 10, 11, 12, 13, 14 or 15 bases.

Here, the proximal domain may have a double strand bond between complementary base sequences therein.

In addition, the proximal domain may have homology with a natural proximal domain, or may be derived from a natural proximal domain. In addition, the proximal domain may have a difference in base sequence according to a species existing in nature, may be derived from a proximal domain of a species existing in nature, or may have partial or complete homology with the proximal domain of a species existing in nature.

In one exemplary embodiment, the proximal domain may have partial, that is, at least 50% or more, or complete homology with a proximal domain of *Streptococcus pyogenes, Campylobacter jejuni, Streptococcus thermophilus, Staphylococcus aureus* or *Neisseria meningitides*, or a proximal domain derived therefrom.

[Tail Domain]

Selectively, in the second strand, the tail domain may be a domain selectively added to the 3' end of the second strand, and the tail domain may be or include a 1 to 50-base sequence. For example, the tail domain may be or include a 1 to 5, 5 to 10, 10 to 15, 15 to 20, 20 to 25, 25 to 30, 30 to 35, 35 to 40, 40 to 45 or 45 to 50-base sequence.

Here, the tail domain may have a double strand bond between complementary base sequences therein.

In addition, the tail domain may have homology with a natural tail domain, or may be derived from a natural tail domain. In addition, the tail domain may have a difference in base sequence according to a species existing in nature, may be derived from a tail domain contained in the species existing in nature, or may have partial or complete homology with the tail domain contained in the species existing in nature.

In one exemplary embodiment, the tail domain may have partial, that is, at least 50% or more, or complete homology with a tail domain of *Streptococcus pyogenes, Campylo-* bacter jejuni, Streptococcus thermophilus, Staphylococcus aureus or Neisseria meningitides, or a tail domain derived therefrom.

In another embodiment, the tail domain may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

Selectively, a part or all of each of the base sequence of the second complementary domain, the proximal domain and/or the tail domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the second strand may consist of 5'-[second complementary domain]-[proximal domain]-3' or 5'-[second complementary domain]-[proximal domain]-[tail domain]-3' as described above.

In addition, the second strand may selectively include an additional base sequence.

In one exemplary embodiment, the second strand may be 5'-$(Z)_h$-$(P)_k$-3'; or 5'-$(X)_d$-$(Z)_h$-$(X)_e$-$(P)_k$-$(X)_f$-3'.

In another embodiment, the second strand may be 5'-$(Z)_h$-$(P)_k$-$(F)_i$-3'; or 5'-$(X)_d$-$(Z)_h$-$(X)_e$-$(P)_k$-$(X)_f$-$(F)_i$-3'.

Here, the $(Z)_h$ is a base sequence including a second complementary domain, which is able to form a complementary bond with the first complementary domain of the first strand. The $(Z)_h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of Streptococcus pyogenes or a second complementary domain derived therefrom, the $(Z)_h$ may be 5'-UAGCAAGUUAAAAU-3' (SEQ ID NO: 295), or a base sequence having at least 50% or more homology with 5'-UAGCAAGUUAAAAU-3' (SEQ ID NO: 295).

In another example, when the second complementary domain has partial or complete homology with a second complementary domain of Campylobacter jejuni or a second complementary domain derived therefrom, the $(Z)_h$ may be 5'-AAGAAAUUUAAAAAGGGACUAAAAU-3' (SEQ ID NO: 297), or a base sequence having at least 50% or more homology with 5'-AAGAAAUUUAAAAAGGGAC-UAAAAU-3' (SEQ ID NO: 297).

In still another example, when the second complementary domain has partial or complete homology with a second complementary domain of Streptococcus thermophilus or a second complementary domain derived therefrom, the $(Z)_h$ may be 5'-CGAAACAACACAGCGAGUUAAAAU-3' (SEQ ID NO: 310), or a base sequence having at least 50% or more homology with 5'-CGAAACAACACAGCGAGUUAAAAU-3' (SEQ ID NO: 310).

The $(P)_k$ is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of Streptococcus pyogenes or a proximal domain derived therefrom, the $(P)_k$ may be 5'-AAGGCUAGUCCG-3' (SEQ ID NO: 301), or a base sequence having at least 50% or more homology with 5'-AAGGCUAGUCCG-3' (SEQ ID NO: 301).

In another example, when the proximal domain has partial or complete homology with a proximal domain of Campylobacter jejuni or a proximal domain derived therefrom, the $(P)_k$ may be 5'-AAAGAGUUUGC-3' (SEQ ID NO: 303), or a base sequence having at least 50% or more homology with 5'-AAAGAGUUUGC-3' (SEQ ID NO: 303).

In still another example, when the proximal domain has partial or complete homology with a proximal domain of Streptococcus thermophilus or a proximal domain derived therefrom, the $(P)_k$ may be 5'-AAGGCUUAGUCCG-3' (SEQ ID NO: 311), or a base sequence having at least 50% or more homology with 5'-AAGGCUUAGUCCG-3' (SEQ ID NO: 311).

The $(F)_i$ may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of Streptococcus pyogenes or a tail domain derived therefrom, the $(F)_i$ may be 5'-UUAUCAACUUGAAAAAGUGGCACCGAGUCGGUGC-3' (SEQ ID NO: 305), or a base sequence having at least 50% or more homology with 5'-UUAUCAACUUGAAAAAGUGGCACCGAGUCGGUGC-3' (SEQ ID NO: 305).

In another example, when the tail domain has partial or complete homology with a tail domain of Campylobacter jejuni or a tail domain derived therefrom, the $(F)_i$ may be 5'-GGGACUCUGCGGGGUUACAAUCCCC-UAAAACCGCUUUU-3' (SEQ ID NO: 307), or a base sequence having at least 50% or more homology with 5'-GGGACUCUGCGGGGUUACAAUCCCC-UAAAACCGCUUUU-3' (SEQ ID NO: 307).

In still another example, when the tail domain has partial or complete homology with a tail domain of Streptococcus thermophilus or a tail domain derived therefrom, the $(F)_i$ may be 5'-UACUCAACUUGAAAAG-GUGGCACCGAUUCGGUGUUUU-3' (SEQ ID NO: 312), or a base sequence having at least 50% or more homology with 5'-UACUCAACUUGAAAAG-GUGGCACCGAUUCGGUGUUUU-3' (SEQ ID NO: 312).

In addition, the $(F)_i$ may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the $(X)_d$, $(X)_e$ and $(X)_f$ may be base sequences selectively added, where the X may be each independently selected from the group consisting of A, U, C and G, and each of the d, e and f may be the number of bases, which is 0 or an integer of 1 to 20.

Single-Stranded gRNA

Single-stranded gRNA may be classified into two types.

i) Single-Stranded gRNA

First, there is single-stranded gRNA in which a first strand or a second strand of the double-stranded gRNA is linked by a linker domain, and here, the single-stranded gRNA consists of 5'-[first strand]-[linker domain]-[second strand]-3'.

Specifically, the single-stranded gRNA may consist of

5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3'.

Each domain except the linker domain is the same as the description of each domain of the first and second strands of the double-stranded gRNA.

Linker Domain

In the single-stranded gRNA, the linker domain is a domain connecting a first strand and a second strand, and specifically, is a nucleic acid sequence which connects a first complementary domain with a second complementary domain to produce single-stranded gRNA. Here, the linker domain may be connected with the first complementary domain and the second complementary domain or connect the first complementary domain with the second complementary domain by covalent or non-covalent bonding.

The linker domain may be or include a 1 to 30-base sequence. For example, the linker domain may be or include a 1 to 5, 5 to 10, 10 to 15, 15 to 20, 20 to 25 or 25 to 30-base sequence.

The linker domain is suitable to be used in a single-stranded gRNA molecule, and may be connected with the first strand and the second strand of the double-stranded gRNA, or connect the first strand with the second strand by covalent or non-covalent bonding to be used in production of the single-stranded gRNA. The linker domain may be connected with crRNA and tracrRNA of the double-stranded gRNA, or connect crRNA with tracrRNA by covalent or non-covalent bonding to be used in production of the single-stranded gRNA.

The linker domain may have homology with a natural sequence, for example, a partial sequence of tracrRNA, or may be derived therefrom.

Selectively, a part or all of the base sequence of the linker domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the single-stranded gRNA may consist of 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3' as described above.

In addition, the single-stranded gRNA may selectively include an additional base sequence.

In one exemplary embodiment, the single-stranded gRNA may be

5'-$(N_{target})$-$(Q)_m$-$(L)_j$-$(Z)_h$-$(P)_k$-3'; or

5'-$(N_{target})$-$(Q)_m$-$(L)_j$-$(Z)_h$-$(P)_k$-$(F)_i$-3'.

In another embodiment, the single-stranded gRNA may be

5'-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-3'; or 5'-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-$(F)_i$-3'.

Here, the $N_{target}$ is a base sequence capable of forming a complementary bond with a target sequence on a target gene or nucleic acid, and a base sequence region capable of being changed according to a target sequence on a target gene or nucleic acid.

The $(Q)_m$ includes a base sequence including the first complementary domain, which is able to form a complementary bond with a second complementary domain. The $(Q)_m$ may be a sequence having partial or complete homology with a first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a first complementary domain derived therefrom, the $(Q)_m$ may be 5'-GUUUUA-GAGCUA-3' (SEQ ID NO: 290), or a base sequence having at least 50% or more homology with 5'-GUUUUA-GAGCUA-3' (SEQ ID NO: 290).

In another example, when the first complementary domain has partial or complete homology with a first complementary domain of *Campylobacter jejuni* or a first complementary domain derived therefrom, the $(Q)_m$ may be 5'-GUUUUAGUCCCUUUUUAAAUUUCUU-3' (SEQ ID NO: 292), or a base sequence having at least 50% or more homology with 5'-GUUUUAGUCCC-UUUUUAAAUUUCUU-3' (SEQ ID NO: 292).

In still another example, when the first complementary domain has partial or complete homology with a first complementary domain of *Streptococcus thermophilus* or a first complementary domain derived therefrom, the $(Q)_m$ may be 5'-GUUUUAGAGCUGUGUUGUUUCG-3' (SEQ ID NO: 309), or a base sequence having at least 50% or more homology with 5'-GUUUUAGAGCUGUGUUGUUUCG-3' (SEQ ID NO: 309).

In addition, the $(L)_j$ is a base sequence including the linker domain, and connecting the first complementary domain with the second complementary domain, thereby producing single-stranded gRNA. Here, the L may be each independently selected from the group consisting of A, U, C and G, and the j may be the number of bases, which is an integer of 1 to 30.

The $(Z)_h$ is a base sequence including the second complementary domain, which is able to have a complementary bond with the first complementary domain. The $(Z)_h$ may be a sequence having partial or complete homology with the second complementary domain of a species existing in nature, and the base sequence of the second complementary domain may be changed according to the species of origin. The Z may be each independently selected from the group consisting of A, U, C and G, and the h is the number of bases, which may be an integer of 5 to 50.

For example, when the second complementary domain has partial or complete homology with a second complementary domain of *Streptococcus pyogenes* or a second complementary domain derived therefrom, the (Z)$_h$ may be 5'-UAGCAAGUUAAAAU-3' (SEQ ID NO: 295), or a base sequence having at least 50% or more homology with 5'-UAGCAAGUUAAAAU-3' (SEQ ID NO: 295).

In another example, when the second complementary domain has partial or complete homology with a second complementary domain of *Campylobacter jejuni* or a second complementary domain derived therefrom, the (Z)$_h$ may be 5'-AAGAAAUUUAAAAAGGGACUAAAAU-3' (SEQ ID NO: 297), or a base sequence having at least 50% or more homology with 5'-AAGAAAUUUAAAAAGGGAC-UAAAAU-3' (SEQ ID NO: 297).

In still another example, when the second complementary domain has partial or complete homology with a second complementary domain of *Streptococcus thermophilus* or a second complementary domain derived therefrom, the (Z)$_h$ may be 5'-CGAAACAACACAGCGAGUUAAAAU-3' (SEQ ID NO: 310), or a base sequence having at least 50% or more homology with 5'-CGAAACAACACAGCGAGUUAAAAU-3' (SEQ ID NO: 310).

The (P)$_k$ is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the (P)$_k$ may be 5'-AAGGCUAGUCCG-3' (SEQ ID NO: 301), or a base sequence having at least 50% or more homology with 5'-AAGGCUAGUCCG-3' (SEQ ID NO: 301).

In another example, when the proximal domain has partial or complete homology with a proximal domain of *Campylobacter jejuni* or a proximal domain derived therefrom, the (P)$_k$ may be 5'-AAAGAGUUUGC-3' (SEQ ID NO: 303), or a base sequence having at least 50% or more homology with 5'-AAAGAGUUUGC-3' (SEQ ID NO: 303).

In still another example, when the proximal domain has partial or complete homology with a proximal domain of *Streptococcus thermophilus* or a proximal domain derived therefrom, the (P)$_k$ may be 5'-AAGGCUUAGUCCG-3' (SEQ ID NO: 311), or a base sequence having at least 50% or more homology with 5'-AAGGCUUAGUCCG-3' (SEQ ID NO: 311).

The (F)$_i$ may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the (F)$_i$ may be 5'-UUAU-CAACUUGAAAAAGUGGCACCGAGUCGGUGC-3' (SEQ ID NO: 305), or a base sequence having at least 50% or more homology with 5'-UUAUCAAC-UUGAAAAAGUGGCACCGAGUCGGUGC-3' (SEQ ID NO: 305).

In another example, when the tail domain has partial or complete homology with a tail domain of *Campylobacter jejuni* or a tail domain derived therefrom, the (F)$_i$ may be 5'-GGGACUCUGCGGGGUUACAAUCCC-UAAAACCGCUUUU-3' (SEQ ID NO: 307), or a base sequence having at least 50% or more homology with 5'-GGGACUCUGCGGGGUUACAAUCCC-UAAAACCGCUUUU-3' (SEQ ID NO: 307).

In still another example, when the tail domain has partial or complete homology with a tail domain of *Streptococcus thermophilus* or a tail domain derived therefrom, the (F)$_i$ may be 5'-UACUCAACUUGAAAAG-GUGGCACCGAUUCGGUGUUUU-3' (SEQ ID NO: 312), or a base sequence having at least 50% or more homology with 5'-UACUCAACUUGAAAAG-GUGGCACCGAUUCGGUGUUUU-3' (SEQ ID NO: 312).

In addition, the (F)$_i$ may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the (X)$_a$, (X)$_b$, (X)$_c$, (X)$_d$, (X)$_e$ and (X)$_f$ may be base sequences selectively added, where the X may be each independently selected from the group consisting of A, U, C and G, and each of the a, b, c, d, e and f may be the number of bases, which is 0 or an integer of 1 to 20.

ii) Single-Stranded gRNA

Second, the single-stranded gRNA may be single-stranded gRNA consisting of a guide domain, a first complementary domain and a second complementary domain, and here, the single-stranded gRNA may consist of:

5'-[second complementary domain]-[first complementary domain]-[guide domain]-3'; or 5'-[second complementary domain]-[linker domain]-[first complementary domain]-[guide domain]-3'.

Guide Domain

In the single-stranded gRNA, the guide domain includes a complementary guide sequence capable of forming a complementary bond with a target sequence on a target gene or nucleic acid. The guide sequence may be a nucleic acid sequence having complementarity to the target sequence on the target gene or nucleic acid, which has, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

Here, the guide domain may be or include a 5 to 50-base sequence. For example, the guide domain may be or include a 16, 17, 18, 19, 20, 21, 22, 23, 24 or 25-base sequence.

In addition, the guide domain may include a guide sequence.

Here, the guide sequence may be a complementary base sequence capable of forming a complementary bond with a target sequence on a target gene or nucleic acid, which has, for example, at least 70%, 75%, 80%, 85%, 90% or 95% or more complementarity or complete complementarity.

Here, the guide sequence may be or include a 5 to 50-base sequence. For example, the guide sequence may be or include a 16, 17, 18, 19, 20, 21, 22, 23, 24 or 25-base sequence.

Selectively, the guide domain may include a guide sequence and an additional base sequence.

Here, the additional base sequence may be a 1 to 35-base sequence. For example, the additional base sequence may be a 1, 2, 3, 4, 5, 6, 7, 8, 9 or 10-base sequence.

In one exemplary embodiment, the additional base sequence may be a single base sequence, guanine (G), or a sequence of two bases, GG.

Here, the additional base sequence may be located at the 5' end of the guide domain, or at the 5' end of the guide sequence.

The additional base sequence may be located at the 3' end of the guide domain, or at the 3' end of the guide sequence.

First Complementary Domain

The first complementary domain is a domain including a nucleic acid sequence complementary to the second complementary domain, and having enough complementarity so as to form a double strand with the second complementary domain.

Here, the first complementary domain may be or include a 5 to 35-base sequence. For example, the first complementary domain may be or include a 5, 6, 7, 8, 9, 10, 11, 12, 13, 14, 15, 16, 17, 18, 19, 20, 21, 22, 23, 24 or 25-base sequence.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of Parcubacteia bacterium (GWC2011_GWC2_44_17), Lachnospirameae bacterium (MC2017), Butyrivibrio proteoclasiicus, Peregrinibacteria bacterium (GW2011_GWA_33_10), Acidaminococcus sp. (BV3L6), Porphyromonas macacae, Lachnospiraceae bacterium (ND2006), Porphyromonas crevioricanis, Prevotella disiens, Moraxella bovoculi (237), Smiihella sp. (SC_KO8D17), Leptospira inadai, Lachnospiraceae bacterium (MA2020), Francisella novicida (U112), Candidatus Methanoplasma termitum or Eubacterium eligens, or a first complementary domain derived therefrom.

Selectively, the first complementary domain may include an additional base sequence which does not undergo complementary bonding with the second complementary domain.

Here, the additional base sequence may be a 1 to 15-base sequence. For example, the additional base sequence may be a 1 to 5, 5 to 10, or 10 to 15-base sequence.

Second Complementary Domain

The second complementary domain includes a nucleic acid sequence complementary to the first complementary domain, and has enough complementarity so as to form a double strand with the first complementary domain. The second complementary domain may include a base sequence complementary to the first complementary domain, and a base sequence having no complementarity with the first complementary domain, for example, a base sequence not forming a double strand with the first complementary domain, and may have a longer base sequence than the first complementary domain.

Here, the second complementary domain may be or include a 5 to 35-base sequence. For example, the second complementary domain may be a 5, 6, 7, 8, 9, 10, 11, 12, 13, 14, 15, 16, 17, 18, 19, 20, 21, 22, 23, 24 or 25-base sequence.

The second complementary domain may have homology with a natural second complementary domain, or may be derived from the natural second complementary domain. In addition, the second complementary domain may have a difference in base sequence of the second complementary domain according to a species existing in nature, and may be derived from second complementary domain contained in the species existing in nature, or may have partial or complete homology with the second complementary domain contained in the species existing in nature.

In one exemplary embodiment, the second complementary domain may have partial, that is, at least 50% or more, or complete homology with a second complementary domain of Parcubacteria bacterium (GWC2011_GWC2_44_17), Lachnospiraceae bacterium (MC2017), Butyrivibrio proteoclasiicus, Peregrinibacteria bacterium (GW2011_GWA_33_10), Acidaminococcus sp. (BV3L6), Porphyromonas macacae, Lachnospiraceae bacterium (ND2006), Porphyromonas crevioricanis, Prevotella disiens, Moraxella bovoculi (237), Smiihella sp. (SC_KO8D17), Leptospira inadai, Lachnospiraceae bacterium (MA2020), Francisella novicida (U112), Candidatus Methanoplasma termitum or Eubacterium eligens, or a second complementary domain derived therefrom.

Selectively, the second complementary domain may include an additional base sequence which does not undergo complementary bonding with the first complementary domain.

Here, the additional base sequence may be a 1 to 15-base sequence. For example, the additional base sequence may be a 1 to 5, 5 to 10, or 10 to 15-base sequence.

Linker Domain

Selectively, the linker domain is a nucleic acid sequence connecting a first complementary domain with a second complementary domain to produce single-stranded gRNA. Here, the linker domain may be connected with the first complementary domain and the second complementary domain, or may connect the first and second complementary domains by covalent or non-covalent bonding.

The linker domain may be or include a 1 to 30-base sequence. For example, the linker domain may be or include a 1 to 5, 5 to 10, 10 to 15, 15 to 20, 20 to 25 or 25 to 30-base sequence.

Selectively, a part or all of the base sequence of the guide domain, the first complementary domain, the second complementary domain and the linker domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the single-stranded gRNA may consist of 5'-[second complementary domain]-[first complementary domain]-[guide domain]-3' or 5'-[second complementary domain]-[linker domain]-[first complementary domain]-[guide domain]-3' as described above.

In addition, the single-stranded gRNA may selectively include an additional base sequence.

In one exemplary embodiment, the single-stranded gRNA may be

5'-$(Z)_h$-$(Q)_m$-$(N_{target})$-3'; or

5'-$(X)_a$-$(Z)_h$-$(X)_b$-$(Q)_m$-$(X)_c$-$(N_{target})$-3'.

In another embodiment, the single-stranded gRNA may be

5'-(Z)$_h$-(L)$_j$-(Q)$_m$-(N$_{target}$)-3'; or

5'-(X)$_a$-(Z)$_h$-(L)$_j$-(Q)$_m$-(X)$_c$-(N$_{target}$)-3'.

Here, the N$_{target}$ is a base sequence capable of forming a complementary bond with a target sequence on a target gene or nucleic acid, and a base sequence region which may be changed according to a target sequence on a target gene or nucleic acid.

The (Q)$_m$ is a base sequence including the first complementary domain, which is able to form a complementary bond with the second complementary domain of the second strand. The (Q)$_m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of Parcubacteia *bacterium* or a first complementary domain derived therefrom, the (Q)$_m$ may be 5'-UUUGUAGAU-3', or a base sequence having at least 50% or more homology with 5'-UUUGUAGAU-3'.

The (Z)$_h$ is a base sequence including a second complementary domain, which is able to form a complementary bond with the first complementary domain of the first strand. The (Z)$_h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of Parcubacteria *bacterium* or a Parcubacteria *bacterium*-derived second complementary domain, the (Z)$_h$ may be 5'-AAAUUUCUACU-3' (SEQ ID NO: 299), or a base sequence having at least 50% or more homology with 5'-AAAUUUCUACU-3' (SEQ ID NO: 299).

In addition, the (L)$_j$ is a base sequence including the linker domain, which connects the first complementary domain with the second complementary domain. Here, the L may be each independently selected from the group consisting of A, U, C and G, and the j may be the number of bases, which is an integer of 1 to 30.

In addition, each of the (X)$_a$, (X)$_b$ and (X)$_c$ is selectively an additional base sequence, where the X may be each independently selected from the group consisting of A, U, C and G, and the a, b and c may be the number of bases, which is 0 or an integer of 1 to 20.

2. Editor Protein

An editor protein refers to a peptide, polypeptide or protein which is able to directly bind to or interact with, without direct binding to, a nucleic acid. Conceptually, it is sometimes referred to as "gene scissors" or RGEN (RNA-Guided Endonuclease).

The nucleic acid may be a nucleic acid contained in a target nucleic acid, gene or chromosome.

The nucleic acid may be a guide nucleic acid.

The editor protein may be an enzyme.

The editor protein may be a fusion protein.

Here, the fusion protein refers to a protein produced by fusing an enzyme with an additional domain, peptide, polypeptide or protein.

The enzyme refers to a protein including a domain which is able to cleave a nucleic acid, gene, chromosome or protein.

The enzyme may be a nuclease, protease or restriction enzyme.

The additional domain, peptide, polypeptide or protein may be a functional domain, peptide, polypeptide or protein, which has a function the same as or different from the enzyme.

The fusion protein may include an additional domain, peptide, polypeptide or protein at one or more of an N-terminus of an enzyme or the proximity thereof; a C-terminus of the enzyme or the proximity thereof; the middle region of an enzyme; and a combination thereof.

The fusion protein may include a functional domain, peptide, polypeptide or protein at one or more of an N-terminus of an enzyme or the proximity thereof; a C-terminus of the enzyme or the proximity thereof; the middle region of an enzyme; and a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV (SEQ ID NO: 313); NLS derived from nucleoplasmin (e.g., nucleoplasmin bipartite NLS with a sequence KRPAATKKAGQAKKKK (SEQ ID NO: 314)); c-myc NLS with an amino acid sequence PAAKRVKLD (SEQ ID NO: 315) or RQRRNELKRSP (SEQ ID NO: 316); hRNPA1 M9 NLS with a sequence NQSSNFGPMKGGNFGGRSSGPYGGGGQYFAKPRNQGGY (SEQ ID NO: 317; an importin-α-derived IBB domain sequence RMRIZFKNKGKDTAELRRRRVEVSVELRKAKKD-EQILKRRNV (SEQ ID NO: 318); myoma T protein sequences VSRKRPRP (SEQ ID NO: 319) and PPKKARED (SEQ ID NO: 320); human p53 sequence PQPKKKPL (SEQ ID NO: 321) POPKKKPL; a mouse c-abl IV sequence SALIKKKKKMAP (SEQ ID NO: 322); influenza virus NS1 sequences DRLRR (SEQ ID NO: 323) and PKQKKRK (SEQ ID NO: 324); a hepatitis virus-6 antigen sequence RKLKKKIKKL (SEQ ID NO: 325); a mouse Mx1 protein sequence REKKKFLKRR (SEQ ID NO: 326); a human poly(ADP-ribose) polymerase sequence KRKGDEVDGVDEVAKKKSKK (SEQ ID NO: 327; or steroid hormone receptor (human) glucocorticoid sequence RKCLQAGMNLEARKTKK (SEQ ID NO: 328), but the present invention is not limited thereto.

The editor protein may include a complete active enzyme.

Here, the "complete active enzyme" refers to an enzyme having the same function as a function of a wild-type enzyme, and for example, the wild-type enzyme cleaving the double strand of DNA has complete enzyme activity of entirely cleaving the double strand of DNA.

In addition, the complete active enzyme includes an enzyme having an improved function compared to the function of the wild-type enzyme, and for example, a specific modification or manipulation type of the wild-type enzyme cleaving the double strand of DNA has full enzyme activity which is improved compared to the wild-type enzyme, that is, activity of cleaving the double strand of DNA.

The editor protein may include an incomplete or partially active enzyme.

Here, the "incomplete or partially active enzyme" refers to an enzyme having some of the functions of the wild-type enzyme, and for example, a specific modification or manipulation type of the wild-type enzyme cleaving the double strand of DNA has incomplete or partial enzyme activity of cleaving a part of the double strand, that is, a single strand of DNA.

The editor protein may include an inactive enzyme.

Here, the "inactive enzyme" refers to an enzyme in which the function of a wild-type enzyme is completely inactivated. For example, a specific modification or manipulation type of the wild-type enzyme cleaving the double strand of DNA has inactivity so as not to completely cleave the DNA double strand.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

In addition, the modification may be substitution, removal, addition of some bases in the base sequence encoding the editor protein, or a combination thereof.

As one exemplary embodiment of the editor protein of the present invention, a CRISPR enzyme will be described below.

CRISPR Enzyme

The term "CRISPR enzyme" is a main protein component of a CRISPR-Cas system, and forms a complex with gRNA, resulting in the CRISPR-Cas system.

The CRISPR enzyme is a nucleic acid or polypeptide (or a protein) having a sequence encoding the CRISPR enzyme, and representatively, a Type II CRISPR enzyme or Type V CRISPR enzyme is widely used.

The Type II CRISPR enzyme is Cas9, which may be derived from various microorganisms such as Actinobacteria (e.g., *Actinomyces naeslundii*), Aquifcae Cas9, Bacteroidetes Cas 9, Chlamydiae Cas9, Chloroflexi Cas9, Cyanobacteria Cas9, Elusimicrobia Cas9, Fibrobacteres Cas9, Firmicutes Cas9 (e.g., *Streptococcus pyogenes* Cas9, *Streptococcus thermophilus* Cas9, *Listeria innocua* Cas9, *Streptococcus agalactiae* Cas9, *Streptococcus mutans* Cas9 and *Enterococcus faecium* Cas9), Fusobacteria Cas9, Proteobacteria (e.g., *Neisseria meningitides, Campylobacter jejuni*) Cas9, and Spirochaetes (e.g., *Treponema denticola*) Cas9.

The term "Cas9" is an enzyme which binds to gRNA so as to cleave or modify a target sequence or position on a target gene or nucleic acid, and may consist of an HNH domain capable of cleaving a nucleic acid strand forming a complementary bond with gRNA, an RuvC domain capable of cleaving a nucleic acid strand forming a complementary bond with gRNA, an REC domain recognizing a target and a PI domain recognizing PAM. Hiroshi Nishimasu et al. (2014) Cell 156:935-949 may be referenced for specific structural characteristics of Cas9.

In addition, the Type V CRISPR enzyme may be Cpf1, which may be derived from *Streptococcus, Campylobacter, Nitratifractor, Staphylococcus, Parvibaculum, Roseburia, Neisseria, Gluconacetobacter*, Azospirillum, Sphaerochaeta, *Lactobacillus, Eubacterium*, Corynebacter, Camobacterium, Rhodobacter, Listeria, Paludibacter, *Clostridium*, Lachnospiraceae, Clostridiaridium, Leptotrichia, *Francisella, Legionella, Alicyclobacillus, Methanomethyophilus, Porphyromonas, Prevotella*, Bacteroidetes, *Helcococcus*, Letospira, *Desulfovibrio, Desulfonatronum*, Opitutaceae, *Tuberibacillus, Bacillus, Brevibacillus*, Methylobacteium or *Acidaminococcus*.

The Cpf1 may consist of a RuvC domain similar and corresponding to the RuvC domain of Cas9, an Nuc domain without the HNH domain of Cas9, an REC domain recognizing a target, a WED domain and a PI domain recognizing PAM. For specific structural characteristics of Cpf1, Takashi Yamano et al. (2016) Cell 165:949-962 may be referenced.

The CRISPR enzyme of the Cas9 or Cpf1 protein may be isolated from a microorganism existing in nature or non-naturally produced by a recombinant or synthetic method.

Type II CRISPR Enzyme

The crystal structure of the type II CRISPR enzyme was determined according to studies on two or more types of natural microbial type II CRISPR enzyme molecules (Jinek et al., Science, 343(6176):1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 and REC2 domains play an important role in recognizing a double strand formed in gRNA, for example, single-stranded gRNA, double-stranded gRNA or tracrRNA.

The NUC lobe includes an RuvC domain, an HNH domain and a PAM-interaction (PI) domain. Here, the RuvC domain encompasses RuvC-like domains, or the HNH domain is used to include HNH-like domains.

Here, the RuvC domain shares structural similarity with members of the microorganism family existing in nature having the type II CRISPR enzyme, and cleaves a single strand, for example, a non-complementary strand of a target gene or nucleic acid, that is, a strand not forming a complementary bond with gRNA. The RuvC domain is sometimes referred to as a RuvCI domain, RuvCII domain or RuvCIII domain in the art, and generally called an RuvC I, RuvCII or RuvCII. For example, in the case of SpCas9, the RuvC domain is assembled from each of three divided RuvC domains (RuvC I, RuvCII and RuvCIII) located at the sequences of amino acids 1 to 59, 718 to 769 and 909 to 1098 of SpCas9, respectively.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs. For example, in the case of SpCas9, the HNH domain is located at amino acid sequence 775 to 908 of SpCas9.

The PI domain recognizes a specific base sequence in a target gene or nucleic acid, that is, a protospacer adjacent motif (PAM) or interacts with PAM. For example, in the case of SpCas9, the PI domain is located at the sequence of amino acids 1099 to 1368 of SpCas9.

Here, the PAM may vary according to the origin of the type II CRISPR enzyme. For example, when the CRISPR enzyme is SpCas9, PAM may be 5'-NGG-3', when the CRISPR enzyme is *Streptococcus thermophilus* Cas9 (StCas9), PAM may be 5'-NNAGAAW-3'(W=A or T), when the CRISPR enzyme is *Neisseria meningitides* Cas9 (NmCas9), PAM may be 5'-NNNNGATT-3', and when the CRISPR enzyme is *Campylobacter jejuni* Cas9 (CjCas9), PAM may be 5'-NNNVRYAC-3' (V=G or C or A, R=A or G, Y=C or T), where the N may be A, T, G or C; or A, U, G or C.

Type V CRISPR Enzyme

Type V CRISPR enzyme includes similar RuvC domains corresponding to the RuvC domains of the type II CRISPR enzyme, and may consist of an Nuc domain, instead of the HNH domain of the type II CRISPR enzyme, REC and WED domains, which recognize a target, and a PI domain recognizing PAM. For specific structural characteristics of the type V CRISPR enzyme, Takashi Yamano et al. (2016) Cell 165:949-962 may be referenced.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a target gene or nucleic acid is dependent on the PAM sequence.

The PAM sequence is a sequence present in a target gene or nucleic acid, and may be recognized by the PI domain of the type V CRISPR enzyme. The PAM sequence may vary according to the origin of the type V CRISPR enzyme. That is, there are different PAM sequences which are able to be specifically recognized depending on a species.

In one example, the PAM sequence recognized by Cpf1 may be 5'-TTN-3' (N is A, T, C or G).

CRISPR Enzyme Activity

A CRISPR enzyme cleaves a double or single strand of a target gene or nucleic acid, and has nuclease activity causing breakage or deletion of the double or single strand. Generally, the wild-type type II CRISPR enzyme or type V CRISPR enzyme cleaves the double strand of the target gene or nucleic acid.

To manipulate or modify the above-described nuclease activity of the CRISPR enzyme, the CRISPR enzyme may be manipulated or modified, such a manipulated or modified CRISPR enzyme may be modified into an incompletely or partially active or inactive enzyme.

Incompletely or Partially Active Enzyme

A CRISPR enzyme modified to change enzyme activity, thereby exhibiting incomplete or partial activity is called a nickase.

The term "nickase" refers to a CRISPR enzyme manipulated or modified to cleave only one strand of the double strand of the target gene or nucleic acid, and the nickase has nuclease activity of cleaving a single strand, for example, a strand that is not complementary or complementary to gRNA of the target gene or nucleic acid. Therefore, to cleave the double strand, nuclease activity of the two nickases is needed.

For example, the nickase may have nuclease activity by the RuvC domain. That is, the nickase may include nuclease activity of the HNH domain, and to this end, the HNH domain may be manipulated or modified.

In one example, provided that the CRISPR enzyme is the type II CRISPR enzyme, when the residue 840 in the amino acid sequence of SpCas9 is mutated from histidine to alanine, the nuclease activity of the HNH domain is inactivated to be used as a nickase. Since the nickase produced thereby has nuclease activity of the RuvC domain, it is able to cleave a strand which does not form a complementary bond with a non-complementary strand of the target gene or nucleic acid, that is, gRNA.

In another exemplary embodiment, when the residue 559 in the amino acid sequence of CjCas9 is mutated from histidine to alanine, the nuclease activity of the HNH domain is inactivated to be used as a nickase. The nickase produced thereby has nuclease activity by the RuvC domain, and thus is able to cleave a non-complementary strand of the target gene or nucleic acid, that is, a strand that does not form a complementary bond with gRNA.

For example, the nickase may have nuclease activity by the HNH domain. That is, the nickase may include the nuclease activity of the RuvC domain, and to this end, the RuvC domain may be manipulated or modified.

In one example, provided that the CRISPR enzyme is the type II CRISPR enzyme, in one exemplary embodiment, when the residue 10 in the amino acid sequence of SpCas9 is mutated from aspartic acid to alanine, the nuclease activity of the RuvC domain is inactivated to be used as a nickase. The nickase produced thereby has the nuclease activity of the HNH domain, and thus is able to cleave a complementary strand of the target gene or nucleic acid, that is, a strand that forms a complementary bond with gRNA.

In another exemplary embodiment, when the residue 8 in the amino acid sequence of CjCas9 is mutated from aspartic acid to alanine, the nuclease activity of the RuvC domain is inactivated to be used as a nickase. The nickase produced thereby has the nuclease activity of the HNH domain, and thus is able to cleave a complementary strand of the target gene or nucleic acid, that is, a strand that forms a complementary bond with gRNA.

Inactive Enzyme

A CRISPR enzyme which is modified to make enzyme activity completely inactive is called an inactive CRISPR enzyme.

The term "inactive CRISPR enzyme" refers to a CRISPR enzyme which is modified not to completely cleave the double strand of the target gene or nucleic acid, and the inactive CRISPR enzyme has nuclease inactivity due to the mutation in the domain with nuclease activity of the wild-type CRISPR enzyme. The inactive CRISPR enzyme may be one in which the nuclease activities of the RuvC domain and the HNH domain are inactivated.

For example, the inactive CRISPR enzyme may be manipulated or modified in the RuvC domain and the HNH domain so as to inactive nuclease activity.

In one example, provided that the CRISPR enzyme is the type II CRISPR enzyme, in one exemplary embodiment, when the residues 10 and 840 in the amino acid sequence of SpCas9 are mutated from aspartic acid and histidine to alanine, respectively, nuclease activities by the RuvC domain and the HNH domain are inactivated, such that the double strand may not cleave completely the double strand of the target gene or nucleic acid.

In another exemplary embodiment, when the residues 8 and 559 in the amino acid sequence of CjCas9 are mutated from aspartic acid and histidine to alanine, the nuclease activities by the RuvC domain and the HNH domain are inactivated, such that the double strand may not cleave completely the double strand of the target gene or nucleic acid.

Other Activities

The CRISPR enzyme may have endonuclease activity, exonuclease activity or helicase activity, that is, an ability to anneal the helix structure of the double-stranded nucleic acid, in addition to the above-described nuclease activity.

In addition, the CRISPR enzyme may be modified to completely, incompletely, or partially activate the endonuclease activity, exonuclease activity or helicase activity.

Targeting of CRISPR Enzyme

The CRISPR enzyme may interact with gRNA, thereby forming a gRNA-CRISPR enzyme complex, that is, a CRISPR complex, and lead a guide sequence to approach a target sequence including a PAM sequence in cooperation with gRNA. Here, the ability of the CRISPR enzyme to interact with the target gene or nucleic acid is dependent on the PAM sequence.

The PAM sequence is a sequence present in the target gene or nucleic acid, which may be recognized by the PI domain of the CRISPR enzyme. The PAM sequence may vary depending on the origin of the CRISPR enzyme. That is, there are various PAM sequences which are able to be specifically recognized according to species.

In one example, provided that the CRISPR enzyme is the type II CRISPR enzyme, in the case of SpCas9, the PAM sequence may be 5'-NGG-3', 5'-NAG-3' and/or 5'-NGA-3', in the case of StCas9, the PAM sequence may be 5'-NGGNG-3' and/or 5'-NNAGAAW-3' (W=A or T), in the case of NmCas9, the PAM sequence may be 5'-NNNNGATT-3' and/or 5'-NNNGCTT-3', in the case of CjCas9, the PAM sequence may be 5'-NNNVRYAC-3' (V=G, C or A; R=A or G; Y=C or T), in the case of *Streptococcus mutans* Cas9 (SmCas9), the PAM sequence may be 5'-NGG-3' and/or 5'-NAAR-3' (R=A or G), and in the case of *Staphylococcus aureus* Cas9 (SaCas9), the PAM sequence may be 5'-NNGRR-3', 5'-NNGRRT-3' and/or 5'-NNGRRV-3' (R=A or G; V=G, C or A).

In another example, provided that the CRISPR enzyme is the type V CRISPR enzyme, in the case of Cpf1, the PAM sequence may be 5'-TTN-3'. Here, the N may be A, T, G or C; or A, U, G or C.

The CRISPR enzyme capable of recognizing a specific PAM sequence may be manipulated or modified using the PAM sequence capable of being specifically recognized according to species. For example, the PI domain of SpCas9 may be replaced with the PI domain of CjCas9 so as to have the nuclease activity of SpCas9 and recognize a CjCas9-specific PAM sequence, thereby producing SpCas9 recognizing the CjCas9-specific PAM sequence. A specifically recognized PAM sequence may be changed by substitution or replacement of the PI domain.

CRISPR Enzyme Mutant

The CRISPR enzyme may be modified to improve or inhibit various characteristics such as nuclease activity, helicase activity, an ability to interact with gRNA, and an ability to approach the target gene or nucleic acid, for example, PAM recognizing ability of the CRISPR enzyme.

In addition, the CRISPR enzyme mutant may be a CRISPR enzyme which interacts with gRNA to form a gRNA-CRISPR enzyme complex, that is, a CRISPR complex, and is modified or manipulated to improve target specificity, when approaching or localized to the target gene or nucleic acid, such that only a double or single strand of the target gene or nucleic acid is cleaved without cleavage of a double or single strand of a non-target gene or nucleic acid which partially forms a complementary bond with gRNA and a non-target gene or nucleic acid which does not form a complementary bond therewith.

Here, an effect of cleaving the double or single strand of the non-target gene or nucleic acid partially forming a complementary bond with gRNA and the non-target gene or nucleic acid not forming a complementary bond therewith is referred to as an off-target effect, a position or base sequence of the non-target gene or nucleic acid partially forming a complementary bond with gRNA and the non-target gene or nucleic acid not forming a complementary bond therewith is referred to as an off-target. Here, there may be one or more off-targets. One the other hand, the cleavage effect of the double or single strand of the target gene or nucleic acid is referred to as an on-target effect, and a location or target sequence of the target gene or nucleic acid is referred to as an on-target.

The CRISPR enzyme mutant is modified in at least one of the amino acids of a naturally-occurring CRISPR enzyme, and may be modified, for example, improved or inhibited in one or more of the various characteristics such as nuclease activity, helicase activity, an ability to interact with gRNA, an ability to approach the target gene or nucleic acid and target specificity, compared to the unmodified CRISPR enzyme. Here, the modification may be substitution, removal, addition of an amino acid, or a mixture thereof.

In the CRISPR enzyme mutant,
the modification may be a modification of one or two or more amino acids located in a region consisting of amino acids having positive charges, present in the naturally-occurring CRISPR enzyme.

For example, the modification may be a modification of one or two or more amino acids of the positively-charged amino acids such as lysine (K), arginine (R) and histidine (H), present in the naturally-occurring CRISPR enzyme.

The modification may be a modification of one or two or more amino acids located in a region composed of non-positively-charged amino acids present in the naturally-occurring CRISPR enzyme.

For example, the modification may be a modification of one or two or more amino acids of the non-positively-charged amino acids, that is, aspartic acid (D), glutamic acid (E), serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In another example, the modification may be a modification of one or two or more amino acids of non-charged amino acids, that is, serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In addition, the modification may be a modification of one or two or more of the amino acids having hydrophobic residues present in the naturally-occurring CRISPR enzyme.

For example, the modification may be a modification of one or two or more amino acids of glycine (G), alanine (A), valine (V), isoleucine (I), leucine (L), methionine (M), phenylalanine (F), tyrosine (Y) and tryptophan (W), present in the naturally-occurring CRISPR enzyme.

The modification may be a modification of one or two or more of the amino acids having polar residues, present in the naturally-occurring CRISPR enzyme.

For example, the modification may be a modification of one or two or more amino acids of serine (S), threonine (T), asparagine (N), glutamine (Q), cysteine (C), proline (P), lysine (K), arginine (R), histidine (H), aspartic acid (D) and glutamic acid (E), present in the naturally-occurring CRISPR enzyme.

In addition, the modification may be a modification of one or two or more of the amino acids including lysine (K), arginine (R) and histidine (H), present in the naturally-occurring CRISPR enzyme.

For example, the modification may be a substitution of one or two or more of the amino acids including lysine (K), arginine (R) and histidine (H), present in the naturally-occurring CRISPR enzyme.

The modification may be a modification of one or two or more of the amino acids including aspartic acid (D) and glutamic acid (E), present in the naturally-occurring CRISPR enzyme.

For example, the modification may be a substitution of one or two or more of the amino acids including aspartic acid (D) and glutamic acid (E), present in the naturally-occurring CRISPR enzyme.

The modification may be a modification of one or two or more of the amino acids including serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

For example, the modification may be a substitution of one or two or more of the amino acid including serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In addition, the modification may be a modification of one, two, three, four, five, six, seven or more of the amino acids present in the naturally-occurring CRISPR enzyme.

In addition, in the CRISPR enzyme mutant,
the modification may be a modification of one or two or more of the amino acids present in the RuvC domain of the CRISPR enzyme. Here, the RuvC domain may be an RuvCI, RuvCII or RuvCIII domain.

The modification may be a modification of one or two or more of the amino acids present in the HNH domain of the CRISPR enzyme.

The modification may be a modification of one or two or more of the amino acids present in the REC domain of the CRISPR enzyme.

The modification may be one or two or more of the amino acids present in the PI domain of the CRISPR enzyme.

The modification may be a modification of two or more of the amino acids contained in at least two or more domains of the REC, RuvC, HNH and PI domains of the CRISPR enzyme.

In one example, the modification may be a modification of two or more of the amino acids contained in the REC and RuvC domains of the CRISPR enzyme.

In one exemplary embodiment, in the SpCas9 mutant, the modification may be a modification of at least two or more of the A203, H277, G366, F539, I601, M763, D965 and F1038 amino acids contained in the REC and RuvC domains of SpCas9.

In another example, the modification may be a modification of two or more of the amino acids contained in the REC and HNH domains of the CRISPR enzyme.

In one exemplary embodiment, in the SpCas9 mutant, the modification may be a modification of at least two or more of the A203, H277, G366, F539, I601 and K890 amino acids contained in the REC and HNH domains of SpCas9.

In one example, the modification may be a modification of two or more of the amino acids contained in the REC and PI domains of the CRISPR enzyme.

In one exemplary embodiment, in the SpCas9 mutant, the modification may be a modification of at least two or more of the A203, H277, G366, F539, I601, T1102 and D1127 amino acids contained in the REC and PI domains of SpCas9.

In another example, the modification may be a modification of three or more of the amino acids contained in the REC, RuvC and HNH domains of the CRISPR enzyme.

In one exemplary embodiment, in the SpCas9 mutant, the modification may be a modification of at least three or more of the A203, H277, G366, F539, I601, M763, K890, D965 and F1038 amino acids contained in the REC, RuvC and HNH domains of SpCas9.

In one example, the modification may be a modification of three or more of the amino acids contained in the REC, RuvC and PI domains contained in the CRISPR enzyme.

In one exemplary embodiment, in the SpCas9 mutant, the modification may be a modification of at least three or more of the A203, H277, G366, F539, I601, M763, D965, F1038, T1102 and D1127 amino acids contained in the REC, RuvC and PI domains of SpCas9.

In another example, the modification may be a modification of three or more of the amino acids contained in the REC, HNH and PI domains of the CRISPR enzyme.

In one exemplary embodiment, in the SpCas9 mutant, the modification may be a modification of at least three or more of the A203, H277, G366, F539, I601, K890, T1102 and D1127 amino acids contained in the REC, HNH and PI domains of SpCas9.

In one example, the modification may be a modification of three or more of the amino acids contained in the RuvC, HNH and PI domains of the CRISPR enzyme.

In one exemplary embodiment, in the SpCas9 mutant, the modification may be a modification of at least three or more of the M763, K890, D965, F1038, T1102 and D1127 amino acids contained in the RuvC, HNH and PI domains of SpCas9.

In another example, the modification may be a modification of four or more of the amino acids contained in the REC, RuvC, HNH and PI domains of the CRISPR enzyme.

In one exemplary embodiment, in the SpCas9 mutant, the modification may be a modification of at least four or more of the A203, H277, G366, F539, I601, M763, K890, D965, F1038, T1102 and D1127 amino acids contained in the REC, RuvC, HNH and PI domains of SpCas9.

In addition, in the CRISPR enzyme mutant,
the modification may be a modification of one or two or more of the amino acids participating in the nuclease activity of the CRISPR enzyme.

For example, in the SpCas9 mutant, the modification may be a modification of one or two or more of the group consisting of the amino acids D10, E762, H840, N854, N863 and D986, or one or two or more of the group consisting of the amino acids corresponding to other Cas9 orthologs.

The modification may be a modification for partially inactivating the nuclease activity of the CRISPR enzyme, and such a CRISPR enzyme mutant may be a nickase.

Here, the modification may be a modification for inactivating the nuclease activity of the RuvC domain of the CRISPR enzyme, and such a CRISPR enzyme mutant may not cleave a non-complementary strand of a target gene or nucleic acid, that is, a strand which does not form a complementary bond with gRNA.

In one exemplary embodiment, in the case of SpCas9, when residue 10 of the amino acid sequence of SpCas9 is mutated from aspartic acid to alanine, that is, when mutated to D10A, the nuclease activity of the RuvC domain is inactivated, and thus the SpCas9 may be used as a nickase. The nickase produced thereby may not cleave a non-complementary strand of the target gene or nucleic acid, that is, a strand that does not form a complementary bond with gRNA.

In another exemplary embodiment, in the case of CjCas9, when residue 8 of the amino acid sequence of CjCas9 is mutated from aspartic acid to alanine, that is, when mutated to D8A, the nuclease activity of the RuvC domain is inactivated, and thus the CjCas9 may be used as a nickase. The nickase produced thereby may not cleave a non-complementary strand of the target gene or nucleic acid, that is, a strand that does not form a complementary bond with gRNA.

In addition, here, the modification may be a modification for inactivating the nuclease activity of the HNH domain of the CRISPR enzyme, and such a CRISPR enzyme mutant may not cleave a complementary strand of the target gene or nucleic acid, that is, a strand forming a complementary bond with gRNA.

In one exemplary embodiment, in the case of SpCas9, when residue 840 of the amino acid sequence of SpCas9 is mutated from histidine to alanine, that is, when mutated to H840A, the nuclease activity of the HNH domain is inactivated, and thus the SpCas9 may be used as a nickase. The nickase produced thereby may not cleave a complementary strand of the target gene or nucleic acid, that is, a strand that forms a complementary bond with gRNA.

In another exemplary embodiment, in the case of CjCas9, when residue 559 of the amino acid sequence of CjCas9 is mutated from histidine to alanine, that is, when mutated to H559A, the nuclease activity of the HNH domain is inactivated, and thus the CjCas9 may be used as a nickase. The nickase produced thereby may not cleave a complementary strand of the target gene or nucleic acid, that is, a strand that forms a complementary bond with gRNA.

In addition, the modification may be a modification for completely inactivating the nuclease activity of the CRISPR enzyme, and such a CRISPR enzyme mutant may be an inactive CRISPR enzyme.

Here, the modification may be a modification for inactivating the nuclease activities of the RuvC and HNH domains of the CRISPR enzyme, and such a CRISPR enzyme mutant may does not cleave a double strand of the target gene or nucleic acid.

In one exemplary embodiment, in the case of SpCas9, when the residues 10 and 840 in the amino acid sequence of SpCas9 are mutated from aspartic acid and histidine to alanine, that is, mutated to D10A and H840A, respectively, the nuclease activities of the RuvC domain and the HNH domain are inactivated, the double strand of the target gene or nucleic acid may not be completely cleaved.

In another exemplary embodiment, in the case of CjCas9, when residues 8 and 559 of the amino acid sequence of CjCas9 are mutated from aspartic acid and histidine to alanine, that is, mutated to D8A and H559A, respectively, the nuclease activities by the RuvC and HNH domains are inactivated, and thus the double strand of the target gene or nucleic acid may not be completely cleaved.

In addition, the CRISPR enzyme mutant may further include an optionally functional domain, in addition to the innate characteristics of the CRISPR enzyme, and such a CRISPR enzyme mutant may have an additional characteristic in addition to the innate characteristics.

Here, the functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The functional domain, peptide, polypeptide or protein may be a deaminase.

For example, an incomplete or partial CRISPR enzyme may additionally include a cytidine deaminase as a functional domain. In one exemplary embodiment, a cytidine deaminase, for example, apolipoprotein B editing complex 1 (APOBEC1) may be added to SpCas9 nickase, thereby producing a fusion protein. The [SpCas9 nickase]-[APOBEC1] formed thereby may be used in base repair or editing of C into T or U, or G into A.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain may be a nuclear localization sequence or signal (NLS) or a nuclear export sequence or signal (NES).

In one example, the CRISPR enzyme may include one or more NLSs. Here, one or more NLSs may be included at an N-terminus of a CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV (SEQ ID NO: 313); NLS from nucleoplasmin (e.g., nucleoplasmin bipartite NLS having the sequence KRPAATKKAGQAKKKK (SEQ ID NO: 314)); c-myc NLS having the amino acid sequence PAAKRVKLD (SEQ ID NO: 315) or RQRRNELKRSP (SEQ ID NO: 316); hRNPA1 M9 NLS having the sequence NQSSNFGPMKGGNFGGRSSGPYGGGGQYFAKPRNQGGY (SEQ ID NO: 317); the sequence RMRIZFKNKGKDTAELRRRRVEVSVELRKAKKDEQILKRRNV (SEQ ID NO: 318) of the IBB domain from importin-α; the sequences VSRKRPRP (SEQ ID NO: 319) and PPKKARED (SEQ ID NO: 320) of a myoma T protein; the sequence PQPKKKPL (SEQ ID NO: 321) POPKKKPL of human p53; the sequence SALIK- KKKKMAP (SEQ ID NO: 322) of mouse c-abl IV; the sequences DRLRR (SEQ ID NO: 323) and PKQKKRK (SEQ ID NO: 324) of influenza virus NS1; the sequence RKLKKKIKKL (SEQ ID NO: 325) of a hepatitis delta virus antigen; the sequence REKKKFLKRR (SEQ ID NO: of a mouse Mx1 protein; the sequence KRKGDEVDGVDE-VAKKKSKK (SEQ ID NO: 327) of a human poly (ADP-ribose) polymerase; or the NLS sequence RKCLQAGMN-LEARKTKK (SEQ ID NO: 328), derived from a sequence of a steroid hormone receptor (human) glucocorticoid.

In addition, the CRISPR enzyme mutant may include a split-type CRISPR enzyme prepared by dividing the CRISPR enzyme into two or more parts. The term "split" refers to functional or structural division of a protein or random division of a protein into two or more parts.

Here, the split-type CRISPR enzyme may be a completely, incompletely or partially active enzyme or inactive enzyme.

For example, the SpCas9 may be divided into two parts between the residue 656, tyrosine, and the residue 657, threonine, thereby generating split SpCas9.

In addition, the split-type CRISPR enzyme may selectively include an additional domain, peptide, polypeptide or protein for reconstitution.

Here, the "reconstitution" refers to formation of the split-type CRISPR enzyme to be structurally the same or similar to the wild-type CRISPR enzyme.

The additional domain, peptide, polypeptide or protein for reconstitution may be FRB and FKBP dimerization domains; intein; ERT and VPR domains; or domains which form a heterodimer under specific conditions.

For example, the SpCas9 may be divided into two parts between the residue 713, serine, and the residue 714, glycine, thereby generating split SpCas9. The FRB domain may be connected to one of the two parts, and the FKBP domain may be connected to the other one. In the split SpCas9 produced thereby, the FRB domain and the FKBP domain may be formed in a dimer in an environment in which rapamycine is present, thereby producing a reconstituted CRISPR enzyme.

The CRISPR enzyme or CRISPR enzyme mutant described in the present invention may be a polypeptide, protein or nucleic acid having a sequence encoding the same, and may be codon-optimized for a subject to introduce the CRISPR enzyme or CRISPR enzyme mutant.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized by optimal gene expression in a given organism based on codon optimization.

3. Target Sequence

The term "target sequence" is a base sequence present in a target gene or nucleic acid, and has complementarity to a guide sequence contained in a guide domain of a guide nucleic acid. The target sequence is a base sequence which may vary according to a target gene or nucleic acid, that is, a subject for gene manipulation or correction, which may be designed in various forms according to the target gene or nucleic acid.

The target sequence may form a complementary bond with the guide sequence contained in the guide domain of the guide nucleic acid, and a length of the target sequence may be the same as that of the guide sequence.

The target sequence may be a 5 to 50-base sequence.

In an embodiment, the target sequence may be a 16, 17, 18, 19, 20, 21, 22, 23, 24 or 25-base sequence.

The target sequence may be a nucleic acid sequence complementary to the guide sequence contained in the guide domain of the guide nucleic acid, which has, for example, at least 70%, 75%, 80%, 85%, 90% or 95% or more complementarity or complete complementarity.

In one example, the target sequence may be or include a 1 to 8-base sequence, which is not complementary to the guide sequence contained in the guide domain of the guide nucleic acid.

In addition, the target sequence may be a base sequence adjacent to a nucleic acid sequence that is able to be recognized by an editor protein.

In one example, the target sequence may be a continuous 5 to 50-base sequence adjacent to the 5' end and/or 3' end of the nucleic acid sequence that is able to be recognized by the editor protein.

In one exemplary embodiment, target sequences for a gRNA-CRISPR enzyme complex will be described below.

When the target gene or nucleic acid is targeted by the gRNA-CRISPR enzyme complex, the target sequence has complementarity to the guide sequence contained in the guide domain of gRNA. The target sequence is a base sequence which varies according to the target gene or nucleic acid, that is, a subject for gene manipulation or correction, which may be designed in various forms according to the target gene or nucleic acid.

In addition, the target sequence may be a base sequence adjacent to a PAM sequence which is able to be recognized by the CRISPR enzyme, that is, Cas9 or Cpf1.

In one example, the target sequence may be a continuous 5 to 50-base sequence adjacent to the 5' end and/or 3' end of the PAM sequence which is recognized by the CRISPR enzyme.

In one exemplary embodiment, when the CRISPR enzyme is SpCas9, the target sequence may be a continuous 16 to 25-base sequence adjacent to the 5' end and/or 3' end of a 5'-NGG-3', 5'-NAG-3' and/or 5'-NGA-3' (N=A, T, G or C; or A, U, G or C) sequence.

In another exemplary embodiment, when the CRISPR enzyme is StCas9, the target sequence may be a continuous 16 to 25-base sequence adjacent to the 5' end and/or 3' end of a 5'-NGGNG-3' and/or 5'-NNAGAAW-3' (W=A or T, and N=A, T, G or C; or A, U, G or C) sequence.

In still another exemplary embodiment, when the CRISPR enzyme is NmCas9, the target sequence may be a continuous 16 to 25-base sequence adjacent to the 5' end and/or 3' end of a 5'-NNNNGATT-3' and/or 5'-NNNGCTT-3' (N=A, T, G or C; or A, U, G or C) sequence.

In one exemplary embodiment, when the CRISPR enzyme is CjCas9, the target sequence may be a continuous 16 to 25-base sequence adjacent to the 5' end and/or 3' end of a 5'-NNNVRYAC-3' (V=G, C or A; R=A or G, Y=C or T, N=A, T, G or C; or A, U, G or C) sequence.

In another exemplary embodiment, when the CRISPR enzyme is SmCas9, the target sequence may be a continuous 16 to 25-base sequence adjacent to the 5' end and/or 3' end of a 5'-NGG-3' and/or 5'-NAAR-3'(R=A or G, N=A, T, G or C; or A, U, G or C) sequence.

In yet another exemplary embodiment, when the CRISPR enzyme is SaCas9, the target sequence may be a continuous 16 to 25-base sequence adjacent to the 5' end and/or 3' end of a 5'-NNGRR-3', 5'-NNGRRT-3' and/or 5'-NNGRRV-3' (R=A or G, V=G, C or A, N=A, T, G or C; or A, U, G or C) sequence.

In one exemplary embodiment, when the CRISPR enzyme is Cpf1, the target sequence may be a continuous 16 to 25-base sequence adjacent to the 5' end and/or 3' end of a 5'-TTN-3' (N=A, T, G or C; or A, U, G or C) sequence.

4. Guide Nucleic Acid-Editor Protein Complex and Use Thereof

A guide nucleic acid-editor protein complex may modify a target.

The target may be a target nucleic acid, gene, chromosome or protein.

For example, the guide nucleic acid-editor protein complex may be used to ultimately regulate (e.g., inhibit, suppress, reduce, increase or promote) the expression of a protein of interest, remove a protein, regulate (e.g., inhibit, suppress, reduce, increase or promote) protein activity, or express a new protein.

Here, the guide nucleic acid-editor protein complex may act at a DNA, RNA, gene or chromosomal level.

For example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of the target DNA.

In another example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of target RNA.

In one example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of a target gene.

In another example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of a target chromosome.

The guide nucleic acid-editor protein complex may act at gene transcription and translation stages.

In one example, the guide nucleic acid-editor protein complex may promote or suppress the transcription of a target gene, thereby regulating (e.g., inhibiting, suppressing, reducing, increasing or promoting) the expression of a protein encoded by the target gene.

In another example, the guide nucleic acid-editor protein complex may promote or suppress the translation of a target gene, thereby regulating (e.g., inhibiting, suppressing, reducing, increasing or promoting) the expression of a protein encoded by the target gene.

The guide nucleic acid-editor protein complex may act at a protein level.

In one example, the guide nucleic acid-editor protein complex may manipulate or modify a target protein, thereby removing the target protein or regulating (e.g., inhibiting, suppressing, reducing, increasing or promoting) protein activity.

As a specific example of the use of the guide nucleic acid-editor protein complex of the present invention, the manipulation or modification of the target DNA, RNA, gene or chromosome using the gRNA-CRISPR enzyme complex is described below.

Gene Manipulation

A target gene or nucleic acid may be manipulated or corrected using the above-described gRNA-CRISPR enzyme complex, that is, the CRISPR complex. Here, the manipulation or correction of the target gene or nucleic acid includes all of the stages of i) cleaving or damaging the target gene or nucleic acid and ii) repairing the damaged target gene or nucleic acid.

i) Cleavage or Damage of Target Gene or Nucleic Acid i) The cleavage or damage of the target gene or nucleic acid may be cleavage or damage of the target gene or nucleic acid using the CRISPR complex, and particularly, cleavage or damage of a target sequence in the target gene or nucleic acid.

In one example, the cleavage or damage of the target gene or nucleic acid using the CRISPR complex may be complete cleavage or damage to the double strand of a target sequence.

In one exemplary embodiment, when wild-type SpCas9 is used, the double strand of a target sequence forming a complementary bond with gRNA may be completely cleaved.

In another exemplary embodiment, when SpCas9 nickase (D10A) and SpCas9 nickase (H840A) are used, a complementary single strand of a target sequence forming a complementary bond with gRNA may be cleaved by the SpCas9 nickase (D10A), and a non-complementary single strand of the target sequence forming a complementary bond with gRNA may be cleaved by the SpCas9 nickase (H840A), and the cleavages may take place sequentially or simultaneously.

In still another exemplary embodiment, when SpCas9 nickase (D10A) and SpCas9 nickase (H840A), and two gRNAs having different target sequences are used, a complementary single strand of a target sequence forming a complementary bond with the first gRNA may be cleaved by the SpCas9 nickase (D10A), a non-complementary single strand of a target sequence forming a complementary bond with the second gRNA may be cleaved by the SpCas9 nickase (H840A), and the cleavages may take place sequentially or simultaneously.

In another example, the cleavage or damage of a target gene or nucleic acid using the CRISPR complex may be cleavage or damage to only the single strand of a target sequence. Here, the single strand may be a complementary single strand of a target sequence forming a complementary bond with gRNA, or a non-complementary single strand of the target sequence forming a complementary bond with gRNA.

In one exemplary embodiment, when SpCas9 nickase (D10A) is used, a complementary single strand of a target sequence forming a complementary bond with gRNA may be cleaved by the SpCas9 nickase (D10A), but a non-complementary single strand of the target sequence forming a complementary bond with gRNA may not be cleaved.

In another exemplary embodiment, when SpCas9 nickase (H840A) is used, a non-complementary single strand of a target sequence forming a complementary bond with gRNA may be cleaved by the SpCas9 nickase (H840A), but a complementary single strand of the target sequence forming a complementary bond with gRNA may not be cleaved.

In yet another example, the cleavage or damage of a target gene or nucleic acid using the CRISPR complex may be partial removal of a nucleic acid fragment.

In one exemplary embodiment, when two gRNAs having different target sequences and wild-type SpCas9 are used, a double strand of a target sequence forming a complementary bond with the first gRNA may be cleaved, and a double strand of a target sequence forming a complementary bond with the second gRNA may be cleaved, resulting in the removal of nucleic acid fragments by the first and second gRNAs and SpCas9.

In another exemplary embodiment, when two gRNAs having different target sequences, wild-type SpCas9, SpCas9 nickase (D10A) and SpCas9 nickase (H840A) are used, a double strand of a target sequence forming a complementary bond with the first gRNA may be cleaved by the wild-type SpCas9, a complementary single strand of a target sequence forming a complementary bond with the second gRNA may be cleaved by the SpCas9 nickase (D10A), and a non-complementary single strand nay be cleaved by the SpCas9 nickase (H840A), resulting in the removal of nucleic acid fragments by the first and second gRNAs, the wild-type SpCas9, the SpCas9 nickase (D10A) and the SpCas9 nickase (H840A).

In still another exemplary embodiment, when two gRNAs having different target sequences, SpCas9 nickase (D10A) and SpCas9 nickase (H840A) are used, a complementary single strand of a target sequence forming a complementary bond with the first gRNA may be cleaved by the SpCas9 nickase (D10A), a non-complementary single strand may be cleaved by the SpCas9 nickase (H840A), a complementary double strand of a target sequence forming a complementary bond with the second gRNA may be cleaved by the SpCas9 nickase (D10A), and a non-complementary single strand may be cleaved by the SpCas9 nickase (H840A), resulting in the removal of nucleic acid fragments by the first and second gRNAs, the SpCas9 nickase (D10A) and the SpCas9 nickase (H840A).

In yet another exemplary embodiment, when three gRNAs having different target sequences, wild-type SpCas9, SpCas9 nickase (D10A) and SpCas9 nickase (H840A) are used, a double strand of a target sequence forming a complementary bond with the first gRNA may be cleaved by the wild-type SpCas9, a complementary single strand of a target sequence forming a complementary bond with the second gRNA may be cleaved by the SpCas9 nickase (D10A), and a non-complementary single strand of a target sequence forming a complementary bond with the third gRNA may be cleaved by the SpCas9 nickase (H840A), resulting in the removal of nucleic acid fragments by the first gRNA, the second gRNA, the third gRNA, the wild-type SpCas9, the SpCas9 nickase (D10A) and the SpCas9 nickase (H840A).

In yet another exemplary embodiment, when four gRNAs having different target sequences, SpCas9 nickase (D10A) and SpCas9 nickase (H840A) are used, a complementary single strand of a target sequence forming a complementary bond with the first gRNA may be cleaved by the SpCas9 nickase (D10A), a non-complementary single strand of a target sequence forming a complementary bond with the second gRNA may be cleaved by the SpCas9 nickase (H840A), a complementary single strand of a target sequence forming a complementary bond with the third gRNA may be cleaved by the SpCas9 nickase (D10A), and a non-complementary single strand of a target sequence forming a complementary bond with fourth gRNA may be cleaved by the SpCas9 nickase (H840A), resulting in the removal of nucleic acid fragments by the first gRNA, the second gRNA, the third gRNA, the fourth gRNA, the SpCas9 nickase (D10A) and the SpCas9 nickase (H840A).

ii) Repair or Restoration of Damaged Target Gene or Nucleic Acid

The target gene or nucleic acid cleaved or damaged by the CRISPR complex may be repaired or restored through NHEJ and homology-directed repairing (HDR).

Non-Homologous End Joining (NHEJ)

NHEJ is a method of restoration or repairing double strand breaks in DNA by joining both ends of a cleaved double or single strand together, and generally, when two compatible ends formed by breaking of the double strand (for example, cleavage) are frequently in contact with each other to completely join the two ends, the broken double strand is recovered. The NHEJ is a restoration method that is able to be used in the entire cell cycle, and usually occurs when there is no homologous genome to be used as a template in cells, like the G1 phase.

In the repair process of the damaged gene or nucleic acid using NHEJ, some insertions and/or deletions (indels) in the nucleic acid sequence occur in the NHEJ-repaired region, such insertions and/or deletions cause the leading frame to be shifted, resulting in frame-shifted transcriptome mRNA. As a result, innate functions are lost because of nonsense-mediated decay or the failure to synthesize normal proteins. In addition, while the leading frame is maintained, mutations in which insertion or deletion of a considerable amount of sequence may be caused to destroy the functionality of the proteins. The mutation is locus-dependent because the mutation in a significant functional domain is probably less tolerated than mutations in a non-significant region of a protein.

While it is impossible to expect indel mutations produced by NHEJ in a natural state, a specific indel sequence is preferred in a given broken region, and can come from a small region of micro homology. Conventionally, the deletion length ranges from 1 bp to 50 bp, insertions tend to be shorter, and frequently include a short repeat sequence directly surrounding a broken region.

In addition, the NHEJ is a process causing a mutation, and when it is not necessary to produce a specific final sequence, may be used to delete a motif of the small sequence.

A specific knockout of a gene targeted by the CRISPR complex may be performed using such NHEJ. A double strand or two single strands of a target gene or nucleic acid may be cleaved using the CRISPR enzyme such as Cas9 or Cpf1, and the broken double strand or two single strands of the target gene or nucleic acid may have indels through the NHEJ, thereby inducing specific knockout of the target gene or nucleic acid. Here, the site of a target gene or nucleic acid cleaved by the CRISPR enzyme may be a non-coding or coding region, and in addition, the site of the target gene or nucleic acid restored by NHEJ may be a non-coding or coding region.

Homology Directed Repairing (HDR)

HDR is a correction method without an error, which uses a homologous sequence as a template to repair or restoration a damaged gene or nucleic acid, and generally, to repair or restoration broken DNA, that is, to restore innate information of cells, the broken DNA is repaired using information of a complementary base sequence which is not modified or information of a sister chromatid. The most common type of HDR is homologous recombination (HR). HDR is a repair or restoration method usually occurring in the S or G2/M phase of actively dividing cells.

To repair or restore damaged DNA using HDR, rather than using a complementary base sequence or sister chromatin of the cells, a DNA template artificially synthesized using information of a complementary base sequence or homologous base sequence, that is, a nucleic acid template including a complementary base sequence or homologous base sequence may be provided to the cells, thereby repairing the broken DNA. Here, when a nucleic acid sequence or nucleic acid fragment is further added to the nucleic acid template to repair the broken DNA, the nucleic acid sequence or nucleic acid fragment further added to the broken DNA may be subjected to knockin. The further added nucleic acid sequence or nucleic acid fragment may be a nucleic acid sequence or nucleic acid fragment for correcting the target gene or nucleic acid modified by a mutation to a normal gene or nucleic acid, or a gene or nucleic acid to be expressed in cells, but the present invention is not limited thereto.

In one example, a double or single strand of a target gene or nucleic acid may be cleaved using the CRISPR complex, a nucleic acid template including a base sequence complementary to a base sequence adjacent to the cleavage site may be provided to cells, and the cleaved base sequence of the target gene or nucleic acid may be repaired or restored through HDR.

Here, the nucleic acid template including the complementary base sequence may have broken DNA, that is, a cleaved double or single strand of a complementary base sequence, and further include a nucleic acid sequence or nucleic acid fragment to be inserted into the broken DNA. An additional nucleic acid sequence or nucleic acid fragment may be inserted into a cleaved site of the broken DNA, that is, the target gene or nucleic acid using the nucleic acid template including a nucleic acid sequence or nucleic acid fragment to be inserted into the complementary base sequence. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The complementary base sequence may be a base sequence having complementary bonds with broken DNA, that is, right and left base sequences of the cleaved double or single strand of the target gene or nucleic acid. Alternatively, the complementary base sequence may be a base sequence having complementary bonds with broken DNA, that is, 3' and 5' ends of the cleaved double or single strand of the target gene or nucleic acid. The complementary base sequence may be a 15 to 3000-base sequence, a length or size of the complementary base sequence may be suitably designed according to a size of the nucleic acid template or the target gene. Here, as the nucleic acid template, a double- or single-stranded nucleic acid may be used, or it may be linear or circular, but the present invention is not limited thereto.

In another example, a double- or single-stranded target gene or nucleic acid is cleaved using the CRISPR complex, a nucleic acid template including a homologous base sequence with a base sequence adjacent to a cleavage site is provided to cells, and the cleaved base sequence of the target gene or nucleic acid may be repaired or restored by HDR.

Here, the nucleic acid template including the homologous base sequence may be broken DNA, that is, a cleaved double- or single-stranded homologous base sequence, and further include a nucleic acid sequence or nucleic acid fragment to be inserted into the broken DNA. An additional nucleic acid sequence or nucleic acid fragment may be inserted into broken DNA, that is, a cleaved site of a target gene or nucleic acid using the nucleic acid template including a homologous base sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The homologous base sequence may be broken DNA, that is, a base sequence having homology with cleaved double-stranded base sequence or right and left single-stranded base sequences of a target gene or nucleic acid. Alternatively, the complementary base sequence may be a base sequence having homology with broken DNA, that is, the 3' and 5' ends of a cleaved double or single strand of a target gene or nucleic acid. The homologous base sequence may be a 15 to 3000-base sequence, and a length or size of the homologous base sequence may be suitably designed according to a size of the nucleic acid template or a target gene or nucleic acid. Here, as the nucleic acid template, a double- or single-stranded nucleic acid may be used and may be linear or circular, but the present invention is not limited thereto.

Other than the NHEJ and HDR, there are methods of repairing or restoring broken DNA.

Single-Strand Annealing (SSA)

SSA is a method of repairing double strand breaks between two repeat sequences present in a target nucleic acid, and generally uses a repeat sequence of more than 30 bases. The repeat sequence is cleaved (to have sticky ends) to have a single strand with respect to a double strand of the target nucleic acid at each of the broken ends, and after the cleavage, a single-strand overhang containing the repeat sequence is coated with an RPA protein such that it is prevented from inappropriately annealing the repeat sequences to each other. RAD52 binds to each repeat sequence on the overhang, and a sequence capable of annealing a complementary repeat sequence is arranged. After annealing, a single-stranded flap of the overhang is cleaved, and synthesis of new DNA fills a certain gap to restore a DNA double strand. As a result of this repair, a DNA sequence between two repeats is deleted, and a deletion length may be dependent on various factors including the locations of the two repeats used herein, and a path or degree of the progress of cleavage.

SSA, similar to HDR, utilizes a complementary sequence, that is, a complementary repeat sequence, and in contrast, does not requires a nucleic acid template for modifying or correcting a target nucleic acid sequence.

Single-Strand Break Repair (SSBA)

Single strand breaks in a genome are repaired through a separate mechanism, SSBR, from the above-described repair mechanisms. In the case of single-strand DNA breaks, PARP1 and/or PARP2 recognize the breaks and recruit a repair mechanism. PARP1 binding and activity with respect to the DNA breaks are temporary, and SSBR is promoted by promoting the stability of an SSBR protein complex in the damaged regions. The most important protein in the SSBR complex is XRCC1, which interacts with a protein promoting 3' and 5' end processing of DNA to stabilize the DNA. End processing is generally involved in repairing the damaged 3' end to a hydroxylated state, and/or the damaged 5' end to a phosphatic moiety, and after the ends are processed, DNA gap filling takes place. There are two methods for the DNA gap filling, that is, short patch repair and long patch repair, and the short patch repair involves insertion of a single base. After DNA gap filling, a DNA ligase promotes end joining.

Mismatch Repair (MMR)

MMR works on mismatched DNA bases. Each of an MSH2/6 or MSH2/3 complex has ATPase activity and thus plays an important role in recognizing a mismatch and initiating a repair, and the MSH2/6 primarily recognizes base-base mismatches and identifies one or two base mismatches, but the MSH2/3 primarily recognizes a larger mismatch.

Base Excision Repair (BER)

BER is a repair method which is active throughout the entire cell cycle, and used to remove a small non-helix-distorting base damaged region from the genome. In the damaged DNA, damaged bases are removed by cleaving an N-glycoside bond joining a base to the phosphate-deoxyribose backbone, and then the phosphodiester backbone is cleaved, thereby generating breaks in single-strand DNA. The broken single strand ends formed thereby were removed, a gap generated due to the removed single strand is filled with a new complementary base, and then an end of the newly-filled complementary base is ligated with the backbone by a DNA ligase, resulting in repair of the damaged DNA.

Nucleotide Excision Repair (NER)

NER is an excision mechanism important for removing large helix-distorting damage from DNA, and when the damage is recognized, a short single-strand DNA segment containing the damaged region is removed, resulting in a single strand gap of 22 to 30 bases. The generated gap is filled with a new complementary base, and an end of the newly filled complementary base is ligated with the backbone by a DNA ligase, resulting in the repair of the damaged DNA.

Gene Manipulation Effects

Manipulation or correction of a target gene or nucleic acid may largely lead to effects of knockout, knockdown, and knockin.

Knockout

The term "knockout" refers to inactivation of a target gene or nucleic acid, and the "inactivation of a target gene or nucleic acid" refers to a state in which transcription and/or translation of a target gene or nucleic acid does not occur. Transcription and translation of a gene causing a disease or a gene having an abnormal function may be inhibited through knockout, resulting in the prevention of protein expression.

For example, when a target gene or nucleic acid is edited or corrected using a gRNA-CRISPR enzyme complex, that is, a CRISPR complex, the target gene or nucleic acid may be cleaved using the CRISPR complex. The damaged target gene or nucleic acid may be repaired through NHEJ using the CRISPR complex. The damaged target gene or nucleic acid may have indels due to NHEJ, and thereby, specific knockout for the target gene or nucleic acid may be induced.

Knockdown

The term "knockdown" refers to a decrease in transcription and/or translation of a target gene or nucleic acid or the expression of a target protein. The onset of a disease may be prevented or a disease may be treated by regulating the overexpression of a gene or protein through the knockdown.

For example, when a target gene or nucleic acid is edited or corrected using a gRNA-CRISPR inactive enzyme-transcription inhibitory activity domain complex, that is, a CRISPR inactive complex including a transcription inhibitory activity domain, the CRISPR inactive complex may specifically bind to the target gene or nucleic acid, transcription of the target gene or nucleic acid may be inhibited by the transcription inhibitory activity domain included in the CRISPR inactive complex, thereby inducing knockdown in which expression of the corresponding gene or nucleic acid is inhibited.

Knockin

The term "knockin" refers to insertion of a specific nucleic acid or gene into a target gene or nucleic acid, and in particular, the term "specific nucleic acid" refers to a gene or nucleic acid to be inserted or desired to be expressed. Knockin may be used for the treatment of diseases by precisely correcting a mutant gene that causes a disease or inducing normal gene expression by inserting a normal gene.

In addition, knockin may require an additional donor.

For example, when a target gene or nucleic acid is edited or corrected using a gRNA-CRISPR enzyme complex (i.e., a CRISPR complex), the target gene or nucleic acid may be cleaved using a CRISPR complex. A damaged target gene or nucleic acid may be repaired via HDR using the CRISPR complex. In particular, a specific nucleic acid may be inserted into a damaged gene or nucleic acid using a donor.

The term "donor" refers to a nucleic acid sequence that helps to repair the damaged gene or nucleic acid via HDR, and in particular, the template may include a specific nucleic acid.

The donor may be a double-stranded nucleic acid or single-stranded nucleic acid.

The donor may be linear or circular.

The donor may include a nucleic acid sequence having homology to a target gene or nucleic acid.

For example, the donor may include a nucleic acid sequence which has homology to a nucleotide sequence at positions in which a specific nucleic acid is to be inserted (e.g., the upstream and the downstream of a damaged nucleic acid), respectively. In particular, the specific nucleic acid to be inserted may be located between the nucleic acid sequence having homology to the downstream nucleic acid sequence of the damaged nucleic acid and the nucleic acid sequence having homology to the upstream nucleic acid sequence of the damaged nucleic acid. In particular, the nucleic acid sequence having the above homology may have at least 50%, 55%, 60%, 65%, 70%, 75%, 80%, 85%, 90% or 95% or more of homology, or complete homology.

The donor may optionally include an additional nucleic acid sequence. In particular, the additional nucleic acid sequence may have roles in enhancing the stability, knockin efficiency, or HDR efficiency of the donor.

For example, the additional nucleic acid sequence may be a nucleic acid sequence rich in A and T bases (i.e., an A-T rich domain). Alternatively, the additional nucleic acid sequence may be a scaffold/matrix attachment region (S/MAR).

5. Other Additional Components

An additional component may be selectively added to increase the efficiency of a guide nucleic acid-editor protein complex or improve the repair efficiency of a damaged gene or nucleic acid.

The additional component may be selectively used to improve the efficiency of the guide nucleic acid-editor protein complex.

Activator

The additional component may be used as an activator to increase the cleavage efficiency of a target nucleic acid, gene or chromosome of the guide nucleic acid-editor protein complex.

The term "activator" refers to a nucleic acid serving to stabilize the bonding between the guide nucleic acid-editor protein complex and the target nucleic acid, gene or chromosome, or to allow the guide nucleic acid-editor protein complex to more easily approach the target nucleic acid, gene or chromosome.

The activator may be a double-stranded nucleic acid or single-stranded nucleic acid.

The activator may be linear or circular.

The activator may be divided into a "helper" that stabilizes the bonding between the guide nucleic acid-editor protein complex and the target nucleic acid, gene or chromosome, and an "escorter" that serves to allow the guide nucleic acid-editor protein complex to more easily approach the target nucleic acid, gene or chromosome.

The helper may increase the cleavage efficiency of the guide nucleic acid-editor protein complex with respect to the target nucleic acid, gene or chromosome.

For example, the helper includes a nucleic acid sequence having homology with the target nucleic acid, gene or chromosome. Therefore, when the guide nucleic acid-editor protein complex is bonded to the target nucleic acid, gene or chromosome, the homologous nucleic acid sequence included in the helper may form an additional complementary bond with the target nucleic acid, gene or chromosome to stabilize the bonding between the guide nucleic acid-editor protein complex and the target nucleic acid, gene or chromosome.

The escorter may increase the cleavage efficiency of the guide nucleic acid-editor protein complex with respect to the target nucleic acid, gene or chromosome.

For example, the escorter includes a nucleic acid sequence having homology with the target nucleic acid, gene or chromosome. Here, the homologous nucleic acid sequence included in the escorter may partly form a complementary bond with a guide nucleic acid of the guide nucleic acid-editor protein complex. Therefore, the escorter partly forming a complementary bond with the guide nucleic acid-editor protein complex may partly form a complementary bond with the target nucleic acid, gene or chromosome, and as a result, may allow the guide nucleic acid-editor protein complex to accurately approach the position of the target nucleic acid, gene or chromosome.

The homologous nucleic acid sequence may have at least 50%, 55%, 60%, 65%, 70%, 75%, 80%, 85%, 90% or 95% or more homology, or complete homology.

In addition, the additional component may be selectively used to improve the repair efficiency of the damaged gene or nucleic acid.

Assistor

The additional component may be used as an assistor to improve the repair efficiency of the damaged gene or nucleic acid.

The term "assistor" refers to a nucleic acid that serves to participate in a repair process or increase the repair efficiency of the damaged gene or nucleic acid, for example, the gene or nucleic acid cleaved by the guide nucleic acid-editor protein complex.

The assistor may be a double-stranded nucleic acid or single-stranded nucleic acid.

The assistor may be present in a linear or circular shape.

The assistor may be divided into an "NHEJ assistor" that participates in a repair process using NHEJ or improves repair efficiency and an "HDR assistor" that participates in a repair process using HDR or improves repair efficiency according to a repair method.

The NHEJ assistor may participate in a repair process or improve the repair efficiency of the damaged gene or nucleic acid using NHEJ.

For example, the NHEJ assistor may include a nucleic acid sequence having homology with a part of the damaged nucleic acid sequence. Here, the homologous nucleic acid sequence may include a nucleic acid sequence having homology with the nucleic acid sequence at one end (e.g., the 3' end) of the damaged nucleic acid sequence, and include a nucleic acid sequence having homology with the nucleic acid sequence at the other end (e.g., the 5' end) of the damaged nucleic acid sequence. In addition, a nucleic acid sequence having homology with each of the base sequences upstream and downstream of the damaged nucleic acid sequence may be included. The nucleic acid sequence having such homology may assist two parts of the damaged nucleic acid sequence to be placed in close proximity, thereby increasing the repair efficiency of the damaged nucleic acid by NHEJ.

The HDR assistor may participate in the repair process or improve repair efficiency of the damaged gene or nucleic acid using HDR.

For example, the HDR assistor may include a nucleic acid sequence having homology with a part of the damaged nucleic acid sequence. Here, the homologous nucleic acid sequence may include a nucleic acid sequence having homology with the nucleic acid sequence at one end (e.g., the 3' end) of the damaged nucleic acid sequence, and a nucleic acid sequence having homology with the nucleic acid sequence at the other end (e.g., the 5' end) of the damaged nucleic acid sequence. Alternatively, a nucleic acid sequence having homology with each of the base sequences upstream and downstream of the damaged nucleic acid sequence may be included. The nucleic acid sequence having such homology may serve as a template of the damaged nucleic acid sequence to increase the repair efficiency of the damaged nucleic acid by HDR.

In another example, the HDR assistor may include a nucleic acid sequence having homology with a part of the damaged nucleic acid sequence and a specific nucleic acid, for example, a nucleic acid or gene to be inserted. Here, the homologous nucleic acid sequence may include a nucleic acid sequence having homology with each of the base sequences upstream and downstream of the damaged nucleic acid sequence. The specific nucleic acid may be located between a nucleic acid sequence having homology with a base sequence downstream of the damaged nucleic acid and a nucleic acid sequence having homology with a base sequence upstream of the damaged nucleic acid. The nucleic acid sequence having such homology and specific nucleic acid may serve as a donor to insert a specific nucleic acid into the damaged nucleic acid, thereby increasing HDR efficiency for knockin.

The homologous nucleic acid sequence may have at least 50%, 55%, 60%, 65%, 70%, 75%, 80%, 85%, 90% or 95% or more homology or complete homology.

6. Subject

The term "subject" refers to an organism into which a guide nucleic acid, editor protein or guide nucleic acid-editor protein complex is introduced, an organism in which a guide nucleic acid, editor protein or guide nucleic acid-editor protein complex operates, or a specimen or sample obtained from the organism.

The subject may be an organism including a target nucleic acid, gene, chromosome or protein of the guide nucleic acid-editor protein complex.

The organism may be cells, tissue, a plant, an animal or a human.

The cells may be prokaryotic cells or eukaryotic cells.

The eukaryotic cells may be plant cells, animal cells or human cells, but the present invention is not limited thereto.

The tissue may be animal or human body tissue such as skin, liver, kidney, heart, lung, brain or muscle tissue.

The subject may be a specimen or sample including a target nucleic acid, gene, chromosome or protein of the guide nucleic acid-editor protein complex.

The specimen or sample may be obtained from an organism including a target nucleic acid, gene, chromosome or protein and may be saliva, blood, skin tissue, cancer cells or stem cells.

As an embodiment of the subjects in the present invention, the subjects containing a target gene or nucleic acid of a guide nucleic acid-editor protein complex are described below.

For example, PD-1 gene, CTLA-4 gene, TNFAIP3 gene, DGKA gene, DGKZ gene, Fas gene, EGR2 gene, PPP2R2D gene, PSGL-1 gene, KDM6A gene, and/or TET2 gene may be the target genes.

In an embodiment, the target sequence of each of the above genes may be one or more selected from the sequences described in Table 1, excluding the PAM sequence (where T is changed to U). This target sequence may serve as a basis in designing a guide nucleic acid.

That is, the nucleotide sequence of the target sequence region for each gene and the corresponding targeting sequence region of a guide RNA (a targeting sequence region of a guide RNA and a targeting sequence region of a guide RNA having a nucleotide sequence that can be hybridized with the target sequence region) are summarized in Table 1 above (the target sequence regions shown in Table 1 are described in a state where the PAM sequence (5'-NGG-3') is included at the 3' end).

These target sequence regions are characterized in that they are sequences without any 0 bp to 2 bp mismatch region in the genome of a gene except the target sequence, and have a low off-target effect and a high efficiency of gene correction.

The target sequence may target two or more kinds simultaneously.

The gene may target two or more kinds simultaneously.

Two or more target sequences in a homologous gene or two or more target sequences in a heterologous gene may be targeted simultaneously.

A non-coding region or coding region within the gene (e.g., promoter region, enhancer, 3'UTR, and/or polyadenylation signal sequence, or transcription sequence (e.g., intron or exon sequence)) may be targeted.

The upper 50% of the coding regions of the genes may be targeted.

In an exemplary embodiment, DGKa or DGKz may be targeted, respectively.

In an exemplary embodiment, DGKa and DGKz may be targeted simultaneously.

In an embodiment of the present invention, for the artificial manipulation of each gene, guide nucleic acid sequences corresponding to the target sequences of SEQ ID NOS: 1 to 289 are provided.

In an embodiment of the present invention, for the artificial manipulation of each gene, editor proteins (e.g., proteins that form a complex) which interact with guide nucleic acid sequences corresponding to the target sequences of SEQ ID NOS: 1 to 289 are provided.

In an embodiment of the present invention, a nucleic acid modification product of each gene, in which artificial manipulation has occurred in the target sequence regions of SEQ ID NOS: 1 to 289, and an expression product thereof are provided.

In an embodiment of the present invention, for the artificial manipulation of each gene, complexes between guide nucleic acid sequences corresponding to one or more target sequences among SEQ ID NOS: 6 and 11 (A20),
SEQ ID NOS: 19, 20, 21, and 23 (DGKa)
SEQ ID NO: 25 (EGR2)
SEQ ID NO: 64 (PPP2R2D)
SEQ ID NOS: 87 and 89 (PD-1)
SEQ ID NOS: 109, 110, 111, 112 and 113 (Dgkζ)
SEQ ID NOS: 126,128 and 129 (Tet-2)
SEQ ID NO: 182 (PSGL-1)
SEQ ID NOS: 252, 254, 257 and 264 (FAS); and
SEQ ID NO: 285 (KDM6A),
and editor proteins interacting therewith are provided.

In an embodiment of the present invention, a nucleic acid modification product of each gene, in which artificial manipulation has occurred in the target sequence regions of SEQ ID NO: 6 and 11 (A20), SEQ ID NO: 19, 20, 21, and 23 (DGKa), SEQ ID NO: 25 (EGR2), SEQ ID NO: 64 (PPP2R2D), SEQ ID NO: 87 and 89 (PD-1), SEQ ID NO: 109, 110, 111, 112 and 113 (Dgkζ), SEQ ID NO: 126,128 and 129 (Tet-2), SEQ ID NO: 182 (PSGL-1), SEQ ID NO: 252, 254, 257 and 264 (FAS), and SEQ ID NO: 285 (KDM6A), and an expression product thereof are provided.

7. Delivery

The guide nucleic acid, editor protein or guide nucleic acid-editor protein complex may be delivered or introduced into a subject by various delivering methods and various forms.

The guide nucleic acid may be delivered or introduced into a subject in the form of DNA, RNA or a mixed form.

The editor protein may be delivered or introduced into a subject in the form of DNA, RNA, a DNA/RNA mixture, a peptide, a polypeptide, which encodes the editor protein, or a protein.

The guide nucleic acid-editor protein complex may be delivered or introduced into a target in the form of DNA, RNA or a mixture thereof, which encodes each component, that is, a guide nucleic acid or an editor protein.

The guide nucleic acid-editor protein complex may be delivered or introduced into a subject as a complex of a guide nucleic acid having a form of DNA, RNA or a mixture thereof and an editor protein having a form of a peptide, polypeptide or protein.

In addition, an additional component capable of increasing or inhibiting the efficiency of the guide nucleic acid-editor protein complex may be delivered or introduced into a subject by various delivering methods and in various forms.

i) Delivery in Form of DNA, RNA or Mixture Thereof

The form of DNA, RNA or a mixture thereof, which encodes the guide nucleic acid and/or editor protein may be delivered or introduced into a subject by a method known in the art.

Or, the form of DNA, RNA or a mixture thereof, which encodes the guide nucleic acid and/or editor protein may be delivered or introduced into a subject by a vector, a non-vector or a combination thereof.

The vector may be a viral or non-viral vector (e.g., a plasmid).

The non-vector may be naked DNA, a DNA complex or mRNA.

Vector-Based Introduction

The nucleic acid sequence encoding the guide nucleic acid and/or editor protein may be delivered or introduced into a subject by a vector.

The vector may include a nucleic acid sequence encoding a guide nucleic acid and/or editor protein.

For example, the vector may simultaneously include nucleic acid sequences, which encode the guide nucleic acid and the editor protein, respectively.

For example, the vector may include the nucleic acid sequence encoding the guide nucleic acid.

As an example, domains included in the guide nucleic acid may be contained all in one vector, or may be divided and then contained in different vectors.

For example, the vector may include the nucleic acid sequence encoding the editor protein.

In one example, in the case of the editor protein, the nucleic acid sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the guide nucleic acid may be a H1, EF-1a, tRNA or U6 promoter. For example, a promoter useful for the editor protein may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector including a guide nucleic acid or an editor protein or a viral vector including both of a guide nucleic acid and an editor protein may be designed. Alternatively, a viral vector including a guide nucleic acid, an editor protein and additional components may be designed.

In one example, a nucleic acid sequence encoding a guide nucleic acid and/or editor protein may be delivered or introduced by a recombinant lentivirus.

In another example, a nucleic acid sequence encoding a guide nucleic acid and/or editor protein may be delivered or introduced by a recombinant adenovirus.

In still another example, a nucleic acid sequence encoding a guide nucleic acid and/or editor protein may be delivered or introduced by recombinant AAV.

In yet another example, a nucleic acid sequence encoding a guide nucleic acid and/or editor protein may be delivered or introduced by a hybrid virus, for example, one or more hybrids of the virus listed herein.

Non-Vector-Based Introduction

A nucleic acid sequence encoding a guide nucleic acid and/or editor protein may be delivered or introduced into a subject using a non-vector.

The non-vector may include a nucleic acid sequence encoding a guide nucleic acid and/or editor protein.

The non-vector may be naked DNA, a DNA complex, mRNA, or a mixture thereof.

The non-vector may be delivered or introduced into a subject by electroporation, particle bombardment, sonoporation, magnetofection, transient cell compression or squeezing (e.g., described in the literature [Lee, et al, (2012) Nano Lett., 12, 6322-6327]), lipid-mediated transfection, a dendrimer, nanoparticles, calcium phosphate, silica, a silicate (Ormosil), or a combination thereof.

As an example, the delivery through electroporation may be performed by mixing cells and a nucleic acid sequence encoding a guide nucleic acid and/or editor protein in a cartridge, chamber or cuvette, and applying electrical stimuli with a predetermined duration and amplitude to the cells.

In another example, the non-vector may be delivered using nanoparticles. The nanoparticles may be inorganic nanoparticles (e.g., magnetic nanoparticles, silica, etc.) or organic nanoparticles (e.g., a polyethylene glycol (PEG)-coated lipid, etc.). The outer surface of the nanoparticles may be conjugated with a positively-charged polymer which is attachable (e.g., polyethyleneimine, polylysine, polyserine, etc.).

ii) Delivery in Form of Peptide, Polypeptide or Protein

An editor protein in the form of a peptide, polypeptide or protein may be delivered or introduced into a subject by a method known in the art The peptide, polypeptide or protein form may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The peptide, polypeptide or protein may be delivered with a nucleic acid sequence encoding a guide nucleic acid.

In one example, the transfer through electroporation may be performed by mixing cells into which the editor protein will be introduced with or without a guide nucleic acid in a cartridge, chamber or cuvette, and applying electrical stimuli with a predetermined duration and amplitude to the cells.

iii) Delivery in Form of Nucleic Acid-Protein Mixture

The guide nucleic acid and the editor protein may be delivered or introduced into a subject in the form of a guide nucleic acid-editor protein complex.

For example, the guide nucleic acid may be DNA, RNA or a mixture thereof. The editor protein may be a peptide, polypeptide or protein.

In one example, the guide nucleic acid and the editor protein may be delivered or introduced into a subject in the form of a guide nucleic acid-editor protein complex containing an RNA-type guide nucleic acid and a protein-type editor protein, that is, a ribonucleoprotein (RNP).

In the present invention, as an embodiment of a method for delivering the guide nucleic acid and/or editor protein into a subject, the delivery of gRNA, a CRISPR enzyme or a gRNA-CRISPR enzyme complex will be described below.

8. Transformant

The term "transformant" refers to an organism into which a guide nucleic acid, editor protein or guide nucleic acid-editor protein complex is introduced, an organism in which a guide nucleic acid, editor protein or guide nucleic acid-editor protein complex is expressed, or a specimen or sample obtained from the organism.

The transformant may be an organism into which a guide nucleic acid, editor protein or guide nucleic acid-editor protein complex is introduced in the form of DNA, RNA or a mixture thereof.

For example, the transformant may be an organism into which a vector including a nucleic acid sequence encoding a guide nucleic acid and/or editor protein is introduced. Here, the vector may be a non-viral vector, viral vector or recombinant viral vector.

In another example, the transformant may be an organism into which a nucleic acid sequence encoding a guide nucleic acid and/or editor protein is introduced in a non-vector form. Here, the non-vector may be naked DNA, a DNA complex, mRNA or a mixture thereof.

The transformant may be an organism into which a guide nucleic acid, editor protein or guide nucleic acid-editor protein complex is introduced in the form of a peptide, polypeptide or protein.

The transformant may be an organism into which a guide nucleic acid, editor protein or guide nucleic acid-editor protein complex is introduced in the form of DNA, RNA, a peptide, a polypeptide, a protein or a mixture thereof.

For example, the transformant may be an organism into which a guide nucleic acid-editor protein complex including an RNA-type guide nucleic acid and a protein-type editor protein is introduced.

The transformant may be an organism including a target nucleic acid, gene, chromosome or protein of the guide nucleic acid-editor protein complex.

The organism may be cells, tissue, a plant, an animal or a human.

The cells may be prokaryotic cells or eukaryotic cells.

The eukaryotic cells may be plant cells, animal cells, or human cells, but the present invention is not limited thereto.

The tissue may be an animal or human body tissue such as skin, liver, kidney, heart, lung, brain, or muscle tissue.

The transformant may be an organism into which a guide nucleic acid, editor protein or guide nucleic acid-editor protein complex is introduced or expressed, or a specimen or sample obtained from the organism.

The specimen or sample may be saliva, blood, skin tissue, cancer cells or stem cells.

Additionally, in an embodiment, the present invention provides a guide nucleic acid-editor protein complex, which is used for nucleic acid modification in the target sites of PD-1, CTLA-4, TNFAIP3, DGKA, DGKZ, Fas, EGR2, PPP2R2D, PSGL-1, KDM6A and/or TET2 gene.

In particular, gRNA molecules which contain a domain capable of forming a complementary bond with a target site from a gene (e.g., isolated or non-naturally occurring gRNA molecules and DNAs encoding the same) may be provided. The sequences of the gRNA molecules and DNAs encoding the same may be designed so that these sequences can have a complementary binding with the target site sequences of Table 1.

Additionally, the target sites of the gRNA molecules are constituted such that a third immune regulatory factor is provided, in which the third immune regulatory factor is associated with the change in the target position of an immune cell (e.g., breaks of double strands or breaks of single strands); or has a specific function in the target position, in PD-1, CTLA-4, TNFAIP3, DGKA, DGKZ, Fas, EGR2, PPP2R2D, PSGL-1, KDM6A and/or TET2 gene.

Additionally, when two or more gRNAs are used to locate two or more cleavage events (e.g., breaks of double strands or single strands) in a target nucleic acid, two or more cleavage events may be generated by the same or different Cas9 proteins.

The gRNAs may be, for example, may be able to target two or more genes among PD-1, CTLA-4, TNFAIP3, DGKA, DGKZ, Fas, EGR2, PPP2R2D, PSGL-1, KDM6A, and/or TET2 gene;

may be able to target two or more sites within each of the PD-1, CTLA-4, TNFAIP3, DGKA, DGKZ, Fas, EGR2, PPP2R2D, PSGL-1, KDM6A and/or TET2 gene;

may be able to induce independently the cleavage of a double strand and/or single strand of the PD-1, CTLA-4, TNFAIP3, DGKA, DGKZ, Fas, EGR2, PPP2R2D, PSGL-1, KDM6A and/or TET2 gene; or may be able to induce the insertion of one or more exogenous nucleotide in the cleavage site of the PD-1, CTLA-4, TNFAIP3, DGKA, DGKZ, Fas, EGR2, PPP2R2D, PSGL-1, KDM6A and/or TET2 gene.

Additionally, in another embodiment of the present invention, the nucleic acid constituting a guide nucleic acid-editor protein complex may include:

(a) a sequence encoding a gRNA molecule which includes a guide domain complementary to a target site sequence in the PD-1, CTLA-4, TNFAIP3, DGKA, DGKZ, Fas, EGR2, PPP2R2D, PSGL-1, KDM6A, and/or TET2 gene as disclosed herein; and (b) a sequence encoding an editor protein.

In particular, two or more may be present in (a) according to the target site, and homologous or two or more editor proteins may be used in (b).

In an embodiment, the nucleic acid is constituted so as to target an enzymatically inactive editor protein, which is close enough to the knockdown target position of an immune cell, or a fusion protein thereof (e.g., a fusion of transcription repressor domains), for reducing, decreasing, or inhibiting the expression of the PD-1, CTLA-4, TNFAIP3, DGKA, DGKZ, Fas, EGR2, PPP2R2D, PSGL-1, KDM6A, and/or TET2 gene.

Additionally, in an embodiment of the present invention, the manipulation of the immune cell-expressed genes (e.g., PD-1, CTLA-4, TNFAIP3, DGKA, DGKZ, Fas, EGR2, PPP2R2D, PSGL-1, KDM6A, and/or TET2 gene) by a guide nucleic acid-editor protein complex may be mediated by any mechanism.

Examples of the mechanism include, but are not limited to, non-homologous end joining (NHEJ), microhomology-mediated end joining (MMEJ), homology-directed repair (HDR), synthesis-dependent strand annealing (SDSA), or single strand penetration.

In addition, it will be apparent that all features of the structure, function, and utilization of the guide nucleic acid-editor protein complex described above may be used for the manipulation of the PD-1, CTLA-4, TNFAIP3, DGKA, DGKZ, Fas, EGR2, PPP2R2D, PSGL-1, KDM6A, and/or TET2 gene.

In an embodiment of the present invention, the immune system factor, which is the resulting product obtained using the "guide nucleic acid-editor protein complex", may be, for example, a manipulated gene, a product expressed by the manipulated gene, a cell, composition, transformant, etc. containing the same.

In an embodiment of the present invention, the immune system factor is an immune regulatory gene artificially manipulated by a guide nucleic acid-editor protein complex, or an expressed protein thereof; and a cell containing the same.

In an embodiment of the present invention, the immune system factor is an immune regulatory gene genetically manipulated by a guide nucleic acid-editor protein complex, or an expressed protein thereof; and a cell containing the same.

In an embodiment of the present invention, the immune system factor is a nucleic acid sequence or amino acid sequence of an immune regulatory gene genetically manipulated by a guide nucleic acid-editor protein complex.

In an embodiment of the present invention, the immune system factor is an immune regulatory gene genetically manipulated by a guide nucleic acid-editor protein complex; an expressed protein thereof; a cell containing the manipulated immune regulatory factor and/or protein; or a composition containing the manipulated immune regulatory factor, protein and/or cell.

In an embodiment of the present invention, the immune system factor is a transformant, which is formed by introduction of one or more among an immune regulatory gene genetically manipulated by a guide nucleic acid-editor protein complex; an expressed protein thereof; a cell containing the manipulated immune regulatory factor and/or protein; or a composition containing the manipulated immune regulatory factor, protein and/or cell.

The immune factor, which is a resulting product obtained using the guide nucleic acid-editor protein complex may include independently two or more of each of the factors, and may further include two or more per factor.

For example,
the immune factor may be provided in a form simultaneously including two or more among the artificially manipulated immune regulatory gene, an expressed protein thereof, and a cell containing the same;
artificially manipulated, one or two or more kinds of immune regulatory genes may be provided simultaneously;
artificially manipulated, one or two or more kinds of immune regulatory proteins may be provided simultaneously;
artificially manipulated, one or two or more kinds of immune cells may be provided simultaneously; and
a combination of two or more of the artificially manipulated immune factors may be provided simultaneously.

Preferred examples of the immune system factor, which is the product obtained using a "guide nucleic acid-editor protein complex" may have the following constitutions.

In an embodiment, when the immune regulatory factor is a gene, the constitution of the immune regulatory gene artificially manipulated by a guide nucleic acid-editor protein complex may include:
in a proto-spacer-adjacent Motif (PAM) sequence in a nucleic acid sequence constituting the immune regulatory gene or in a continuous 1 bp to 50 bp, 1 bp to 40 bp, 1 bp to 30 bp, and preferably 3 bp to 25 bp nucleotide sequence region adjacent to the 5' end and/or 3' end thereof, one or more nucleic acid modifications among:
deletion or insertion of one or more nucleotides;
substitution with one or more nucleotides different from a wild-type gene; and
insertion of one or more foreign nucleotides.

Additionally, the constitution of the immune regulatory gene artificially manipulated by a guide nucleic acid-editor protein complex may include a chemical modification of one or more nucleotides in a nucleic acid sequence constituting the immune regulatory gene.

In particular, the term "foreign nucleotide" is a concept which includes all of those produced from the outside (e.g., nucleotides derived from a heterologous biooranism or artificially synthesized nucleotides), not those nucleotides possessed by an immune regulatory gene. The foreign nucleotide includes not only a small size oligonucleotide of 50 bp or less, but also a large size nucleotide (e.g., a few hundreds, a few thousands, or a few tens of thousands bp) for the expression of a protein with a specific function. Such a "foreign nucleotide" may be referred to as a donor.

The chemical modification includes methylation, acetylation, phosphorylation, ubiquitination, ADP-ribosylation, myristylation, and glycosylation, e.g., part of the functional group of the nucleotide is substituted with, but is not limited to, any one of a hydrogen atom, a fluorine atom, —O-alkyl group, —O-acyl group, and amino group. Additionally, for increasing the ability of transferring a nucleic acid molecule, part of the functional group of the nucleotide may be substituted with any one among —Br, —Cl, —R, —R'OR, —SH, —SR, —N3 and —CN (R=alkyl, aryl, alkylene). Additionally, a phosphate backbone of at least one nucleotide is substituted with any one among an alkylphosphonate form, phosphoroamidate form and boranophosphate form. Additionally, the chemical modification may be characterized in that at least one nucleotide included in the nucleic acid molecule is substituted with any one among locked nucleic acid (LNA), unlocked nucleic acid (UNA), Morpholino, and peptide nucleic acid (PNA), and the chemical modification may be characterized in that the nucleic acid molecule is bound to one or more selected from the group consisting of lipids, cell penetrating peptides, and cell targeting ligands.

In order to form a desired immune system, a nucleic acid that artificially constitutes an immune regulatory gene may be modified by a guide nucleic acid-editor protein complex.

The site, which is capable of forming a desired immune system, containing the modification of the nucleic acid of an immune regulatory gene is referred to as a target sequence or a target site.

The "target sequence" may be a target of a guide nucleic acid-editor protein complex, and the target sequence may include, but is not limited to, a protospacer-adjacent motif (PAM) sequence recognized by the editor protein. The target sequence may provide the practitioner with important criteria for the design of a guide nucleic acid.

Such modification of the nucleic acid includes "cleavage" of a nucleic acid.

The "cleavage" at a target site refers to a breakage of a covalent backbone of a polynucleotide. The cleavage may include, but is not limited to, enzymatic or chemical hydrolysis of a phosphodiester linkage, and may be performed by various other methods. Both the cleavage of a single strand and cleavage of a double strand may be possible, and the cleavage of a double strand may occur as a result of the cleavage of two distinct single strands. The cleavage of double strands may produce blunt ends or staggered ends.

When an inactivated editor protein is used, factors possessing a specific function may be induced to be located close to any part of the target site or immune regulatory gene, without the cleavage process. Depending on this particular function, the chemical modification of one or more nucleotides may be included in the nucleic acid sequence of an immune regulatory gene.

In an embodiment, various insertion and deletion (indel) may occur due to target and non-target activity through the cleavage of a nucleic acid formed by a guide nucleic acid-editor protein complex.

The term "indel" collectively refers to a mutation in which some nucleotides are inserted or deleted in the nucleotide sequence of DNA.

As described above, when a guide nucleic acid-editor protein complex cleaves the nucleic acid (DNA, RNA) of an immune regulatory gene, indel may be one which is introduced to a target sequence in the process of repair by homologous recombination or non-homologous end-joining (NHEJ) mechanism.

The artificially manipulated immune regulatory gene of the present invention means one in which the nucleic acid sequence of the original gene was modified by cleavage and indel of the nucleic acid, insertion of a donor, etc., and the artificially manipulated immune regulatory gene contributes to the establishment of a desired immune system (e.g., exhibition of the effect of promoting or suppressing or supplementing specific immune functions).

For example, the expression and activity of a specific protein may be promoted by the artificially manipulated immune regulatory gene.

A specific protein may be inactivated by the artificially manipulated immune regulatory gene.

In one example, the specific target sites of the immune regulatory genes that downregulate the immune response in the genome (e.g., PD-1, CTLA-4, TNFAIP3, DGKA (Dgkα), DGKAZ (Dgkζ), Fas, EGR2, PPP2R2D, PSGL-1, and/or TET2 gene) may be cleaved to knock down or knock out these genes.

In another example, for the alteration of transcription, for example, for blocking, decreasing, or reducing the transcription of PD-1, CTLA-4, TNFAIP3, DGKA (Dgkα), DGKAZ (Dgkζ), Fas, EGR2, PPP2R2D, PSGL-1, and/or TET2 gene, the targeted knockdown may be mediated by targeting an editor protein, which is fused to a transcription repressor domain or chromatin modification protein and is enzymatically inactive.

The activity of immune cells may be regulated by the artificially manipulated immune regulatory gene. The proliferation, survival, cytotoxicity, infiltration, cytokine-release of the immune cells, etc. can be regulated.

Therapeutic effects (e.g., immunity function, antitumor function, anti-inflammatory function, etc.) can be obtained by the artificially manipulated immune regulatory gene.

Depending on the constitutional features of a guide nucleic acid-editor protein complex, the major PAM sequences possessed by the target site of the immune regulatory gene may vary.

Hereinafter, the present invention will be described with respect to representative examples of editor proteins and immune regulatory genes, but these embodiments are for specific illustration purposes only and the present invention is not limited to these embodiments.

For example, when the editor protein is a *Streptococcus pyogenes*-derived Cas9 protein, the PAM sequence may be 5'-NGG-3' (N is A, T, G, or C); and the nucleotide sequence region to be cleaved (target site) may be a nucleotide sequence region with a continuous 1 bp to 25 bp (e.g., 17 bp to 23 bp or 21 bp to 23 bp) adjacent to the 5' end and/or 3' end of the 5'-NGG-3' sequence within a target gene.

Artificially manipulated immune regulatory genes (e.g., artificially manipulated PD-1 gene, CTLA-4 gene, TNFAIP3 gene, DGKA gene, DGKZ gene, Fas gene, EGR2 gene, PPP2R2D gene, PSGL-1 gene, KDM6A gene, and TET2 gene) due to the following modifications in immune regulatory genes may be provided:

a) deletion of one or more nucleotides in a nucleotide sequence region of a continuous 1 bp to 25 bp (e.g., 17 bp to 23 bp) adjacent to the 5' end and/or 3' end of the 'NGG' (N is A, T, C, or G) sequence;

b) substitution of one or more nucleotides with one or more nucleotides, which are different from a wild type gene, in a nucleotide sequence region of a continuous 1 bp to 25 bp (e.g., 17 bp to 23 bp) adjacent to the 5' end and/or 3' end of the 'NGG' sequence;

c) insertion of one or more nucleotides into a nucleotide sequence region of a continuous 1 bp to 25 bp (e.g., 17 bp to 23 bp) adjacent to the 5' end and/or 3' end of the 'NGG' sequence; or d) a combination of two or more selected from a) to c).

For example, when the editor protein is a *Campylobacter jejuni*-derived Cas9 protein, the PAM sequence may be 5'-NNNNRYAC-3' (N is each independently A, T, C or G, R is A or G, and Y is C or T); and the nucleotide sequence region to be cleaved (target site) may be a nucleotide sequence region with a continuous 1 bp to 25 bp (e.g., 17 bp to 23 bp or 21 bp to 23 bp) adjacent to the 5' end and/or 3' end of the 5'-NNNNRYAC-3' sequence within a target gene.

Artificially manipulated immune regulatory genes (e.g., artificially manipulated PD-1 gene, CTLA-4 gene, TNFAIP3 gene, DGKA gene, DGKZ gene, Fas gene, EGR2 gene, PPP2R2D gene, PSGL-1 gene, KDM6A gene, and TET2 gene) due to the following modifications in immune regulatory genes may be provided:

a') deletion of one or more nucleotides in a nucleotide sequence region of a continuous 1 bp to 25 bp (e.g., 17 bp to 23 bp) adjacent to the 5' end and/or 3' end of the 'NNNNRYAC' (N is each independently A, T, C or G, R is A or G, and Y is C or T) sequence;

b') substitution of one or more nucleotides with one or more nucleotides, which are different from a wild type gene, in a nucleotide sequence region of a continuous 1 bp to 25 bp (e.g., 17 bp to 23 bp) adjacent to the 5' end and/or 3' end of the 'NNNNRYAC' sequence;

(c') insertion of one or more nucleotides into a nucleotide sequence region of a continuous 1 bp to 25 bp (e.g., 17 bp to 23 bp) adjacent to the 5' end and/or 3' end of the 'NNNNRYAC' sequence; or d') a combination of two or more selected from a') to c').

For example, when the editor protein is a *Streptococcus thermophilus*-derived Cas9 protein, the PAM sequence may be 5'-NNAGAAW-3' (N is each independently A, T, C or G, and W is A or T); and the nucleotide sequence region to be cleaved (target site) may be a nucleotide sequence region with a continuous 1 bp to 25 bp (e.g., 17 bp to 23 bp or 21 bp to 23 bp) adjacent to the 5' end and/or 3' end of the 5'-NNAGAAW-3' sequence within a target gene.

Artificially manipulated immune regulatory genes (e.g., artificially manipulated PD-1 gene, CTLA-4 gene, TNFAIP3 gene, DGKA gene, DGKZ gene, Fas gene, EGR2 gene, PPP2R2D gene, PSGL-1 gene, KDM6A gene, and TET2 gene) due to the following modifications in immune regulatory genes may be provided:

- a") deletion of one or more nucleotides in a nucleotide sequence region of a continuous 1 bp to 25 bp (e.g., 17 bp to 23 bp) adjacent to the 5' end and/or 3' end of the 'NNAGAAW' (N is each independently A, T, C or G, and W is A or T) sequence;
- b") substitution of one or more nucleotides with one or more nucleotides, which are different from a wild type gene, in a nucleotide sequence region of a continuous 1 bp to 25 bp (e.g., 17 bp to 23 bp) adjacent to the 5' end and/or 3' end of the 'NNAGAAW' sequence;
- c") insertion of one or more nucleotides into a nucleotide sequence region of a continuous 1 bp to 25 bp (e.g., 17 bp to 23 bp) adjacent to the 5' end and/or 3' end of the 'NNAGAAW' sequence; or
- d") a combination of two or more selected from a") to c").

For example, when the editor protein is a *Neisseria meningitidis*-derived Cas9 protein, the PAM sequence may be 5'-NNNNGATT-3' (N is each independently A, T, C or G); and the nucleotide sequence region to be cleaved (target site) may be a nucleotide sequence region with a continuous 1 bp to 25 bp (e.g., 17 bp to 23 bp or 21 bp to 23 bp) adjacent to the 5' end and/or 3' end of the 5'-NNNNGATT-3' sequence within a target gene.

Artificially manipulated immune regulatory genes (e.g., artificially manipulated PD-1 gene, CTLA-4 gene, TNFAIP3 gene, DGKA gene, DGKZ gene, Fas gene, EGR2 gene, PPP2R2D gene, PSGL-1 gene, KDM6A gene, and TET2 gene) due to the following modifications in immune regulatory genes may be provided:

- a''') deletion of one or more nucleotides in a nucleotide sequence region of a continuous 1 bp to 25 bp (e.g., 17 bp to 23 bp) adjacent to the 5' end and/or 3' end of the 'NNNNGATT' (N is each independently A, T, C or G) sequence;
- b''') substitution of one or more nucleotides with one or more nucleotides, which are different from a wild type gene, in a nucleotide sequence region of a continuous 1 bp to 25 bp (e.g., 17 bp to 23 bp) adjacent to the 5' end and/or 3' end of the 'NNNNGATT' sequence;
- c''') insertion of one or more nucleotides into a nucleotide sequence region of a continuous 1 bp to 25 bp (e.g., 17 bp to 23 bp) located adjacent to the 5' end and/or 3' end of the 'NNNNGATT' sequence; or
- d''') a combination of two or more selected from a''') to c''').

For example, when the editor protein is a *Staphylococcus aureus*-derived Cas9 protein, the PAM sequence may be 5'-NNGRR(T)-3' (N is each independently A, T, C or G, R is A or G, and (T) is any sequence that can be optionally included); and the nucleotide sequence region to be cleaved (target site) may be a nucleotide sequence region with a continuous 1 bp to 25 bp (e.g., 17 bp to 23 bp or 21 bp to 23 bp) adjacent to the 5' end or 3' end of the 5'-NNGRR(T)-3' sequence within a target gene.

Artificially manipulated immune regulatory genes (e.g., artificially manipulated PD-1 gene, CTLA-4 gene, TNFAIP3 gene, DGKA gene, DGKZ gene, Fas gene, EGR2 gene, PPP2R2D gene, PSGL-1 gene, KDM6A gene, and TET2 gene) due to the following modifications in immune regulatory genes may be provided:

- a'''') deletion of one or more nucleotides in a nucleotide sequence region of a continuous 1 bp to 25 bp (e.g., 17 bp to 23 bp) adjacent to the 5' end and/or 3' end of the 5'-NNGRR(T)-3' (N is each independently A, T, C or G; R is A or G, and; Y is C or T) sequence;
- b'''') substitution of one or more nucleotides with one or more nucleotides, which are different from a wild type gene, in a nucleotide sequence region of a continuous 1 bp to 25 bp (e.g., 17 bp to 23 bp) adjacent to the 5' end and/or 3' end of the 5'-NNGRR(T)-3' sequence;
- c'''') insertion of one or more nucleotides into a nucleotide sequence region of a continuous 1 bp to 25 bp (e.g., 17 bp to 23 bp) adjacent to the 5' end and/or 3' end of the 5'-NNGRR(T)-3' sequence; or
- d'''') a combination of two or more selected from a'''') to c'''').

For example, when a Cpf1 protein is used as the editor protein, the PAM sequence may be 5'-TTN-3' (N is A, T, C or G); and the nucleotide sequence region to be cleaved (target site) may be a nucleotide sequence region with a continuous 10 bp to 30 bp (e.g., 15 bp to 26 bp, 17 bp to 30 bp, or 17 bp to 26 bp) adjacent to the 5' end or 3' end of the 5'-TTN-3' sequence within a target gene.

The Cpf1 protein may be one derived from a microorganism such as Parcubacteria bacterium (GWC2011_GWC2_44_17), Lachnospiraceae bacterium (MC2017), *Butyrivibrio* proteoclasiicus, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Smiihella* sp. (SC_KO8D17), *Leptospira inadai*, Lachnospiraceae bacterium (MA2020), *Francisella novicida* (U112), *Candidatus* Methanoplasma *termitum, Eubacterium eligens*, etc.), and for example, those derived from Parcubacteria bacterium (GWC2011_GWC2_44_17), Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Leptospira inadai*, Lachnospiraceae bacterium (MA2020), *Francisella novicida* (U112), *Candidatus* Methanoplasma *termitum*, or Eubacterum *eligens*, but the microorganism is not limited thereto.

Artificially manipulated immune regulatory genes (e.g., artificially manipulated PD-1 gene, CTLA-4 gene, TNFAIP3 gene, DGKA gene, DGKZ gene, Fas gene, EGR2 gene, PPP2R2D gene, PSGL-1 gene, KDM6A gene, and TET2 gene) due to the following modifications in immune regulatory genes may be provided:

- a''''') deletion of one or more nucleotides in a nucleotide sequence region of a continuous 10 bp to 30 bp (e.g., 15 bp to 26 bp) adjacent to the 5' end and/or 3' end of the 5'-TTN-3' (N is A, T, C or G) sequence;
- b''''') substitution of one or more nucleotides with one or more nucleotides, which are different from a wild type gene, in a nucleotide sequence region of a continuous 10 bp to 30 bp (e.g., 15 bp to 26 bp) adjacent to the 5' end and/or 3' end of the 5'-TTN-3' sequence;
- c''''') insertion of one or more nucleotides into a nucleotide sequence region of a continuous 10 bp to 30 bp (e.g., 15 bp to 26 bp) located adjacent to the 5' end and/or 3' end of the 5'-TTN-3' sequence; or d"""') a combination of two or more selected from a"""') to c"""').

In another embodiment, when the immune regulatory factor is a protein, the artificially manipulated protein may include all of the proteins involved in a new or altered immune response formed by the direct/indirect action of a guide nucleic acid-editor protein complex.

For example, the immune regulatory factor may be, but is not limited to, a protein expressed by an artificially manipulated immune regulatory gene by a guide nucleic acid-editor protein complex, or other proteins in which the expression is increased or decreased by the influence of the activity of the protein.

The artificially manipulated immune regulatory protein may have an amino acid constitution and activity corresponding to those of the artificially manipulated immune regulatory genes.

In an embodiment, (i) An artificially manipulated protein in which the expression characteristics are altered may be provided.

For example, protein modifications having one of the following characteristics may be included in a nucleotide sequence region of a continuous 1 bp to 50 bp, 1 bp to 40 bp, 1 bp to 30 bp, and preferably 3 bp to 25 bp, located in the proto-spacer-adjacent motif (PAM) sequence or adjacent to the 5' end and/or 3' end of the PAM sequence within the nucleic acid sequence of an immune regulatory gene;
- a decrease or increase in the expression amount due to deletion or insertion of one or more nucleotides;
- a decrease or increase in the expression amount due to substitution with one or more nucleotides different from the wild type gene;
- a decrease or increase in the expression level due to insertion of one or more foreign nucleotides, or an expression of a fusion protein or independent expression of a specific protein; and
- a decrease or increase in the expression level of a third protein which is affected by the expression characteristics of the proteins described above.

(ii) An Artificially Manipulated Protein in which the Structural Characteristics are Changed May be Provided.

For example, protein modifications having one of the following characteristics may be included in a nucleotide sequence region of a continuous 1 bp to 50 bp, 1 bp to 40 bp, 1 bp to 30 bp, and preferably 3 bp to 25 bp, located in the proto-spacer-adjacent motif (PAM) sequence or adjacent to the 5' end and/or 3' end of the PAM sequence within the nucleic acid sequence of an immune regulatory gene;
- changes in codons, changes in amino acids, and changes in three-dimensional structures due to deletion or insertion of one or more nucleotides;
- changes in codons, changes in amino acids, and subsequent changes in three-dimensional structures due to substitution with one or more nucleotides different from the wild type gene;
- changes in codons, changes in amino acids, and changes in three-dimensional structures due to insertion of one or more foreign nucleotides, or a fusion structure with a specific protein or an independent structure in which a specific protein is separated; and
- changes in codons, changes in amino acids, and changes in three-dimensional structures of a third protein affected by a protein in which the structural characteristics described above are changed.

(iii) An Artificially Manipulated Protein in which the Characteristics of Immune Functions are Changed May be Provided.

For example, protein modifications having one of the following characteristics may be included in a nucleotide sequence region of a continuous 1 bp to 50 bp, 1 bp to 40 bp, 1 bp to 30 bp, and preferably 3 bp to 25 bp, located in the proto-spacer-adjacent motif (PAM) sequence or adjacent to the 5' end and/or 3' end of the PAM sequence within the nucleic acid sequence of an immune regulatory gene;
- activation or inactivation of specific immune functions or introduction of new immune functions by protein modification due to deletion or insertion of one or more nucleotides;
- activation or inactivation of specific immune functions or introduction of new immune functions by protein modification due to substitution with one or more nucleotides different from the wild type gene;
- activation or inactivation of specific immune functions or introduction of a new immune function by protein modification due to insertion of one or more foreign nucleotides (in particular, a third function may be introduced into an existing immune function by a fusion expression or independent expression of a specific protein); and
- a change in the function of a third protein affected by a protein in which the immune function characteristics described above are changed.

Additionally, a protein artificially manipulated by chemical modification of one or more nucleotides within a nucleic acid sequence constituting an immune regulatory gene may be included.

For example, one or more characteristics among the expression characteristics, structural characteristics, and immune function characteristics of proteins by methylation, acetylation, phosphorylation, ubiquitination, ADP-ribosylation, myristylation, and glycosylation may be changed.

For example, a third structure and function may be rendered by the binding of a third protein to the nucleic acid sequence of a gene by chemical modification of nucleotides.

In another embodiment, an artificially manipulated cell, which is an immune system factor as a product obtained using "a guide nucleic acid-editor protein complex", is provided.

The artificially manipulated cell may be a cell which includes one or more of the followings:
- an immune regulatory gene artificially manipulated by a guide nucleic acid-editor protein complex; and
- a protein which is involved in a new or altered immune response which is formed by direct/indirect action of a guide nucleic acid-editor protein complex. In an embodiment, the cell may be an immune cell or stem cell.

These cells possess immune functions exhibited by artificially manipulated immune regulatory genes and/or proteins described above and the subsequent functions involved in the intracellular mechanisms thereof.

In still another embodiment, a composition that induces a desired immune response, which is an immune system factor as a product obtained using "a guide nucleic acid-editor protein complex", is provided. This composition may be referred to as a pharmaceutical composition or therapeutic composition.

The composition that induces a desired immune response may contain one or more of the followings as an active ingredient:
- an immune regulatory gene artificially manipulated by a guide nucleic acid-editor protein complex;
- a protein which is involved in a new or altered immune response which is formed by direct/indirect action of a guide nucleic acid-editor protein complex; and
- a cell including the immune regulatory gene and/or protein.

These compositions possess possesses immune functions exhibited by an artificially manipulated immune regulatory genes, proteins, and/or cells described above and the subsequent functions involved in the various mechanisms thereof in the body.

The compositions (e.g., a cell therapeutic agent) may be used for the prevention and/or treatment of immune related diseases (e.g., cancer).

[Preparation Method]

As one embodiment of the present invention, there is provided an artificially manipulated immune regulatory factor and a method for preparing immune cells including the same.

The description of the artificially manipulated immune regulatory factor may be referred to the description above. Hereinafter, the above method will be described being focused on representative embodiments of manipulated immune cells.

Cell Culture

To produce manipulated immune cells, cells are first harvested from healthy donors and cultured. For example, immune cells (e.g., T cells, NK cells, NKT cells, etc.) are collected from a donor using a known method and cultured in an appropriate cell culture medium.

As described later, some of the immune regulatory factors expressed by cultured immune cells are selected and artificially manipulated. For example, PD-1, CTLA-4, TNFAIP3, DGKA (Dgkα), DGKAZ (Dgkζ), Fas, EGR2, PPP2R2D, PSGL-1, and/or TET2 gene are genetically manipulated. The detailed description of genetic manipulation may be referred to the above.

Alternatively, immune cells are transfected and then cultured to produce manipulated immune cells.

Method of Producing Functionally Manipulated Immune Cells

Functionally manipulated immune cells may be produced by inserting or removing a protein as an immune regulatory factor.

Functionally manipulated immune cells may be produced by modifying a gene as an immune regulatory factor.

Functionally manipulated immune cells may be produced by knockdown (KD) or knockout (KO) of a wild-type receptor or an immune regulatory gene. Knock-down or knockout refers to the suppression of gene expression via cleavage of a target gene, transcriptional inhibitor of DNA, and RNA translation inhibitor (e.g., complementary microRNA, etc.), etc.

Knock-down or knockout may be achieved via microRNA.

Knock-down or knockout may be preferably achieved by a guide nucleic acid-editor protein complex of the present invention.

Knock-down or knockout may be achieved via NHEJ using a genetic scissor.

Knock-down or knockout may be achieved via HR using a genetic scissor and a template of nucleotides.

In one example, knockdown or knockout may be achieved by cleaving specific target sites of PD-1, CTLA-4, TNFAIP3, DGKA (Dgkα), DGKAZ (Dgkζ), Fas, EGR2, PPP2R2D, PSGL-1, and/or TET2 gene.

Functionally manipulated immune cells may include modification of a target region, for example,
- insertion or deletion of one or more nucleotides in the coding region that are very close to or within the coding region of a gene (for example, NHEJ-mediated insertion or deletion);
- deletion of a genomic sequence containing at least part of the gene (e.g., NHEJ-mediated deletion); and
- modification of knockdown or knockout of a gene mediated by an enzymatically inactive editor protein by targeting a non-coding region of a gene (e.g., a promoter region).

Additionally, functionally manipulated immune cells may be produced by transfection of a wild-type receptor or an immune regulatory gene.

The method of transfection includes insertion of episomes containing a target gene or fusion into the genome.

Transfection may be achieved by inserting an episome. An episome vector refers to a vector that acts as an exogenous gene in the nucleus of a eukaryotic organism and is not fused to the genome. In particular, the episome may be a plasmid.

Transfection may be achieved via HR using a guide nucleic acid-editor protein complex and a template of nucleotides.

Additionally, functionally manipulated immune cells may be produced by transfection of a different wild type receptor or immune regulatory gene while simultaneously knocking out a wild-type receptor or an immune regulatory gene. Transfection methods include insertion of episomes containing a target gene or fusion to the genome.

In particular, the gene to be transfected may be fused to the position of the gene to be knocked out.

Transfection may be achieved by inserting an episome.

Transfection may be achieved via HR using a guide nucleic acid-editor protein complex and a template of nucleotides.

Method of Producing Artificial Structure Supplemented Immune Cells

Artificial structure supplemented immune cells may be produced by directly supplementing an artificial structure to the immune cells in the form of a protein.

Artificial structure supplemented immune cells may be produced by transfection of a gene that encodes an artificial structure.

The method of transfection includes insertion of episomes containing a target gene or fusion into the genome.

Transfection may be achieved by inserting an episome.

Transfection may be achieved via HR using a guide nucleic acid-editor protein complex and a template of nucleotides.

In an embodiment, there is provided a method of inactivating one or more immune regulatory genes in an immune cell, which includes introducing a guide nucleic acid and an editor protein into the immune cell (transfection).

In an embodiment, there is provided a method of preparing a transfected immune cell, which includes introducing a guide nucleic acid and an editor protein into the immune cell (transfection).

Method of Producing Hybrid Manipulated Immune Cells

A hybrid manipulated immune cell may be prepared by a method of producing functionally manipulated immune cells and a method of manipulating a protein or gene described in the method of producing artificial structure supplemented immune cells.

The method of producing a hybrid manipulated immune cell includes knocking out a wild-type receptor or immune regulatory factor, or performing transfection. This step may be achieved according to the method described in the method of producing the functionally manipulated immune cells.

The method of producing a hybrid manipulated immune cell includes transfecting an artificial structure. This step may be achieved according to the method described in the method of producing artificial structure supplemented immune cells.

A preferred aspect of the method of producing hybrid manipulated immune cells is to perform transfection of an artificial structure while simultaneously knocking out wild-type receptors of an immune cell.

In one example, the method is to perform transfection of an artificial structure while simultaneously knockout PD-1 and CTLA-4 of an immune cell.

In another example, the method of producing hybrid manipulated immune cells is to perform transfection of an artificial structure while knocking out TNFAIP3 (A20), DGK-alpha, DGK-zeta, Fas, EGR2, PPP2R2D, PSGL-1, KDM6A and/or TET2.

In particular, the gene to be transfected may be fused to the same position as the gene to be knocked out.

The manipulated immune described above may be produced using a known method, for example, commonly employing a recombinant vector.

Recombinant Expression Vector for Immune Cells

The term "expression target sequence" refers to a means for modifying a protein or gene of a target cell, or a nucleotide sequence encoding a gene to be newly expressed. In an embodiment of the present invention, the expression target sequence may include sequences encoding a guide nucleic acid and an editor protein, and additional sequences for expression of the guide nucleic acid and the editor protein.

The term "recombinant vector" refers to a transporter that functions to transport an expression target sequence to a target cell, including, for example, plasmids, episome vectors, viral vectors, etc.

The term "recombinant expression vector", which is an embodiment of a recombinant vector, refers to an artificially constructed vector that exhibits even the function of the expression target sequence linked to the recombinant vector to be expressed in a target cell.

The recombinant expression vector for immune cells, which is a recombinant expression vector, is a means for modifying a protein or gene of an immune cell so as to express the immune cell as a manipulated immune cell; or a recombinant expression vector for encoding a gene to be newly expressed.

The recombinant expression vector for immune cells includes the recombinant expression vector for the expression of a guide nucleic acid-editor protein complex described above.

In an embodiment, the manipulated immune cells may be obtained only by transfecting one kind of a recombinant expression vector for immune cells.

The manipulated immune cells may be obtained by transfecting two or more kinds of a recombinant expression vector for immune cells.

The recombinant expression vector for immune cells may be designed by dividing the recombinant expression vector into an appropriate number of recombinant expression vectors according to the size of the nucleotide sequence to be finally expressed.

(Functionally Manipulated Recombinant Expression Vector)

In an embodiment, there is provided a recombinant expression vector for preparing functionally manipulated immune cells.

In an embodiment, the functionally manipulated recombinant expression vector includes a recombinant nucleotide sequence for knocking out a wild-type receptor or an immune regulatory factor gene.

The recombinant expression vector for knocking out a gene includes a recombinant expression vector for expressing a guide nucleic acid-editor protein complex described above. In particular, the target sequence of gRNA may have complementarity with the nucleotide sequence of a wild-type receptor or a nucleotide sequence of the immune regulatory factor. Additionally, the recombinant expression vector may include a template of nucleotides to be inserted at a position cleaved by a guide nucleic acid-editor protein complex, as necessary.

In an embodiment, the functionally manipulated recombinant expression vector includes a recombinant nucleotide sequence for the transfection of a wild-type receptor or an immune regulatory factor gene.

In particular, the functionally manipulated recombinant expression vector may be an episome vector. The episome vector may include a promoter for gene expression.

In an embodiment, the functionally manipulated recombinant expression vector may be one which has a function to be fused to the genome of a living body. In particular, the functionally manipulated recombinant expression vector may be a viral vector. In particular, a preferred viral vector may be an adeno-associated viral vector.

In an embodiment, the functionally manipulated recombinant expression vector may include a nucleotide sequence that is homologous to the insertion target site. The nucleotide sequence may be a template of nucleotides to be inserted during the HR process. The template of nucleotides may be homologous to the sequenece of the region to be cleaved by a guide nucleic acid-editor protein complex.

In an embodiment, the functionally manipulated recombinant expression vector may include independently a sequence for the expression of the guide nucleic acid-editor protein complex as described above, either in the same vector or in a different vector.

In another aspect, the functionally manipulated recombinant expression vector includes a recombinant nucleotide sequence for knocking out a wild-type receptor or an immune regulatory factor gene, or for the transfection of a different wild-type receptor or immune regulatory factor gene.

The recombinant nucleotide sequence for knocking out a gene includes a nucleotide sequence of the recombinant expression vector for expressing a guide nucleic acid-editor protein complex described above. In particular, the target sequence of gRNA may have complementarity with the nucleotide sequence of the immune regulatory factor.

The recombinant expression vector for transfection may be an episome vector. In particular, the episome vector may include a promoter for gene expression.

The recombinant expression vector for transfection may have a function to be fused to the genome of a living body.

The recombinant expression vector for transfection may be a viral vector. In particular, a preferred viral vector may be an adeno-associated viral vector.

The recombinant expression vector for transfection may include a nucleotide sequence that is homologous to the insertion target site. The nucleotide sequence may be a template of nucleotides to be inserted during the HR process. The template of nucleotides may be homologous to the sequence of the region to be cleaved by a guide nucleic acid-editor protein complex.

Additionally, the functionally manipulated recombinant expression vector may include a recombinant expression vector for the expression of the guide nucleic acid-editor protein complex described above.

(Artificial Structure Supplemented Recombinant Expression Vector)

In an embodiment, there is provided a recombinant expression vector for preparing artificial structure supplemented immune cells.

The artificial structure supplemented recombinant expression vector includes a recombinant nucleotide sequence for transfecting an immune regulatory factor gene.

In one example, the artificial structure supplemented recombinant expression vector may be an episome vector. An episome vector refers to a vector that acts as an exogenous gene in the nucleus of a eukaryotic organism and is not fused to the genome. In particular, the episome vector may include a promoter for gene expression.

In another example, the artificial structure supplemented recombinant expression vector may have a function to be fused to the genome of a living body.

In particular, the artificial structure supplemented recombinant expression vector may be a viral vector. In particular, a preferred viral vector may be an adeno-associated viral vector.

Additionally, the artificial structure supplemented recombinant expression vector may include a nucleotide sequence that is homologous to the insertion site. The nucleotide sequence may be a template of nucleotides to be inserted during the HR process. The template of nucleotides may be homologous to the sequence to be cleaved by a guide nucleic acid-editor protein complex.

Additionally, the artificial structure supplemented recombinant expression vector may include a recombinant expression vector for the expression of the guide nucleic acid-editor protein complex described above.

(Hybrid Manipulated Recombinant Expression Vector)

The hybrid manipulated recombinant expression vector may include a recombinant nucleotide sequence for knocking out a wild-type receptor or immune regulatory factor gene and transfecting a different gene with an artificial structure.

The recombinant nucleotide sequence for knocking out a gene may include a nucleotide sequence of the recombinant expression vector for expressing a guide nucleic acid-editor protein complex described above. In particular, the target sequence of gRNA may have complementarity with the nucleotide sequence of the immune regulatory factor.

In one example, the recombinant expression vector for transfection may be an episome vector. In particular, the episome vector may include a promoter for gene expression.

In another example, the recombinant expression vector for transfection may have a function to be fused to the genome of a living body.

In particular, the recombinant expression vector for transfection may be a viral vector. In particular, a preferred viral vector may be an adeno-associated viral vector.

Additionally, the recombinant expression vector for transfection may include a nucleotide sequence that is homologous to the insertion target site. The nucleotide sequence may be a template of nucleotides to be inserted during the HR process. The template of nucleotides may be homologous to the sequence to be cleaved by a guide nucleic acid-editor protein complex.

Additionally, the functionally manipulated recombinant expression vector may include a recombinant expression vector for the expression of the guide nucleic acid-editor protein complex described above.

Meanwhile, in a specific exemplary embodiment of the present invention, there is provided a method for preparing immune cells which includes an artificially manipulated immune regulatory factor by a guide nucleic acid-editor protein complex.

In an embodiment, the method may be one for preparing manipulated immune cells, in which the sequence of a target nucleic acid in the cell is altered, which include bringing cells into contact with (a) one or more guide nucleic acids (e.g., gRNA) which targets PD-1, CTLA-4, TNFAIP3, DGKA (Dgkα), DGKAZ (Dgkζ), Fas, EGR2, PPP2R2D, PSGL-1 and/or TET2 gene; and (b) an editor protein (e.g., Cas9 protein).

The contacting method may be to introduce the guide nucleic acid and the editor protein directly into the immune cells by a conventional method.

The contacting method may be to introduce each DNA molecule encoding the guide nucleic acid and the editor protein into the immune cells in a state where they are contained in one vector or in a separate vector.

The contact method may be achieved using a vector. The vector may be a viral vector. The viral vector may be, for example, a retrovirus, adeno-associated vector.

In the method, a variety of methods known in the art (e.g., electroporation, liposomes, viral vectors, nanoparticles as well as protein translocation domain (PTD) fusion protein method, etc.) may be employed for the transport into immune cells.

The method may further include introducing gRNA targeting different genes into a cell, or introducing a nucleic acid encoding such gRNA into a cell.

The method may be to proceed in vivo or in vitro, for example, ex vivo.

For example, the contacting may be performed in vitro and the contacted cells may be returned to the body of the subject after the contacting.

The method may employ immune cells or organisms in vivo, for example, immune cells isolated from the human body or artificially produced immune cells. In one example, contacting the cells from the subject suffering from cancer may be included.

The immune cells used in the above method may be immune cells derived from mammals including primates (e.g., humans, monkeys, etc.) and rodents (e.g., mice, rats, etc.). For example, the immune cells may be NKT cells, NK cells, T cells, etc. In particular, the immune cells may be manipulated immune cells to which immune receptors are supplemented (e.g., chimeric antigen receptors (CAR) or manipulated T-cell receptors (TCR) are supplemented). The immune cells may be manipulated such that the immune receptors (e.g., TCR or CAR) are expressed before, after, or simultaneously with regard to the introduction of a target position mutation of immune cells in one or more genes among PD-1, CTLA-4, TNFAIP3, DGKA (Dgkα), DGKAZ (Dgkζ), Fas, EGR2, PPP2R2D, PSGL-1, and/or TET2 gene.

The method may be performed in an appropriate medium for immune cells, which can contain serum (e.g., bovine fetal serum or human serum), interleukin-2 (IL-2), insulin, IFN-gamma, IL-4, IL-7, GM-CSF, IL-10, IL-15, TGF-beta, and TNF-alpha; or in an appropriate medium which may contain factors necessary for proliferation and viability, including other additives for growth of cells known to those skilled in the art (e.g., minimal essential media, RPMI Media 1640, or X-vivo-10, -15, -20, (Lonza)), but the medium is not limited thereto.

[Use]

In an embodiment, the present invention relates to use for the treatment of diseases using immunotherapy approach, which includes administration of artificially manipulated cells (e.g., genetically manipulated immune cells or stem cells) to a subject.

The subject to be treated may be a mammal including primates (e.g., humans, monkeys, etc.) and rodents (e.g., mice, rats, etc.).

Pharmaceutical Composition

One embodiment of the present invention is a composition for use in the treatment of diseases using an immune response, for example, a composition containing an artificially manipulated immune regulatory gene or an immune cell including the same. The composition may be referred to as a therapeutic composition, a pharmaceutical composition, or a cell therapeutic agent.

In an embodiment, the composition may contain immune cells.

In an embodiment, the composition may contain an artificially manipulated gene for immune regulatory and/or a protein expressed thereby.

The immune cells may be immune cells that have already undergone differentiation.

The immune cells may be extracted from bone marrow or umbilical cord blood.

The immune cells may be stem cells. In particular, the stem cells may be hematopoietic stem cells.

The composition may contain manipulated immune cells.

The composition may contain functionally manipulated immune cells.

The composition may contain artificial structure supplemented immune cells.

In another embodiment, the composition may further contain additional factors.

The composition may contain an antigen binding agent.

The composition may contain cytokines.

The composition may contain a secretagogue or inhibitor of cytokines.

The composition may contain a suitable carrier for the delivery of the manipulated immune cell into the body.

The immune cells contained in the composition may be allogenic to the patient.

Method of Treatment

Another embodiment of the present invention is a method of treating a disease in a patient, which includes administering the composition, in which the production of the composition and an effective amount of the composition are described above, to a patient in need thereof.

In an embodiment, the method may be one which utilizes adoptive immunotherapy.

Disease to be Treated

Adoptive immunotherapy may be to treat any specific disease.

The any specific disease may be an immune disease. In particular, immune disease may be a disease in which immune competence is deteriorated.

The immune disease may be an autoimmune disease.

For example, the autoimmune disease may include graft versus host disease (GVHD), systemic lupus erythematosus, celiac disease, diabetes mellitus type 1, graves disease, inflammatory bowel disease, psoriasis, rheumatoid arthritis, multiple sclerosis, etc.

The immune disease may be a hyperplastic disease.

For example, the immune disease may be hematologic malignancy or solid cancer. Representative hematologic malignancies include acute lymphoblastic leukemia (ALL), acute myelogenous leukemia (AML), chronic myelogenous leukemia (CML), chronic eosinophils leukemia (CEL), myelodysplastic syndrome (MDS), non-Hodgkin's lymphoma (NHL), and multiple myeloma (MM). Examples of solid tumors include biliary tract cancer, bladder cancer, bone and soft tissue carcinoma, brain tumor, breast cancer, uterine cervical cancer, colon cancer, colon adenocarcinoma, colorectal cancer, desmoid tumor, embryonic cancer, endometrial cancer, esophageal cancer, gastric cancer, gastric adenocarcinoma, glioblastoma multiforme, gynecologic tumors, head and neck squamous cell carcinoma, hepatic cancer, lung cancer, malignant melanoma, osteosarcoma, ovarian cancer, pancreatic cancer, pancreatic duct adenocarcinoma, primary astrocytic tumor, primary thyroid cancer, prostate cancer, kidney cancer, renal cell carcinoma, rhabdomyosarcoma, skin cancer, soft tissue sarcoma, testicular germ cell tumor, urinary epithelial cell cancer, uterine sarcoma, uterine cancer, etc.

A wide range of cancers, including solid malignant tumors and hematologic malignancies, may be subject diseases to be treated.

For example, the types of cancer that can be treated include breast, prostate, pancreas, colon and rectal adenocarcinoma; bronchogenic carcinoma of lungs in all forms (including squamous cell carcinoma, adenocarcinoma, small cell lung cancer and non-small cell lung cancer); myeloma; melanoma; hepatoma; neuroblastoma; papilloma; apudoma; choristoma; branchial cleft cyst; malignant carcinoid syndrome; carcinoid heart disease; and carcinoma (e.g., Walker, basal cell, basosquamous, Brown-Pierce, duct, Ehrlich tumor, Krebs-2, Merkel cells, mucinous, non-small cell lung, oat cell, papillary, scirrhous, bronchiolar, bronchogenic, squamous cell and transitional cell).

For example, additional types of cancer that may be treated include: histiocytocytic disorder; leukemia; malignant histiocytosis; Hodgkin's disease; non-Hodgkin's lymphoma; plasmacytoma, reticuloendothelioma; melanoma; renal cell carcinoma; chondroblastoma; chondroma; chondrosarcoma; fibroma; fibrosarcoma; giant cell tumors; histiocytoma, lipoma, liposarcoma; mesothelioma; myxoma; myxosarcoma; osteoma; osteosarcoma; chordoma, craniopharyngioma; dysgerminoma; hamartoma; mesenchymoma; mesonephroma; myosarcoma; adamantio; cementoma; odontoma; teratoma; thymoma; and trophoblastic tumor.

Further, the following types of cancers may also be considered as amenable to treatment: adenoma; cholangioma; cholesteatoma; cylindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; uterine leiomyoma; uterine sarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; and glioblastoma multiforme.

The types of cancers that may be treated also include angiokeratoma; angiolymphoid hyperplasia with eosinophilia; vascular sclerosis; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangio sarcoma; myosarcoma; myxosarcoma; ovarian carcinoma; rhabdomyosarcoma; sarcoma; neoplasm; neurofibromatosis, and cervical dysplasia.

Additionally, any specific disease may be a refractory disease for which pathogens are known but the treatment is unknown.

The refractory disease may be a viral infection disease.

The refractory disease may be a disease caused by a prion pathogen.

Any specific disease may be a bacterial disease.

Any specific disease may be an inflammatory disease.

Any specific disease may be an aging-related disease.

Immunity-Enhancing Treatment

For patients with significantly decreased immunity, even mild infections can result in fatal consequences. Decreased immunity is caused by the functional decline of immune cells, a decreased amount of immune cell production, etc. As methods for enhancing immunity to treat the deterioration in immune function, one may be a permanent treatment method that activates the production of normal immune cells, and the other may be a temporary treatment method in which immune cells are temporarily injected.

The immunity-enhancing treatment may be intended to inject the therapeutic composition into the body of a patient to permanently enhance the immunity.

The immunity-enhancing treatment may be a method of injecting the therapeutic composition into a specific body part of the patient. In particular, the specific body part may be a part having tissues supply immune cell sources.

The immunity-enhancing treatment may be to create a new source of immune cells in the body of the patient. In particular, in one example, the therapeutic composition may include stem cells. In particular, the stem cells may be hematopoietic stem cells.

The immunity-enhancing treatment may be intended to inject the therapeutic composition into the body of a patient to temporarily enhance the immunity.

The immunity-enhancing treatment may be to inject a therapeutic composition into the body of a patient.

In particular, a preferred therapeutic composition may contain differentiated immune cells.

The therapeutic composition used in the immunity-enhancing treatment may contain a specific number of immune cells.

The specific number may vary depending on the degree of deterioration of the immunity.

The specific number may vary depending on the volume of the body.

The specific number can be adjusted according to the amount of cytokines released from the patient.

Treatment of Refractory Disease

Immune cell manipulation techniques may provide a method for treating diseases in which complete treatment for pathogens such as HIV, prions, and cancer is not known. Although pathogens for these diseases are known, in many cases, these diseases are difficult to treat because there are problems in that antibodies are hardly formed, the diseases are rapidly progressed and inactivate immune system of the patient, and the pathogens have a latent period in the body. Manipulated immune cells may be a powerful means to solve these problems.

Treatment of refractory disease may be performed by injecting the therapeutic composition into the body. In particular, a preferred therapeutic composition may contain manipulated immune cells. In addition, the therapeutic composition may be injected into a specific part of the body.

Manipulated immune cells may be those in which the immune cells have an improved ability of recognizing the pathogen of the target disease.

Manipulated immune cells may be those in which the intensity or activity of the immune response is enhanced.

Gene-Correction Treatment

In addition to the treatment method using exogenously extracted immune cells, there may be a treatment method that directly affects the expression of immune cells by manipulating the gene of a living body. Such a treatment method may be achieved by directly injecting a gene-correction composition for manipulating a gene into the body.

The gene-correction composition may contain a guide nucleic acid-editor protein complex.

The gene-correction composition may be injected into a specific part of the body.

The specific part of the body can be an immune cell source, for example, bone marrow.

One embodiment of the present invention relates to a method of treating an immune-related disease by administering to a subject an effective amount of a composition containing the components of an artificially manipulated immune system described above.

In any embodiment, the treatment methods provide a use of cell populations manipulated or modified in a recombinant manner ex vivo, e.g., via viral vectors. In a further embodiment, the modified cell population is a homologous, allogeneic, or autologous cell. In any of the aforementioned embodiments, the manipulated or modified cell population may be further formulated with a pharmaceutically acceptable carrier, diluent, or excipient as described herein.

The subject to be administered may be a mammal including primates, e.g., humans, monkeys, etc.; and rodents, e.g., mice, rats, etc.

Administration refers to the delivering objects to a subject, regardless of the route or mode of the delivery. The administration may be performed continuously or intermittently, and parenterally.

In certain embodiments, co-administration with an adjuvant therapeutic agent may involve simultaneous and/or sequential delivery of multiple agents in any order and any dosage regimen (for example, administration of one or more cytokines together with antigen-specific recombinant host T cells and antigen expressing cells; immunosuppressive therapy, for example, calcineurin inhibitors, corticosteroids, microtubule inhibitors, low-dose mycophenolic acid prodrugs, or any combination thereof).

In certain embodiments, the administration may be repeated multiple times and for a period of a few weeks, a few months, or up to two years.

The composition may be administered in a manner suitable for the disease or conditions being treated or prevented, as determined by those skilled in the medical arts. An appropriate dose, a suitable duration, and frequency for administration of the composition will be determined by factors, such as the health condition of the patient, the size of the patient (i.e., weight, mass, body area), the type and severity of the patient's disease, the particular form of the active ingredient, and the method of administration.

For example, administration of the composition may be performed in any convenient manner, e.g., injection, transfusion, implantation, transplantation, etc.). The route of administration may be selected from subcutaneous, intradermal, intratumoral, intranodal, intramedullary, intramuscular, intravenous, intralymphatic, intraperitoneal, intraperitoneal, intraperitoneal administrations, etc.

A single dose of the composition (a pharmaceutically effective amount for achieving the desired effect) may be selected from among all the integer values in the range of about $10^4$ to $10^9$ cells/kg of body weight of the subject (e.g., about $10^5$ to $10^6$ cells/kg (body weight)) to be administered, but the dose is not limited thereto, and the single dose of the composition may be appropriately prescribed considering the age, health conditions and weight of the subject to be administered, kind of concurrent treatment, if any, frequency of treatment, and the nature of the desired effect.

When an artificially manipulated immune regulatory factor is regulated by the methods, compositions of the present specification, the immune efficacy involved in survival, proliferation, persistency, cytotoxicity, cytokine-release and/or infiltration, etc. of immune cells may be improved.

EXAMPLES

Example 1: Cell Preparation (Activation & Culture) and Transfection

Jurkat cells (ATCC TIB-152; immortalized cell line of human T-cells) were cultured in RPMI 1640 medium supplemented with 10% (v/v) fetal bovine serum (GeneAll). The cells were incubated in an incubator under 37° C. and 5% $CO_2$ conditions.

Human Naive T-cells (STEMCELL Technology) were cultured in X-VIVO 15 medium (Lonza) supplemented with 10% (v/v) fetal bovine serum (GeneAll) and/or IL-2 (50 U/mL), IL-7 (5 ng/mL), and IL-15 (5 ng/mL)(PEPROTECH). For cell activation, the concentration of cells in the medium had kept as 1×10^6 cells/mL, respectively.

CD2/CD3/CD28 beads (anti-CD2/3/CD28 Dynabeads; Miltenyi Biotec) were added at a ratio of 3:1 (beads:cells; Number of beads and cells), and the cells were incubated in an incubator under 37° C. and 5% $CO_2$ conditions. After performing the cell activation for 72 hours, the CD2/CD3/CD28 beads were removed using a magnet, and the cells were further cultured for 12-24 hours in the absence of beads.

In order to find a gRNA capable of knocking out a specific gene at a high efficiency, 1 ug of in vitro transcribed sgRNA and 4 ug of Cas9 protein (Toolgen, Korea) were introduced into 1×10^6 Jurkat cells by electroporation (in vitro) as described in Examples 2 and 3 below. Using 10 uL tip of Neon Transfection System (ThermoFisher Scientific, Grand Island, NY), the gene was introduced under the following conditions:

Jurkats (Buffer R): 1,400 V, 20 ms, 2 pulses.

Similarly, 1 ug gRNA and 4 ug Cas9 protein (Toolgen, Korea) were introduced into 1×10^6 human primary T cells by electroporation to knock-out specific genes in T cells. The gRNA used in this study is in vitro transcribed and AP (alkaline phosphatase) treated sgRNA; or chemically synthesized crRNA and tracrRNA complex (Integrated DNA Technologies). For electroporation, a 10 uL tip of Neon Transfection System (ThermoFisher Scientific, Grand Island, NY) was used to introduce the gene under the following conditions:

Human primary T-cells (Buffer T): 1,550 V, 10 ms, 3 pulses;

The cells were plated on 500 ul of non-antibiotic medium and cultured in an incubator at 37° C. and 5% $CO_2$.

Example 2: Design and Synthesis of sgRNA 2.1. Design of sgRNA

CRISPR/Cas9 target regions of human PD-1 gene (PDCD1; NCBI Accession No. NM_005018.2), CTLA-4 gene (NCBI Accession No. NM_001037631.2), A20 gene (TNFAIP3; NCBI Accession No. NM_001270507.1), Dgk-alpha gene (NCBI Accession No. NM_001345.4), Dgk-zeta gene (NCBI Accession No. NM_001105540.1), Egr2 gene (NCBI Accession No. NM_000399.4), PPP2r2d gene (NCBI Accession No. NM_001291310.1), PSGL-1 gene (NCBI Accession No. NP_001193538.1), and Tet2 gene (NCBI Accession No. NM_017628.4) were selected using CRISPR RGEN Tools (Institute for Basic Science, Korea) and estimated by off-target test. For CRISPR/Cas9 target regions, DNA sequences without 0-, 1-, or 2 bp mismatch sites were selected as target regions of the sgRNA, except for the on-target sequence regions in the human genome (GRCh38/hg38).

2.2 Synthesis of sgRNA

Templates for sgRNA synthesis were PCR-amplified by annealing and extending two complementary oligonucleotides.

The target regions sequence used at this time, the primer sequence for amplifying them, and the DNA target sequence targeted by the sgRNA obtained therefrom are described in Table 2 below.

In vitro transcription was performed using T7 RNA polymerase (New England Biolabs) for the template DNA (except for 'NGG' at the 3' end of the target sequence), RNA was synthesized according to the manufacturer's instructions, and then DNAase (Ambion) was used to remove template DNA. The transcribed RNA was purified by Expin Combo kit (GeneAll) and isopropanol precipitation In experiments using T cells, in order to minimize the immunogenicity and degradation of sgRNA, the 5'terminal phosphate residues were removed from the sgRNA synthesized by the above method using alkaline phosphatase (New England Biolabs) and then the RNA was purified again by the Expin Combo kit (GeneAll) and isopropanol precipitation. In addition, chemically synthesized sgRNA (Trilink) was used in some T cell experiments.

The chemically synthesized sgRNA used in a certain example was sgRNA modified with 2'OMe and phosphorothioate.

For example, DGKα sgRNA #11 used in this example has a structure of 5'-2'OMe(C(ps)U(ps)C(ps)) UCA AGC UGA GUG GGU CCG UUU UAG AGC UAG AAA UAG CAA GUU AAA AUA AGG CUA GUC CGU UAU CAA CUU GAA AAA GUG GCA CCG AGU CGG UGC 2'OMe(U (ps)U(ps)U(ps)U-3' (2'OMe=2'-methyl RNA and ps=phosphorothioate) (SEQ ID NO: 329).

In another example, A20 sgRNA #1 used in this embodiment is GCUUGUGGCGCUGAAAACGAAGUUUUA-GAGCUAGAAAUAGCAAGUUAAAAUAAG GCUA-GUCCGUUAUCAACUUGAAAAAGUGGCACCGA GUCGGUGCUUUUUUU (SEQ ID NO: 330) (the bold part is the sequence being that hybridizes to the target sequence region; sgRNA for other target gene or other target sequence is that the bold sequence has a target sequence Oust, T is changed to U)), modified thereof in which the three nucleotides at the 3' end of the sequence and the three nucleotides at the 5' end is modified with 2'-OMe and a phosphorothioate backbone introduction)

TABLE 2

| Gene | # | DNA target sequence | Forward primer sequence | Reverse primer | SEQ ID NO |
|---|---|---|---|---|---|
| A20 | 1 | CTTGTGGCGCTGA AAACGAACGG | GAAATTAATACGAC TCACTATAGCTTGT GGCGCTGAAAACG AAGTTTTAGAGCTA GAAATAGC | AAAAAAAGC ACCGACTCG GTGCCACTTT TTCAAGTTGA TAACGGACT | SEQ ID NO 1 |
|  | 2 | ATGCCACTTCTCA GTACATGTGG | GAAATTAATACGAC TCACTATAGATGCC ACTTCTCAGTACAT GGTTTTAGAGCTAG AAATAGC | AGCCTTATTT TAACTTGCTA TTTCTAGCTC TAAAAC | SEQ ID NO 2 |
|  | 3 | GCCACTTCTCAGT ACATGTGGG | GAAATTAATACGAC TCACTATAGGCCAC TTCTCAGTACATGT GGTTTTAGAGCTAG AAATAGC |  | SEQ ID NO 3 |
|  | 4 | GCCCCACATGTAC TGAGAAGTGG | GAAATTAATACGAC TCACTATAGGCCCC ACATGTACTGAGAA GGTTTTAGAGCTAG AAATAGC |  | SEQ ID NO 4 |
|  | 5 | TCAGTACATGTGG GGCGTTCAGG | GAAATTAATACGAC TCACTATAGTCAGT ACATGTGGGGCGTT CGTTTTAGAGCTAG AAATAGC |  | SEQ ID NO 5 |
|  | 6 | GGGCGTTCAGGA CACAGACTTGG | GAAATTAATACGAC TCACTATAGGGCG TTCAGGACACAGAC TGTTTTAGAGCTAG AAATAGC |  | SEQ ID NO 6 |
|  | 7 | CACAGACTTGGTA CTGAGGAAGG | GAAATTAATACGAC TCACTATAGCACAG ACTTGGTACTGAGG AGTTTTAGAGCTAG AAATAGC |  | SEQ ID NO 7 |
|  | 8 | GGCGCTGTTCAGC ACGCTCAAGG | GAAATTAATACGAC CACTATAGGGCGC TGTTCAGCACGCTC AGTTTTAGAGCTAG AAATAGC |  | SEQ ID NO 8 |
|  | 9 | CACCAACTTTAA | GAAATTAATACGAC TCACTATAGCACGC AACTTTAAATTCCG CGTTTTAGAGCTAG AAATAGC |  | SEQ ID NO 9 |
|  | 10 | CGGGGCTTTGCTA TGATACTCGG | GAAATTAATACGAC TCACTATAGCGGGG CTTTGCTATGATACT GTTTTAGAGCTAGA AATAGC |  | SEQ ID NO 10 |
|  | 11 | GGCTTCCACAGA CACACCCATGG | GAAATTAATACGAC TCACTATAGGGCTT CCACAGACACACCC AGTTTTAGAGCTAG AAATAGC |  | SEQ ID NO 11 |
|  | 12 | TGAAGTCCACTTC GGGCCATGGG | GAAATTAATACGAC TCACTATAGTGAAG TCCACTTCGGGCCA TGTTTTAGAGCTAG AAATAGC |  | SEQ ID NO 12 |

| Gene | # | DNA target sequence | Forward primer sequence | Reverse primer | SEQ ID NO |
|---|---|---|---|---|---|
| DGKα | 1 | CTGTACGACACG GACAGAAATGG | GAAATTAATACGAC TCACTATAGCTGTA CGACACGGACAGA AAGTTTTAGAGCTA GAAATAGC | AAAAAAAGC ACCGACTCG GTGCCACTTT TTCAAGTTGA TAACGGACT | SEQ ID NO 13 |
|  | 2 | TGTACGACACGG ACAGAAATGGG | GAAATTAATACGAC TCACTATAGTGTAC GACACGGACAGAA ATGTTTTAGAGCTA GAAATAGC | AGCCTTATTT TAACTTGCTA TTTCTAGCTC TAAAAC | SEQ ID NO 14 |

TABLE 2-continued

| | # | DNA target sequence | Forward primer sequence | Reverse primer | SEQ ID NO |
|---|---|---|---|---|---|
| | 3 | CACGGACAGAAA TGGGATCCTGG | GAAATTAATACGAC TCACTATAGCACGG ACAGAAATGGGATC CGTTTTAGAGCTAG AAATAGC | | SEQ ID NO 15 |
| | 4 | GATGCGAGTGGC TGAATACCTGG | GAAATTAATACGAC TCACTATAGGATGC GAGTGGCTGAATAC CGTTTTAGAGCTAG AAATAGC | | SEQ ID NO 16 |
| | 5 | GAGTGGCTGAAT ACCTGGATTGG | GAAATTAATACGAC TCACTATAGGAGTG GCTGAATACCTGGA TGTTTTAGAGCTAG AAATAGC | | SEQ ID NO 17 |
| | 6 | AGTGGCTGAATAC CTGGATTGGG | GAAATTAATACGAC TCACTATAGAGTGG CTGAATACCTGGAT TGTTTTAGAGCTAG AAATAGC | | SEQ ID NO 18 |
| | 7 | ATTGGGATGTGT CTGAGCTGAGG | GAAATTAATACGAC TCACTATAGATTGG GATGTGTCTGAGCT GGTTTTAGAGCTAG AAATAGC | | SEQ ID NO 19 |
| | 8 | ATGAAAGAGATT GACTATGATGG | GAAATTAATACGAC TCACTATAGATGAA AGAGATTGACTATG AGTTTTAGAGCTAG AAATAGC | | SEQ ID NO 20 |
| | 9 | CTCTGTCTCTCAA GCTGAGTGGG | GAAATTAATACGAC TCACTATAGCTCTG TCTCTCAAGCTGAG TGTTTTAGAGCTAG AAATAGC | | SEQ ID NO 21 |
| | 10 | TCTCTCAAGCTGA GTGGGTCCGG | GAAATTAATACGAC TCACTATAGTCTCTC AAGCTGAGTGGGTC GTTTTAGAGCTAGA AATAGC | | SEQ ID NO 22 |
| | 11 | CTCTCAAGCTGA GTGGGTCCGGG | GAAATTAATACGAC TCACTATAGCTCTC AAGCTGAGTGGGTC CGTTTTAGAGCTAG AAATAGC | | SEQ ID NO 23 |
| | 12 | CAAGCTGAGTGG GTCCGGGCTGG | GAAATTAATACGAC TCACTATAGCAAGC TGAGTGGGTCCGG GCGTTTTAGAGCTA GAAATAGC | | SEQ ID NO 24 |

| Gene | # | DNA target sequence | Forward primer sequence | Reverse primer | SEQ ID NO |
|---|---|---|---|---|---|
| EGR2 | 1 | TTGACATGACTG GAGAGAAGAGG | GAAATTAATACGAC TCACTATAGTTGAC ATGACTGGAGAGA AGGTTTTAGAGCTA GAAATAGC | AAAAAAGC ACCGACTCG GTGCCACTTT TTCAAGTTGA TAACGGACT | SEQ ID NO 25 |
| | 2 | GACTGGAGAGAA GAGGTCGTTGG | GAAATTAATACGAC TCACTATAGGACTG GAGAGAAGAGGTC GTGTTTTAGAGCTA GAAATAGC | AGCCTTATTT TAACTTGCTA TTTCTAGCTC TAAAAC | SEQ ID NO 26 |
| | 3 | GAGACGGGAGCA AAGCTGCTGGG | GAAATTAATACGAC TCACTATAGGAGAC GGGAGCAAAGCTG CTGTTTTAGAGCTA GAAATAGC | | SEQ ID NO 27 |
| | 4 | AGAGACGGGAGC AAAGCTGCTGG | GAAATTAATACGAC TCACTATAGAGAGA CGGGAGCAAAGCT GCGTTTTAGAGCTA GAAATAGC | | SEQ ID NO 28 |
| | 5 | AGAGACGGGAGC AAAGCTGCTGG | GAAATTAATACGAC TCACTATAGTGGTTT CTAGGTGCAGAGAC GTTTTAGAGCTAGA AATAGC | | SEQ ID NO 29 |

TABLE 2-continued

| | | | |
|---|---|---|---|
| 6 | TAAGTGAAGGTCT GGTTTCTAGG | GAAATTAATACGAC TCACTATAGTAAGT GAAGGTCTGGTTTC TGTTTTAGAGCTAG AAATAGC | SEQ ID NO 30 |
| 7 | TGCCCATGTAAGT GAAGGTCTGG | GAAATTAATACGAC TCACTATAGTGCCC ATGTAAGTGAAGGT CGTTTTAGAGCTAG AAATAGC | SEQ ID NO 31 |
| 8 | GAACTTGCCCATG TAAGTGAAGG | GAAATTAATACGAC TCACTATAGGAACT TGCCCATGTAAGTG AGTTTTAGAGCTAG AAATAGC | SEQ ID NO 32 |
| 9 | TCCATTGACCCTC AGTACCCTGG | GAAATTAATACGAC TCACTATAGTCCATT GACCCTCAGTACCC GTTTTAGAGCTAGA AATAGC | SEQ ID NO 33 |
| 10 | TATGCCTTCTGGG TAGCAGCTGG | GAAATTAATACGAC TCACTATAGTATGC CTTCTGGGTAGCAG CGTTTTAGAGCTAG AAATAGC | SEQ ID NO 34 |
| 11 | TGAGTGCAGGCAT CTTGCAAGGG | GAAATTAATACGAC TCACTATAGTGAGT GCAGGCATCTTGCA AGTTTTAGAGCTAG AAATAGC | SEQ ID NO 35 |
| 12 | GAGTGCAGGCAT CTTGCAAGGGG | GAAATTAATACGAC TCACTATAGGAGTG CAGGCATCTTGCAA GGTTTTAGAGCTAG AAATAGC | SEQ ID NO 36 |
| 13 | GATGAGGCTGTG GTTGAAGCTGG | GAAATTAATACGAC TCACTATAGGATGA GGCTGTGGTTGAAG CGTTTTAGAGCTAG AAATAGC | SEQ ID NO 37 |
| 14 | CCACTGGCCACA GGACCCCTGGG | GAAATTAATACGAC TCACTATAGCCACT GGCCACAGGACCC CTGTTTTAGAGCTA GAAATAGC | SEQ ID NO 38 |
| 15 | GGGACATGGTGC ACACACCCAGG | GAAATTAATACGAC TCACTATAGGGGAC ATGGTGCACACACC CGTTTTAGAGCTAG AAATAGC | SEQ ID NO 39 |
| 16 | GAGTACAGGTGG TCCAGGTCAGG | GAAATTAATACGAC TCACTATAGGAGTA CAGGTGGTCCAGGT CGTTTTAGAGCTAG AAATAGC | SEQ ID NO 40 |
| 17 | GCGGAGAGTACA GGTGGTCCAGG | GAAATTAATACGAC TCACTATAGGCGGA GAGTACAGGTGGTC CGTTTTAGAGCTAG AAATAGC | SEQ ID NO 41 |
| 18 | GCGGTGGCGGAG AGTACAGGTGG | GAAATTAATACGAC TCACTATAGGCGGT GGCGGAGAGTACA GGGTTTTAGAGCTA GAAATAGC | SEQ ID NO 42 |
| 19 | TCTCCTGCACAGC CAGAATAAGG | GAAATTAATACGAC TCACTATAGTCTCCT GCACAGCCAGAAT AGTTTTAGAGCTAG AAATAGC | SEQ ID NO 43 |
| 20 | ACGCAGAAGGGT CCTGGTAGAGG | GAAATTAATACGAC TCACTATAGACGCA GAAGGGTCCTGGTA GGTTTTAGAGCTAG AAATAGC | SEQ ID NO 44 |
| 21 | AGGTGGTGGGTA GGCCAGAGAGG | GAAATTAATACGAC TCACTATAGAGGTG GTGGGTAGGCCAG AGGTTTTAGAGCTA GAAATAGC | SEQ ID NO 45 |

TABLE 2-continued

| | | DNA target sequence | Forward primer sequence | Reverse primer | SEQ ID NO |
|---|---|---|---|---|---|
| | 22 | CCCAAGCCAGCC ACGGACCCAGG | GAAATTAATACGAC TCACTATAGCCCAA GCCAGCCACGGAC CCGTTTTAGAGCTA GAAATAGC | | SEQ ID NO 46 |
| | 23 | ACCTGGGTCCGTG GCTGGCTTGG | GAAATTAATACGAC TCACTATAGACCTG GGTCCGTGGCTGGC TGTTTTAGAGCTAG AAATAGC | | SEQ ID NO 47 |
| | 24 | AAGAGACCTGGG TCCGTGGCTGG | GAAATTAATACGAC TCACTATAGAAGAG ACCTGGGTCCGTGG CGTTTTAGAGCTAG AAATAGC | | SEQ ID NO 48 |
| | 25 | GGATCATTGGGA AGAGACCTGGG | GAAATTAATACGAC TCACTATAGGGATC ATTGGGAAGAGAC CTGTTTTAGAGCTA GAAATAGC | | SEQ ID NO 49 |
| | 26 | GGGATCATTGGG AAGAGACCTGG | GAAATTAATACGAC TCACTATAGGGGAT CATTGGGAAGAGA CCGTTTTAGAGCTA GAAATAGC | | SEQ ID NO 50 |
| | 27 | CAGGATAGTCTGG GATCATTGGG | GAAATTAATACGAC TCACTATAGCAGGA TAGTCTGGGATCAT TGTTTTAGAGCTAG AAATAGC | | SEQ ID NO 51 |
| | 28 | GGAAAGAATCCA GGATAGTCTGG | GAAATTAATACGAC TCACTATAGGGAAA GAATCCAGGATAGT CGTTTTAGAGCTAG AAATAGC | | SEQ ID NO 52 |
| | 29 | CAGTGCCAGAGA GACCTACATGG | GAAATTAATACGAC TCACTATAGCAGTG CCAGAGAGACCTAC AGTTTTAGAGCTAG AAATAGC | | SEQ ID NO 53 |
| | 30 | CTGTACCATGTAG GTCTCTCTGG | GAAATTAATACGAC TCACTATAGCTGTA CCATGTAGGTCTC CGTTTTAGAGCTAG AAATAGC | | SEQ ID NO 54 |
| | 31 | AGAGACCTACAT GGTACAGCTGG | GAAATTAATACGAC TCACTATAGAGA CCTACATGGTACAG CGTTTTAGAGCTAG AAATAGC | | SEQ ID NO 55 |
| | 32 | CTGGGCCAGCTGT ACCATGTAGG | GAAATTAATACGAC TCACTATAGCTGGG CCAGCTGTACCATG TGTTTTAGAGCTAG AAATAGC | | SEQ ID NO 56 |
| | 33 | AGGGAAAGGGCT TACGGTCTGGG | GAAATTAATACGAC TCACTATAGAGGGA AAGGGCTTACGGTC TGTTTTAGAGCTAG AAATAGC | | SEQ ID NO 57 |
| | 34 | CAGGGAAAGGGC TTACGGTCTGG | GAAATTAATACGAC TCACTATAGCAGGG AAAGGGCTTACGGT CGTTTTAGAGCTAG AAATAGC | | SEQ ID NO 58 |

| Gene | # | DNA target sequence | Forward primer sequence | Reverse primer | SEQ ID NO |
|---|---|---|---|---|---|
| PPP2R2D | 5 | TCTGGAGATCTTC TTGCAACAGG | GAAATTAATACGAC TCACTATAGTCTGG AGATCTTCTTGCAA CGTTTTAGAGCTAG AAATAGC | | SEQ ID NO 59 |
| | 6 | CTCCGGTTCATGA CTTTGAAAGG | GAAATTAATACGAC TCACTATAGCTCCG GTTCATGACTTTGA AGTTTTAGAGCTAG AAATAGC | | SEQ ID NO 60 |

TABLE 2-continued

| | | | |
|---|---|---|---|
| 7 | GTCTTCCATCTTC GTCTTTCAGG | GAAATTAATACGAC TCACTATAGGTCTT CCATCTTCGTCTTTC GTTTTAGAGCTAGA AATAGC | SEQ ID NO 61 |
| 8 | GAAGACTTCGAG ACCCATTTAGG | GAAATTAATACGAC TCACTATAGGAAGA CTTCGAGACCCATT TGTTTTAGAGCTAG AAATAGC | SEQ ID NO 62 |
| 9 | TCGAGACCCATTT AGGATCACGG | GAAATTAATACGAC TCACTATAGTCGAG ACCCATTTAGGATC AGTTTTAGAGCTAG AAATAGC | SEQ ID NO 63 |
| 10 | GTAGCGCCGTGA TCCTAAATGGG | GAAATTAATACGAC TCACTATAGGTAGC GCCGTGATCCTAAA TGTTTTAGAGCTAG TGTTTTAGAGCTAG AAATAGC | SEQ ID NO 64 |
| 11 | CGTAGCGCCGTG ATCCTAAATGG | GAAATTAATACGAC TCACTATAGCGTAG CGCCGTGATCCTAA AGTTTTAGAGCTAG AAATAGC | SEQ ID NO 65 |
| 12 | CATTTAGGATCAC GGCGCTACGG | GAAATTAATACGAC TCACTATAGCATTTA GGATCACGGCGCTA GTTTTAGAGCTAGA AATAGC | SEQ ID NO 66 |
| 13 | GGTCCCAATATTG AAGCCCATGG | GAAATTAATACGAC TCACTATAGGGTCC CAATATTGAAGCCC AGTTTTAGAGCTAG AAATAGC | SEQ ID NO 67 |
| 14 | GATCCATGGGCTT CAATATTGGG | GAAATTAATACGAC TCACTATAGGATCC ATGGGCTTCAATAT TGTTTTAGAGCTAG AAATAGC | SEQ ID NO 68 |
| 15 | AGATCCATGGGCT TCAATATTGG | GAAATTAATACGAC TCACTATAGAGATC CATGGGCTTCAATA TGTTTTAGAGCTAG AAATAGC | SEQ ID NO 69 |
| 16 | GCTTCTACCATAA GATCCATGGG | GAAATTAATACGAC TCACTATAGGCTTC TACCATAAGATCCA TGTTTTAGAGCTAG AAATAGC | SEQ ID NO 70 |
| 17 | CGCTTCTACCATA AGATCCATGG | GAAATTAATACGAC TCACTATAGCGCTT CTACCATAAGATCC AGTTTTAGAGCTAG AAATAGC | SEQ ID NO 71 |
| 18 | GCATTTGCAAAAA TTCGCCGTGG | GAAATTAATACGAC TCACTATAGGCATT TGCAAAAATTCGCC GGTTTTAGAGCTAG AAATAGC | SEQ ID NO 72 |
| 19 | ATGACCTGAGAAT TAATTTATGG | GAAATTAATACGAC TCACTATAGATGAC CTGAGAATTAATTT AGTTTTAGAGCTAG AAATAGC | SEQ ID NO 73 |
| 20 | CCATGCACTCCCA GACATCGTGG | GAAATTAATACGAC TCACTATAGCCATG CACTCCCAGACATC GGTTTTAGAGCTAG AAATAGC | SEQ ID NO 74 |
| 21 | GCACTGGTGCGG GTGGAACTCGG | GAAATTAATACGAC TCACTATAGGCACT GGTGCGGGTGGAA CTGTTTTAGAGCTA GAAATAGC | SEQ ID NO 75 |

TABLE 2-continued

| | # | DNA target sequence | Forward primer sequence | Reverse primer | SEQ ID NO |
|---|---|---|---|---|---|
| | 22 | ACACGTTGCACTG GTGCGGGTGG | GAAATTAATACGAC TCACTATAGACACG TTGCACTGGTGCGG GGTTTTAGAGCTAG AAATAGC | | SEQ ID NO 76 |
| | 23 | CGAACACGTTGCA CTGGTGCGGG | GAAATTAATACGAC TCACTATAGCGAAC ACGTTGCACTGGTG CGTTTTAGAGCTAG AAATAGC | | SEQ ID NO 77 |
| | 24 | ACGAACACGTTGC ACTGGTGCGG | GAAATTAATACGAC TCACTATAGACGAA CACGTTGCACTGGT GGTTTTAGAGCTAG AAATAGC | | SEQ ID NO 78 |
| | 25 | TGTAGACGAAGA CGTTGCACTGG | GAAATTAATACGAC TCACTATAGTGTAG ACGAACACGTTGCA CGTTTTAGAGCTAG AAATAGC | | SEQ ID NO 79 |
| | 26 | GCGCATGTCACA AGGCGGATGG | GAAATTAATACGAC TCACTATAGGCGCA TGTCACACAGGCGG AGTTTTAGAGCTAG AAATAGC | | SEQ ID NO 80 |
| | 27 | AGGAGCGCATGT CACACGGCGG | GAAATTAATACGAC TCACTATAGAGGAG CGCATGTCACACAG GGTTTTAGAGCTAG AAATAGC | | SEQ ID NO 81 |
| | 28 | CCGAGGAGCGCA TGTCACACAGG | GAAATTAATACGAC TCACTATAGCCGAG GAGCGCATGTCACA CGTTTTAGAGCTAG AAATAGC | | SEQ ID NO 82 |
| | 29 | CCTGTGTGACATG CGCTCCTCGG | GAAATTAATACGAC TCACTATAGCCTGT GTGACATGCGCTCC TGTTTTAGAGCTAG AAATAG | | SEQ ID NO 83 |

| Gene | # | DNA target sequence | Forward primer sequence | Reverse primer | SEQ ID NO |
|---|---|---|---|---|---|
| PD-1 | 1 | CGACTGGCCAGG GCGCCTGTGGG | GAAATTAATACGAC TCACTATAGCGACT GGCCAGGGCGCCT TGTTTTAGAGCTA GAAATAGC | AAAAAAAGC ACCGACTCG GTGCCACTTT TTCAAGTTGA TAACGGACT | SEQ ID NO 84 |
| | 2 | ACCGCCCAGACG ACTGGCCAGGG | GAAATTAATACGAC TCACTATAGACCGC CCAGACGACTGGCC AGTTTTAGAGCTAG AAATAGC | AGCCTTATTT TAACTTGCTA TTTCTAGCTC TAAAAC | SEQ ID NO 85 |
| | 3 | CACCGCCCAGAC GACTGGCCAGG | GAAATTAATACGAC TCACTATAGCACCG CCCAGACGACTGGC CGTTTTAGAGCTAG AAATAGC | | SEQ ID NO 86 |
| | 4 | GTCTGGGCGGTG CTACAACTGGG | GAAATTAATACGAC TCACTATAGGTCTG GGCGGTGCTACAAC TGTTTTAGAGCTAG AAATAGC | | SEQ ID NO 87 |
| | 5 | CTACAACTGGGCT GGCGGCCAGG | GAAATTAATACGAC TCACTATAGCTACA ACTGGGCTGGCGG CCGTTTTAGAGCTA GAAATAGC | | SEQ ID NO 88 |
| | 6 | CACCTACCTAAG AACCATCCTGG | GAAATTAATACGAC TCACTATAGCACCT ACCTAAGAACCATC CGTTTTAGAGCTAG AAATAGC | | SEQ ID NO 89 |
| | 7 | CGGTCACCACGA GCAGGGCTGGG | GAAATTAATACGAC TCACTATAGCGGTC ACCACGAGCAGGG CTGTTTTAGAGCTA GAAATAGC | | SEQ ID NO 90 |

TABLE 2-continued

| | # | DNA target sequence | Forward primer sequence | Reverse primer | SEQ ID NO |
|---|---|---|---|---|---|
| | 8 | GCCCTGCTCGTGG TGACCGAAGG | GAAATTAATACGAC TCACTATAGGCCCT GCTCGTGGTGACCG AGTTTTAGAGCTAG AAATAGC | | SEQ ID NO 91 |
| | 9 | CGGAGAGCTTCGT GCTAAACTGG | GAAATTAATACGAC TCACTATAGCGGAG AGCTTCGTGCTAAA CGTTTTAGAGCTAG AAATAGC | | SEQ ID NO 92 |
| | 10 | CAGCTTGTCCGTC TGGTTGCTGG | GAAATTAATACGAC TCACTATAGCAGCT TGTCCGTCTGGTTG CGTTTTAGAGCTAG AAATAGC | | SEQ ID NO 93 |
| | 11 | AGGCGGCCAGCT TGTCCGTCTGG | GAAATTAATACGAC TCACTATAGAGGCG GCCAGCTTGTCCGT CGTTTTAGAGCTAG AAATAGC | | SEQ ID NO 94 |
| | 12 | CCGGGCTGGCTG CGGTCCTCGGG | GAAATTAATACGAC TCACTATAGCCGGG CTGGCTGCGGTCCT CGTTTTAGAGCTAG AAATAGC | | SEQ ID NO 95 |
| | 13 | CGTTGGGCAGTTG TGTGACACGG | GAAATTAATACGAC TCACTAAGCGTTG GGCAGTTGTGTGAC AGTTTTAGAGCTAG AAATAGC | | SEQ ID NO 96 |

| Gene | # | DNA target sequence | Forward primer sequence | Reverse primer | SEQ ID NO |
|---|---|---|---|---|---|
| CTLA-4 | 1 | CATAAAGCCATG GCTTGCCTTGG | GAAATTAATACGAC TCACTATAGCATAA AGCCATGGCTTGCC TGTTTTAGAGCTAG AAATAGC | AAAAAAAGC ACCGACTCG GTGCCACTTT TTCAAGTTGA TACGGACT | SEQ ID NO 97 |
| | 2 | CCTTGGATTTCAG CGGCACAAGG | GAAATTAATACGAC TCACTATAGCCTTG GATTTCAGCGGCAC AGTTTTAGAGCTAG AAATAGC | AGCCTTATTT TAACTTGCTA TTTCTAGCTC TAAAAC | SEQ ID NO 98 |
| | 3 | CCTTGTGCCGCTG AAATCCAAGG | GAAATTAATACGAC TCACTATAGCCTTG TGCCGCTGAAATCC AGTTTTAGAGCTAG AAATAGC | | SEQ ID NO 99 |
| | 4 | CACTCACCTTTGC AGAAGACAGG | GAAATTAATACGAC TCACTATAGCACTC ACCTTTGCAGAAGA CGTTTTAGAGCTAG AAATAGC | | SEQ ID NO 100 |
| | 5 | TTCCATGCTAGCA ATGCACGTGG | GAAATTAATACGAC TCACTATAGTTCCAT GCTAGCAATGCACG GTTTTAGAGCTAGA AATAGC | | SEQ ID NO 101 |
| | 6 | GGCCACGTGCATT GCTAGCATGG | GAAATTAATACGAC TCACTATAGGGCCA CGTGCATTGCTAGC AGTTTTAGAGCTAG AAATAGC | | SEQ ID NO 102 |
| | 7 | GGCCCAGCCTGCT GTGGTACTGG | GAAATTAATACGAC TCACTATAGGGCCC AGCCTGCTGTGGTA CGTTTTAGAGCTAG AAATAGC | | SEQ ID NO 103 |
| | 8 | AGGTCCGGGTGA CAGTGCTTCGG | GAAATTAATACGAC TCACTATAGAGGTC CGGGTGACAGTGCT TGTTTTAGAGCTAG AAATAGC | | SEQ ID NO 104 |
| | 9 | CCGGGTGACAGT GCTTCGGCAGG | GAAATTAATACGAC TCACTATAGCCGGG TGACAGTGCTTCGG CGTTTTAGAGCTAG AAATAGC | | SEQ ID NO 105 |

TABLE 2-continued

| Gene | # | DNA target sequence | Forward primer sequence | Reverse primer | SEQ ID NO |
|---|---|---|---|---|---|
| | 10 | CTGTGCGGCAACC TACATGATGG | GAAATTAATACGAC TCACTATAGCTGTG CGGCAACCTACATG AGTTTTAGAGCTAG AAATAGC | | SEQ ID NO 106 |
| | 11 | CAACTCATTCCCC ATCATGTAGG | GAAATTAATACGAC TCACTATAGCAACT CATTCCCCATCATG TGTTTTAGAGCTAG AAATAGC | | SEQ ID NO 107 |
| | 12 | CTAGATGATTCCA TCTGCACGGG | GAAATTAATACGAC TCACTATAGCTAGA TGATTCCATCTGCA CGTTTTAGAGCTAG AAATAGC | | SEQ ID NO 108 |

| Gene | # | DNA target sequence | Forward primer sequence | Reverse primer | SEQ ID NO |
|---|---|---|---|---|---|
| DGKζ | 1 | GGCTAGGAGTCA GCGACATATGG | GAAATTAATACGAC TCACTATAGGGCTA GGAGTCAGCGACAT GTTTTAGAGCTAG AAATAGC | AAAAAAGC ACCGACTCG GTGCCACTTT TTCAAGTTGA TAACGGACT | SEQ ID NO 109 SEQ ID NO 110 |
| | 2 | GCTAGGAGTCAG CGACATATGGG | GAAATTAATACGAC TCACTATAGGCTAG GAGTCAGCGACATA TGTTTTAGAGCTAG AAATAGC | AGCCTTATTT TAACTTGCCTA TTTCTAGCTC TAAAAC | |
| | 3 | CTAGGAGTCAGC GACATATGGGG | GAAATTAATACGAC TCACTATAGCTAGG AGTCAGCGACATAT GGTTTTAGAGCTAG AAATAGC | | SEQ ID NO 111 |
| | 4 | GTACTGTGTAGC CAGGATGCTGG | GAAATTAATACGAC TCACTATAGGTACT GTGTAGCCAGGATG CGTTTTAGAGCTAG AAATAGC | | SEQ ID NO 112 |
| | 5 | ACGAGCACTCAC CAGCATCCTGG | GAAATTAATACGAC TCACTATAGACGAG CACTCACCAGCATC CGTTTTAGAGCTAG AAATAGC | | SEQ ID NO 113 |
| | 6 | AGGCTCCAGGAA TGTCCGCGAGG | GAAATTAATACGAC TCACTATAGAGGCT CCAGGAATGTCCGC GGTTTTAGAGCTAG AAATAGC | | SEQ ID NO 114 |
| | 7 | ACTTACCTCGCGG ACATTCCTGG | GAAATTAATACGAC TCACTATAGACTTA CCTCGCGGACATTC CGTTTTAGAGCTAG AAATAGC | | SEQ ID NO 115 |
| | 8 | CACCCTGGGCACT TACCTCGCGG | GAAATTAATACGAC TCACTATAGCACCC TGGGCACTTACCTC GGTTTTAGAGCTAG AAATAGC | | SEQ ID NO 116 |
| | 9 | GTGCCGTACAAA GGTTGGCTGGG | GAAATTAATACGAC TCACTATAGGTGCC GTACAAAGGTTGGC TGTTTTAGAGCTAG AAATAGC | | SEQ ID NO 117 |
| | 10 | GGTGCCGTACAA AGGTTGGCTGG | GAAATTAATACGAC TCACTATAGGGTGC CGTACAAAGGTTGG CGTTTTAGAGCTAG AAATAGC | | SEQ ID NO 118 |
| | 11 | CTCTCCTCAGTAC CACAGCAAGG | GAAATTAATACGAC TCACTATAGCTCTC CTCAGTACCACAGC AGTTTTAGAGCTAG AAATAGC | | SEQ ID NO 119 |
| | 12 | CCTGGGCCTCC GGGCGCGGAGG | GAAATTAATACGAC TCACTATAGCCTGG GCCTCCGGGCGC GGGTTTTAGAGCTA GAAATAGC | | SEQ ID NO 120 |

TABLE 2-continued

| | | | | | |
|---|---|---|---|---|---|
| | 13 | AGTACTCACCTGG GGCCTCCGGG | GAAATTAATACGAC TCACTATAGAGAC TCACCTGGGGCCTC CGTTTTAGAGCTAG AAATAGC | | SEQ ID NO 121 |
| | 14 | AGGGTCTCCAGC GGCCCCCTGG | GAAATTAATACGAC TCACTATAGAGGGT CTCCAGCGGCCCTC CGTTTTAGAGCTAG AAATAGC | | SEQ ID NO 122 |
| | 15 | GCAAGTACTTACG CCTCCTTGGG | GAAATTAATACGAC TCACTATAGGCAAG TACTTACGCCTCCTT GTTTTAGAGCTAGA AATAGC | | SEQ ID NO 123 |
| | 16 | TTGCGGTACATCT CCAGCCTGGG | GAAATTAATACGAC TCACTATAGTTGCG GTACATCTCCAGCC TGTTTTAGAGCTAG AAATAGC | | SEQ ID NO 124 |
| | 17 | TTTGCGGTACATC TCCAGCCTGG | GAAATTAATACGAC TCACTATAGTTTGC GGTACATCTCCAGC CGTTTTAGAGCTAG AAATAGC | | SEQ ID NO 125 |

| Gene | # | DNA target sequence | Forward primer sequence | Reverse primer | SEQ ID NO |
|---|---|---|---|---|---|
| Tet2 | 1 | GCAAAACCTGTC CACTCTTATGG | GAAATTAATACGAC TCACTATAGGCAAA ACCTGTCCACTCTT AGTTTTAGAGCTAG AAATAGC | AAAAAAAGC ACCGACTCG GTGCCACTTT TTCAAGTTGA TAACGGACT | SEQ ID NO 126 |
| | 2 | TTGGTGCCATAAG AGTGGACAGG | GAAATTAATACGAC TCACTATAGTTGGT GCCATAAGAGTGG ACGTTTTAGAGCTA GAAATAGC | AGCCTTATTT TAACTTGCTA TTTCTAGCTC TAAAAC | SEQ ID NO 127 |
| | 3 | GGTGCAAGTTTC TTATATGTTGG | GAAATTAATACGAC TCACTATAGGGTGC AAGTTTCTTATATGT GTTTTAGAGCTAGA AATAGC | | SEQ ID NO 128 |
| | 4 | ACCTGATGCATA TAATAATCAGG | GAAATTAATACGAC TCACTATAGACCTG ATGCATATAATAAT CGTTTTAGAGCTAG AAATAGC | | SEQ ID NO 129 |
| | 5 | ACCTGATTATTAT ATGCATCAGG | GAAATTAATACGAC TCACTATAGACCTG ATTATTATATGCATC GTTTTAGAGCTAGA AATAGC | | SEQ ID NO 130 |
| | 6 | CAGAGCACCAGA GTGCCGTCTGG | GAAATTAATACGAC TCACTATAGCAGAG CACCAGAGTGCCGT CGTTTTAGAGCTAG AAATAGC | | SEQ ID NO 131 |
| | 7 | AGAGCACCAGAG TGCCGTCTGGG | GAAATTAATACGAC TCACTATAGAGAGC ACCAGAGTGCCGTC TGTTTTAGAGCTAG AAATAGC | | SEQ ID NO 132 |
| | 8 | AGAGTGCCGTCTG GGTCTGAAGG | GAAATTAATACGAC TCACTATAGAGAGT GCCGTCTGGGTCTG AGTTTTAGAGCTAG AAATAGC | | SEQ ID NO 133 |
| | 9 | AGGAAGGCCGTC CATTCTCAGGG | GAAATTAATACGAC TCACTATAGAGGAA GGCCGTCCATTCTC AGTTTTAGAGCTAG AAATAGC | | SEQ ID NO 134 |
| | 10 | GGATAGAACCAA CCATGTTGAGG | GAAATTAATACGAC TCACTATAGGGATA GAACCAACCATGTT GGTTTTAGAGCTAG AAATAGC | | SEQ ID NO 135 |

TABLE 2-continued

| | | | |
|---|---|---|---|
| 11 | TCTGTTGCCCTCA ACATGGTTGG | GAAATTAATACGAC TCACTATAGTCTGTT GCCCTCAACATGGT GTTTTAGAGCTAGA AATAGC | SEQ ID NO 136 |
| 12 | TTAGTCTGTTGCC CTCAACATGG | GAAATTAATACGAC TCACTATAGTTAGT CTGTTGCCCTCAAC AGTTTTAGAGCTAG AAATAGC | SEQ ID NO 137 |
| 13 | GTCTGGCAAATGG GAGGTGATGG | GAAATTAATACGAC TCACTATAGGTCTG GCAAATGGGAGGT GAGTTTTAGAGCTA GAAATAGC | SEQ ID NO 138 |
| 14 | CAGAGGTTCTGTC TGGCAAATGG | GAAATTAATACGAC TCACTATAGCAGAG GTTCTGTCTGGCAA AGTTTTAGAGCTAG AAATAGC | SEQ ID NO 139 |
| 15 | TTGTAGCCAGAGG TTCTGTCTGG | GAAATTAATACGAC TCACTATAGTTGTA GCCAGAGGTTCTGT CGTTTTAGAGCTAG AAATAGC | SEQ ID NO 140 |
| 16 | ACTTCTGGATGAG CTCTCTCAGG | GAAATTAATACGAC TCACTATAGACTTCT GGATGAGCTCTCTC GTTTTAGAGCTAGA AATAGC | SEQ ID NO 141 |
| 17 | AGAGCTCATCCAG AAGTAAATGG | GAAATTAATACGAC TCACTATAGAGAGC TCATCCAGAAGTAA AGTTTTAGAGCTAG AAATAGC | SEQ ID NO 142 |
| 18 | TTGGTGTCTCCAT TTACTTCTGG | GAAATTAATACGAC TCACTATAGTTGGT GTCTCCATTTACTTC GTTTTAGAGCTAGA AATAGC | SEQ ID NO 143 |
| 19 | TTCTGGCTTCCCTT CATACAGGG | GAAATTAATACGAC TCACTATATTCTG GCTTCCCTTCATAC AGTTTTAGAGCTAG AAATAGC | SEQ ID NO 144 |
| 20 | CAGGACTCACAC GACTATTCTGG | GAAATTAATACGAC TCACTATAGCAGGA CTCACACGACTATT CGTTTTAGAGCTAG AAATAGC | SEQ ID NO 145 |
| 21 | CTACTTTCTTGTGT AAAGTCAGG | GAAATTAATACGAC TCACTATAGCTACTT TCTTGTGTAAAGTC GTTTTAGAGCTAGA AATAGC | SEQ ID NO 146 |
| 22 | GACTTTACACAAG AAAGTAGAGG | GAAATTAATACGAC TCACTATAGGACTT TACACAAGAAAGTA GGTTTTAGAGCTAG AAATAGC | SEQ ID NO 147 |
| 23 | GTCTTTCTCCATTA GCCTTTTGG | GAAATTAATACGAC TCACTATAGGTCTTT CTCCATTAGCCTTTG TTTTAGAGCTAGAA ATAGC | SEQ ID NO 148 |
| 24 | AATGGAGAAAGA CGTAACTTCGG | GAAATTAATACGAC TCACTATAGAATGG AGAAAGACGTAACT TGTTTTAGAGCTAG AAATAGC | SEQ ID NO 149 |
| 25 | ATGGAGAAAGAC GTAACTTCGGG | GAAATTAATACGAC TCACTATAGATGGA GAAAGACGTAACTT CGTTTTAGAGCTAG AAATAGC | SEQ ID NO 150 |
| 26 | TGGAGAAAGACG TAACTTCGGGG | GAAATTAATACGAC TCACTATAGTGGAG AAAGACGTAACTTC GGTTTTAGAGCTAG AAATAGC | SEQ ID NO 151 |

TABLE 2-continued

| | # | DNA target sequence | Forward primer sequence | Reverse primer | SEQ ID NO |
|---|---|---|---|---|---|
| | 27 | TTTGGTTGACTGC TTTCACCTGG | GAAATTAATACGAC TCACTATAGTTTGGT TGACTGCTTTCACC GTTTTAGAGCTAGA AATAGC | | SEQ ID NO 152 |
| | 28 | TCACTCAAATCGG AGACATTTGG | GAAATTAATACGAC TCACTATAGTCACT CAAATCGGAGACAT TGTTTTAGAGCTAG AAATAGC | | SEQ ID NO 153 |
| | 29 | ATCTGAAGCTCTG GATTTTCAGG | GAAATTAATACGAC TCACTATAGATCTG AAGCTCTGGATTTT CGTTTTAGAGCTAG AAATAGC | | SEQ ID NO 154 |
| | 30 | GCTTCAGATTCTG AATGAGCAGG | GAAATTAATACGAC TCACTATAGGCTTC AGATTCTGAATGAG CGTTTTAGAGCTAG AAATAGC | | SEQ ID NO 155 |
| | 31 | CAGATTCTGAATG AGCAGGAGGG | GAAATTAATACGAC TCACTATAGCAGAT TCTGAATGAGCAGG AGTTTTAGAGCTAG AAATAGC | | SEQ ID NO 156 |
| | 32 | AAGGCAGTGCTA ATGCCTAATGG | GAAATTAATACGAC TCACTATAGAAGGC AGTGCTAATGCCTA AGTTTTAGAGCTAG AAATAGC | | SEQ ID NO 157 |
| | 33 | GCAGAAACTGTA GCACCATTAGG | GAAATTAATACGAC TCACTATAGGCAGA AACTGTAGCACCAT TGTTTTAGAGCTAG AAATAGC | | SEQ ID NO 158 |
| | 34 | ACCGCAATGGAA ACACAATCTGG | GAAATTAATACGAC TCACTATAGACCGC AATGGAAACACAAT CGTTTTAGAGCTAG AAATAGC | | SEQ ID NO 159 |
| | 35 | TGTGGTTTTCTGC ACCGCAATGG | GAAATTAATACGAC TCACTATAGTGTGG TTTTCTGCACCGCA AGTTTTAGAGCTAG AAATAGC | | SEQ ID NO 160 |
| | 36 | CATAAATGCCATT AACAGTCAGG | GAAATTAATACGAC TCACTATAGCATAA ATGCCATTAACAGT CGTTTTAGAGCTAG AAATAGC | | SEQ ID NO 161 |
| | 37 | ATTAGTAGCCTGA CTGTTAATGG | GAAATTAATACGAC TCACTATAGATTAG TAGCCTGACTGTTA AGTTTTAGAGCTAG AAATAGC | | SEQ ID NO 162 |
| | 38 | CGATGGGTGAGT GATCTCACAGG | GAAATTAATACGAC TCACTATAGCGATG GGTGAGTGATCTCA CGTTTTAGAGCTAG AAATAGC | | SEQ ID NO 163 |
| | 39 | ACTCACCCATCGC ATACCTCAGG | GAAATTAATACGAC TCACTATAGCTCAC CCCATCGCATACCT CTTTTAGAGCTAG AAATAGC | | SEQ ID NO 164 |
| | 40 | CTCACCCATCGCA TACCTCAGGG | GAAATTAATACGAC TCACTATAGCTCAC CCATCGCATACCTC AGTTTTAGAGCTAG AAATAGC | | SEQ ID NO 165 |

| Gene | # | DNA target sequence | Forward primer sequence | Reverse primer | SEQ ID NO |
|---|---|---|---|---|---|
| PSGL-1 | 1 | AGCAACAGGAGG AGTTGCAGAGG | GAAATTAATACGAC TCACTATAGAGCAA CAGGAGGAGTTGC AGGTTTTAGAGCTA GAAATAGC | AAAAAAGC ACCGACTCG GTGCCACTTT TTCAAGTTGA TAACGGACT | SEQ ID NO 166 |

TABLE 2-continued

| | | | | |
|---|---|---|---|---|
| 2 | CCAGTAGGATCA GCAACAGGAGG | GAAATTAATACGAC TCACTATAGCCAGT AGGATCAGCAACA GGGTTTTAGAGCTA GAAATAGC | AGCCTTATTT TAACTTGCTA TTTCTAGCTC TAAAAC | SEQ ID NO 167 |
| 3 | CTCCTGTTGCTGA TCCTACTGGG | GAAATTAATACGAC TCACTATAGCTCCT GTTGCTGATCCTAC TGTTTTAGAGCTAG AAATAGC | | SEQ ID NO 168 |
| 4 | GGCCCAGTAGGA TCAGCAACAGG | GAAATTAATACGAC TCACTATAGGGCCC AGTAGGATCAGCAA CGTTTTAGAGCTAG AAATAGC | | SEQ ID NO 169 |
| 5 | TTGCTGATCCTAC TGGGCCCTGG | GAAATTAATACGAC TCACTATAGTTGCT GATCCTACTGGGCC CGTTTTAGAGCTAG AAATAGC | | SEQ ID NO 170 |
| 6 | TGGCAACAGCTTG CAGCTGTGGG | GAAATTAATACGAC TCACTATAGTGGCA ACAGCTTGCAGCTG TGTTTTAGAGCTAG AAATAGC | | SEQ ID NO 171 |
| 7 | CTTGGGTCCCCTG CTTGCCCGGG | GAAATTAATACGAC TCACTATAGCTTGG GTCCCTGCTTGCC CGTTTTAGAGCTAG AAATAGC | | SEQ ID NO 172 |
| 8 | GTCCCCTGCTTGC CCGGGACCGG | GAAATTAATACGAC TCACTATAGGTCCC CTGCTTGCCCGGGA CGTTTTAGAGCTAG AAATAGC | | SEQ ID NO 173 |
| 9 | CTCCGGTCCCGG GCAAGCAGGGG | GAAATTAATACGAC TCACTATAGCTCCG GTCCCGGGCAAGC AGGTTTTAGAGCTA GAAATAGC | | SEQ ID NO 14 |
| 10 | TCTCCGGTCCCGG GCAAGCAGGG | GAAATTAATACGAC TCACTATAGTCTCC GGTCCCGGGCAAG CAGTTTTAGAGCTA GAAATAGC | | SEQ ID NO 175 |
| 11 | GTCTCCGGTCCCG GGCAAGCAGG | GAAATTAATACGAC TCACTATAGGTCTC CGGTCCCGGGCAA GCGTTTTAGAGCTA GAAATAGC | | SEQ ID NO 176 |
| 12 | GCTTGCCCGGGA CCGGAGACAGG | GAAATTAATACGAC TCACTATAGGCTTG CCCGGGACCGGAG ACGTTTTAGAGCTA GAAATAGC | | SEQ ID NO 177 |
| 13 | GGTGGCCTGTCTC CGGTCCCGGG | GAAATTAATACGAC TCACTATAGGGTGG CCTGTCTCCGGTCC CGTTTTAGAGCTAG AAATAGC | | SEQ ID NO 178 |
| 14 | CGGTGGCCTGTCT CCGGTCCCGG | GAAATTAATACGAC TCACTATAGCGGTG GCCTGTCTCCGGTC CGTTTTAGAGCTAG AAATAGC | | SEQ ID NO 179 |
| 15 | CATATTCGGTGGC CTGTCTCCGG | GAAATTAATACGAC TCACTATAGCATATT CGGTGGCCTGTCTC GTTTTAGAGCTAGA AATAGC | | SEQ ID NO 180 |
| 16 | ATCTAGGTACTCA TATTCGGTGG | GAAATTAATACGAC TCACTATAGATCTA GGTACTCATATTCG GGTTTTAAGCTAG AAATAGC | | SEQ ID NO 181 |
| 17 | ATAATCTAGGTA CTCATATTCGG | GAAATTAATACGAC TCACTATAGATAAT CTAGGTACTCATAT TGTTTTAGAGCTAG AAATAGC | | SEQ ID NO 182 |

TABLE 2-continued

| | | | |
|---|---|---|---|
| 18 | TTATGATTCCTG CCAGAAACGG | GAAATTAATACGAC TCACTATAGTTATG ATTTCCTGCCAGAA AGTTTTAGAGCTAG AAATAGC | SEQ ID NO 183 |
| 19 | ATTTCTGGAGGCT CCGTTTCTGG | GAAATTAATACGAC TCACTATAGATTTCT GGAGGCTCCGTTTC GTTTTAGAGCTAG AATAGC | SEQ ID NO 184 |
| 20 | ACTGACACCACTC CTCTGACTGG | GAAATTAATACGAC TCACTATAGACTGA CACCACTCCTCTGA CGTTTTAGAGCTAG AAATAGC | SEQ ID NO 185 |
| 21 | CTGACACCACTCC TCTGACTGGG | GAAATTAATACGAC TCACTATAGCTGAC ACCACTCCTCTGAC TGTTTTAGAGCTAG AAATAGC | SEQ ID NO 186 |
| 22 | ACCACTCCTCTGA CTGGGCCTGG | GAAATTAATACGAC TCACTATAGACCAC TCCTCTGACTGGGC CGTTTTAGAGCTAG AAATAGC | SEQ ID NO 187 |
| 23 | AACCCCTGAGTCT ACCACTGTGG | GAAATTAATACGAC TCACTATAGAACCC CTGAGTCTACCACT GGTTTTAGAGCTAG AAATAGC | SEQ ID NO 188 |
| 24 | CTCCACAGTGGTA GACTCAGGGG | GAAATTAATACGAC TCACTATAGCTCCA CAGTGGTAGACTCA GGTTTTAGAGCTAG AAATAGC | SEQ ID NO 189 |
| 25 | GCTCCACAGTGGT GACTCAGGG | GAAATTAATACGAC TCACTATAGGCTCC ACAGTGGTAGACTC AGTTTTAGAGCTAG AAATAGC | SEQ ID NO 190 |
| 26 | GGCTCCACAGTG GTAGACTCAGG | GAAATTAATACGAC TCACTATAGGGCTC CACAGTGGTAGACT CGTTTTAGAGCTAG AAATAGC | SEQ ID NO 191 |
| 27 | CCTGCTGCAAGGC GTTCTACTGG | GAAATTAATACGAC TCACTATAGCCTGC TGCAAGGCGTTCTA CGTTTTAGAGCTAG AAATAGC | SEQ ID NO 192 |
| 28 | CCAGTAGAACGC CTTGCAGCAGG | GAAATTAATACGAC TCACTATAGCCAGT AGAACGCCTTGCAG CGTTTTAGAGCTAG AAATAGC | SEQ ID NO 193 |
| 29 | CGTTCTACTGGCC TGGATGCAGG | GAAATTAATACGAC TCACTATAGCGTTC TACTGGCCTGGATG CGTTTTAGAGCTAG AAATAGC | SEQ ID NO 194 |
| 30 | TCTACTGGCCTGG ATGCAGGAGG | GAAATTAATACGAC TCACTATAGTCTACT GGCCTGGATGCAG GGTTTTAGAGCTAG AAATAGC | SEQ ID NO 195 |
| 31 | CCACGGAGCTGG CCAACATGGGG | GAAATTAATACGAC TCACTATAGCCACG GAGCTGGCCAACAT GGTTTTAGAGCTAG AAATAGC | SEQ ID NO 196 |
| 32 | CGTGGACAGGTTC CCCATGTTGG | GAAATTAATACGAC TCACTATAGCGTGG ACAGGTTCCCCATG TGTTTTAGAGCTAG AAATAGC | SEQ ID NO 197 |
| 33 | GTCCACGGATTCA GCAGCTATGG | GAAATTAATACGAC TCACTATAGGTCCA CGGATTCAGCAGCT AGTTTTAGAGCTAG AAATAGC | SEQ ID NO 198 |

TABLE 2-continued

| 34 | GACCACTCAACCA GTGCCCACGG | GAAATTAATACGAC TCACTATAGGACCA CTCAACCAGTGCCC CGTTTTAGAGCTAG AAATAGC | SEQ ID NO 199 |
| --- | --- | --- | --- |
| 35 | GGAGTGGTCTGTG CCTCCGTGGG | GAAATTAATACGAC TCACTATAGGGAGT GGTCTGTGCCTCCG TGTTTTAGAGCTAG AAATAGC | SEQ ID NO 200 |
| 36 | GGCACAGACAAC CGACTGACGG | GAAATTAATACGAC TCACTATAGGGCAC AGACAACTCGACTG AGTTTTAGAGCTAG AAATAGC | SEQ ID NO 201 |
| 37 | GACAACTCGACTG ACGGCCACGG | GAAATTAATACGAC TCACTATAGGACAA CTCGACTGACGGCC AGTTTTAGAGCTAG AAATAGC | SEQ ID NO 202 |
| 38 | AACTCGACTGACG GCCACGGAGG | GAAATTAATACGAC TCACTATAGAACTC GACTGACGGCCAC GGGTTTTAGAGCTA GAAATAGC | SEQ ID NO 203 |
| 39 | CACAGAACCCAG TGCCACAGAGG | GAAATTAATACGAC TCACTATAGCACAG AACCCAGTGCCACA GGTTTTAGAGCTAG AAATAGC | SEQ ID NO 204 |
| 40 | GGTAGTAGGTTCC ATGGACAGGG | GAAATTAATACGAC TCACTATAGGGTAG TAGGTTCCATGGAC AGTTTTAGAGCTAG AAATAGC | SEQ ID NO 205 |
| 41 | TGGTAGTAGGTTC CATGGACAGG | GAAATTAATACGAC TCACTATAGTGGTA GTAGGTTCCATGGA CGTTTTAGAGCTAG AAATAGC | SEQ ID NO 206 |
| 42 | TCTTTTGGTAGTA GGTTCCATGG | GAAATTAATACGAC TCACTATAGTCTTTT GGTAGTAGGTTCCA GTTTTAGAGCTAGA AATAGC | SEQ ID NO 207 |
| 43 | ATGGAACCTACTA CCAAAAGAGG | GAAATTAATACGAC TCACTATAGATGGA ACCTACTACCAAAA GGTTTTAGAGCTAG AAATAGC | SEQ ID NO 208 |
| 44 | AACAGACCTCTTT TGGTAGTAGG | GAAATTAATACGAC TCACTATAGAACAG ACCTCTTTTGGTAGT GTTTTAGAGCTAGA AATAGC | SEQ ID NO 209 |
| 45 | GGGTATGAACAG ACCTCTTTTGG | GAAATTAATACGAC TCACTATAGGGGTA TGAACAGACCTCTT TGTTTTAGAGCTAG AAATAGC | SEQ ID NO 210 |
| 46 | TGTGTCCTCTGTT ACTCACAAGG | GAAATTAATACGAC TCACTATAGTGTGT CCTCTGTTACTCAC AGTTTTAGAGCTAG AAATAGC | SEQ ID NO 211 |
| 47 | GTGTCCTCTGTTA CTCACAAGGG | GAAATTAATACGAC TCACTATAGGTGTC CTCTGTTACTCACA AGTTTTAGAGCTAG AAATAGC | SEQ ID NO 212 |
| 48 | GTAGTTGACGGAC AAATTGCTGG | GAAATTAATACGAC TCACTATAGGTAGT TGACGGACAAATTG CGTTTTAGAGCTAG AAATAGC | SEQ ID NO 213 |
| 49 | TTTGTCCGTCAAC TACCCAGTGG | GAAATTAATACGAC TCACTATAGTTTGTC CGTCAACTACCCAG GTTTTAGAGCTAGA AATAGC | SEQ ID NO 214 |

TABLE 2-continued

| 50 | TTGTCCGTCAACT ACCCAGTGGG | GAAATTAATACGAC TCACTATAGTTGTC CGTCAACTACCCAG TGTTTTAGAGCTAG AAATAGC | SEQ ID NO 215 |
| 51 | TGTCCGTCAACTA CCCAGTGGGG | GAAATTAATACGAC TCACTATAGTGTCC GTCAACTACCCAGT GGTTTTAGAGCTAG AAATAGC | SEQ ID NO 216 |
| 52 | GTCCGTCAACTAC CCAGTGGGGG | GAAATTAATACGAC TCACTATAGGTCCG TCAACTACCCAGTG GGTTTTAGAGCTAG AAATAGC | SEQ ID NO 217 |
| 53 | CTCTGTGAAGCAG TGCCTGCTGG | GAAATTAATACGAC TCACTATAGCTCTG TGAAGCAGTGCCTG CGTTTTAGAGCTAG AAATAGC | SEQ ID NO 218 |
| 54 | CCTGCTGGCCATC CTAATCTTGG | GAAATTAATACGAC TCACTATAGCCTGC TGGCCATCCTAATC TGTTTTAGAGCTAG AAATAGC | SEQ ID NO 219 |
| 55 | CCAAGATTAGGAT GGCCAGCAGG | GAAATTAATACGAC TCACTATAGCCAAG ATTAGGATGGCCAG CGTTTTAGAGCTAG AAATAGC | SEQ ID NO 220 |
| 56 | GGCCATCCTAATC TTGGCGCTGG | GAAATTAATACGAC TCACTATAGGGCCA TCCTAATCTTGGCG CGTTTTAGAGCTAG AAATAGC | SEQ ID NO 221 |
| 57 | CACCAGCGCCAA GATTAGGATGG | GAAATTAATACGAC TCACTATAGCACCA GCGCCAAGATTAGG AGTTTTAGAGCTAG AAATAGC | SEQ ID NO 222 |
| 58 | AGTGCACACGAA GAAGATAGTGG | GAAATTAATACGAC TCACTATAGAGTGC ACACGAAGAAGAT AGGTTTTAGAGCTA GAAATAGC | SEQ ID NO 223 |
| 59 | TATCTTCTTCGTGT GCACTGTGG | GAAATTAATACGAC TCACTATAGTATCTT CTTCGTGTGCACTG GTTTTAGAGCTAGA AATAGC | SEQ ID NO 224 |
| 60 | CTTCGTGTGCACT GTGGTGCTGG | GAAATTAATACGAC TCCACTATAGCTTCG TGTGCACTGTGGTG CGTTTTAGAGCTAG AAATAGC | SEQ ID NO 225 |
| 61 | GGCGGTCCGCCT CTCCCGCAAGG | GAAATTAATACGAC TCACTATAGGGCGG TCCGCCTCTCCCGC AGTTTTAGAGCTAG AAATAGC | SEQ ID NO 226 |
| 62 | GCGGTCCGCCTCT CCCGCAAGGG | GAAATTAATACGAC TCACTATAGGCGGT CCGCCTCTCCCGCA AGTTTTAGAGCTAG AAATAGC | SEQ ID NO 227 |
| 63 | AATTACGCACGG GGTACATGTGG | GAAATTAATACGAC TCACTATAGAATTA CGCACGGGGTACAT GGTTTTAGAGCTAG AAATAGC | SEQ ID NO 228 SEQ ID NO 229 |
| 64 | TGGGGGAGTAATT ACGCACGGGG | GAAATTAATACGAC TCACTATAGTGGGG GAGTAATTACGCAC GGTTTTAGAGCTAG AAATAGC | SEQ ID NO 230 |
| 65 | GTGGGGGAGTAA TTACGCACGGG | GAAATTAATACGAC TCACTATAGGTGGG GGAGTAATTACGCA CGTTTTAGACGCTAG AAATAGC | SEQ ID NO 231 |

TABLE 2-continued

| 66 | GGTGGGGGAGTA ATTACGCACGG | GAAATTAATACGAC TCACTATAGGGTGG GGGAGTAATTACGC AGTTTTAGAGCTAG AAATAGC | SEQ ID NO 232 |
| --- | --- | --- | --- |
| 67 | TAATTACTCCCCC ACCGAGATGG | GAAATTAATACGAC TCACTATAGTAATT ACTCCCCCACCGAG AGTTTTAGAGCTAG AAATAGC | |
| 68 | AGATGCAGACCA TCTCGGTGGGG | GAAATTAATACGAC TCACTATAGAGATG CAGACCATCTCGGT GGTTTTAGAGCTAG AAATAGC | SEQ ID NO 233 |
| 69 | GAGATGCAGACC ATCTCGGTGGG | GAAATTAATACGAC TCACTATAGGAGAT GCAGACCATCTCGG TGTTTTAGAGCTAG AAATAGC | SEQ ID NO 234 |
| 70 | TGAGATGCAGAC CATCTCGGTGG | GAAATTAATACGAC TCACTAGTGAGA TGCAGACCATCTCG GGTTTTAGAGCTAG AAATAGC | SEQ ID NO 235 |
| 71 | GGATGAGATGCA GACCATCTCGG | GAAATTAATACGAC TCACTATAGGGATG AGATGCAGACCATC TGTTTTAGAGCTAG AAATAGC | SEQ ID NO 236 |
| 72 | ATCTCATCCCTGT TGCCTGATGG | GAAATTAATACGAC TCACTATAGATCTC ATCCCTGTTGCCTG AGTTTTAGAGCTAG AAATAGC | SEQ ID NO 237 |
| 73 | TCATCCCTGTTGC CTGATGGGGG | GAAATTAATACGAC TCACTATAGTCATC CCTGTTGCCTGAT GGTTTTAGAGCTAG | SEQ ID NO 238 |
| 74 | CTCACCCCCATCA GGCAACAGGG | GAAATTAATACGAC TCACTATAGCTCAC CCCCATCAGGCAAC AGTTTTAGAGCTAG AAATAGC | SEQ ID NO 239 |
| 75 | GAGGGCCCCTCA CCCCCATCAGG | GAAATTAATACGAC TCACTATAGGAGGG CCCCTCACCCCCAT CGTTTTAGAGCTAG AAATAGC | SEQ ID NO 240 |
| 76 | GGGCCCTCTGCCA CAGCCAATGG | GAAATTAATACGAC TCACTATAGGGGCC CTCTGCCACAGCCA AGTTTTAGAGCTAG AAATAGC | SEQ ID NO 241 |
| 77 | CCCTCTGCCACAG CCAATGGGGG | GAAATTAATACGAC TCACTATAGCCCTC TGCCACAGCCAATG GGTTTTAGAGCTAG AAATAGC | SEQ ID NO 242 |
| 78 | CCCCCATTGGCTG TGGCAGAGGG | GAAATTAATACGAC TCACTATAGCCCCC ATTGGCTGTGGCAG AGTTTTAGAGCTAG AAATAGC | SEQ ID NO 243 |
| 79 | GCCCCCATTGGCT GTGGCAGAGG | GAAATTAATACGAC TCACTATAGGCCCC CATTGGCTGTGGCA GGTTTTAGAGCTAG AAATAGC | SEQ ID NO 244 |
| 80 | GGACAGCCCCC ATTGGCTGTGG | GAAATTAATACGAC TCACTATAGGGACA GCCCCCATTGGCT GGTTTTAGAGCTAG AAATAGC | SEQ ID NO 245 |
| 81 | CCGGGCTCTTGGC CTTGGACAGG | GAAATTAATACGAC TCACTATAGCCGGG CTCTTGGCCTTGGA CGTTTTAGAGCTAG AAATAGC | SEQ ID NO 246 |

TABLE 2-continued

| | | | | | |
|---|---|---|---|---|---|
| | 82 | CTGTCCAAGGCCA AGAGCCCGGG | GAAATTAATACGAC TCACTATAGCTGTC CAAGGCCAAGAGC CCGTTTTAGAGCTA GAAATAGC | | SEQ ID NO 247 |
| | 83 | TGGCGTCAGGCC CGGGCTCTTGG | GAAATTAATACGAC TCACTATAGTGGCG TCAGGCCCGGGCTC TGTTTTAGAGCTAG AAATAGC | | SEQ ID NO 248 |
| | 84 | CGGGCCTGACGC CAGAGCCCAGG | GAAATTAATACGAC TCACTATAGCGGGC CTGACGCCAGAGCC CGTTTTAGAGCTAG AAATAGC | | SEQ ID NO 249 |

| Gene | # | DNA target sequence | Forward primer sequence | Reverse primer | SEQ ID NO |
|---|---|---|---|---|---|
| FAS | 1 | CAACAACCATGCT GGGCATCTGG | GAAATTAATACGAC TCACTATAGCAACA ACCATGCTGGGCAT CGTTTTAGAGCTAG AAATAGC | AAAAAAGC ACCGACTCG GTGCCACTTT TTCAAGTTGA TAACGGACT | SEQ ID NO 250 |
| | 2 | GAGGGTCCAGAT GCCCAGCATGG | GAAATTAATACGAC TCACTATAGGAGGG TCCAGATGCCCAGC AGTTTTAGAGCTAG AAATAGC | AGCCTTATTT TAACTTGCTA TTTCTAGCTC TAAAAC | SEQ ID NO 251 |
| | 3 | CATCTGGACCCT CCTACCTCTGG | GAAATTAATACGAC TCACTATAGCATCT GGACCCTCCTACCT CGTTTTAGAGCTAG AAATAGC | | SEQ ID NO 252 |
| | 4 | AGGGCTCACCAG AGGTAGGAGGG | GAAATTAATACGAC TCACTATAGAGGGC TCACCAGAGGTAGG AGTTTTAGAGCTAG AAATAGC | | SEQ ID NO 253 |
| | 5 | GGAGTTGATGTC AGTCACTTGGG | GAAATTAATACGAC TCACTATAGGGAGT TGATGTCAGTCACT TGTTTTAGAGCTAG AAATAGC | | SEQ ID NO 254 |
| | 6 | TGGAGTTGATGTC AGTCACTTGG | GAAATTAATACGAC TCACTATAGTGGAG TTGATGTCAGTCAC TGTTTTAGAGCTAG AAATAGC | | SEQ ID NO 255 |
| | 7 | AGTGACTGACATC AACTCCAAGG | GAAATTAATACGAC TCACTATAGAGTGA CTGACATCAACTCC AGTTTTAGAGCTAG AAATAGC | | SEQ ID NO 256 |
| | 8 | GTGACTGACATC AACTCCAAGGG | GAAATTAATACGAC TCACTATAGGTGAC TGACATCAACTCCA AGTTTTAGAGCTAG AAATAGC | | SEQ ID NO 257 |
| | 9 | ACTCCAAGGGATT GGAATTGAGG | GAAATTAATACGAC TCACTATAGACTCC AAGGGATTGGAATT GGTTTTAGAGCTAG AAATAGC | | SEQ ID NO 258 |
| | 10 | CTTCCTCAATTCC AATCCCTTGG | GAAATTAATACGAC TCACTATAGCTTCCT CAATTCCAATCCCT GTTTTAGAGCTAGA AATAGC | | SEQ ID NO 259 |
| | 11 | TACAGTTGAGACT CAGAACTTGG | GAAATTAATACGAC TCACTATAGTACAG TTGAGACTCAGAAC TGTTTTAGAGCTAG AAATAGC | | SEQ ID NO 260 |
| | 12 | TTGGAAGGCCTGC ATCATGATGG | GAAATTAATACGAC TCACTATAGTTGGA AGGCCTGCATCATG AGTTTTAGAGCTAG AAATAGC | | SEQ ID NO 261 |

TABLE 2-continued

| Gene | # | DNA target sequence | Forward primer sequence | Reverse primer | SEQ ID NO |
|---|---|---|---|---|---|
| | 13 | AGAATTGGCCATC ATGATGCAGG | GAAATTAATACGAC TCACTATAGAGAAT TGGCCATCATGATG CGTTTTAGAGCTAG AAATAGC | | SEQ ID NO 262 |
| | 14 | GACAGGGCTTATG GCAGAATTGG | GAAATTAATACGAC TCACTATAGGACAG GGCTTATGGCAGAA TGTTTTAGAGCTAG AAATAGC | | SEQ ID NO 263 |
| | 15 | TGTAACATACCT GGAGGACAGGG | GAAATTAATACGAC TCACTATAGTGTAA CATACCTGGAGGAC AGTTTTAGAGCTAG AAATAGC | | SEQ ID NO 264 |
| | 16 | GTGTAACATACCT GGAGGACAGG | GAAATTAATACGAC TCACTATAGGTGTA ACATACCTGGAGGA CGTTTTAGAGCTAG AAATAGC | | SEQ ID NO 265 |

| Gene | # | DNA target sequence | Forward primer sequence | Reverse primer | SEQ ID NO |
|---|---|---|---|---|---|
| KDM6A | 1 | CGTACCTGTGCAA CTCCTGTTGG | GAAATTAATACGAC TCACTATAGCGTAC CTGTGCAACTCCTG TGTTTTAGAGCTAG AAATAGC | AAAAAAAGC ACCGACTCG GTGCCACTTT TTCAAGTTGA TAACGGACT | SEQ ID NO 266 |
| | 2 | GATCTACTGGAAT TCCTAATGGG | GAAATTAATACGAC TCACTATAGGATCT ACTGGAATTCCTAA TGTTTTAGAGCTAG AAATAGC | GCCTTATTT TAACTTGCTA TTTCTAGCTC TAAAAC | SEQ ID NO 267 |
| | 3 | GAGTCAGCTGTTG GCCCATTAGG | GAAATTAATACGAC TCACTATAGGAGTC AGCTGTTGGCCCAT TGTTTTAGAGCTAG AAATAGC | | SEQ ID NO 268 |
| | 4 | CTGCCTACAAACT CAGTCTCTGG | GAAATTAATACGAC TCACTATAGCTGCC TACAAACTCAGTCT CGTTTTAGAGCTAG AAATAGC | | SEQ ID NO 269 |
| | 5 | GGGCAGGCAGGA CGGACTCCAGG | GAAATTAATACGAC TCACTATAGGGGCA GGCAGGACGGACT CCGTTTTAGAGCTA GAAATAGC | | SEQ ID NO 270 |
| | 6 | GGAGTCCGTCCTG CCTGCCCTGG | GAAATTAATACGAC TCACTATAGGGAGT CCGTCCTGCCTGCC CGTTTTAGAGCTAG AAATAGC | | SEQ ID NO 271 |
| | 7 | GAGTCCGTCCTGC CTGCCCTGG | GAAATTAATACGAC TCACTATAGGAGTC CGTCCTGCCTGCCC TGTTTTAGAGCTAG AAATAGC | | SEQ ID NO 272 |
| | 8 | GAAAAGGGTCCA TTGGCCAAAGG | GAAATTAATACGAC TCACTATAGGAAAA GGGTCCATTGGCCA AGTTTTAGAGCTAG AAATAGC | | SEQ ID NO 273 |
| | 9 | GCCTGCAGAAAA GGGTCCATTGG | GAAATTAATACGAC TCACTATAGGCCTG CAGAAAAGGGTCC ATGTTTTAGAGCTA GAAATAGC | | SEQ ID NO 274 |
| | 10 | TTGATGTGCTACA GGGAACATGG | GAAATTAATACGAC TCACTATAGTTGAT GTGCTACAGGGAAC AGTTTTAGAGCTAG AAATAGC | | SEQ ID NO 275 |
| | 11 | AGCGTTCTTGATG TGCTACAGGG | GAAATTAATACGAC TCACTATAGAGCGT TCTTGATGTGCTAC AGTTTTAGAGCTAG AAATAGC | | SEQ ID NO 276 |

TABLE 2-continued

| | | | |
|---|---|---|---|
| 12 | CAGCGTTCTTGAT GTGCTACAGG | GAAATTAATACGAC TCACTATAGCAGCG TTCTTGATGTGCTAC GTTTTAGAGCTAGA AATAGC | SEQ ID NO 277 |
| 13 | CTGTAGCACATCA AGAACGCTGG | GAAATTAATACGAC TCACTATAGCTGTA GCACATCAAGAAC GCGTTTTAGAGCTA GAAATAGC | SEQ ID NO 278 |
| 14 | TGTAGCACATCAA GAACGCTGGG | GAAATTAATACGAC TCACTATAGTGTAG CACATCAAGAACGC TGTTTTAGAGCTAG AAATAGC | SEQ ID NO 279 |
| 15 | ATAGGCAATAATC ATATAACAGG | GAAATTAATACGAC TCACTATAGATAGG CAATAATCATATAA CGTTTTAGAGCTAG AAATAGC | SEQ ID NO 280 |
| 16 | AGTGCGTTTCGCT GCAGGTAAGG | GAAATTAATACGAC TCACTATAGAGTGC GTTTCGCTGCAGGT AGTTTTAGAGCTAG AAATAGC | SEQ ID NO 281 |
| 17 | GAGTGAGTGCGTT TCGCTGCAGG | GAAATTAATACGAC TCACTATAGGAGTG AGTGCGTTTCGCTG CGTTTTAGAGCTAG AAATAGC | SEQ ID NO 282 |
| 18 | GTCAGGTTTGTGC GGTTATGAGG | GAAATTAATACGAC TCACTATAGGTCAG GTTTGTGCGGTTAT GGTTTTAGAGCTAG AAATAGC | SEQ ID NO 283 |
| 19 | CGCTGCTGGTCAG GTTTGTGCGG | GAAATTAATACGAC TCACTATAGCGCTG CTGGTCAGGTTTGT GGTTTTAGAGCTAG AAATAGC | SEQ ID NO 284 |
| 20 | AAACCTGACCAG CAGCGCAGAGG | GAAATTAATACGAC TCACTATAGAAACC TGACCAGCAGCGC AGGTTTTAGAGCTA GAAATAGC | SEQ ID NO 285 |
| 21 | CCAGCAGCGCAG AGGAGCCGTGG | GAAATTAATACGAC TCACTATAGCCCAGC AGCGCAGAGGAGC CGGTTTTAGAGCTA GAAATAGC | SEQ ID NO 286 |
| 22 | CCACGGCTCCTCT GCGCTGCTGG | GAAATTAATACGAC TCACTATAGCCACG GCTCCTCTGCGCTG CGTTTTAGAGCTAG AAATAGC | SEQ ID NO 287 |
| 23 | CCAACTATCTAAC TCCACTCAGG | GAAATTAATACGAC TCACTATAGCCAAC TATCTAACTCCACTC GTTTTAGAGCTAGA AATAGC | SEQ ID NO 288 |
| 24 | CCTGAGTGGAGTT AGATAGTTGG | GAAATTAATACGAC TCACTATAGCCTGA GTGGAGTTAGATAG TGTTTTAGAGCTAG AATAGC | SEQ ID NO 289 |

2.3 Deep Sequencing

On-target and off-target sites were PCR-amplified to 200-300 bp size using Hipi Plus DNA polymerase (Elpisbio). The PCR product obtained by the above method was sequenced using Mi-seq. equipment (Illumina) and analyzed by Cas Analyzer of CRISPR RGEN tool (www.rgenome.net). Insertions/deletions within 5 bp from the CRISPR/Cas9 cleavage site were considered as a mutation induced by RGEN.

As shown in Table 4 and Table 6, as a result of deep sequencing, it was confirmed that the indel mutation occurred at high efficiency in various immune cells when the CRISPR-Cas9 was delivered.

Example 3: Preparation of sgRNA 3.1. Screening of sqRNAs in Jurkat Cells

The activity of sgRNAs targeting the exons of A20, DGKα, EGR2, PPP2R2D, EGR2, PPP2r2dPPP2R2D, PD-1, CTLA-4, DGKζ, PSGL-1, KDM6A, FAS and TET2TET2TET2 obtained by the method described in Example 2 was tested in Jurkat cells.

Each of the sgRNAs obtained in Example 2 was tested by comparing the indel ratio between in Jurkat cells transfected with Cas9 by the method of Example 1 and in Jurkat cells without transduction. Table 3 shows the number of mismatch sites having the similar target sequences in the CRISPR/Cas9 target sequence and the human genome, and Table 4 shows the indel ratio of each sgRNA. Among the gRNAs targeting each gene, the DNA target region of those with good activity is displayed in bold.

TABLE 3

| Gene | # | DNA target sequence | Mismatch 0 bp | 1 bp | 2 bp |
|---|---|---|---|---|---|
| A20 | 1 | CTTGTGGCGCTGAAAACGAACGG | 1 | 0 | 0 |
| | 2 | ATGCCACTTCTCAGTACATGTGG | 1 | 0 | 0 |
| | 3 | GCCACTTCTCAGTACATGTGGGG | 1 | 0 | 0 |
| | 4 | GCCCCACATGTACTGAGAAGTGG | 1 | 0 | 0 |
| | 5 | TCAGTACATGTGGGGCGTTCAGG | 1 | 0 | 0 |
| | 6 | GGGCGTTCAGGACACAGACTTGG | 1 | 0 | 0 |
| | 7 | CACAGACTTGGTACTGAGGAAGG | 1 | 0 | 0 |
| | 8 | GGCGCTGTTCAGCACGCTCAAGG | 1 | 0 | 0 |
| | 9 | CACGCAACTTTAAATTCCGCTGG | 1 | 0 | 0 |
| | 10 | CGGGGCTTTGCTATGATACTCGG | 1 | 0 | 0 |
| | 11 | GGCTTCCACAGACACACCCATGG | 1 | 0 | 0 |
| | 12 | TGAAGTCCACTTCGGGCCATGGG | 1 | 0 | 0 |
| DGKα | 1 | CTGTACGACACGGACAGAAATGG | 1 | 0 | 0 |
| | 2 | TGTACGACACGGACAGAAATGGG | 1 | 0 | 0 |
| | 3 | CACGGACAGAAATGGGATCCTGG | 1 | 0 | 0 |
| | 4 | GATGCGAGTGGCTGAATACCTGG | 1 | 0 | 0 |
| | 5 | GAGTGGCTGAATACCTGGATTGG | 1 | 0 | 0 |
| | 6 | AGTGGCTGAATACCTGGATTGGG | 1 | 0 | 0 |
| | 7 | ATTGGGATGTGTCTGAGCTGAGG | 1 | 0 | 0 |
| | 8 | ATGAAAGAGATTGACTATGATGG | 1 | 0 | 0 |
| | 9 | CTCTGTCTCTCAAGCTGAGTGGG | 1 | 0 | 0 |
| | 10 | TCTCTCAAGCTGAGTGGGTCCGG | 1 | 0 | 0 |
| | 11 | CTCTCAAGCTGAGTGGGTCCGGG | 1 | 0 | 0 |
| | 12 | CAAGCTGAGTGGGTCCGGGCTGG | 1 | 0 | 0 |
| EGR2 | 1 | TTGACATGACTGGAGAGAAGAGG | 1 | 0 | 0 |
| | 2 | GACTGGAGAGAAGAGGTCGTTGG | 1 | 0 | 0 |
| | 3 | GAGACGGGAGCAAAGCTGCTGGG | 1 | 0 | 0 |
| | 4 | AGAGACGGGAGCAAAGCTGCTGG | 1 | 0 | 0 |
| | 5 | TGGTTTCTAGGTGCAGAGACGGG | 1 | 0 | 0 |
| | 6 | TAAGTGAAGGTCTGGTTTCTAGG | 1 | 0 | 0 |
| | 7 | TGCCCATGTAAGTGAAGGTCTGG | 1 | 0 | 0 |
| | 8 | GAACTTGCCCATGTAAGTGAAGG | 1 | 0 | 0 |
| | 9 | TCCATTGACCCTCAGTACCCTGG | 1 | 0 | 0 |
| | 10 | TATGCCTTCTGGGTAGCAGCTGG | 1 | 0 | 0 |
| | 11 | TGAGTGCAGGCATCTTGCAAGGG | 1 | 0 | 0 |
| | 12 | GAGTGCAGGCATCTTGCAAGGGG | 1 | 0 | 0 |
| | 13 | GATGAGGCTGTGGTTGAAGCTGG | 1 | 0 | 0 |
| | 14 | CCACTGGCCACAGGACCCCTGGG | 1 | 0 | 0 |
| | 15 | GGGACATGGTGCACACACCCAGG | 1 | 0 | 0 |
| | 16 | GAGTACAGGTGGTCCAGGTCAGG | 1 | 0 | 0 |
| | 17 | GCGGAGAGTACAGGTGGTCCAGG | 1 | 0 | 0 |
| | 18 | GCGGTGGCGGAGAGTACAGGTGG | 1 | 0 | 0 |
| | 19 | TCTCCTGCACAGCCAGAATAAGG | 1 | 0 | 0 |
| | 20 | ACGCAGAAGGGTCCTGGTAGAGG | 1 | 0 | 0 |
| | 21 | AGGTGGTGGGTAGGCCAGAGAGG | 1 | 0 | 0 |
| | 22 | CCCAAGCAGCCACGGACCCCAGG | 1 | 0 | 0 |
| | 23 | ACCTGGGTCCGTGGCTGGCTTGG | 1 | 0 | 0 |
| | 24 | AAGAGACCTGGGTCCGTGGCTGG | 1 | 0 | 0 |
| | 25 | GGATCATTGGGAAGAGACCTGGG | 1 | 0 | 0 |
| | 26 | GGATCATTGGGAAGAGACCTGGG | 1 | 0 | 0 |
| | 27 | CAGGATAGTCTGGGATCATTGGG | 1 | 0 | 0 |
| | 28 | GGAAAGAATCCAGGATAGTCTGG | 1 | 0 | 0 |
| | 29 | CAGTGCCAGAGAGACCTACATGG | 1 | 0 | 0 |
| | 30 | CTGTACATGTAGGTCTCTCTGG | 1 | 0 | 0 |
| | 31 | AGAGACCTACATGGTACAGCTGG | 1 | 0 | 0 |
| | 32 | CTGGGCCAGCTGTACCATGTAGG | 1 | 0 | 0 |
| | 33 | AGGGAAAGGGCTTACGGTCTGGG | 1 | 0 | 0 |
| | 34 | CAGGGAAAGGGCTTACGGTCTGG | 1 | 0 | 0 |

TABLE 3-continued

| Gene | # | DNA target sequence | Mismatch 0 bp | 1 bp | 2 bp |
|---|---|---|---|---|---|
| PPP2R2D | 5 | TCTGGAGATCTTCTTGCAACAGG | 1 | 0 | 0 |
| | 6 | CTCCGGTTCATGACTTTGAAAGG | 1 | 0 | 0 |
| | 7 | GTCTTCCATCTTCGTCTTTCAGG | 1 | 0 | 0 |
| | 8 | GAAGACTTCGAGACCCATTTAGG | 1 | 0 | 0 |
| | 9 | TCGAGACCCATTTAGGATCACGG | 1 | 0 | 0 |
| | 10 | GTAGCGCCGTGATCCTAAATGGG | 1 | 0 | 0 |
| | 11 | CGTAGCGCCGTGATCCTAAATGG | 1 | 0 | 0 |
| | 12 | CATTTAGGATCACGGCGCTACGG | 1 | 0 | 0 |
| | 13 | GGTCCCAATATTGAAGCCCATGG | 1 | 0 | 0 |
| | 14 | GATCCATGGGCTTCAATATTGGG | 1 | 0 | 0 |
| | 15 | AGATCCATGGGCTTCAATATTGG | 1 | 0 | 0 |
| | 16 | GCTTCTACCATAAGATCCATGGG | 1 | 0 | 0 |
| | 17 | CGCTTCTACCATAAGATCCATGG | 1 | 0 | 0 |
| | 18 | GCATTTGCAAAAATTCGCCGTGG | 1 | 0 | 0 |
| | 19 | ATGACCTGAGAATTAATTTATGG | 1 | 0 | 0 |
| | 20 | CCATGCACTCCCAGACATGTGTG | 1 | 0 | 0 |
| | 21 | GCACTGGTGCGGGTGGAACTCGG | 1 | 0 | 0 |
| | 22 | ACACGTTGCACTGGTGCGGGTGG | 1 | 0 | 0 |
| | 23 | CGAACACGTTGCACTGGTGCGGG | 1 | 0 | 0 |
| | 24 | ACGAACACGTTGCACTGGTGCGG | 1 | 0 | 0 |
| | 25 | TGTAGACGAACACGTTGCACTGG | 1 | 0 | 0 |
| | 26 | GCGCATGTCACACAGGCGGATGG | 1 | 0 | 0 |
| | 27 | AGGAGCGCATGTCACACAGGCGG | 1 | 0 | 0 |
| | 28 | CCGAGGAGCGCATGTCACACAGG | 1 | 0 | 0 |
| | 29 | CCTGTGTGACATGCGCTCCTCGG | 1 | 0 | 0 |
| PD-1 | 1 | CGACTGGCCAGGGCGCCTGTGGG | 1 | 0 | 0 |
| | 2 | ACCGCCCAGACGACTGGCCAGGG | 1 | 0 | 0 |
| | 3 | CACCGCCCAGACGACTGGCCAGG | 1 | 0 | 0 |
| | 4 | GTCTGGGCGGTGCTACAACTGGG | 1 | 0 | 0 |
| | 5 | CTACAACTGGGCTGGCGGCCAGG | 1 | 0 | 0 |
| | 6 | CACCTACCTAAGAACCATCCTGG | 1 | 0 | 0 |
| | 7 | CGGTCACCACGAGCAGGGCTGGG | 1 | 0 | 0 |
| | 8 | GCCCTGCTCGTGGTGACCGAAGG | 1 | 0 | 0 |
| | 9 | CGGAGAGCTTCGTGCTAAACTGG | 1 | 0 | 0 |
| | 10 | CAGCTTGTCCGTCTGGTTGCTGG | 1 | 0 | 0 |
| | 11 | AGGCGGCCAGCTTGTCCGTCTGG | 1 | 0 | 0 |
| | 12 | CCGGGCTGGCTGCGTCCTCGGG | 1 | 0 | 0 |
| | 13 | CGTTGGGCAGTTGTGTGACACGG | 1 | 0 | 0 |
| CTLA-4 | 1 | CATAAAGCCATGGCTTGCCTTGG | 1 | 0 | 0 |
| | 2 | CCTTGGATTTCAGCGGCACAAGG | 1 | 0 | 0 |
| | 3 | CCTTGTGCCGCTGAAATCCAAGG | 1 | 0 | 0 |
| | 4 | CACTCACCTTTGCAGAAGACAGG | 1 | 0 | 0 |
| | 5 | TTCCATGCTAGCAATGCACGTGG | 1 | 0 | 0 |
| | 6 | GGCCACGTGCATTGCTAGCATGG | 1 | 0 | 0 |
| | 7 | GGCCCAGCCTGCTGTGGTACTGG | 1 | 0 | 0 |
| | 8 | AGGTCCGGGTGACAGTGCTTCGG | 1 | 0 | 0 |
| | 9 | CCGGGTGACAGTGCTTCGGCAGG | 1 | 0 | 0 |
| | 10 | CTGTGCCGCAACCTACATGATGG | 1 | 0 | 0 |
| | 11 | CAACTCATTCCCCATCATGTAGG | 1 | 0 | 0 |
| | 12 | CTAGATGATTCCATCTGCACGGG | 1 | 0 | 0 |
| DGKζ | 1 | GGCTAGGAGTCAGCGACATATGG | 1 | 0 | 0 |
| | 2 | GCTAGGAGTCAGCGACATATGGG | 1 | 0 | 0 |
| | 3 | CTAGGAGTCAGCGACATATGGGG | 1 | 0 | 0 |
| | 4 | GTACTGTGTAGCCAGGATGCTGG | 1 | 0 | 0 |
| | 5 | ACGAGCACTCACCAGCATCCTGG | 1 | 0 | 0 |
| | 6 | AGGCTCCAGGAATGTCCGCAGG | 1 | 0 | 0 |
| | 7 | ACTTACCTGCGGACATTCCTGG | 1 | 0 | 0 |
| | 8 | CACCCTGGGCACTTACCTCGCGG | 1 | 0 | 0 |
| | 9 | GTGCCGTACAAAGGTTGGCTGGG | 1 | 0 | 0 |
| | 10 | GGTGCCGTACAAAGGTTGGCTGG | 1 | 0 | 0 |
| | 11 | CTCTCCTCAGTACCACAGCAAGG | 1 | 0 | 0 |
| | 12 | CCTGGGGCCTCCGGGCGGAGG | 1 | 0 | 0 |
| | 13 | AGTACTCACCTGGGGCCTCCGGG | 1 | 0 | 0 |
| | 14 | AGGGTCTCCAGGCCCGCCCTCGG | 1 | 0 | 0 |
| | 15 | GCAAGTACTTACGCCTCCTTGGG | 1 | 0 | 0 |
| | 16 | TTGCGGTACATCTCCAGCCTGGG | 1 | 0 | 0 |
| | 17 | TTTGCGGTACATCTCCAGCCTGG | 1 | 0 | 0 |
| Tet2 | 1 | GCAAAACCTGTCCACTCTTATGG | 1 | 0 | 0 |
| | 2 | TTGGTGCCATAAGAGTGGACAGG | 1 | 0 | 0 |
| | 3 | GGTGCAAGTTTCTTATATGTTGG | 1 | 0 | 0 |
| | 4 | ACCTGATGCATATAATAATCAGG | 1 | 0 | 0 |
| | 5 | ACCTGATTATTATATGCATCAGG | 1 | 0 | 0 |

TABLE 3-continued

| Gene | # | DNA target sequence | Mismatch 0 bp | 1 bp | 2 bp |
|---|---|---|---|---|---|
| | 6 | CAGAGCACCAGAGTGCCGTCTGG | 1 | 0 | 0 |
| | 7 | AGAGCACCAGAGTGCCGTCTGGG | 1 | 0 | 0 |
| | 8 | AGAGTGCCGTCTGGGTCTGAAGG | 1 | 0 | 0 |
| | 9 | AGGAAGGCCGTCCATTCTCAGGG | 1 | 0 | 0 |
| | 10 | GGATAGAACCAACCATGTTGAGG | 1 | 0 | 0 |
| | 11 | TCTGTTGCCCTCAACATGGTTGG | 1 | 0 | 0 |
| | 12 | TTAGTCTGTTGCCCTCAACATGG | 1 | 0 | 0 |
| | 13 | GTCTGGCAAATGGGAGGTGATGG | 1 | 0 | 0 |
| | 14 | CAGAGGTTCTGTCTGGCAAATGG | 1 | 0 | 0 |
| | 15 | TTGTAGCCAGAGGTTCTGTCTGG | 1 | 0 | 0 |
| | 16 | ACTTCTGGATGAGCTCTCTCAGG | 1 | 0 | 0 |
| | 17 | AGAGCTCATCCAGAAGTAAATGG | 1 | 0 | 0 |
| | 18 | TTGGTGTCTCCATTTACTTCTGG | 1 | 0 | 0 |
| | 19 | TTCTGGCTTCCCTTCATACAGGG | 1 | 0 | 0 |
| | 20 | CAGGACTCACACGACTATTCTGG | 1 | 0 | 0 |
| | 21 | CTACTTTCTTGTGTAAAGTCAGG | 1 | 0 | 0 |
| | 22 | GACTTTACACAAGAAAGTAGAGG | 1 | 0 | 0 |
| | 23 | GTCTTTCTCCATTAGCCTTTTGG | 1 | 0 | 0 |
| | 24 | AATGGAGAAAGACGTAACTTCGG | 1 | 0 | 0 |
| | 25 | ATGGAGAAAGACGTAACTTCGGG | 1 | 0 | 0 |
| | 26 | TGGAGAAAGACGTAACTTCGGGG | 1 | 0 | 0 |
| | 27 | TTTGGTTGACTGCTTTCACCTGG | 1 | 0 | 0 |
| | 28 | TCACTCAAATCGGAGACATTTGG | 1 | 0 | 0 |
| | 29 | ATCTGAAGCTCTGGATTTTCAGG | 1 | 0 | 0 |
| | 30 | GCTTCAGATTCTGAATGAGCAGG | 1 | 0 | 0 |
| | 31 | CAGATTCTGAATGAGCAGGAGGG | 1 | 0 | 0 |
| | 32 | AAGGCAGTGCTAATGCCTAATGG | 1 | 0 | 0 |
| | 33 | GCAGAAACTGTAGCACCATTAGG | 1 | 0 | 0 |
| | 34 | ACCGCAATGGAAACACAATCTGG | 1 | 0 | 0 |
| | 35 | TGTGGTTTTCTGCACCGCAATGG | 1 | 0 | 0 |
| | 36 | CATAAATGCCATTAACAGTCAGG | 1 | 0 | 0 |
| | 37 | ATTAGTAGCCTGACTGTTAATGG | 1 | 0 | 0 |
| | 38 | CGATGGGTGAGTGATCTCACAGG | 1 | 0 | 0 |
| | 39 | ACTCACCCATCGCATACCTCAGG | 1 | 0 | 0 |
| | 40 | CTCACCCATCGCATACCTCAGGG | 1 | 0 | 0 |
| PSGL-1 | 1 | AGCAACAGGAGGAGTTGCAGAGG | 1 | 0 | 0 |
| | 2 | CCAGTAGGATCAGCAACAGGAGG | 1 | 0 | 0 |
| | 3 | CTCCTGTTGCTGATCCTACTGGG | 1 | 0 | 0 |
| | 4 | GGCCCAGTAGGATCAGCAACAGG | 1 | 0 | 0 |
| | 5 | TTGCTGATCCTACTGGGCCCTGG | 1 | 0 | 0 |
| | 6 | TGGCAACAGCTTGCAGCTGTGGG | 1 | 0 | 0 |
| | 7 | CTTGGGTCCCCTGCTTGCCCGGG | 1 | 0 | 0 |
| | 8 | GTCCCCTGCTTGCCCGGGACCGG | 1 | 0 | 0 |
| | 9 | CTCCGGTCCCGGGCAAGCAGGGG | 1 | 0 | 0 |
| | 10 | TCTCCGGTCCCGGGCAAGCAGGG | 1 | 0 | 0 |
| | 11 | GTCTCCGGTCCCGGGCAAGCAGG | 1 | 0 | 0 |
| | 12 | GCTTGCCCGGGACCGGAGACAGG | 1 | 0 | 0 |
| | 13 | GGTGGCCTGTCTCCGGTCCCGGG | 1 | 0 | 0 |
| | 14 | CGGTGGCCTGTCTCCGGTCCCGG | 1 | 0 | 0 |
| | 15 | CATATTCGGTGGCCTGTCTCCGG | 1 | 0 | 0 |
| | 16 | ATCTAGGTACTCATATTCGGTGG | 1 | 0 | 0 |
| | 17 | ATAATCTAGGTACTCATATTCGG | 1 | 0 | 0 |
| | 18 | TTATGATTTCTGCCAGAAACTGG | 1 | 0 | 0 |
| | 19 | ATTTCTGGAGGCTCCGTTTCTGG | 1 | 0 | 0 |
| | 20 | ACTGACACCACTCCTCTGACTGG | 1 | 0 | 0 |
| | 21 | CTGACACCACTCCTCTGACTGGG | 1 | 0 | 0 |
| | 22 | ACCACTCCTCTGACTGGGCCTGG | 1 | 0 | 0 |
| | 23 | AACCCCTGAGTCTACCACTGTGG | 1 | 0 | 0 |
| | 24 | CTCCACAGTGGTAGACTCAGGGG | 1 | 0 | 0 |
| | 25 | GCTCCACAGTGGTAGACTCAGGG | 1 | 0 | 0 |
| | 26 | GGCTCCACAGTGGTAGACTCAGG | 1 | 0 | 0 |
| | 27 | CCTGCTGCAAGGCGTTCTACTGG | 1 | 0 | 0 |
| | 28 | CCAGTAGAACGCCTTGCAGCAGG | 1 | 0 | 0 |
| | 29 | CGTTCTACTGGCCTGGATGCAGG | 1 | 0 | 0 |
| | 30 | TCTACTGGCCTGGATGCAGGAGG | 1 | 0 | 0 |
| | 31 | CCACGGAGCTGGCCAACATGGGG | 1 | 0 | 0 |
| | 32 | CGTGGACAGGTTCCCCATGTTGG | 1 | 0 | 0 |
| | 33 | GTCCACGGATTCAGCAGCTATGG | 1 | 0 | 0 |
| | 34 | GACCACTCAACCAGTGCCCACGG | 1 | 0 | 0 |
| | 35 | GGGTGGTCTGCCTCCGTGGG | 1 | 0 | 0 |
| | 36 | GGCACAGACAACTCGACTGACGG | 1 | 0 | 0 |
| | 37 | GACAACTCGACTGACGGCCACGG | 1 | 0 | 0 |
| | 38 | AACTCGACTGACGGCCACGGAGG | 1 | 0 | 0 |
| | 39 | CACAGAACCCAGTGCCACAGAGG | 1 | 0 | 0 |
| | 40 | GGTAGTAGGTTCCATGGACAGGG | 1 | 0 | 0 |
| | 41 | TGGTAGTAGGTTCCATGGACAGG | 1 | 0 | 0 |
| | 42 | TCTTTTGGTAGTAGGTTCCATGG | 1 | 0 | 0 |
| | 43 | ATGGAACCTACTACCAAAAGAGG | 1 | 0 | 0 |
| | 44 | AACAGACCTCTTTTGGTAGTAGG | 1 | 0 | 0 |
| | 45 | GGGTATGAACAGACCTCTTTTGG | 1 | 0 | 0 |
| | 46 | TGTGTCCTCTGTTACTCACAAGG | 1 | 0 | 0 |
| | 47 | GTGTCCTCTGTTACTCACAAGGG | 1 | 0 | 0 |
| | 48 | GTAGTTGACGGACAAATTGCTGG | 1 | 0 | 0 |
| | 49 | TTTGTCCGTCAACTACCCAGTGG | 1 | 0 | 0 |
| | 50 | TTGTCCGTCAACTACCCAGTGGG | 1 | 0 | 0 |
| | 51 | TGTCCGTCAACTACCCAGTGGGG | 1 | 0 | 0 |
| | 52 | GTCCGTCAACTACCCAGTGGGGG | 1 | 0 | 0 |
| | 53 | CTCTGTGAAGCAGTGCCTGCTGG | 1 | 0 | 0 |
| | 54 | CCTGCTGGCCATCCTAATCTTGG | 1 | 0 | 0 |
| | 55 | CCAAGATTAGGATGGCCAGCAGG | 1 | 0 | 0 |
| | 56 | GGCCATCCTAATCTTGGCGCTGG | 1 | 0 | 0 |
| | 57 | CACCAGCGCCAAGATTAGGATGG | 1 | 0 | 0 |
| | 58 | AGTGCACACGAAGAAGATAGTGG | 1 | 0 | 0 |
| | 59 | TATCTTCTTCGTGTGCACTGTGG | 1 | 0 | 0 |
| | 60 | CTTCGTGTGCACTGTGGTGCTGG | 1 | 0 | 0 |
| | 61 | GGCGGTCCGCCTCTCCCGCAAGG | 1 | 0 | 0 |
| | 62 | GCGGTCCGCCTCTCCCGCAAGGG | 1 | 0 | 0 |
| | 63 | AATTACGCACGGGGTACATGTGG | 1 | 0 | 0 |
| | 64 | TGGGGGAGTAATTACGCACGGGG | 1 | 0 | 0 |
| | 65 | GTGGGGGAGTAATTACGCACGGG | 1 | 0 | 0 |
| | 66 | GGTGGGGGAGTAATTACGCACGG | 1 | 0 | 0 |
| | 67 | TAATTACTCCCCCACCGAGATGG | 1 | 0 | 0 |
| | 68 | AGATGCAGACCATCTCGGTGGGG | 1 | 0 | 0 |
| | 69 | GAGATGCAGACCATCTCGGTGGG | 1 | 0 | 0 |
| | 70 | TGAGATGCAGACCATCTCGGTGG | 1 | 0 | 0 |
| | 71 | GGATGAGATGCAGACCATCTCGG | 1 | 0 | 0 |
| | 72 | ATCTCATCCCTGTTGCCTGATGG | 1 | 0 | 0 |
| | 73 | TCATCCCTGTTGCCTGATGGGGG | 1 | 0 | 0 |
| | 74 | CTCACCCCCATCAGGCAACAGGG | 1 | 0 | 0 |
| | 75 | GAGGGCCCCTCACCCCCATCAGG | 1 | 0 | 0 |
| | 76 | GGGCCCTCTGCCACAGCCAATGG | 1 | 0 | 0 |
| | 77 | CCCCTCTGCCACAGCCAATGGGG | 1 | 0 | 0 |
| | 78 | CCCCCATTGGCTGTGGCAGAGGG | 1 | 0 | 0 |
| | 79 | GCCCCATTGGCTGTGGCAGAGGG | 1 | 0 | 0 |
| | 80 | GGACAGGCCCCATTGGCTGTGGG | 1 | 0 | 0 |
| | 81 | CCGGGCTCTTGGCCTTGGACAGG | 1 | 0 | 0 |
| | 82 | CTGTCCAAGGCCAAGAGCCCGGG | 1 | 0 | 0 |
| | 83 | TGGCGTCAGGCCCGGGCTCTTGG | 1 | 0 | 0 |
| | 84 | CGGGCCTGACGCCAGAGCCCAGG | 1 | 0 | 0 |
| FAS | 1 | CAACAACCATGCTGGGCATCTGG | 1 | 0 | 0 |
| | 2 | GAGGGTCCAGATGCCCAGCATGG | 1 | 0 | 0 |
| | 3 | CATCTGGACCCTCCTACCTCTGG | 1 | 0 | 0 |
| | 4 | AGGGCTCACCAGAGGTAGGAGGG | 1 | 0 | 0 |
| | 5 | GGAGTTGATGTCAGTCACTTGGG | 1 | 0 | 0 |
| | 6 | TGGAGTTGATGTCAGTCACTTGG | 1 | 0 | 0 |
| | 7 | AGTGACTGACATCAACTCCAAGG | 1 | 0 | 0 |
| | 8 | GTGACTGACATCAACTCCAAGGG | 1 | 0 | 0 |
| | 9 | ACTCCAAGGGATTGGAATTGAGG | 1 | 0 | 0 |
| | 10 | CTTCCTCAATTCCAATCCCTTGG | 1 | 0 | 0 |
| | 11 | TACAGTTGAGACTCAGAACTTGG | 1 | 0 | 0 |
| | 12 | TTGGAAGGCCTGCATCATGATGG | 1 | 0 | 0 |
| | 13 | AGAATTGACCATCATGATGCAGG | 1 | 0 | 0 |
| | 14 | GACAGGGCTTATGCAGAATTGG | 1 | 0 | 0 |
| | 15 | TGTAACATACCTGGAGGACAGGG | 1 | 0 | 0 |
| | 16 | GTGTAACATACCTGGAGGACAGG | 1 | 0 | 0 |
| KDM6A | 1 | CGTACCTGTGCAACTCCTGTTGG | 1 | 0 | 0 |
| | 2 | GATCTACTGGAATTCCTAATGGG | 1 | 0 | 0 |
| | 3 | GAGTCAGCTGTTGGCCCATTAGG | 1 | 0 | 0 |
| | 4 | CTGCCTACAAACTCAGTCTCTGG | 1 | 0 | 0 |
| | 5 | GGGCAGGCAGGACGGACTCCAGG | 1 | 0 | 0 |
| | 6 | GGAGTCCGTCCTGCCTGCCCTGG | 1 | 0 | 0 |
| | 7 | GAGTCCGTCCTGCCTGCCCTGGG | 1 | 0 | 0 |
| | 8 | GAAAAGGGTCCATTGGCCAAAGG | 1 | 0 | 0 |
| | 9 | GCCTGCAGAAAAGGGTCCATTGG | 1 | 0 | 0 |
| | 10 | TTGATGTGCTACAGGGAACATGG | 1 | 0 | 0 |
| | 11 | AGCGTTCTTGATGTGCTACAGGG | 1 | 0 | 0 |
| | 12 | CAGCGTTCTTGATGTGCTACAGG | 1 | 0 | 0 |
| | 13 | CTGTAGCACATCAAGAACGCTGG | 1 | 0 | 0 |
| | 14 | TGTAGCACATCAAGAACGCTGGG | 1 | 0 | 0 |

TABLE 3-continued

| Gene | # | DNA target sequence | Mismatch 0 bp | 1 bp | 2 bp |
|---|---|---|---|---|---|
| | 15 | ATAGGCAATAATCATATAACAGG | 1 | 0 | 0 |
| | 16 | AGTGCGTTTCGCTGCAGGTAAGG | 1 | 0 | 0 |
| | 17 | GAGTGAGTGCGTTTCGCTGCAGG | 1 | 0 | 0 |
| | 18 | GTCAGGTTTGTGCGGTTATGAGG | 1 | 0 | 0 |
| | 19 | CGCTGCTGGTCAGGTTTGTGCGG | 1 | 0 | 0 |
| | 20 | AAACCTGACCAGCAGCGCAGAGG | 1 | 0 | 0 |
| | 21 | CCAGCAGCGCAGAGGAGCCGTGG | 1 | 0 | 0 |
| | 22 | CCACGGCTCCTCTGCGCTGCTGG | 1 | 0 | 0 |
| | 23 | CCAACTATCTAACTCCACTCAGG | 1 | 0 | 0 |
| | 24 | CCTGAGTGGAGTTAGATAGTTGG | 1 | 0 | 0 |

TABLE 4

The activity of each sgRNA on the Jurkat cells for the target sequence

| Gene | # | Cas9/sgRNA Transfection Total Leads | Ins | Del | Indel ratio(%) | Cas9/sgRNA Transfection Total Leads | Ins | Del | Indel ratio(%) |
|---|---|---|---|---|---|---|---|---|---|
| A20 | 1 | 58003 | 46 | 55 | 0.20% | 63455 | 17711 | 9469 | 42.80% |
| | 2 | 40652 | 0 | 18 | 0.00% | 46245 | 12025 | 6331 | 39.70% |
| | 3 | 40652 | 0 | 18 | 0.00% | 41702 | 301 | 92 | 0.90% |
| | 4 | 40652 | 0 | 18 | 0.00% | 4 | 2 | 2 | 0.00% |
| | 5 | 40652 | 0 | 18 | 0.00% | 52838 | 36339 | 4989 | 78.20% |
| | 6 | 40652 | 0 | 18 | 0.00% | 10641 | 5864 | 3460 | 87.60% |
| | 7 | 40652 | 0 | 18 | 0.00% | 40168 | 10298 | 4194 | 36.10% |
| | 8 | 40652 | 0 | 18 | 0.00% | 43044 | 9494 | 13398 | 53.20% |
| | 9 | 40652 | 0 | 18 | 0.00% | 46853 | 6629 | 2620 | 19.70% |
| | 10 | 40652 | 0 | 18 | 0.00% | 44573 | 17644 | 5168 | 51.20% |
| | 11 | 63969 | 37 | 103 | 0.20% | 61003 | 26844 | 22740 | 81.30% |
| | 12 | 63969 | 37 | 103 | 0.20% | 63321 | 949 | 1464 | 3.80% |
| DGKα | 1 | 61246 | 0 | 4 | 0.00% | 70438 | 4171 | 793 | 7.00% |
| | 2 | 61246 | 0 | 4 | 0.00% | 55262 | 7413 | 662 | 14.60% |
| | 3 | 61246 | 0 | 4 | 0.00% | 62354 | 19424 | 1546 | 33.60% |
| | 4 | 59349 | 0 | 44 | 0.10% | 58402 | 20072 | 5137 | 43.20% |
| | 5 | 59349 | 0 | 44 | 0.10% | 60718 | 14921 | 2484 | 28.70% |
| | 6 | 59349 | 0 | 44 | 0.10% | 67024 | 18760 | 2365 | 31.50% |
| | 7 | 49807 | 0 | 0 | 0.00% | 49459 | 26142 | 2877 | 58.70% |
| | 8 | 49807 | 0 | 0 | 0.00% | 65141 | 29740 | 3324 | 50.80% |
| | 9 | 49807 | 0 | 0 | 0.00% | 50760 | 30324 | 3742 | 67.10% |
| | 10 | 49807 | 0 | 0 | 0.00% | 61315 | 8953 | 4772 | 22.40% |
| | 11 | 49807 | 0 | 0 | 0.00% | 78876 | 61415 | 8416 | 88.50% |
| | 12 | 49807 | 0 | 0 | 0.00% | 64641 | 12255 | 1780 | 21.70% |
| EGR2 | 1 | 37189 | 0 | 0 | 0.00% | 53321 | 11060 | 4974 | 30.10% |
| | 2 | 37189 | 0 | 0 | 0.00% | 48475 | 6809 | 1965 | 18.10% |
| | 3 | 37189 | 0 | 0 | 0.00% | 43800 | 8688 | 7796 | 37.60% |
| | 4 | 37189 | 0 | 0 | 0.00% | 43670 | 2921 | 569 | 8.00% |
| | 5 | 37189 | 0 | 0 | 0.00% | 34730 | 3002 | 497 | 10.10% |
| | 6 | 37189 | 0 | 0 | 0.00% | 46018 | 10502 | 1408 | 25.90% |
| | 7 | 37189 | 0 | 0 | 0.00% | 48537 | 5271 | 2475 | 16.00% |
| | 8 | 37189 | 0 | 0 | 0.00% | 36551 | 6457 | 686 | 19.50% |
| | 9 | 37189 | 0 | 0 | 0.00% | 37903 | 6210 | 1671 | 20.80% |
| | 10 | 37189 | 0 | 0 | 0.00% | 44855 | 9524 | 2320 | 26.40% |
| | 11 | 37189 | 0 | 0 | 0.00% | 39615 | 9368 | 2622 | 30.30% |
| | 12 | 37189 | 0 | 0 | 0.00% | 43995 | 2542 | 563 | 7.10% |
| | 13 | | | | | 46228 | 289 | 62 | 0.76% |
| | 14 | | | | | 50220 | 1323 | 821 | 4.27% |
| | 15 | | | | | 33478 | 5638 | 1156 | 20.29% |
| | 16 | | | | | 20489 | 1731 | 483 | 10.81% |
| | 17 | | | | | 26353 | 3835 | 495 | 16.43% |
| | 18 | | | | | 23901 | 1456 | 896 | 9.84% |
| | 19 | | | | | 24352 | 3956 | 1672 | 23.11% |
| | 20 | | | | | 11 | 0 | 0 | 0.00% |
| | 21 | | | | | 34764 | 1522 | 359 | 5.41% |
| | 22 | | | | | 31546 | 91 | 0 | 0.29% |
| | 23 | | | | | 42734 | 10 | 0 | 0.02% |
| | 24 | | | | | 32492 | 59 | 0 | 0.18% |
| | 25 | | | | | 32243 | 1917 | 304 | 6.89% |
| | 26 | | | | | 39333 | 868 | 328 | 3.04% |
| | 27 | | | | | 36373 | 806 | 556 | 3.74% |
| | 28 | | | | | 45819 | 2 | 26 | 0.06% |
| | 29 | | | | | 53425 | 1159 | 584 | 3.26% |
| | 30 | | | | | 36877 | 169 | 47 | 0.59% |
| | 31 | | | | | 36317 | 0 | 76 | 0.21% |
| | 32 | | | | | 37941 | 829 | 122 | 2.51% |
| | 33 | | | | | 47730 | 167 | 2 | 0.35% |
| | 34 | | | | | 38753 | 347 | 62 | 1.06% |

TABLE 4-continued

The activity of each sgRNA on the Jurkat cells for the target sequence

| | | Cas9/sgRNA Transfection | | | | Cas9/sgRNA Transfection | | | |
|---|---|---|---|---|---|---|---|---|---|
| Gene | # | Total Leads | Ins | Del | Indel ratio(%) | Total Leads | Ins | Del | Indel ratio(%) |
| PPP2R2D | 5 | 38644 | 0 | 31 | 0.10% | 48997 | 2891 | 240 | 6.40% |
| | 6 | 50653 | 2 | 19 | 0.00% | 48327 | 7669 | 1403 | 18.80% |
| | 7 | 36764 | 0 | 0 | 0.00% | 54465 | 670 | 70 | 1.40% |
| | 8 | 36764 | 0 | 0 | 0.00% | 45004 | 11382 | 1569 | 28.80% |
| | 9 | 36764 | 0 | 0 | 0.00% | 54094 | 17825 | 3635 | 39.70% |
| | 10 | 36764 | 0 | 0 | 0.00% | 47800 | 19253 | 3432 | 47.50% |
| | 11 | 36764 | 0 | 0 | 0.00% | 50362 | 966 | 129 | 2.20% |
| | 12 | 36764 | 0 | 0 | 0.00% | 42667 | 12810 | 2318 | 35.50% |
| | 13 | | | | | 67258 | 1380 | 1050 | 3.61% |
| | 14 | | | | | 69925 | 13321 | 3599 | 24.20% |
| | 15 | | | | | 1E+05 | 21836 | 3254 | 24.10% |
| | 16 | | | | | 77282 | 19219 | 7372 | 34.41% |
| | 17 | | | | | 66732 | 3687 | 2227 | 8.86% |
| | 18 | | | | | 96593 | 9524 | 1111 | 11.01% |
| | 19 | | | | | 63082 | 11415 | 4155 | 24.68% |
| | 20 | | | | | 57937 | 4360 | 676 | 8.69% |
| | 21 | | | | | 67752 | 20314 | 4900 | 37.22% |
| | 22 | | | | | 72814 | 2244 | 1198 | 4.73% |
| | 23 | | | | | 79305 | 14047 | 1175 | 19.19% |
| | 24 | | | | | 73629 | 2914 | 571 | 4.73% |
| | 25 | | | | | 85222 | 5472 | 1905 | 8.66% |
| | 26 | | | | | 73094 | 1937 | 288 | 3.04% |
| | 27 | | | | | 94017 | 9895 | 6171 | 17.09% |
| | 28 | | | | | 93118 | 8847 | 2464 | 12.15% |
| | 29 | | | | | 77821 | 5007 | 1962 | 8.96% |
| PD-1 | 1 | 68258 | 581 | 105 | 1.00% | 77910 | 29123 | 7725 | 47.30% |
| | 2 | 68258 | 581 | 105 | 1.00% | 77866 | 1270 | 3816 | 6.50% |
| | 3 | 68258 | 581 | 105 | 1.00% | 66362 | 912 | 94 | 1.50% |
| | 4 | 68258 | 581 | 105 | 1.00% | 55936 | 41594 | 10324 | 92.80% |
| | 5 | 68258 | 581 | 105 | 1.00% | 65077 | 2554 | 192 | 4.20% |
| | 6 | 68258 | 581 | 105 | 1.00% | 71898 | 50678 | 10542 | 85.10% |
| | 7 | 68258 | 581 | 105 | 1.00% | 83902 | 17154 | 3246 | 24.30% |
| | 8 | 68258 | 581 | 105 | 1.00% | 79724 | 28304 | 7542 | 45.00% |
| | 9 | 68258 | 581 | 105 | 1.00% | 65936 | 10471 | 649 | 16.90% |
| | 10 | 68258 | 581 | 105 | 1.00% | 66937 | 0 | 29 | 0.00% |
| | 11 | 68258 | 581 | 105 | 1.00% | 77994 | 1135 | 754 | 2.40% |
| | 12 | 68258 | 581 | 105 | 1.00% | 67631 | 0 | 8 | 0.00% |
| | 13 | 68258 | 581 | 105 | 1.00% | 67161 | 30099 | 8037 | 56.80% |
| CTLA-4 | 7 | 68230 | 0 | 0 | 0 | 51173 | 3216 | 714 | 7.70% |
| | 10 | 53694 | 3 | 18 | 0 | 40995 | 11760 | 1803 | 33.10% |
| | 11 | 53694 | 3 | 18 | 0 | 55767 | 33107 | 3935 | 66.40% |
| | 12 | 53333 | 0 | 0 | 0 | 54992 | 19469 | 8396 | 50.70% |
| DGKζ | 1 | 26039 | 3 | 2 | 0.00% | 25450 | 10061 | 2453 | 49.20% |
| | 2 | 26039 | 3 | 2 | 0.00% | 24907 | 17380 | 2591 | 80.20% |
| | 3 | 26039 | 3 | 2 | 0.00% | 21950 | 14819 | 3291 | 82.50% |
| | 4 | 26039 | 3 | 2 | 0.00% | 20959 | 17708 | 1027 | 89.40% |
| | 5 | 26039 | 3 | 2 | 0.00% | 29570 | 26290 | 2120 | 96.10% |
| | 6 | 37268 | 0 | 0 | 0.00% | 32463 | 3663 | 1878 | 17.10% |
| | 7 | 37268 | 0 | 0 | 0.00% | 34154 | 6884 | 1706 | 25.20% |
| | 8 | 37268 | 0 | 0 | 0.00% | 32920 | 13190 | 4952 | 55.10% |
| | 9 | 22544 | 7 | 12 | 0.10% | 40374 | 5391 | 1209 | 16.30% |
| | 10 | 22544 | 7 | 12 | 0.10% | 28637 | 879 | 702 | 5.50% |
| | 11 | 21780 | 0 | 0 | 0.00% | 27636 | 9279 | 1859 | 40.30% |
| | 12 | 21780 | 0 | 0 | 0.00% | 20548 | 9474 | 2164 | 56.60% |
| | 13 | 21780 | 0 | 0 | 0.00% | 19161 | 9909 | 3016 | 67.50% |
| | 14 | 53786 | 0 | 6 | 0.00% | 36736 | 13 | 45 | 0.20% |
| | 15 | 24528 | 0 | 10 | 0.00% | 24319 | 12791 | 1446 | 58.50% |
| | 16 | 24528 | 0 | 10 | 0.00% | 20768 | 1520 | 140 | 8.00% |
| | 17 | 24528 | 0 | 10 | 0.00% | 26158 | 301 | 56 | 1.40% |
| Tet2 | 1 | 42428 | 375 | 573 | 2.23% | 48887 | 35150 | 5438 | 83.02% |
| | 2 | 42428 | 375 | 573 | 2.23% | 44082 | 852 | 1852 | 6.13% |
| | 3 | 42428 | 375 | 573 | 2.23% | 49662 | 24418 | 7469 | 64.21% |
| | 4 | 42428 | 375 | 573 | 2.23% | 39571 | 20708 | 6428 | 68.58% |
| | 5 | 42428 | 375 | 573 | 2.23% | 52562 | 11325 | 2524 | 26.35% |
| | 6 | 38575 | 7 | 14 | 0.10% | 38990 | 3873 | 6433 | 26.43% |
| | 7 | 38575 | 7 | 14 | 0.10% | 36884 | 8795 | 1143 | 26.94% |
| | 8 | 38575 | 7 | 14 | 0.10% | 34674 | 5096 | 1843 | 20.01% |
| | 9 | 38575 | 7 | 14 | 0.10% | 38693 | 16101 | 4895 | 54.26% |
| | 10 | | | | | 17614 | 4770 | 780 | 31.51% |
| | 11 | | | | | 19411 | 1855 | 1416 | 16.85% |
| | 12 | | | | | 14049 | 6887 | 1565 | 60.16% |
| | 13 | | | | | 16272 | 2960 | 2087 | 31.02% |
| | 14 | | | | | 18553 | 110 | 79 | 1.02% |

TABLE 4-continued

The activity of each sgRNA on the Jurkat cells for the target sequence

| Gene | # | Cas9/sgRNA Transfection | | | | Cas9/sgRNA Transfection | | | |
|---|---|---|---|---|---|---|---|---|---|
| | | Total Leads | Ins | Del | Indel ratio(%) | Total Leads | Ins | Del | Indel ratio(%) |
| | 15 | | | | | 18062 | 1434 | 591 | 11.21% |
| | 16 | | | | | 12053 | 2969 | 2423 | 44.74% |
| | 17 | | | | | 14802 | 738 | 444 | 7.99% |
| | 18 | | | | | 16943 | 395 | 154 | 3.24% |
| | 19 | | | | | 18051 | 2953 | 1070 | 22.29% |
| | 20 | | | | | 14729 | 3041 | 474 | 23.86% |
| | 21 | | | | | 18590 | 1074 | 320 | 7.50% |
| | 22 | | | | | 19329 | 3304 | 1481 | 24.76% |
| | 23 | | | | | 17420 | 36 | 19 | 0.32% |
| | 24 | | | | | 20994 | 5582 | 1354 | 33.04% |
| | 25 | | | | | 16860 | 2573 | 370 | 17.46% |
| | 26 | | | | | 15137 | 1509 | 998 | 16.56% |
| | 27 | | | | | 16035 | 635 | 185 | 5.11% |
| | 28 | | | | | 14636 | 2734 | 1750 | 30.64% |
| | 29 | | | | | 18893 | 133 | 45 | 0.94% |
| | 30 | | | | | 15959 | 0 | 0 | 0.00% |
| | 31 | | | | | 22627 | 216 | 126 | 1.51% |
| | 32 | | | | | 15361 | 368 | 361 | 4.75% |
| | 33 | | | | | 14501 | 1358 | 1939 | 22.74% |
| | 34 | | | | | 3225 | 171 | 21 | 5.95% |
| | 35 | | | | | 20968 | 725 | 209 | 4.45% |
| | 36 | | | | | 15689 | 147 | 155 | 1.92% |
| | 37 | | | | | 17405 | 239 | 18 | 1.48% |
| | 38 | | | | | 20122 | 166 | 134 | 1.49% |
| | 39 | | | | | 12585 | 370 | 106 | 3.78% |
| | 40 | | | | | 15027 | 344 | 378 | 4.80% |
| PSGL-1 | 5 | 29368 | 0 | 9 | 0.03% | 36584 | 8978 | 2453 | 31.25% |
| | 6 | 29368 | 0 | 9 | 0.03% | 35183 | 6859 | 639 | 21.31% |
| | 7 | 33707 | 125 | 13 | 0.41% | 24237 | 14697 | 2248 | 69.91% |
| | 9 | 33707 | 125 | 13 | 0.41% | 23911 | 9948 | 2001 | 49.97% |
| | 10 | 33707 | 125 | 13 | 0.41% | 30152 | 804 | 207 | 3.35% |
| | 11 | 33707 | 125 | 13 | 0.41% | 28425 | 95 | 6 | 0.36% |
| | 12 | 33707 | 125 | 13 | 0.41% | 25153 | 8931 | 1355 | 40.89% |
| | 15 | 33707 | 125 | 13 | 0.41% | 24798 | 2996 | 414 | 13.75% |
| | 16 | 33707 | 125 | 13 | 0.41% | 23116 | 8737 | 1192 | 42.95% |
| | 17 | 33707 | 125 | 13 | 0.41% | 19094 | 10638 | 2066 | 66.53% |
| | 27 | 29168 | 0 | 3 | 0.41% | 29561 | 9316 | 1202 | 35.58% |
| | 29 | 29168 | 0 | 3 | 0.01% | 36720 | 5836 | 396 | 16.97% |
| | 30 | 29168 | 0 | 3 | 0.01% | 41685 | 3815 | 976 | 11.49% |
| FAS | 1 | | | | | 33594 | 14802 | 6170 | 62.43% |
| | 2 | | | | | 24634 | 7187 | 2668 | 40.01% |
| | 3 | | | | | 32994 | 21062 | 10555 | 95.83% |
| | 4 | | | | | 30374 | 1328 | 529 | 6.11% |
| | 5 | | | | | 40549 | 33991 | 4118 | 93.98% |
| | 6 | | | | | 51209 | 7460 | 1737 | 17.96% |
| | 7 | | | | | 24583 | 8997 | 9498 | 75.23% |
| | 8 | | | | | 28815 | 20681 | 6053 | 92.78% |
| | 9 | | | | | 29188 | 17689 | 4990 | 77.70% |
| | 10 | | | | | 25433 | 10120 | 9482 | 77.07% |
| | 11 | | | | | 29184 | 15700 | 7500 | 79.50% |
| | 12 | | | | | 25410 | 18254 | 1737 | 78.67% |
| | 13 | | | | | 28564 | 18560 | 1575 | 70.49% |
| | 14 | | | | | 2482 | 1241 | 325 | 63.09% |
| | 15 | | | | | 29819 | 14067 | 10479 | 82.32% |
| | 16 | | | | | 31325 | 8422 | 3600 | 38.38% |
| KDM6A | 1 | | | | | 33935 | 4337 | 1753 | 17.95% |
| | 2 | | | | | 42016 | 10713 | 3625 | 34.13% |
| | 3 | | | | | 56988 | 1195 | 951 | 3.77% |
| | 4 | | | | | 25006 | 3298 | 1295 | 18.37% |
| | 5 | | | | | 38511 | 43 | 16 | 0.15% |
| | 6 | | | | | 20361 | 598 | 340 | 4.61% |
| | 7 | | | | | 32084 | 2785 | 1161 | 12.30% |
| | 8 | | | | | 31373 | 1616 | 523 | 6.82% |
| | 9 | | | | | 5215 | 199 | 228 | 8.19% |
| | 10 | | | | | 32955 | 4524 | 1097 | 17.06% |
| | 11 | | | | | 38820 | 5726 | 1940 | 19.75% |
| | 12 | | | | | 24536 | 72 | 12 | 0.34% |
| | 13 | | | | | 42251 | 2640 | 475 | 7.37% |
| | 14 | | | | | 44333 | 2018 | 628 | 5.97% |
| | 15 | | | | | 33618 | 722 | 290 | 3.01% |
| | 16 | | | | | 36221 | 466 | 250 | 1.98% |
| | 17 | | | | | 40214 | 1357 | 261 | 4.02% |
| | 18 | | | | | 31381 | 1958 | 714 | 8.51% |

TABLE 4-continued

The activity of each sgRNA on the Jurkat cells for the target sequence

| Gene | # | Cas9/sgRNA Transfection | | | | Cas9/sgRNA Transfection | | | |
|---|---|---|---|---|---|---|---|---|---|
| | | Total Leads | Ins | Del | Indel ratio(%) | Total Leads | Ins | Del | Indel ratio(%) |
| | 19 | | | | | 40205 | 345 | 151 | 1.23% |
| | 20 | | | | | 32494 | 9665 | 1761 | 35.16% |
| | 21 | | | | | 37911 | 1286 | 381 | 4.40% |
| | 22 | | | | | 30751 | 677 | 103 | 2.54% |
| | 23 | | | | | 38635 | 8932 | 2445 | 29.45% |
| | 24 | | | | | 44475 | 1263 | 978 | 5.04% |

3.2. Selection of sgRNAs in Human Primary T-Cells

Based on the results of sgRNA activity in the Jurkat cells obtained in Example 3.1 above, sgRNAs with relatively high activity in Jurkat cells (see bold in Table 3 and Table 4) were selected to be tested in human primary T-cells.

Single or dual gRNA and Cas9 were transferred to human primary T cells. The CRISPR/Cas9 target sequences tested are shown in Table 5, and the indel ratios by the sgRNAs are summarized in Table 6, respectively.

TABLE 5

Target sequences and mismatches in human primary T-cells

| Gene | # | DNA target sequence | SEQ ID NO | Mismatch 0 bp | 1 bp | 2 bp |
|---|---|---|---|---|---|---|
| A20 | 6 | GGGCGTTCAGGA CACAGACTTGG | SEQ ID NO 6 | 1 | 0 | 0 |
| | 11 | GGCTTCCACAGA CACACCCATGG | SEQ ID NO 1 | 1 | 0 | 0 |
| DGKα | 7 | ATTGGGATGTGT CTGAGCTGAGG | SEQ ID NO 19 | 1 | 0 | 0 |
| | 8 | ATGAAAGAGATT GACTATGATGG | SEQ ID NO 20 | 1 | 0 | 0 |
| | 9 | CTCTGTCTCTCA AGCTGAGTGGG | SEQ ID NO 21 | 1 | 0 | 0 |
| | 11 | CTCTCAAGCTGA GTGGGTCCGGG | SEQ ID NO 23 | 1 | 0 | 0 |
| | 8 + 11 | ATGAAAGAGATT GACTATGATGG + CTCTCAAGCTGA GTGGGTCCGGG | SEQ ID NO 20 + SEQ ID NO 23 | 1 | 0 | 0 |
| | 9 + 11 | CTCTGTCTCTCA AGCTGAGTGGG + CTCTCAAGCTGA GTGGGTCCGGG | SEQ ID NO 21 + SEQ ID NO 23 | 1 | 0 | 0 |
| EGR2 | 1 | TTGACATGACTG GAGAGAAGAGG | SEQ ID NO 25 | 1 | 0 | 0 |
| PPP2R2D | 10 | GTAGCGCCGTGA TCCTAAATGGG | SEQ ID NO 64 | 1 | 0 | 0 |
| PD-1 | 4 | GTCTGGGCGGTG CTACAACTGGG | SEQ ID NO 87 | 1 | 0 | 0 |
| | 6 | CACCTACCTAAG AACCATCCTGG | SEQ ID NO 89 | 1 | 0 | 0 |
| DGKζ | 1 | GGCTAGGAGTCA GCGACATATGG | SEQ ID NO 109 | 1 | 0 | 0 |
| | 2 | GCTAGGAGTCAG CGACATATGGG | SEQ ID NO 110 | 1 | 0 | 0 |
| | 3 | CTAGGAGTCAGC GACATATGGGG | SEQ ID NO 111 | 1 | 0 | 0 |
| | 4 | GTACTGTGTAGC CAGGATGCTGG | SEQ ID NO 112 | 1 | 0 | 0 |
| | 5 | ACGAGCACTCAC CAGCATCCTGG | SEQ ID NO 113 | 1 | 0 | 0 |

TABLE 6

Activity of each gRNA on the target sequence in human primary T immune cells

| Gene | # | Cas9/sgRNA Transfection | | | | Cas9/sgRNA No-Transfection | | | |
|---|---|---|---|---|---|---|---|---|---|
| | | Total Leads | Ins | Del | Indel ratio(%) | Total Leads | Ins | Del | Indel ratio(%) |
| A20 | 6 | 32158 | 0 | 26 | 0.10% | 31976 | 190 | 3865 | 12.68% |
| | 11 | 32158 | 0 | 26 | 0.10% | 30008 | 354 | 3324 | 12.26% |
| DGKα | 7 | 35903 | 15 | 7 | 0.10% | 29446 | 332 | 4465 | 16.29% |
| | 8 | 35903 | 15 | 7 | 0.10% | 40656 | 395 | 13739 | 34.76% |
| | 9 | 35903 | 15 | 7 | 0.10% | 48602 | 353 | 3263 | 7.44% |
| | 11 | 35903 | 15 | 7 | 0.10% | 43261 | 1222 | 17621 | 43.56% |
| | 8 + 11 | 35903 | 15 | 7 | 0.10% | 42504 | 184 | 21684 | 51.45% |
| | 9 + 11 | 35903 | 15 | 7 | 0.10% | 42025 | 41 | 5546 | 13.29% |
| EGR2 | 1 | 55074 | 26 | 67 | 0.20% | 42275 | 986 | 5176 | 14.58% |
| PPP2R2D | 10 | 35903 | 15 | 7 | 0.10% | 46205 | 1505 | 5532 | 15.23% |
| PD-1 | 4 | 31063 | 0 | 13 | 0.00% | 62882 | 8104 | 23113 | 49.64% |
| | 6 | 31063 | 0 | 13 | 0.00% | 93252 | 2431 | 8707 | 11.94% |

TABLE 6-continued

Activity of each gRNA on the target sequence in human primary T immune cells

| Gene | # | Cas9/sgRNA Transfection | | | | Cas9/sgRNA No-Transfection | | | |
|---|---|---|---|---|---|---|---|---|---|
| | | Total Leads | Ins | Del | Indel ratio(%) | Total Leads | Ins | Del | Indel ratio(%) |
| DGKζ | 1 | 20278 | 0 | 11 | 0.10% | 56415 | 1384 | 3898 | 9.36% |
| | 2 | 20278 | 0 | 11 | 0.10% | 49114 | 2390 | 4923 | 14.89% |
| | 5 | 20278 | 0 | 11 | 0.10% | 65225 | 6738 | 3929 | 16.35% |
| | 4 | 20278 | 0 | 11 | 0.10% | 36502 | 1303 | 3477 | 13.10% |
| | 5 | 20278 | 0 | 11 | 0.10% | 28580 | 2945 | 10392 | 46.67% |

Similarly, based on the results of sgRNA activity in Jurkat cells obtained in Example 3.1 above, PSGL-1 #17 sgRNA having a relatively high activity in Jurkat cells was selected to test its activity in human primary T-cells.

In addition, the activated human primary T cells were transfected with 4 ug of SpCas9 protein; and 1 ug of in vitro transcribed and AP-treated sgRNA through electroporation (Neon, Thermo Scientific). Five days later, gDNA was isolated and extracted from each T cell, and the indel efficiency was analyzed by the targeted deep sequencing (FIG. 18 A). In addition, PSGL-1 expression on T cell surface was analyzed by flow cytometry (Attune Flow cytometry, Thermo Scientific) to confirm a PSGL-1 knockout (FIG. 18 B, C).

FIGS. 17a to 17c show the results of analysis for hPSGL-1 sgRNA screening in Jurkat cells. These figures are graph showing the indel efficiency and the degree of Jurtat cells not expressing PSGL-1 (hPSGL-1 negative cells) after knockout (17a); and the expression level of PSGL-1 on the surface of Jurkat cells after knockout (17b, 17c).

FIG. 18 shows the results of hPSGL-1 knockout (KO) experiments in human primary T cells, which is showing (A) the indel efficiency, (B) the degree of T cell not expressing PSGL-1 after knockout, and (C) the degree of expression of PSGL-1 on the T cell surface after knockout. As a result, it was confirmed that PSGL-1 was effectively knocked out through Cas9 protein and gRNA complex delivery, thereby, PSGL-1, which is a surface protein, could not be observed by flow cytometry.

Example 4: Activation of Jurkat Cells and Promotion of Cytokine Secretion

In the Jurkat cells into which the Cas9 protein and the sgRNA are introduced, the genomic DNA sequence corresponding to the target region of the introduced sgRNA is cleaved, and the region around the cleaved DNA sequence is mutated by deletion, insertion and/or substitution through NHEJ, resulting in knocking-out gene on which the cleaved DNA sequence locates.

Jurkat cells transfected with Cas9 protein and sgRNA by electroporation as described in Example 1 were cultured for 7 days after electroporation and activated using CD3 dynabeads (Miltenyi Biotec) or CD3/28 dynabeads (Miltenyi Biotec).

After 24 hours, the expression of CD25 which is IL-2 receptor and the release level of IFN-gamma were analyzed by flow cytometry and ELISA, respectively.

First, the expression level of CD25, an IL-2 receptor, was measured by flow cytometry. Jurkat cells transfected with Cas9 protein and sgRNA were cultured for 7 days after each introduction and re-stimulated using CD3 or CD3/28 dynabeads (Miltenyi Biotec) at a ratio of 3:1 (bead:cells; number), and then expression of CD25 was measured.

Phenotypic analysis was performed at 1 day after cell activation. The bead-restimulated (activated) cells were washed with PBS (phosphate-buffered saline) supplemented with 1% (v/v) fetal bovine serum (FBS) and stained with PE-conjugated anti-CD25 antibody (BD Bioscience) for 30 min at 4° C.

The obtained cells were washed and resuspended in PBS, followed by flow cytometry on BD ACCURI C6 (BD Biosciences) and the level of CD25 expression was measured by median fluorescence intensity (MFI).

For comparison, flow cytometry was performed in the same manner on wild-type cells in which Cas9 protein and sgRNA were not introduced, and on cells with which CD3 or CD3/28 dynabeads were not treated.

The obtained CD25 expression level (CD25 MFI) is shown in FIG. 1 to FIG. 4.

Figure 1:
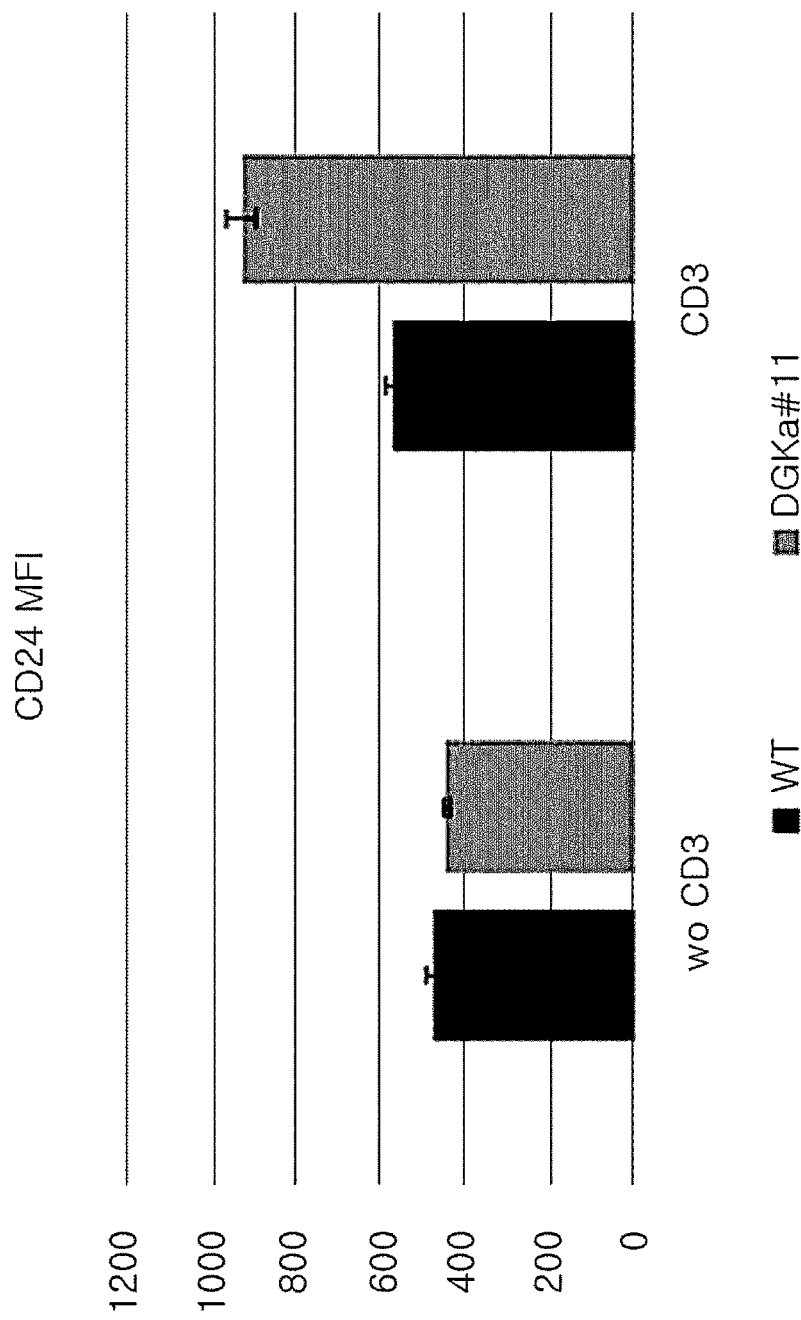
FIG. 1 is a graph showing the median fluorescence intensity (MFI) of CD25 in cells, where the DGK-alpha gene is knocked out, using sgRNA (#11; indicated as DGK-alpha #11) for DGK-alpha.
Figure 2:
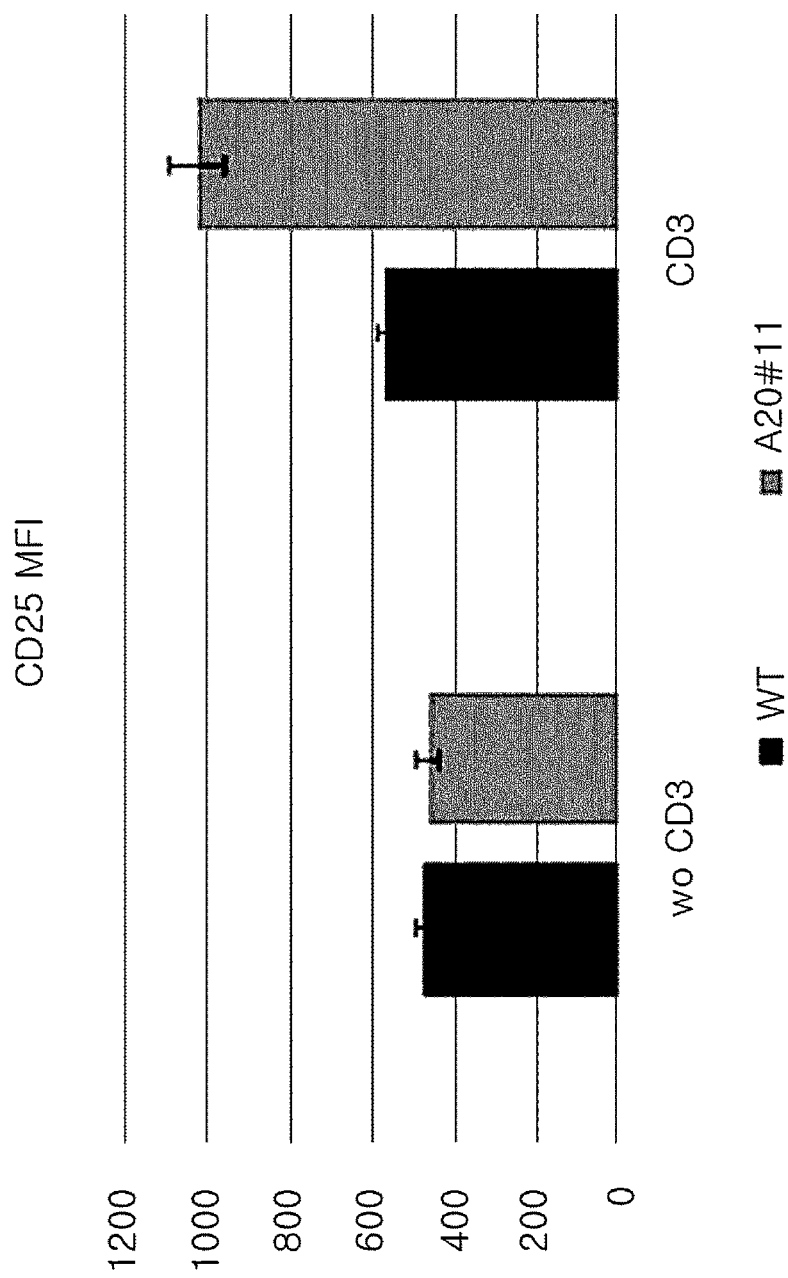
FIG. 2 is a graph showing the MFI of CD25 in cells, where A20 gene is knocked out, using sgRNA (#11; indicated as A20 #11) for A20.
Figure 3:
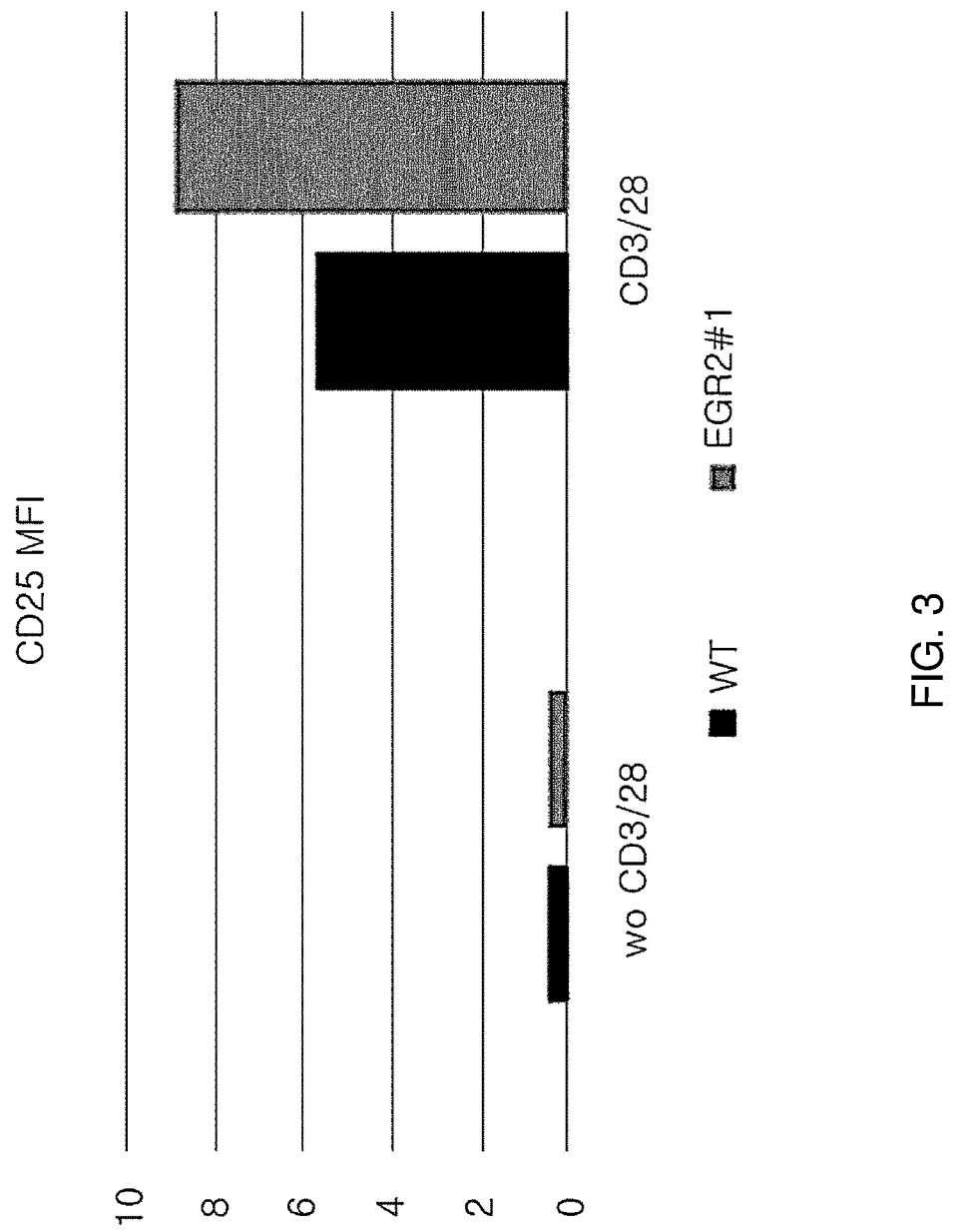
FIG. 3 is a graph showing the MFI of CD25 in cells, where EGR2 gene is knocked out, using sgRNA (#1; indicated as EGR2 #1) for EGR2.
Figure 4:
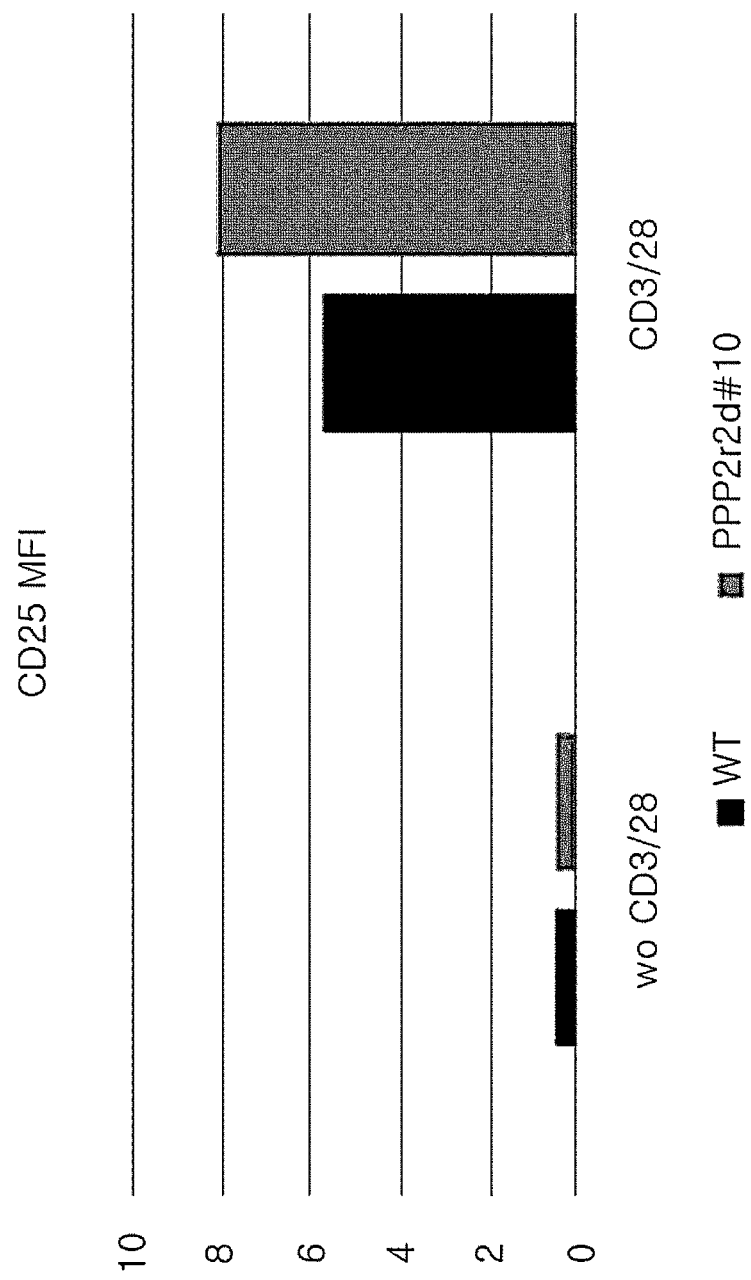
FIG. 4 is a graph showing the MFI of CD25 in cells, where PPP2R2D gene is knocked out, using sgRNA (#10; indicated as PPP2R2D #10) for PPP2R2D.

FIG. 1 shows the CD25 MFI in cells where the DGK-alpha gene was knocked out using sgRNA (#11; denoted DGK-alpha #11) for DGK-alpha, FIG. 2 shows the CD25 MFI in cells where the A20 gene was knocked out using sgRNA (#11; denoted as A20 #11) for A20, FIG. 3 shows the CD25 MFI in cells where the EGR2 gene was knocked out using sgRNA (#1; denoted EGR2 #1) for EGR2, and FIG. 4 shows the CD25 MFI in cells where the PPP2R2D gene was knocked out using sgRNA (#10; denoted PPP2R2D #10) for PPP2R2D, respectively.

As shown in FIGS. 1 to 4, in the case of cells not treated with CD3 or CD3/28 dynabeads, the presence or absence of knockout of the genes did not affect CD25 expression level, whereas in the case of cells treated with CD3 or CD3/28 dynabeads, it was confirmed that the expression level of CD25 was markedly increased when the gene were knockout as compared with wild type.

In addition, secretion levels of IFN-gamma, a kind of cytokine, were tested by ELISA.

As described previously, after re-stimulated Jurkat cells by CD3 or CD3/28 dynabeads were activated for 36 h, the culture medium was collected and diluted to 1/100 or 1/200 ratio (w/v) using a diluent buffer (provided by ELISA kit, Biolegend), and followed being color-developed using an ELISA kit (BioLegend), and quantified using a spectrophotometer (MULTISCAN GO, Thermo Scientific).

For comparison, ELISA was performed in the same manner on wild type cells into which Cas9 protein and sgRNA were not introduced.

The results obtained are shown in FIG. 5.

FIG. 5 shows: a IFN-gamma level in cell culture medium in which the DGK-alpha gene was knocked out using sgRNA (#11; denoted as DGK-alpha #11) for DGK-alpha; a IFN-gamma levels in cell culture medium in which the A20 gene was knocked out using sgRNA (#11; denoted as A20 #11) for A20; a IFN-gamma level in cell culture medium in which the EGR2 gene was knocked out using sgRNA (#1; denoted as EGR2 #1) for EGR2 (IFN-gamma level units: pg/ml).

As shown in FIG. 5, it was confirmed that when the genes were knocked out, the secretion amount of IFN-gamma was significantly increased as compared with the wild type.

Example 5: Activation of Human Primary T-Cells and Enhancement of Cytokine Secretion Referring to the method described in Example 4 above, human primary T-cells transfected with Cas9 protein and sgRNA were activated with CD3 beads (bead:cell ratio of 1:1, 2:1, and 3:1, respectively). After 2 days, secretion levels of IFN-gamma and IL-2 were measured by ELISA (IFN-gamma or IL-2 ELISA kit; Biolegend).

The obtained results are shown in FIG. 6 and FIG. 7.

FIG. 6 shows: a IFN-gamma level in the cell culture medium in which the DGK-alpha gene was knocked out using sgRNA (#11; denoted as DGK-alpha #11) for DGK-alpha; a IFN-gamma level in the cell culture medium in which the DGK-alpha gene was knocked out using sgRNA (using combination with #8 and #11; denoted as DGK-alpha #8+11); a IFN-gamma level in cell culture medium in which the DGK-zeta gene was knocked out using sgRNA (#5; denoted as DGK-zeta #5) for DGK-zeta; and a IFN-gamma level in the cell culture medium in which the A20 gene was knocked out using sgRNA (#11; denoted as A20 #11) for A20 (IFN-gamma level units: pg/ml).

FIG. 7 shows: IL-2 levels in cell culture medium in which DGK-alpha gene was knocked out using DGKalpha #11; IL-2 levels in cell culture medium in which DGK-alpha gene was knocked out using DGK-alpha #8+11; IL-2 levels in cell culture medium in which the DGK-zeta gene was knocked out using DGK-zeta #5; and (IL-2 level unit: pg/ml) in the cell culture medium in which the A20 gene was knocked out using A20 #11 (IL-2 level unit: pg/ml).

In FIGS. 6 and 7, "AAVS1" was used as a negative control for cells where the AAVS1 site was cleaved with the CRISPR system.

As shown in FIGS. 6 and 7, when the genes were knocked out, the secretion amount of cytokines such as IFN-gamma and IL-2 was significantly increased as compared with the wild type.

These results, which showed an increase in CD25 expression and cytokine secretion in Jurkat cells and human primary T cells, indicate that the TCR-mediated activation signal was increased when the genes were knocked out and the immune function of T cells can be enhanced by the increased activity.

Example 6: CAR-T Cell Activation and Cytokine Secretion Enhancement

Human peripheral blood T cells (pan-T cells) were purchased from STEMCELL TECHNOLOGIES. The X-VIVO 15 medium supplemented with 50 U/mL of hIL-2 and 5 ng/mL of hIL-7 was used for cell culture. Anti-CD3/28 Dynabeads (ThermoFisher Scientific) was used to activate the cells, with a ratio of beads to cells of 3:1.

After 24 hours of activation, T cells were mixed with 139-CAR lentivirus for 48 hours on retronectin-coated plates. 139-CAR is a CAR capable of specifically recognizing EGFRvIII and inducing an immune response. Subsequently, 40 µg of recombinant $S.$ $pyogenes$ Cas9 protein (Toolgen, Korea) and 10 µg of chemically synthesized tracr/crRNA (Integrated DNA Technologies) were introduced into the cells by electroporation with 4D-Nucleofecter (Lonza).

For in vitro experiments, pre-stained U87vIII cancer cells with Cell Trace (ThermoFisher Scientific) were co-cultured with 139 CAR-T at appropriate ratios. At this time, the culture was performed with or without 10 ng/mL TGF-β1 or 0.5 µg/mL PGE2. After co-culturing with cancer cell lines, the cells were stained with 7-aminoactinomycin D (7-AAD) for cytotoxicity test experiments. The stained samples were collected on an Attune NxT Acoustic Focusing Cytometer and analyzed with FlowJo.

The cytotoxicity was calculated by the formula [(% lysis sample–% lysis minimum)/(% lysis max [100%]–% lysis minimum]×100%. In addition, the supernatants of co-cultures were also analyzed by ELISA Kit (Biolegend) for the determination of IL-2 and IFN-γ content. For cell proliferation experiment of 139 CAR-T cells, the 139 CAR-T cells stained by CellTrace were co-cultured with the target cancer cell line U87vIII, and then the dilution degree of Cell Trace was measured using flow cytometry in 139 CAR-T cells.

According to the experimental design (FIG. 8a, A), the Indel effect of DGKα and DGKζ was 75.9% and 93.5%, respectively on 139 CAR-T cells delivered with a single Cas9/gRNA ribonucleoprotein (RNP) complex targeting DGKα or DGKζ (FIG. 8 a, B).

Two gRNAs targeting DGKα and DGKζ, respectively, were introduced into cells by electroporation to produce dual-negative 139 CAR-T cells for DGKα and DGKζ. As a result, the Indel effects of DGKα and DGKζ were 49.2% and 92.4%, respectively (FIG. 8a, B).

No significant effects of off-target on the respective gRNA of DGKα and DGKζ were confirmed using the targeted deep-sequencing (FIG. 8b).

In addition, it was observed that DGKα, DGKζ, and DGKαζ KO (knockout) 139 CAR-T cells have a significantly increased cytotoxicity, cytokine production capacity and proliferative capacity, compared to wild type 139 CAR-T cells (FIG. 9a A,B and FIG. 9b).

Interestingly, DGKαζ KO 139 CAR-T cells showed more significantly increased cytokine release compared to single KO 139 CAR-T cells for DGKα or DGKζ, which is thought to be a synergistic effect of DGKα and DGKζ. It is considered that the effector function increase of such DGKs KO 139 CAR-T cells is attributed to the increase of the CD3-terminal signal, namely increase of ERK1/2 and high expression of CAR after antigen exposure (FIG. 10A, B).

In addition, despite of the strongly activated signals in DGKs KO 139 CAR-T cells, no increase in basal cytokine was observed in the absence of target cancer cells, which is suggesting a high safety of DGKs KO (FIG. 11A). Furthermore, the expression of PD-11 and TIM-33, which are exhaustion markers, was not increased in DGKs KO 139 CAR-T cells compared with 139 CAR-T cells. (FIG. 11B). These results suggest that DGKs KO does not promote T cell exhaustion even after prolonged antigen exposure (FIG. 11B).

The anti-cancer effect of 139 CAR-T cells was markedly impaired by treatment with signaling 1 immunosuppressive inhibitors such as TGF-β1 and PGE2, whereas in the case of DGKαζ KO 139 CAR-T cells, it was confirmed that cytotoxicity and cytokine release was maintained even in the presence of inhibitory cytolysis factors (FIG. 12A, B).

These results indicate that T cell function can be activated by inactivating DGK gene using CRISPR/Cas9.

In other words, it was confirmed that the inactivation of DGK gene can enhance the CD3 terminal signal, thereby enhancing the anticancer function and the proliferation of CAR-T cells.

In addition, knockout (KO) CAR-T cells of DGKαζ (two isoforms types not did not show a significant increase in exhaustion markers and were less responsive to immunosuppressive cytolysis factors such as TGF-β and prostaglandin E2 (PGE2).

Thus, it was confirmed that DGK KO by CRISPR/Cas9 can enhance the increased effector function of T cells.

Example 7: NK (Natural Killer) Cell Activation and Cytokine Secretion Enhancement 7.1 NK 92 Cell Line and Human Primary NK Cell Culture NK92 cell lines were purchased from ATCC (CRL-2407), Primary NK cells were purchased from STEMCELL TECHNOLOGY and cultured according to the protocol provided.

NK92 cells were cultured in RPMI 1640 medium (WellGene) containing 10% FCS (fetal calf serum), which is supplemented with 100 μg/ml streptomycin, 100 U/ml penicillin, 2 mM UltraGlutamine I, 200-300 U/ml IL-2 and 10 U/ml IL-15.

7.2 Introduction by Electroporation

In order to knock out DGKα and DGKζ in NK92 cell line, electroporation was performed by Neon electroporator (Thermo Fisher Scientific) at 1200V, 10 ms and 3 pulse. For primary NK cells, 1200 V, 20 ms, and 3 pulses were used.

4 μg of recombinant *S. pyogenes* Cas9 protein (Toolgen, Korea) and 1 μg of chemically synthesized tracr/crRNA (Integrated DNA Technologies) were incubated for 20 minutes to obtain a Cas9 RNP complex.

$2 \times 10^5$ NK92 cells resuspended in R buffer were added (contacted) to the pre-incubated Cas9 RNP complex to perform the electroporation. After that, the cells were plated at a concentration of $4 \times 10^5$ cells/mL in the medium.

The crRNA targeting sequences used in the experiments were as follows:

DGKα:
(SEQ ID NO: 331)
CTCTCAAGCTGAGTGGGTCC

DGKζ:
(SEQ ID NO: 332)
ACGAGCACTCACCAGCATCC.

7.3 In Vitro Killing Assays

To analyze the cytotoxicity of NK92 cells and primary NK cells, the cells were co-cultured with Raji cells stained by CellTrace Far Red (Invitrogen) or $1 \times 10^5$ K562 cells on U-bottom 96 plates. After co-culture for 18 hours, the cells were harvested and stained with 7-AAD and then analyzed by flow cytometry. All cytotoxicity experiments were performed 3 times.

The results are shown in FIG. 13. It was confirmed that the DGKα knockout efficiency (KO efficiency) in NK92 cells and primary NK cells was excellent (FIGS. 13 A and B). In addition, the killing activity of NK-92 was confirmed through the measurement of 7-AAD-positive Raji cells, indicating that the cytotoxicity was increased by DGKα knockout.

In particular, these results confirm that the immune function can be effectively manipulated against NK cells, which are known as being difficult to genetically manipulate.

Example 8: NKT (Natural Killer) Cell Activation and Cytokine Secretion Enhancement 8.1 NKT Cell Culture Human PBMC were purchased from STEMCELL TECHNOLOGY (Canada). These cells were plated at a concentration of $1 \times 10^6$ cells/ml in 10% FBS supplemented RPMI medium which is added with 1000 U/ml interferon-γ (Pepro Tech). 50 ng/ml of anti-human OKT-3 (Biolegend) was added to the culture medium for 5 days and 400 U/ml of IL-2 (Pepro Tech) for 20 days.

8.2 Introduction by Electroporation

In order to knock out DGKα, DGKζ and PD1 in NKT cell line, electroporation was performed by Neon electroporator (Thermo Fisher Scientific) at 1550V, 10 ms, and 3 pulse.

4 μg of recombinant *S. pyogenes* Cas9 protein (Toolgen, Korea) and 1 μg of chemically synthesized tracr/crRNA (Integrated DNA Technologies) were incubated for 20 minutes to obtain a Cas9 RNP complex.

$2 \times 10^5$ NKT cells resuspended in R buffer were added (contacted) to the pre-incubated Cas9 RNP complex to perform the electroporation. After that, the cells were seeded at a concentration of $4 \times 10^5$ cells/mL in the medium.

The crRNA targeting sequences used in the experiments were as follows:

DGKα:
(SEQ ID NO: 331)
CTCTCAAGCTGAGTGGGTCC

DGKζ:
(SEQ ID NO: 332)
ACGAGCACTCACCAGCATCC.

PD-11:
(SEQ ID NO: 87)
GTCTGGGCGGTGCTACAACTGGG 8.3 In Vitro Killing Assays

To analyze the cytotoxicity of NKT cells, the NKT cells were co-cultured with $2 \times 10^4$4 U87vIII cells stained by CellTrace Far Red (Invitrogen) on U-bottom 96 well-plates. After co-culture for 18 hours, the cells were harvested and stained with 7-AAD and then analyzed by flow cytometry. All cytotoxicity experiments were performed 3 times.

As a result, it was confirmed that the knockout of DGKα and DGKζ in human NKT cells was efficiently performed by the CRISPR/Cas9 system as shown in FIG. 14.

Indel efficiency was confirmed by deep sequencing (FIG. 14A), and CRISPR/Cas9 treated NKT cells were analyzed by trypan blue staining to confirm that cell growth (FIG. 14B) and cell viability were maintained well (Viability=Viable cell number/Total cell number). Moreover, through Western blotting, it was confirmed that the knockout of DGKα and DGKζ also occurred well at the protein level (FIG. 14 D)

Furthermore, as shown in FIG. 15, it was confirmed that knockout of DGKα and DGKζ improves the effector function of NKT cells U87vIII, H460 and K562 cells were treated with Cell Trace (Thermo fisher) and cultured for 18 hours at a ratio of E:T (effector cell:target cell ratio) of 20:1 in a 96-well plate. Analysis of the apoptosis level of 7-AAD positive cancer cells by flow cytometry revealed that the knockout of DGKα and DGKζ increased the NKT killing activity of the corresponding NKT cells. The knockout of each of DGKα and DGKζ also had an effect of increasing the killing activity, but it was furthermore confirmed that the killing activity was more improved when the two genes were knocked out simultaneously (FIG. 15 A).

On the other hand, IFN-secretion was measured by ELISA (IFN-kit, Biolegend), and the results showed that the knockout of DGKα and DGKζ increased the IFN-releasing ability of the corresponding cells. Thought the respective knockout of DGKα and DGKζ also had the good effect of enhancing IFN-secretion, it was confirmed that IFN-secretion was further enhanced when both genes were knocked out simultaneously (FIG. 15 B).

In addition, as shown in FIG. 16, it was confirmed that the PD-1 knockout mediated CRISPR/Cas9 in human NKT cells enhanced the effector function of NKT cells. PD-1 knockout was induced using CRISPR-Cas9 in NKT cells, and knockout efficiency of PD-1 was analyzed by targeted deep sequencing. Moreover, U87vIII cells and NKT cells were co-cultured to confirm the function of NKT cells as anti-cancer effectors through PD-1 knockout. U87vIII cells were treated with Cell Trace (Thermo fisher) for 18 hours at a ratio of E:T (effector cell:target cell)=50:1 for 18 hours in a 96-well plate, and 7-AAD positive cancer cells were analyzed by flow cytometry for killing activity.

As a result, it was confirmed that the high indel efficiency in the PD-1 gene by CRISPR/Cas9 was confirmed (FIG. 16A), thereby improving a cytotoxicity thereby (FIG. 16B)

Overall, the above results show that knockout of CRISPR/Cas9-mediated immunomodulatory genes, such as DGK, can have a significant immune enhancement effect in various types of immune cells.

These biological effects of DGK gene knockout show that immune cells including T cells, NK cells and NKT etc. can be developed as immunotherapeutic agents in the form of clinically applicable cells through improving immune functions

INDUSTRIAL APPLICABILITY

An effective immune cell therapeutic can be obtained by the modified immune system in which the functions are artificially manipulated according to the artificially manipulated immune regulatory factors and the cells containing the same.

For example, when the immune regulatory factors are artificially controlled by the method or composition of the present specification, the immune efficacies involved in survival, proliferation, persistency, cytotoxicity, cytokine-release and/or infiltration, etc. of immune cells may be improved.

This application contains references to amino acid sequences and/or nucleic acid sequences which have been submitted concurrently herewith as the sequence listing text file entitled "63066440.TXT", file size 55 KiloBytes (KB), created on 27 Jul. 2022.

SEQUENCE LISTING

```
<160> NUMBER OF SEQ ID NOS: 332

<210> SEQ ID NO 1
<211> LENGTH: 23
<212> TYPE: DNA
<213> ORGANISM: Homo Sapiens

<400> SEQUENCE: 1
cttgtggcgc tgaaaacgaa cgg                                          23

<210> SEQ ID NO 2
<211> LENGTH: 23
<212> TYPE: DNA
<213> ORGANISM: Homo Sapiens

<400> SEQUENCE: 2
atgccacttc tcagtacatg tgg                                          23

<210> SEQ ID NO 3
<211> LENGTH: 23
<212> TYPE: DNA
<213> ORGANISM: Homo Sapiens

<400> SEQUENCE: 3
gccacttctc agtacatgtg ggg                                          23

<210> SEQ ID NO 4
<211> LENGTH: 23
<212> TYPE: DNA
<213> ORGANISM: Homo Sapiens

<400> SEQUENCE: 4
gccccacatg tactgagaag tgg                                          23

<210> SEQ ID NO 5
```

```
<211> LENGTH: 23
<212> TYPE: DNA
<213> ORGANISM: Homo Sapiens

<400> SEQUENCE: 5
tcagtacatg tggggcgttc agg                                              23

<210> SEQ ID NO 6
<211> LENGTH: 23
<212> TYPE: DNA
<213> ORGANISM: Homo Sapiens

<400> SEQUENCE: 6
gggcgttcag gacacagact tgg                                              23

<210> SEQ ID NO 7
<211> LENGTH: 23
<212> TYPE: DNA
<213> ORGANISM: Homo Sapiens

<400> SEQUENCE: 7
cacagacttg gtactgagga agg                                              23

<210> SEQ ID NO 8
<211> LENGTH: 23
<212> TYPE: DNA
<213> ORGANISM: Homo Sapiens

<400> SEQUENCE: 8
ggcgctgttc agcacgctca agg                                              23

<210> SEQ ID NO 9
<211> LENGTH: 23
<212> TYPE: DNA
<213> ORGANISM: Homo Sapiens

<400> SEQUENCE: 9
cacgcaactt taaattccgc tgg                                              23

<210> SEQ ID NO 10
<211> LENGTH: 23
<212> TYPE: DNA
<213> ORGANISM: Homo Sapiens

<400> SEQUENCE: 10
cggggctttg ctatgatact cgg                                              23

<210> SEQ ID NO 11
<211> LENGTH: 23
<212> TYPE: DNA
<213> ORGANISM: Homo Sapiens

<400> SEQUENCE: 11
ggcttccaca gacacaccca tgg                                              23

<210> SEQ ID NO 12
<211> LENGTH: 23
<212> TYPE: DNA
<213> ORGANISM: Homo Sapiens

<400> SEQUENCE: 12
tgaagtccac ttcgggccat ggg                                              23
```

```
<210> SEQ ID NO 13
<211> LENGTH: 23
<212> TYPE: DNA
<213> ORGANISM: Homo sapiens

<400> SEQUENCE: 13
ctgtacgaca cggacagaaa tgg                                              23

<210> SEQ ID NO 14
<211> LENGTH: 23
<212> TYPE: DNA
<213> ORGANISM: Homo Sapiens

<400> SEQUENCE: 14
tgtacgacac ggacagaaat ggg                                              23

<210> SEQ ID NO 15
<211> LENGTH: 23
<212> TYPE: DNA
<213> ORGANISM: Homo Sapiens

<400> SEQUENCE: 15
cacggacaga aatgggatcc tgg                                              23

<210> SEQ ID NO 16
<211> LENGTH: 23
<212> TYPE: DNA
<213> ORGANISM: Homo Sapiens

<400> SEQUENCE: 16
gatgcgagtg gctgaatacc tgg                                              23

<210> SEQ ID NO 17
<211> LENGTH: 23
<212> TYPE: DNA
<213> ORGANISM: Homo Sapiens

<400> SEQUENCE: 17
gagtggctga atacctggat tgg                                              23

<210> SEQ ID NO 18
<211> LENGTH: 23
<212> TYPE: DNA
<213> ORGANISM: Homo Sapiens

<400> SEQUENCE: 18
agtggctgaa tacctggatt ggg                                              23

<210> SEQ ID NO 19
<211> LENGTH: 23
<212> TYPE: DNA
<213> ORGANISM: Homo Sapiens

<400> SEQUENCE: 19
attgggatgt gtctgagctg agg                                              23

<210> SEQ ID NO 20
<211> LENGTH: 23
<212> TYPE: DNA
<213> ORGANISM: Homo Sapiens

<400> SEQUENCE: 20
atgaaagaga ttgactatga tgg                                              23
```

```
<210> SEQ ID NO 21
<211> LENGTH: 23
<212> TYPE: DNA
<213> ORGANISM: Homo Sapiens

<400> SEQUENCE: 21
ctctgtctct caagctgagt ggg                                             23

<210> SEQ ID NO 22
<211> LENGTH: 23
<212> TYPE: DNA
<213> ORGANISM: Homo Sapiens

<400> SEQUENCE: 22
tctctcaagc tgagtgggtc cgg                                             23

<210> SEQ ID NO 23
<211> LENGTH: 23
<212> TYPE: DNA
<213> ORGANISM: Homo Sapiens

<400> SEQUENCE: 23
ctctcaagct gagtgggtcc ggg                                             23

<210> SEQ ID NO 24
<211> LENGTH: 23
<212> TYPE: DNA
<213> ORGANISM: Homo Sapiens

<400> SEQUENCE: 24
caagctgagt gggtccgggc tgg                                             23

<210> SEQ ID NO 25
<211> LENGTH: 23
<212> TYPE: DNA
<213> ORGANISM: Homo Sapiens

<400> SEQUENCE: 25
ttgacatgac tggagagaag agg                                             23

<210> SEQ ID NO 26
<211> LENGTH: 23
<212> TYPE: DNA
<213> ORGANISM: Homo Sapiens

<400> SEQUENCE: 26
gactggagag aagaggtcgt tgg                                             23

<210> SEQ ID NO 27
<211> LENGTH: 23
<212> TYPE: DNA
<213> ORGANISM: Homo Sapiens

<400> SEQUENCE: 27
gagacgggag caaagctgct ggg                                             23

<210> SEQ ID NO 28
<211> LENGTH: 23
<212> TYPE: DNA
<213> ORGANISM: Homo Sapiens

<400> SEQUENCE: 28
agagacggga gcaaagctgc tgg                                             23
```

```
<210> SEQ ID NO 29
<211> LENGTH: 23
<212> TYPE: DNA
<213> ORGANISM: Homo Sapiens

<400> SEQUENCE: 29
tggtttctag gtgcagagac ggg                                              23

<210> SEQ ID NO 30
<211> LENGTH: 23
<212> TYPE: DNA
<213> ORGANISM: Homo Sapiens

<400> SEQUENCE: 30
taagtgaagg tctggtttct agg                                              23

<210> SEQ ID NO 31
<211> LENGTH: 23
<212> TYPE: DNA
<213> ORGANISM: Homo Sapiens

<400> SEQUENCE: 31
tgcccatgta agtgaaggtc tgg                                              23

<210> SEQ ID NO 32
<211> LENGTH: 23
<212> TYPE: DNA
<213> ORGANISM: Homo Sapiens

<400> SEQUENCE: 32
gaacttgccc atgtaagtga agg                                              23

<210> SEQ ID NO 33
<211> LENGTH: 23
<212> TYPE: DNA
<213> ORGANISM: Homo Sapiens

<400> SEQUENCE: 33
tccattgacc ctcagtaccc tgg                                              23

<210> SEQ ID NO 34
<211> LENGTH: 23
<212> TYPE: DNA
<213> ORGANISM: Homo Sapiens

<400> SEQUENCE: 34
tatgccttct gggtagcagc tgg                                              23

<210> SEQ ID NO 35
<211> LENGTH: 23
<212> TYPE: DNA
<213> ORGANISM: Homo Sapiens

<400> SEQUENCE: 35
tgagtgcagg catcttgcaa ggg                                              23

<210> SEQ ID NO 36
<211> LENGTH: 23
<212> TYPE: DNA
<213> ORGANISM: Homo Sapiens

<400> SEQUENCE: 36
```
gagtgcaggc atcttgcaag ggg                                                      23

<210> SEQ ID NO 37
<211> LENGTH: 23
<212> TYPE: DNA
<213> ORGANISM: Homo Sapiens

<400> SEQUENCE: 37
gatgaggctg tggttgaagc tgg                                                      23

<210> SEQ ID NO 38
<211> LENGTH: 23
<212> TYPE: DNA
<213> ORGANISM: Homo Sapiens

<400> SEQUENCE: 38
ccactggcca caggacccct ggg                                                      23

<210> SEQ ID NO 39
<211> LENGTH: 23
<212> TYPE: DNA
<213> ORGANISM: Homo Sapiens

<400> SEQUENCE: 39
gggacatggt gcacacaccc agg                                                      23

<210> SEQ ID NO 40
<211> LENGTH: 23
<212> TYPE: DNA
<213> ORGANISM: Homo Sapiens

<400> SEQUENCE: 40
gagtacaggt ggtccaggtc agg                                                      23

<210> SEQ ID NO 41
<211> LENGTH: 23
<212> TYPE: DNA
<213> ORGANISM: Homo Sapiens

<400> SEQUENCE: 41
gcggagagta caggtggtcc agg                                                      23

<210> SEQ ID NO 42
<211> LENGTH: 23
<212> TYPE: DNA
<213> ORGANISM: Homo Sapiens

<400> SEQUENCE: 42
gcggtggcgg agagtacagg tgg                                                      23

<210> SEQ ID NO 43
<211> LENGTH: 23
<212> TYPE: DNA
<213> ORGANISM: Homo Sapiens

<400> SEQUENCE: 43
tctcctgcac agccagaata agg                                                      23

<210> SEQ ID NO 44
<211> LENGTH: 23
<212> TYPE: DNA
<213> ORGANISM: Homo Sapiens

<400> SEQUENCE: 44
acgcagaagg gtcctggtag agg     23

<210> SEQ ID NO 45
<211> LENGTH: 23
<212> TYPE: DNA
<213> ORGANISM: Homo Sapiens

<400> SEQUENCE: 45
aggtggtggg taggccagag agg     23

<210> SEQ ID NO 46
<211> LENGTH: 23
<212> TYPE: DNA
<213> ORGANISM: Homo Sapiens

<400> SEQUENCE: 46
cccaagccag ccacggaccc agg     23

<210> SEQ ID NO 47
<211> LENGTH: 23
<212> TYPE: DNA
<213> ORGANISM: Homo Sapiens

<400> SEQUENCE: 47
acctgggtcc gtggctggct tgg     23

<210> SEQ ID NO 48
<211> LENGTH: 23
<212> TYPE: DNA
<213> ORGANISM: Homo Sapiens

<400> SEQUENCE: 48
aagagacctg ggtccgtggc tgg     23

<210> SEQ ID NO 49
<211> LENGTH: 23
<212> TYPE: DNA
<213> ORGANISM: Homo Sapiens

<400> SEQUENCE: 49
ggatcattgg gaagagacct ggg     23

<210> SEQ ID NO 50
<211> LENGTH: 23
<212> TYPE: DNA
<213> ORGANISM: Homo Sapiens

<400> SEQUENCE: 50
gggatcattg ggaagagacc tgg     23

<210> SEQ ID NO 51
<211> LENGTH: 23
<212> TYPE: DNA
<213> ORGANISM: Homo Sapiens

<400> SEQUENCE: 51
caggatagtc tgggatcatt ggg     23

<210> SEQ ID NO 52
<211> LENGTH: 23
<212> TYPE: DNA
<213> ORGANISM: Homo Sapiens

<400> SEQUENCE: 52
ggaaagaatc caggatagtc tgg                                              23

<210> SEQ ID NO 53
<211> LENGTH: 23
<212> TYPE: DNA
<213> ORGANISM: Homo Sapiens

<400> SEQUENCE: 53
cagtgccaga gagacctaca tgg                                              23

<210> SEQ ID NO 54
<211> LENGTH: 23
<212> TYPE: DNA
<213> ORGANISM: Homo Sapiens

<400> SEQUENCE: 54
ctgtaccatg taggtctctc tgg                                              23

<210> SEQ ID NO 55
<211> LENGTH: 23
<212> TYPE: DNA
<213> ORGANISM: Homo Sapiens

<400> SEQUENCE: 55
agagacctac atggtacagc tgg                                              23

<210> SEQ ID NO 56
<211> LENGTH: 23
<212> TYPE: DNA
<213> ORGANISM: Homo Sapiens

<400> SEQUENCE: 56
ctgggccagc tgtaccatgt agg                                              23

<210> SEQ ID NO 57
<211> LENGTH: 23
<212> TYPE: DNA
<213> ORGANISM: Homo Sapiens

<400> SEQUENCE: 57
agggaaaggg cttacggtct ggg                                              23

<210> SEQ ID NO 58
<211> LENGTH: 23
<212> TYPE: DNA
<213> ORGANISM: Homo Sapiens

<400> SEQUENCE: 58
cagggaaagg gcttacggtc tgg                                              23

<210> SEQ ID NO 59
<211> LENGTH: 23
<212> TYPE: DNA
<213> ORGANISM: Homo Sapiens

<400> SEQUENCE: 59
tctggagatc ttcttgcaac agg                                              23

<210> SEQ ID NO 60
<211> LENGTH: 23
<212> TYPE: DNA
<213> ORGANISM: Homo Sapiens

```
<400> SEQUENCE: 60
ctccggttca tgactttgaa agg                                              23

<210> SEQ ID NO 61
<211> LENGTH: 23
<212> TYPE: DNA
<213> ORGANISM: Homo Sapiens

<400> SEQUENCE: 61
gtcttccatc ttcgtctttc agg                                              23

<210> SEQ ID NO 62
<211> LENGTH: 23
<212> TYPE: DNA
<213> ORGANISM: Homo Sapiens

<400> SEQUENCE: 62
gaagacttcg agacccattt agg                                              23

<210> SEQ ID NO 63
<211> LENGTH: 23
<212> TYPE: DNA
<213> ORGANISM: Homo Sapiens

<400> SEQUENCE: 63
tcgagaccca tttaggatca cgg                                              23

<210> SEQ ID NO 64
<211> LENGTH: 23
<212> TYPE: DNA
<213> ORGANISM: Homo Sapiens

<400> SEQUENCE: 64
gtagcgccgt gatcctaaat ggg                                              23

<210> SEQ ID NO 65
<211> LENGTH: 23
<212> TYPE: DNA
<213> ORGANISM: Homo Sapiens

<400> SEQUENCE: 65
cgtagcgccg tgatcctaaa tgg                                              23

<210> SEQ ID NO 66
<211> LENGTH: 23
<212> TYPE: DNA
<213> ORGANISM: Homo Sapiens

<400> SEQUENCE: 66
catttaggat cacggcgcta cgg                                              23

<210> SEQ ID NO 67
<211> LENGTH: 23
<212> TYPE: DNA
<213> ORGANISM: Homo Sapiens

<400> SEQUENCE: 67
ggtcccaata ttgaagccca tgg                                              23

<210> SEQ ID NO 68
<211> LENGTH: 23
<212> TYPE: DNA
```

```
<213> ORGANISM: Homo Sapiens

<400> SEQUENCE: 68
gatccatggg cttcaatatt ggg                                           23

<210> SEQ ID NO 69
<211> LENGTH: 23
<212> TYPE: DNA
<213> ORGANISM: Homo Sapiens

<400> SEQUENCE: 69
agatccatgg gcttcaatat tgg                                           23

<210> SEQ ID NO 70
<211> LENGTH: 23
<212> TYPE: DNA
<213> ORGANISM: Homo Sapiens

<400> SEQUENCE: 70
gcttctacca taagatccat ggg                                           23

<210> SEQ ID NO 71
<211> LENGTH: 23
<212> TYPE: DNA
<213> ORGANISM: Homo Sapiens

<400> SEQUENCE: 71
cgcttctacc ataagatcca tgg                                           23

<210> SEQ ID NO 72
<211> LENGTH: 23
<212> TYPE: DNA
<213> ORGANISM: Homo Sapiens

<400> SEQUENCE: 72
gcatttgcaa aaattcgccg tgg                                           23

<210> SEQ ID NO 73
<211> LENGTH: 23
<212> TYPE: DNA
<213> ORGANISM: Homo Sapiens

<400> SEQUENCE: 73
atgacctgag aattaattta tgg                                           23

<210> SEQ ID NO 74
<211> LENGTH: 23
<212> TYPE: DNA
<213> ORGANISM: Homo Sapiens

<400> SEQUENCE: 74
ccatgcactc ccagacatcg tgg                                           23

<210> SEQ ID NO 75
<211> LENGTH: 23
<212> TYPE: DNA
<213> ORGANISM: Homo Sapiens

<400> SEQUENCE: 75
gcactggtgc gggtggaact cgg                                           23

<210> SEQ ID NO 76
<211> LENGTH: 23
```

```
<212> TYPE: DNA
<213> ORGANISM: Homo Sapiens

<400> SEQUENCE: 76
acacgttgca ctggtgcggg tgg                                              23

<210> SEQ ID NO 77
<211> LENGTH: 23
<212> TYPE: DNA
<213> ORGANISM: Homo Sapiens

<400> SEQUENCE: 77
cgaacacgtt gcactggtgc ggg                                              23

<210> SEQ ID NO 78
<211> LENGTH: 23
<212> TYPE: DNA
<213> ORGANISM: Homo Sapiens

<400> SEQUENCE: 78
acgaacacgt tgcactggtg cgg                                              23

<210> SEQ ID NO 79
<211> LENGTH: 23
<212> TYPE: DNA
<213> ORGANISM: Homo Sapiens

<400> SEQUENCE: 79
tgtagacgaa cacgttgcac tgg                                              23

<210> SEQ ID NO 80
<211> LENGTH: 23
<212> TYPE: DNA
<213> ORGANISM: Homo Sapiens

<400> SEQUENCE: 80
gcgcatgtca cacaggcgga tgg                                              23

<210> SEQ ID NO 81
<211> LENGTH: 23
<212> TYPE: DNA
<213> ORGANISM: Homo Sapiens

<400> SEQUENCE: 81
aggagcgcat gtcacacagg cgg                                              23

<210> SEQ ID NO 82
<211> LENGTH: 23
<212> TYPE: DNA
<213> ORGANISM: Homo Sapiens

<400> SEQUENCE: 82
ccgaggagcg catgtcacac agg                                              23

<210> SEQ ID NO 83
<211> LENGTH: 23
<212> TYPE: DNA
<213> ORGANISM: Homo Sapiens

<400> SEQUENCE: 83
cctgtgtgac atgcgctcct cgg                                              23

<210> SEQ ID NO 84
```

```
<211> LENGTH: 23
<212> TYPE: DNA
<213> ORGANISM: Homo Sapiens

<400> SEQUENCE: 84
cgactggcca gggcgcctgt ggg                                            23

<210> SEQ ID NO 85
<211> LENGTH: 23
<212> TYPE: DNA
<213> ORGANISM: Homo Sapiens

<400> SEQUENCE: 85
accgcccaga cgactggcca ggg                                            23

<210> SEQ ID NO 86
<211> LENGTH: 23
<212> TYPE: DNA
<213> ORGANISM: Homo Sapiens

<400> SEQUENCE: 86
caccgcccag acgactggcc agg                                            23

<210> SEQ ID NO 87
<211> LENGTH: 23
<212> TYPE: DNA
<213> ORGANISM: Homo Sapiens

<400> SEQUENCE: 87
gtctgggcgg tgctacaact ggg                                            23

<210> SEQ ID NO 88
<211> LENGTH: 23
<212> TYPE: DNA
<213> ORGANISM: Homo Sapiens

<400> SEQUENCE: 88
ctacaactgg gctggcggcc agg                                            23

<210> SEQ ID NO 89
<211> LENGTH: 23
<212> TYPE: DNA
<213> ORGANISM: Homo Sapiens

<400> SEQUENCE: 89
cacctaccta agaaccatcc tgg                                            23

<210> SEQ ID NO 90
<211> LENGTH: 23
<212> TYPE: DNA
<213> ORGANISM: Homo Sapiens

<400> SEQUENCE: 90
cggtcaccac gagcagggct ggg                                            23

<210> SEQ ID NO 91
<211> LENGTH: 23
<212> TYPE: DNA
<213> ORGANISM: Homo Sapiens

<400> SEQUENCE: 91
gccctgctcg tggtgaccga agg                                            23
```

```
<210> SEQ ID NO 92
<211> LENGTH: 23
<212> TYPE: DNA
<213> ORGANISM: Homo Sapiens

<400> SEQUENCE: 92
cggagagctt cgtgctaaac tgg                                              23

<210> SEQ ID NO 93
<211> LENGTH: 23
<212> TYPE: DNA
<213> ORGANISM: Homo Sapiens

<400> SEQUENCE: 93
cagcttgtcc gtctggttgc tgg                                              23

<210> SEQ ID NO 94
<211> LENGTH: 23
<212> TYPE: DNA
<213> ORGANISM: Homo Sapiens

<400> SEQUENCE: 94
aggcggccag cttgtccgtc tgg                                              23

<210> SEQ ID NO 95
<211> LENGTH: 23
<212> TYPE: DNA
<213> ORGANISM: Homo Sapiens

<400> SEQUENCE: 95
ccgggctggc tgcggtcctc ggg                                              23

<210> SEQ ID NO 96
<211> LENGTH: 23
<212> TYPE: DNA
<213> ORGANISM: Homo Sapiens

<400> SEQUENCE: 96
cgttgggcag ttgtgtgaca cgg                                              23

<210> SEQ ID NO 97
<211> LENGTH: 23
<212> TYPE: DNA
<213> ORGANISM: Homo Sapiens

<400> SEQUENCE: 97
cataaagcca tggcttgcct tgg                                              23

<210> SEQ ID NO 98
<211> LENGTH: 23
<212> TYPE: DNA
<213> ORGANISM: Homo Sapiens

<400> SEQUENCE: 98
ccttggattt cagcggcaca agg                                              23

<210> SEQ ID NO 99
<211> LENGTH: 23
<212> TYPE: DNA
<213> ORGANISM: Homo Sapiens

<400> SEQUENCE: 99
ccttgtgccg ctgaaatcca agg                                              23
```

```
<210> SEQ ID NO 100
<211> LENGTH: 23
<212> TYPE: DNA
<213> ORGANISM: Homo Sapiens

<400> SEQUENCE: 100
cactcacctt tgcagaagac agg                                              23

<210> SEQ ID NO 101
<211> LENGTH: 23
<212> TYPE: DNA
<213> ORGANISM: Homo Sapiens

<400> SEQUENCE: 101
ttccatgcta gcaatgcacg tgg                                              23

<210> SEQ ID NO 102
<211> LENGTH: 23
<212> TYPE: DNA
<213> ORGANISM: Homo Sapiens

<400> SEQUENCE: 102
ggccacgtgc attgctagca tgg                                              23

<210> SEQ ID NO 103
<211> LENGTH: 23
<212> TYPE: DNA
<213> ORGANISM: Homo Sapiens

<400> SEQUENCE: 103
ggcccagcct gctgtggtac tgg                                              23

<210> SEQ ID NO 104
<211> LENGTH: 23
<212> TYPE: DNA
<213> ORGANISM: Homo Sapiens

<400> SEQUENCE: 104
aggtccgggt gacagtgctt cgg                                              23

<210> SEQ ID NO 105
<211> LENGTH: 23
<212> TYPE: DNA
<213> ORGANISM: Homo Sapiens

<400> SEQUENCE: 105
ccgggtgaca gtgcttcggc agg                                              23

<210> SEQ ID NO 106
<211> LENGTH: 23
<212> TYPE: DNA
<213> ORGANISM: Homo Sapiens

<400> SEQUENCE: 106
ctgtgcggca acctacatga tgg                                              23

<210> SEQ ID NO 107
<211> LENGTH: 23
<212> TYPE: DNA
<213> ORGANISM: Homo Sapiens

<400> SEQUENCE: 107
caactcattc cccatcatgt agg                                              23
```

```
<210> SEQ ID NO 108
<211> LENGTH: 23
<212> TYPE: DNA
<213> ORGANISM: Homo Sapiens

<400> SEQUENCE: 108
ctagatgatt ccatctgcac ggg                                              23

<210> SEQ ID NO 109
<211> LENGTH: 23
<212> TYPE: DNA
<213> ORGANISM: Homo Sapiens

<400> SEQUENCE: 109
ggctaggagt cagcgacata tgg                                              23

<210> SEQ ID NO 110
<211> LENGTH: 23
<212> TYPE: DNA
<213> ORGANISM: Homo Sapiens

<400> SEQUENCE: 110
gctaggagtc agcgacatat ggg                                              23

<210> SEQ ID NO 111
<211> LENGTH: 23
<212> TYPE: DNA
<213> ORGANISM: Homo Sapiens

<400> SEQUENCE: 111
ctaggagtca gcgacatatg ggg                                              23

<210> SEQ ID NO 112
<211> LENGTH: 23
<212> TYPE: DNA
<213> ORGANISM: Homo Sapiens

<400> SEQUENCE: 112
gtactgtgta gccaggatgc tgg                                              23

<210> SEQ ID NO 113
<211> LENGTH: 23
<212> TYPE: DNA
<213> ORGANISM: Homo Sapiens

<400> SEQUENCE: 113
acgagcactc accagcatcc tgg                                              23

<210> SEQ ID NO 114
<211> LENGTH: 23
<212> TYPE: DNA
<213> ORGANISM: Homo Sapiens

<400> SEQUENCE: 114
aggctccagg aatgtccgcg agg                                              23

<210> SEQ ID NO 115
<211> LENGTH: 23
<212> TYPE: DNA
<213> ORGANISM: Homo Sapiens

<400> SEQUENCE: 115
```

```
acttacctcg cggacattcc tgg                                              23

<210> SEQ ID NO 116
<211> LENGTH: 23
<212> TYPE: DNA
<213> ORGANISM: Homo Sapiens

<400> SEQUENCE: 116
caccctgggc acttacctcg cgg                                              23

<210> SEQ ID NO 117
<211> LENGTH: 23
<212> TYPE: DNA
<213> ORGANISM: Homo Sapiens

<400> SEQUENCE: 117
gtgccgtaca aaggttggct ggg                                              23

<210> SEQ ID NO 118
<211> LENGTH: 23
<212> TYPE: DNA
<213> ORGANISM: Homo Sapiens

<400> SEQUENCE: 118
ggtgccgtac aaaggttggc tgg                                              23

<210> SEQ ID NO 119
<211> LENGTH: 23
<212> TYPE: DNA
<213> ORGANISM: Homo Sapiens

<400> SEQUENCE: 119
ctctcctcag taccacagca agg                                              23

<210> SEQ ID NO 120
<211> LENGTH: 23
<212> TYPE: DNA
<213> ORGANISM: Homo Sapiens

<400> SEQUENCE: 120
cctggggcct ccgggcgcgg agg                                              23

<210> SEQ ID NO 121
<211> LENGTH: 23
<212> TYPE: DNA
<213> ORGANISM: Homo Sapiens

<400> SEQUENCE: 121
agtactcacc tggggcctcc ggg                                              23

<210> SEQ ID NO 122
<211> LENGTH: 23
<212> TYPE: DNA
<213> ORGANISM: Homo Sapiens

<400> SEQUENCE: 122
agggtctcca gcggccctcc tgg                                              23

<210> SEQ ID NO 123
<211> LENGTH: 23
<212> TYPE: DNA
<213> ORGANISM: Homo Sapiens

<400> SEQUENCE: 123
```
gcaagtactt acgcctcctt ggg                                                   23

<210> SEQ ID NO 124
<211> LENGTH: 23
<212> TYPE: DNA
<213> ORGANISM: Homo Sapiens

<400> SEQUENCE: 124
ttgcggtaca tctccagcct ggg                                                   23

<210> SEQ ID NO 125
<211> LENGTH: 23
<212> TYPE: DNA
<213> ORGANISM: Homo Sapiens

<400> SEQUENCE: 125
tttgcggtac atctccagcc tgg                                                   23

<210> SEQ ID NO 126
<211> LENGTH: 23
<212> TYPE: DNA
<213> ORGANISM: Homo Sapiens

<400> SEQUENCE: 126
gcaaaacctg tccactctta tgg                                                   23

<210> SEQ ID NO 127
<211> LENGTH: 23
<212> TYPE: DNA
<213> ORGANISM: Homo Sapiens

<400> SEQUENCE: 127
ttggtgccat aagagtggac agg                                                   23

<210> SEQ ID NO 128
<211> LENGTH: 23
<212> TYPE: DNA
<213> ORGANISM: Homo Sapiens

<400> SEQUENCE: 128
ggtgcaagtt tcttatatgt tgg                                                   23

<210> SEQ ID NO 129
<211> LENGTH: 23
<212> TYPE: DNA
<213> ORGANISM: Homo Sapiens

<400> SEQUENCE: 129
acctgatgca tataataatc agg                                                   23

<210> SEQ ID NO 130
<211> LENGTH: 23
<212> TYPE: DNA
<213> ORGANISM: Homo Sapiens

<400> SEQUENCE: 130
acctgattat tatatgcatc agg                                                   23

<210> SEQ ID NO 131
<211> LENGTH: 23
<212> TYPE: DNA
<213> ORGANISM: Homo Sapiens

<400> SEQUENCE: 131
cagagcacca gagtgccgtc tgg                                              23

<210> SEQ ID NO 132
<211> LENGTH: 23
<212> TYPE: DNA
<213> ORGANISM: Homo Sapiens

<400> SEQUENCE: 132
agagcaccag agtgccgtct ggg                                              23

<210> SEQ ID NO 133
<211> LENGTH: 23
<212> TYPE: DNA
<213> ORGANISM: Homo Sapiens

<400> SEQUENCE: 133
agagtgccgt ctgggtctga agg                                              23

<210> SEQ ID NO 134
<211> LENGTH: 23
<212> TYPE: DNA
<213> ORGANISM: Homo Sapiens

<400> SEQUENCE: 134
aggaaggccg tccattctca ggg                                              23

<210> SEQ ID NO 135
<211> LENGTH: 23
<212> TYPE: DNA
<213> ORGANISM: Homo Sapiens

<400> SEQUENCE: 135
ggatagaacc aaccatgttg agg                                              23

<210> SEQ ID NO 136
<211> LENGTH: 23
<212> TYPE: DNA
<213> ORGANISM: Homo Sapiens

<400> SEQUENCE: 136
tctgttgccc tcaacatggt tgg                                              23

<210> SEQ ID NO 137
<211> LENGTH: 23
<212> TYPE: DNA
<213> ORGANISM: Homo Sapiens

<400> SEQUENCE: 137
ttagtctgtt gccctcaaca tgg                                              23

<210> SEQ ID NO 138
<211> LENGTH: 23
<212> TYPE: DNA
<213> ORGANISM: Homo Sapiens

<400> SEQUENCE: 138
gtctggcaaa tgggaggtga tgg                                              23

<210> SEQ ID NO 139
<211> LENGTH: 23
<212> TYPE: DNA
<213> ORGANISM: Homo Sapiens

<400> SEQUENCE: 139
cagaggttct gtctggcaaa tgg                                      23

<210> SEQ ID NO 140
<211> LENGTH: 23
<212> TYPE: DNA
<213> ORGANISM: Homo Sapiens

<400> SEQUENCE: 140
ttgtagccag aggttctgtc tgg                                      23

<210> SEQ ID NO 141
<211> LENGTH: 23
<212> TYPE: DNA
<213> ORGANISM: Homo Sapiens

<400> SEQUENCE: 141
acttctggat gagctctctc agg                                      23

<210> SEQ ID NO 142
<211> LENGTH: 23
<212> TYPE: DNA
<213> ORGANISM: Homo Sapiens

<400> SEQUENCE: 142
agagctcatc cagaagtaaa tgg                                      23

<210> SEQ ID NO 143
<211> LENGTH: 23
<212> TYPE: DNA
<213> ORGANISM: Homo Sapiens

<400> SEQUENCE: 143
ttggtgtctc catttacttc tgg                                      23

<210> SEQ ID NO 144
<211> LENGTH: 23
<212> TYPE: DNA
<213> ORGANISM: Homo Sapiens

<400> SEQUENCE: 144
ttctggcttc ccttcataca ggg                                      23

<210> SEQ ID NO 145
<211> LENGTH: 23
<212> TYPE: DNA
<213> ORGANISM: Homo Sapiens

<400> SEQUENCE: 145
caggactcac acgactattc tgg                                      23

<210> SEQ ID NO 146
<211> LENGTH: 23
<212> TYPE: DNA
<213> ORGANISM: Homo Sapiens

<400> SEQUENCE: 146
ctactttctt gtgtaaagtc agg                                      23

<210> SEQ ID NO 147
<211> LENGTH: 23
<212> TYPE: DNA

-continued

```
<213> ORGANISM: Homo Sapiens

<400> SEQUENCE: 147
gactttacac aagaaagtag agg                                            23

<210> SEQ ID NO 148
<211> LENGTH: 23
<212> TYPE: DNA
<213> ORGANISM: Homo Sapiens

<400> SEQUENCE: 148
gtctttctcc attagccttt tgg                                            23

<210> SEQ ID NO 149
<211> LENGTH: 23
<212> TYPE: DNA
<213> ORGANISM: Homo Sapiens

<400> SEQUENCE: 149
aatggagaaa gacgtaactt cgg                                            23

<210> SEQ ID NO 150
<211> LENGTH: 23
<212> TYPE: DNA
<213> ORGANISM: Homo Sapiens

<400> SEQUENCE: 150
atggagaaag acgtaacttc ggg                                            23

<210> SEQ ID NO 151
<211> LENGTH: 23
<212> TYPE: DNA
<213> ORGANISM: Homo Sapiens

<400> SEQUENCE: 151
tggagaaaga cgtaacttcg ggg                                            23

<210> SEQ ID NO 152
<211> LENGTH: 23
<212> TYPE: DNA
<213> ORGANISM: Homo Sapiens

<400> SEQUENCE: 152
tttggttgac tgctttcacc tgg                                            23

<210> SEQ ID NO 153
<211> LENGTH: 23
<212> TYPE: DNA
<213> ORGANISM: Homo Sapiens

<400> SEQUENCE: 153
tcactcaaat cggagacatt tgg                                            23

<210> SEQ ID NO 154
<211> LENGTH: 23
<212> TYPE: DNA
<213> ORGANISM: Homo Sapiens

<400> SEQUENCE: 154
atctgaagct ctggattttc agg                                            23

<210> SEQ ID NO 155
<211> LENGTH: 23
```

```
<212> TYPE: DNA
<213> ORGANISM: Homo Sapiens

<400> SEQUENCE: 155
gcttcagatt ctgaatgagc agg                                         23

<210> SEQ ID NO 156
<211> LENGTH: 23
<212> TYPE: DNA
<213> ORGANISM: Homo Sapiens

<400> SEQUENCE: 156
cagattctga atgagcagga ggg                                         23

<210> SEQ ID NO 157
<211> LENGTH: 23
<212> TYPE: DNA
<213> ORGANISM: Homo Sapiens

<400> SEQUENCE: 157
aaggcagtgc taatgcctaa tgg                                         23

<210> SEQ ID NO 158
<211> LENGTH: 23
<212> TYPE: DNA
<213> ORGANISM: Homo Sapiens

<400> SEQUENCE: 158
gcagaaactg tagcaccatt agg                                         23

<210> SEQ ID NO 159
<211> LENGTH: 23
<212> TYPE: DNA
<213> ORGANISM: Homo Sapiens

<400> SEQUENCE: 159
accgcaatgg aaacacaatc tgg                                         23

<210> SEQ ID NO 160
<211> LENGTH: 23
<212> TYPE: DNA
<213> ORGANISM: Homo Sapiens

<400> SEQUENCE: 160
tgtggttttc tgcaccgcaa tgg                                         23

<210> SEQ ID NO 161
<211> LENGTH: 23
<212> TYPE: DNA
<213> ORGANISM: Homo Sapiens

<400> SEQUENCE: 161
cataaatgcc attaacagtc agg                                         23

<210> SEQ ID NO 162
<211> LENGTH: 23
<212> TYPE: DNA
<213> ORGANISM: Homo Sapiens

<400> SEQUENCE: 162
attagtagcc tgactgttaa tgg                                         23

<210> SEQ ID NO 163
```

```
<211> LENGTH: 23
<212> TYPE: DNA
<213> ORGANISM: Homo Sapiens

<400> SEQUENCE: 163
cgatgggtga gtgatctcac agg                                               23

<210> SEQ ID NO 164
<211> LENGTH: 23
<212> TYPE: DNA
<213> ORGANISM: Homo Sapiens

<400> SEQUENCE: 164
actcacccat cgcatacctc agg                                               23

<210> SEQ ID NO 165
<211> LENGTH: 23
<212> TYPE: DNA
<213> ORGANISM: Homo Sapiens

<400> SEQUENCE: 165
ctcacccatc gcatacctca ggg                                               23

<210> SEQ ID NO 166
<211> LENGTH: 23
<212> TYPE: DNA
<213> ORGANISM: Homo Sapiens

<400> SEQUENCE: 166
agcaacagga ggagttgcag agg                                               23

<210> SEQ ID NO 167
<211> LENGTH: 23
<212> TYPE: DNA
<213> ORGANISM: Homo Sapiens

<400> SEQUENCE: 167
ccagtaggat cagcaacagg agg                                               23

<210> SEQ ID NO 168
<211> LENGTH: 23
<212> TYPE: DNA
<213> ORGANISM: Homo Sapiens

<400> SEQUENCE: 168
ctcctgttgc tgatcctact ggg                                               23

<210> SEQ ID NO 169
<211> LENGTH: 23
<212> TYPE: DNA
<213> ORGANISM: Homo Sapiens

<400> SEQUENCE: 169
ggcccagtag gatcagcaac agg                                               23

<210> SEQ ID NO 170
<211> LENGTH: 23
<212> TYPE: DNA
<213> ORGANISM: Homo Sapiens

<400> SEQUENCE: 170
ttgctgatcc tactgggccc tgg                                               23
```

```
<210> SEQ ID NO 171
<211> LENGTH: 23
<212> TYPE: DNA
<213> ORGANISM: Homo Sapiens

<400> SEQUENCE: 171
tggcaacagc ttgcagctgt ggg                                              23

<210> SEQ ID NO 172
<211> LENGTH: 23
<212> TYPE: DNA
<213> ORGANISM: Homo Sapiens

<400> SEQUENCE: 172
cttgggtccc ctgcttgccc ggg                                              23

<210> SEQ ID NO 173
<211> LENGTH: 23
<212> TYPE: DNA
<213> ORGANISM: Homo Sapiens

<400> SEQUENCE: 173 gtccctgct tgcccgggac cgg                                               23

<210> SEQ ID NO 174
<211> LENGTH: 23
<212> TYPE: DNA
<213> ORGANISM: Homo Sapiens

<400> SEQUENCE: 174
ctccggtccc gggcaagcag ggg                                              23

<210> SEQ ID NO 175
<211> LENGTH: 23
<212> TYPE: DNA
<213> ORGANISM: Homo Sapiens

<400> SEQUENCE: 175
tctccggtcc cgggcaagca ggg                                              23

<210> SEQ ID NO 176
<211> LENGTH: 23
<212> TYPE: DNA
<213> ORGANISM: Homo Sapiens

<400> SEQUENCE: 176
gtctccggtc ccgggcaagc agg                                              23

<210> SEQ ID NO 177
<211> LENGTH: 23
<212> TYPE: DNA
<213> ORGANISM: Homo Sapiens

<400> SEQUENCE: 177
gcttgcccgg gaccggagac agg                                              23

<210> SEQ ID NO 178
<211> LENGTH: 23
<212> TYPE: DNA
<213> ORGANISM: Homo Sapiens

<400> SEQUENCE: 178
ggtggcctgt ctccggtccc ggg                                              23
```

```
<210> SEQ ID NO 179
<211> LENGTH: 23
<212> TYPE: DNA
<213> ORGANISM: Homo Sapiens

<400> SEQUENCE: 179
cggtggcctg tctccggtcc cgg                                             23

<210> SEQ ID NO 180
<211> LENGTH: 23
<212> TYPE: DNA
<213> ORGANISM: Homo Sapiens

<400> SEQUENCE: 180
catattcggt ggcctgtctc cgg                                             23

<210> SEQ ID NO 181
<211> LENGTH: 23
<212> TYPE: DNA
<213> ORGANISM: Homo Sapiens

<400> SEQUENCE: 181
atctaggtac tcatattcgg tgg                                             23

<210> SEQ ID NO 182
<211> LENGTH: 23
<212> TYPE: DNA
<213> ORGANISM: Homo Sapiens

<400> SEQUENCE: 182
ataatctagg tactcatatt cgg                                             23

<210> SEQ ID NO 183
<211> LENGTH: 23
<212> TYPE: DNA
<213> ORGANISM: Homo Sapiens

<400> SEQUENCE: 183
ttatgatttc ctgccagaaa cgg                                             23

<210> SEQ ID NO 184
<211> LENGTH: 23
<212> TYPE: DNA
<213> ORGANISM: Homo Sapiens

<400> SEQUENCE: 184
atttctggag gctccgtttc tgg                                             23

<210> SEQ ID NO 185
<211> LENGTH: 23
<212> TYPE: DNA
<213> ORGANISM: Homo Sapiens

<400> SEQUENCE: 185
actgacacca ctcctctgac tgg                                             23

<210> SEQ ID NO 186
<211> LENGTH: 23
<212> TYPE: DNA
<213> ORGANISM: Homo Sapiens

<400> SEQUENCE: 186
ctgacaccac tcctctgact ggg                                             23
```

```
<210> SEQ ID NO 187
<211> LENGTH: 23
<212> TYPE: DNA
<213> ORGANISM: Homo Sapiens

<400> SEQUENCE: 187
accactcctc tgactgggcc tgg                                              23

<210> SEQ ID NO 188
<211> LENGTH: 23
<212> TYPE: DNA
<213> ORGANISM: Homo Sapiens

<400> SEQUENCE: 188
aacccctgag tctaccactg tgg                                              23

<210> SEQ ID NO 189
<211> LENGTH: 23
<212> TYPE: DNA
<213> ORGANISM: Homo Sapiens

<400> SEQUENCE: 189
ctccacagtg gtagactcag ggg                                              23

<210> SEQ ID NO 190
<211> LENGTH: 23
<212> TYPE: DNA
<213> ORGANISM: Homo Sapiens

<400> SEQUENCE: 190
gctccacagt ggtagactca ggg                                              23

<210> SEQ ID NO 191
<211> LENGTH: 23
<212> TYPE: DNA
<213> ORGANISM: Homo Sapiens

<400> SEQUENCE: 191
ggctccacag tggtagactc agg                                              23

<210> SEQ ID NO 192
<211> LENGTH: 23
<212> TYPE: DNA
<213> ORGANISM: Homo Sapiens

<400> SEQUENCE: 192
cctgctgcaa ggcgttctac tgg                                              23

<210> SEQ ID NO 193
<211> LENGTH: 23
<212> TYPE: DNA
<213> ORGANISM: Homo Sapiens

<400> SEQUENCE: 193
ccagtagaac gccttgcagc agg                                              23

<210> SEQ ID NO 194
<211> LENGTH: 23
<212> TYPE: DNA
<213> ORGANISM: Homo Sapiens

<400> SEQUENCE: 194
```
cgttctactg gcctggatgc agg                                                  23

<210> SEQ ID NO 195
<211> LENGTH: 23
<212> TYPE: DNA
<213> ORGANISM: Homo Sapiens

<400> SEQUENCE: 195
tctactggcc tggatgcagg agg                                                  23

<210> SEQ ID NO 196
<211> LENGTH: 23
<212> TYPE: DNA
<213> ORGANISM: Homo Sapiens

<400> SEQUENCE: 196
ccacggagct ggccaacatg ggg                                                  23

<210> SEQ ID NO 197
<211> LENGTH: 23
<212> TYPE: DNA
<213> ORGANISM: Homo Sapiens

<400> SEQUENCE: 197
cgtggacagg ttccccatgt tgg                                                  23

<210> SEQ ID NO 198
<211> LENGTH: 23
<212> TYPE: DNA
<213> ORGANISM: Homo Sapiens

<400> SEQUENCE: 198
gtccacggat tcagcagcta tgg                                                  23

<210> SEQ ID NO 199
<211> LENGTH: 23
<212> TYPE: DNA
<213> ORGANISM: Homo Sapiens

<400> SEQUENCE: 199
gaccactcaa ccagtgccca cgg                                                  23

<210> SEQ ID NO 200
<211> LENGTH: 23
<212> TYPE: DNA
<213> ORGANISM: Homo Sapiens

<400> SEQUENCE: 200
ggagtggtct gtgcctccgt ggg                                                  23

<210> SEQ ID NO 201
<211> LENGTH: 23
<212> TYPE: DNA
<213> ORGANISM: Homo Sapiens

<400> SEQUENCE: 201
ggcacagaca actcgactga cgg                                                  23

<210> SEQ ID NO 202
<211> LENGTH: 23
<212> TYPE: DNA
<213> ORGANISM: Homo Sapiens

<400> SEQUENCE: 202
gacaactcga ctgacggcca cgg                                           23

<210> SEQ ID NO 203
<211> LENGTH: 23
<212> TYPE: DNA
<213> ORGANISM: Homo Sapiens

<400> SEQUENCE: 203
aactcgactg acggccacgg agg                                           23

<210> SEQ ID NO 204
<211> LENGTH: 23
<212> TYPE: DNA
<213> ORGANISM: Homo Sapiens

<400> SEQUENCE: 204
cacagaaccc agtgccacag agg                                           23

<210> SEQ ID NO 205
<211> LENGTH: 23
<212> TYPE: DNA
<213> ORGANISM: Homo Sapiens

<400> SEQUENCE: 205
ggtagtaggt tccatggaca ggg                                           23

<210> SEQ ID NO 206
<211> LENGTH: 23
<212> TYPE: DNA
<213> ORGANISM: Homo Sapiens

<400> SEQUENCE: 206
tggtagtagg ttccatggac agg                                           23

<210> SEQ ID NO 207
<211> LENGTH: 23
<212> TYPE: DNA
<213> ORGANISM: Homo Sapiens

<400> SEQUENCE: 207
tcttttggta gtaggttcca tgg                                           23

<210> SEQ ID NO 208
<211> LENGTH: 23
<212> TYPE: DNA
<213> ORGANISM: Homo Sapiens

<400> SEQUENCE: 208
atggaaccta ctaccaaaag agg                                           23

<210> SEQ ID NO 209
<211> LENGTH: 23
<212> TYPE: DNA
<213> ORGANISM: Homo Sapiens

<400> SEQUENCE: 209
aacagacctc ttttggtagt agg                                           23

<210> SEQ ID NO 210
<211> LENGTH: 23
<212> TYPE: DNA
<213> ORGANISM: Homo Sapiens

```
<400> SEQUENCE: 210
gggtatgaac agacctcttt tgg                                              23

<210> SEQ ID NO 211
<211> LENGTH: 23
<212> TYPE: DNA
<213> ORGANISM: Homo Sapiens

<400> SEQUENCE: 211
tgtgtcctct gttactcaca agg                                              23

<210> SEQ ID NO 212
<211> LENGTH: 23
<212> TYPE: DNA
<213> ORGANISM: Homo Sapiens

<400> SEQUENCE: 212
gtgtcctctg ttactcacaa ggg                                              23

<210> SEQ ID NO 213
<211> LENGTH: 23
<212> TYPE: DNA
<213> ORGANISM: Homo Sapiens

<400> SEQUENCE: 213
gtagttgacg gacaaattgc tgg                                              23

<210> SEQ ID NO 214
<211> LENGTH: 23
<212> TYPE: DNA
<213> ORGANISM: Homo Sapiens

<400> SEQUENCE: 214
tttgtccgtc aactacccag tgg                                              23

<210> SEQ ID NO 215
<211> LENGTH: 23
<212> TYPE: DNA
<213> ORGANISM: Homo Sapiens

<400> SEQUENCE: 215
ttgtccgtca actacccagt ggg                                              23

<210> SEQ ID NO 216
<211> LENGTH: 23
<212> TYPE: DNA
<213> ORGANISM: Homo Sapiens

<400> SEQUENCE: 216
tgtccgtcaa ctacccagtg ggg                                              23

<210> SEQ ID NO 217
<211> LENGTH: 23
<212> TYPE: DNA
<213> ORGANISM: Homo Sapiens

<400> SEQUENCE: 217
gtccgtcaac tacccagtgg ggg                                              23

<210> SEQ ID NO 218
<211> LENGTH: 23
<212> TYPE: DNA
<213> ORGANISM: Homo Sapiens
```

<400> SEQUENCE: 218
ctctgtgaag cagtgcctgc tgg                                    23

<210> SEQ ID NO 219
<211> LENGTH: 23
<212> TYPE: DNA
<213> ORGANISM: Homo Sapiens

<400> SEQUENCE: 219
cctgctggcc atcctaatct tgg                                    23

<210> SEQ ID NO 220
<211> LENGTH: 23
<212> TYPE: DNA
<213> ORGANISM: Homo Sapiens

<400> SEQUENCE: 220
ccaagattag gatggccagc agg                                    23

<210> SEQ ID NO 221
<211> LENGTH: 23
<212> TYPE: DNA
<213> ORGANISM: Homo Sapiens

<400> SEQUENCE: 221
ggccatccta atcttggcgc tgg                                    23

<210> SEQ ID NO 222
<211> LENGTH: 23
<212> TYPE: DNA
<213> ORGANISM: Homo Sapiens

<400> SEQUENCE: 222
caccagcgcc aagattagga tgg                                    23

<210> SEQ ID NO 223
<211> LENGTH: 23
<212> TYPE: DNA
<213> ORGANISM: Homo Sapiens

<400> SEQUENCE: 223
agtgcacacg aagaagatag tgg                                    23

<210> SEQ ID NO 224
<211> LENGTH: 23
<212> TYPE: DNA
<213> ORGANISM: Homo Sapiens

<400> SEQUENCE: 224
tatcttcttc gtgtgcactg tgg                                    23

<210> SEQ ID NO 225
<211> LENGTH: 23
<212> TYPE: DNA
<213> ORGANISM: Homo Sapiens

<400> SEQUENCE: 225
cttcgtgtgc actgtggtgc tgg                                    23

<210> SEQ ID NO 226
<211> LENGTH: 23
<212> TYPE: DNA

<213> ORGANISM: Homo Sapiens

<400> SEQUENCE: 226
ggcggtccgc ctctcccgca agg                                          23

<210> SEQ ID NO 227
<211> LENGTH: 23
<212> TYPE: DNA
<213> ORGANISM: Homo Sapiens

<400> SEQUENCE: 227
gcggtccgcc tctcccgcaa ggg                                          23

<210> SEQ ID NO 228
<211> LENGTH: 23
<212> TYPE: DNA
<213> ORGANISM: Homo Sapiens

<400> SEQUENCE: 228
aattacgcac ggggtacatg tgg                                          23

<210> SEQ ID NO 229
<211> LENGTH: 23
<212> TYPE: DNA
<213> ORGANISM: Homo Sapiens

<400> SEQUENCE: 229
tgggggagta attacgcacg ggg                                          23

<210> SEQ ID NO 230
<211> LENGTH: 23
<212> TYPE: DNA
<213> ORGANISM: Homo Sapiens

<400> SEQUENCE: 230 gtggggagt aattacgcac ggg                                           23

<210> SEQ ID NO 231
<211> LENGTH: 23
<212> TYPE: DNA
<213> ORGANISM: Homo Sapiens

<400> SEQUENCE: 231
ggtgggggag taattacgca cgg                                          23

<210> SEQ ID NO 232
<211> LENGTH: 23
<212> TYPE: DNA
<213> ORGANISM: Homo Sapiens

<400> SEQUENCE: 232
taattactcc cccaccgaga tgg                                          23

<210> SEQ ID NO 233
<211> LENGTH: 23
<212> TYPE: DNA
<213> ORGANISM: Homo Sapiens

<400> SEQUENCE: 233
agatgcagac catctcggtg ggg                                          23

<210> SEQ ID NO 234
<211> LENGTH: 23

```
<212> TYPE: DNA
<213> ORGANISM: Homo Sapiens

<400> SEQUENCE: 234
gagatgcaga ccatctcggt ggg                                              23

<210> SEQ ID NO 235
<211> LENGTH: 23
<212> TYPE: DNA
<213> ORGANISM: Homo Sapiens

<400> SEQUENCE: 235
tgagatgcag accatctcgg tgg                                              23

<210> SEQ ID NO 236
<211> LENGTH: 23
<212> TYPE: DNA
<213> ORGANISM: Homo Sapiens

<400> SEQUENCE: 236
ggatgagatg cagaccatct cgg                                              23

<210> SEQ ID NO 237
<211> LENGTH: 23
<212> TYPE: DNA
<213> ORGANISM: Homo Sapiens

<400> SEQUENCE: 237
atctcatccc tgttgcctga tgg                                              23

<210> SEQ ID NO 238
<211> LENGTH: 23
<212> TYPE: DNA
<213> ORGANISM: Homo Sapiens

<400> SEQUENCE: 238
tcatccctgt tgcctgatgg ggg                                              23

<210> SEQ ID NO 239
<211> LENGTH: 23
<212> TYPE: DNA
<213> ORGANISM: Homo Sapiens

<400> SEQUENCE: 239
ctcaccccca tcaggcaaca ggg                                              23

<210> SEQ ID NO 240
<211> LENGTH: 23
<212> TYPE: DNA
<213> ORGANISM: Homo Sapiens

<400> SEQUENCE: 240
gagggcccct caccccatc agg                                               23

<210> SEQ ID NO 241
<211> LENGTH: 23
<212> TYPE: DNA
<213> ORGANISM: Homo Sapiens

<400> SEQUENCE: 241
gggccctctg ccacagccaa tgg                                              23

<210> SEQ ID NO 242
```

```
<211> LENGTH: 23
<212> TYPE: DNA
<213> ORGANISM: Homo Sapiens

<400> SEQUENCE: 242
ccctctgcca cagccaatgg ggg                                               23

<210> SEQ ID NO 243
<211> LENGTH: 23
<212> TYPE: DNA
<213> ORGANISM: Homo Sapiens

<400> SEQUENCE: 243
cccccattgg ctgtggcaga ggg                                               23

<210> SEQ ID NO 244
<211> LENGTH: 23
<212> TYPE: DNA
<213> ORGANISM: Homo Sapiens

<400> SEQUENCE: 244
gcccccattg gctgtggcag agg                                               23

<210> SEQ ID NO 245
<211> LENGTH: 23
<212> TYPE: DNA
<213> ORGANISM: Homo Sapiens

<400> SEQUENCE: 245
ggacaggccc ccattggctg tgg                                               23

<210> SEQ ID NO 246
<211> LENGTH: 23
<212> TYPE: DNA
<213> ORGANISM: Homo Sapiens

<400> SEQUENCE: 246
ccgggctctt ggccttggac agg                                               23

<210> SEQ ID NO 247
<211> LENGTH: 23
<212> TYPE: DNA
<213> ORGANISM: Homo Sapiens

<400> SEQUENCE: 247
ctgtccaagg ccaagagccc ggg                                               23

<210> SEQ ID NO 248
<211> LENGTH: 23
<212> TYPE: DNA
<213> ORGANISM: Homo Sapiens

<400> SEQUENCE: 248
tggcgtcagg cccgggctct tgg                                               23

<210> SEQ ID NO 249
<211> LENGTH: 23
<212> TYPE: DNA
<213> ORGANISM: Homo Sapiens

<400> SEQUENCE: 249
cgggcctgac gccagagccc agg                                               23
```

```
<210> SEQ ID NO 250
<211> LENGTH: 23
<212> TYPE: DNA
<213> ORGANISM: Homo Sapiens

<400> SEQUENCE: 250
caacaaccat gctgggcatc tgg                                            23

<210> SEQ ID NO 251
<211> LENGTH: 23
<212> TYPE: DNA
<213> ORGANISM: Homo Sapiens

<400> SEQUENCE: 251
gagggtccag atgcccagca tgg                                            23

<210> SEQ ID NO 252
<211> LENGTH: 23
<212> TYPE: DNA
<213> ORGANISM: Homo Sapiens

<400> SEQUENCE: 252
catctggacc ctcctacctc tgg                                            23

<210> SEQ ID NO 253
<211> LENGTH: 23
<212> TYPE: DNA
<213> ORGANISM: Homo Sapiens

<400> SEQUENCE: 253
agggctcacc agaggtagga ggg                                            23

<210> SEQ ID NO 254
<211> LENGTH: 23
<212> TYPE: DNA
<213> ORGANISM: Homo Sapiens

<400> SEQUENCE: 254
ggagttgatg tcagtcactt ggg                                            23

<210> SEQ ID NO 255
<211> LENGTH: 23
<212> TYPE: DNA
<213> ORGANISM: Homo Sapiens

<400> SEQUENCE: 255
tggagttgat gtcagtcact tgg                                            23

<210> SEQ ID NO 256
<211> LENGTH: 23
<212> TYPE: DNA
<213> ORGANISM: Homo Sapiens

<400> SEQUENCE: 256
agtgactgac atcaactcca agg                                            23

<210> SEQ ID NO 257
<211> LENGTH: 23
<212> TYPE: DNA
<213> ORGANISM: Homo Sapiens

<400> SEQUENCE: 257
gtgactgaca tcaactccaa ggg                                            23
```

```
<210> SEQ ID NO 258
<211> LENGTH: 23
<212> TYPE: DNA
<213> ORGANISM: Homo Sapiens

<400> SEQUENCE: 258
actccaaggg attggaattg agg                                              23

<210> SEQ ID NO 259
<211> LENGTH: 23
<212> TYPE: DNA
<213> ORGANISM: Homo Sapiens

<400> SEQUENCE: 259
cttcctcaat tccatccct tgg                                               23

<210> SEQ ID NO 260
<211> LENGTH: 23
<212> TYPE: DNA
<213> ORGANISM: Homo Sapiens

<400> SEQUENCE: 260
tacagttgag actcagaact tgg                                              23

<210> SEQ ID NO 261
<211> LENGTH: 23
<212> TYPE: DNA
<213> ORGANISM: Homo Sapiens

<400> SEQUENCE: 261
ttggaaggcc tgcatcatga tgg                                              23

<210> SEQ ID NO 262
<211> LENGTH: 23
<212> TYPE: DNA
<213> ORGANISM: Homo Sapiens

<400> SEQUENCE: 262
agaattggcc atcatgatgc agg                                              23

<210> SEQ ID NO 263
<211> LENGTH: 23
<212> TYPE: DNA
<213> ORGANISM: Homo Sapiens

<400> SEQUENCE: 263
gacagggctt atggcagaat tgg                                              23

<210> SEQ ID NO 264
<211> LENGTH: 23
<212> TYPE: DNA
<213> ORGANISM: Homo Sapiens

<400> SEQUENCE: 264
tgtaacatac ctggaggaca ggg                                              23

<210> SEQ ID NO 265
<211> LENGTH: 23
<212> TYPE: DNA
<213> ORGANISM: Homo Sapiens

<400> SEQUENCE: 265
gtgtaacata cctggaggac agg                                              23
```

<210> SEQ ID NO 266
<211> LENGTH: 23
<212> TYPE: DNA
<213> ORGANISM: Homo Sapiens

<400> SEQUENCE: 266
cgtacctgtg caactcctgt tgg                                            23

<210> SEQ ID NO 267
<211> LENGTH: 23
<212> TYPE: DNA
<213> ORGANISM: Homo Sapiens

<400> SEQUENCE: 267
gatctactgg aattcctaat ggg                                            23

<210> SEQ ID NO 268
<211> LENGTH: 23
<212> TYPE: DNA
<213> ORGANISM: Homo Sapiens

<400> SEQUENCE: 268
gagtcagctg ttggcccatt agg                                            23

<210> SEQ ID NO 269
<211> LENGTH: 23
<212> TYPE: DNA
<213> ORGANISM: Homo Sapiens

<400> SEQUENCE: 269
ctgcctacaa actcagtctc tgg                                            23

<210> SEQ ID NO 270
<211> LENGTH: 23
<212> TYPE: DNA
<213> ORGANISM: Homo Sapiens

<400> SEQUENCE: 270
gggcaggcag gacggactcc agg                                            23

<210> SEQ ID NO 271
<211> LENGTH: 23
<212> TYPE: DNA
<213> ORGANISM: Homo Sapiens

<400> SEQUENCE: 271
ggagtccgtc ctgcctgccc tgg                                            23

<210> SEQ ID NO 272
<211> LENGTH: 23
<212> TYPE: DNA
<213> ORGANISM: Homo Sapiens

<400> SEQUENCE: 272
gagtccgtcc tgcctgccct ggg                                            23

<210> SEQ ID NO 273
<211> LENGTH: 23
<212> TYPE: DNA
<213> ORGANISM: Homo Sapiens

<400> SEQUENCE: 273
gaaaagggtc cattggccaa agg                                                23

<210> SEQ ID NO 274
<211> LENGTH: 23
<212> TYPE: DNA
<213> ORGANISM: Homo Sapiens

<400> SEQUENCE: 274
gcctgcagaa aagggtccat tgg                                                23

<210> SEQ ID NO 275
<211> LENGTH: 23
<212> TYPE: DNA
<213> ORGANISM: Homo Sapiens

<400> SEQUENCE: 275
ttgatgtgct acagggaaca tgg                                                23

<210> SEQ ID NO 276
<211> LENGTH: 23
<212> TYPE: DNA
<213> ORGANISM: Homo Sapiens

<400> SEQUENCE: 276
agcgttcttg atgtgctaca ggg                                                23

<210> SEQ ID NO 277
<211> LENGTH: 23
<212> TYPE: DNA
<213> ORGANISM: Homo Sapiens

<400> SEQUENCE: 277
cagcgttctt gatgtgctac agg                                                23

<210> SEQ ID NO 278
<211> LENGTH: 23
<212> TYPE: DNA
<213> ORGANISM: Homo Sapiens

<400> SEQUENCE: 278
ctgtagcaca tcaagaacgc tgg                                                23

<210> SEQ ID NO 279
<211> LENGTH: 23
<212> TYPE: DNA
<213> ORGANISM: Homo Sapiens

<400> SEQUENCE: 279
tgtagcacat caagaacgct ggg                                                23

<210> SEQ ID NO 280
<211> LENGTH: 23
<212> TYPE: DNA
<213> ORGANISM: Homo Sapiens

<400> SEQUENCE: 280
ataggcaata atcatataac agg                                                23

<210> SEQ ID NO 281
<211> LENGTH: 23
<212> TYPE: DNA
<213> ORGANISM: Homo Sapiens

<400> SEQUENCE: 281
agtgcgtttc gctgcaggta agg                                               23

<210> SEQ ID NO 282
<211> LENGTH: 23
<212> TYPE: DNA
<213> ORGANISM: Homo Sapiens

<400> SEQUENCE: 282
gagtgagtgc gtttcgctgc agg                                               23

<210> SEQ ID NO 283
<211> LENGTH: 23
<212> TYPE: DNA
<213> ORGANISM: Homo Sapiens

<400> SEQUENCE: 283
gtcaggtttg tgcggttatg agg                                               23

<210> SEQ ID NO 284
<211> LENGTH: 23
<212> TYPE: DNA
<213> ORGANISM: Homo Sapiens

<400> SEQUENCE: 284
cgctgctggt caggtttgtg cgg                                               23

<210> SEQ ID NO 285
<211> LENGTH: 23
<212> TYPE: DNA
<213> ORGANISM: Homo Sapiens

<400> SEQUENCE: 285
aaacctgacc agcagcgcag agg                                               23

<210> SEQ ID NO 286
<211> LENGTH: 23
<212> TYPE: DNA
<213> ORGANISM: Homo Sapiens

<400> SEQUENCE: 286
ccagcagcgc agaggagccg tgg                                               23

<210> SEQ ID NO 287
<211> LENGTH: 23
<212> TYPE: DNA
<213> ORGANISM: Homo Sapiens

<400> SEQUENCE: 287
ccacggctcc tctgcgctgc tgg                                               23

<210> SEQ ID NO 288
<211> LENGTH: 23
<212> TYPE: DNA
<213> ORGANISM: Homo Sapiens

<400> SEQUENCE: 288
ccaactatct aactccactc agg                                               23

<210> SEQ ID NO 289
<211> LENGTH: 23
<212> TYPE: DNA
<213> ORGANISM: Homo Sapiens

```
<400> SEQUENCE: 289
cctgagtgga gttagatagt tgg                                              23

<210> SEQ ID NO 290
<211> LENGTH: 12
<212> TYPE: RNA
<213> ORGANISM: Artificial sequence
<220> FEATURE:
<223> OTHER INFORMATION: an example of a first complementary domain of
      gRNA

<400> SEQUENCE: 290
guuuuagagc ua                                                          12

<210> SEQ ID NO 291
<211> LENGTH: 13
<212> TYPE: RNA
<213> ORGANISM: Artificial sequence
<220> FEATURE:
<223> OTHER INFORMATION: an example of a first complementary domain of
      gRNA
<220> FEATURE:
<221> NAME/KEY: misc_feature
<222> LOCATION: (13)..(13)
<223> OTHER INFORMATION: n is (X)n, wherein each of the X is selected
      from a, c, g, and u, and wherein n of (X)n represent the number of
      bases, which is an integer of 5 to 15.

<400> SEQUENCE: 291
guuuuagagc uan                                                         13

<210> SEQ ID NO 292
<211> LENGTH: 25
<212> TYPE: RNA
<213> ORGANISM: Artificial sequence
<220> FEATURE:
<223> OTHER INFORMATION: an example of a first complementary domain of
      gRNA

<400> SEQUENCE: 292
guuuuagucc cuuuuuaaau uucuu                                            25

<210> SEQ ID NO 293
<211> LENGTH: 26
<212> TYPE: RNA
<213> ORGANISM: Artificial sequence
<220> FEATURE:
<223> OTHER INFORMATION: an example of a first complementary domain of
      gRNA
<220> FEATURE:
<221> NAME/KEY: misc_feature
<222> LOCATION: (26)..(26)
<223> OTHER INFORMATION: n is (X)n, wherein each of the X is selected
      from a, c, g, and u, and wherein n of (X)n represent the number of
      bases, which is an integer of 5 to 15.

<400> SEQUENCE: 293
guuuuagucc cuuuuuaaau uucuun                                           26

<210> SEQ ID NO 294
<211> LENGTH: 10
<212> TYPE: RNA
<213> ORGANISM: Artificial sequence
<220> FEATURE:
<223> OTHER INFORMATION: an example of a first complementary domain of
      gRNA
<220> FEATURE:
<221> NAME/KEY: misc_feature
<222> LOCATION: (1)..(1)
```

```
<223> OTHER INFORMATION: n is (X)n, wherein each of the X is selected
      from a, c, g, and u, and wherein n of (X)n represent the number of
      bases, which is an integer of 1 to 5.

<400> SEQUENCE: 294 nuuuguagau                                                                    10

<210> SEQ ID NO 295
<211> LENGTH: 14
<212> TYPE: RNA
<213> ORGANISM: Artificial sequence
<220> FEATURE:
<223> OTHER INFORMATION: an example of a second complementary domain of
      gRNA

<400> SEQUENCE: 295
uagcaaguua aaau                                                               14

<210> SEQ ID NO 296
<211> LENGTH: 16
<212> TYPE: RNA
<213> ORGANISM: Artificial sequence
<220> FEATURE:
<223> OTHER INFORMATION: an example of a second complementary domain of
      gRNA
<220> FEATURE:
<221> NAME/KEY: misc_feature
<222> LOCATION: (1)..(1)
<223> OTHER INFORMATION: n is (X)n, wherein each of the X is selected
      from a, c, g, and u, and wherein n of (X)n represent the number of
      bases, which is an integer of 1 to 15.
<220> FEATURE:
<221> NAME/KEY: misc_feature
<222> LOCATION: (16)..(16)
<223> OTHER INFORMATION: n is (X)m, wherein each of the X is selected
      from a, c, g, and u, and wherein m of (X)m represent the number of
      bases, which is an integer of 1 to 6.

<400> SEQUENCE: 296
nuagcaaguu aaaaun                                                             16

<210> SEQ ID NO 297
<211> LENGTH: 25
<212> TYPE: RNA
<213> ORGANISM: Artificial sequence
<220> FEATURE:
<223> OTHER INFORMATION: an example of a second complementary domain of
      gRNA

<400> SEQUENCE: 297
aagaaauuua aaagggacu aaaau                                                    25

<210> SEQ ID NO 298
<211> LENGTH: 27
<212> TYPE: RNA
<213> ORGANISM: Artificial sequence
<220> FEATURE:
<223> OTHER INFORMATION: an example of a second complementary domain of
      gRNA
<220> FEATURE:
<221> NAME/KEY: misc_feature
<222> LOCATION: (1)..(1)
<223> OTHER INFORMATION: n is (X)n, wherein each of the X is selected
      from a, c, g, and u, and wherein n of (X)n represent the number of
      bases, which is an integer of 1 to 15.
<220> FEATURE:
<221> NAME/KEY: misc_feature
<222> LOCATION: (27)..(27)
<223> OTHER INFORMATION: n is (X)m, wherein each of the X is selected
      from a, c, g, and u, and wherein m of (X)m represent the number of
      bases, which is an integer of 1 to 6.
```

-continued

```
<400> SEQUENCE: 298
naagaaauuu aaaaagggac uaaaaun                                    27

<210> SEQ ID NO 299
<211> LENGTH: 11
<212> TYPE: RNA
<213> ORGANISM: Artificial sequence
<220> FEATURE:
<223> OTHER INFORMATION: an example of a second complementary domain of
      gRNA

<400> SEQUENCE: 299
aaauuucuac u                                                     11

<210> SEQ ID NO 300
<211> LENGTH: 13
<212> TYPE: RNA
<213> ORGANISM: Artificial sequence
<220> FEATURE:
<223> OTHER INFORMATION: an example of a second complementary domain of
      gRNA
<220> FEATURE:
<221> NAME/KEY: misc_feature
<222> LOCATION: (1)..(1)
<223> OTHER INFORMATION: n is (X)n, wherein each of the X is selected
      from a, c, g, and u, and wherein n of (X)n represent the number of
      bases, which is an integer of 1 to 10.
<220> FEATURE:
<221> NAME/KEY: misc_feature
<222> LOCATION: (13)..(13)
<223> OTHER INFORMATION: n is (X)m, wherein each of the X is selected
      from a, c, g, and u, and wherein m of (X)m represent the number of
      bases, which is an integer of 1 to 6.

<400> SEQUENCE: 300
naaauuucua cun                                                   13

<210> SEQ ID NO 301
<211> LENGTH: 12
<212> TYPE: RNA
<213> ORGANISM: Artificial sequence
<220> FEATURE:
<223> OTHER INFORMATION: an example of a proximal domain

<400> SEQUENCE: 301
aaggcuaguc cg                                                    12

<210> SEQ ID NO 302
<211> LENGTH: 13
<212> TYPE: RNA
<213> ORGANISM: Artificial sequence
<220> FEATURE:
<223> OTHER INFORMATION: an example of a proximal domain
<220> FEATURE:
<221> NAME/KEY: misc_feature
<222> LOCATION: (13)..(13)
<223> OTHER INFORMATION: n is (X)n, wherein each of the X is selected
      from a, c, g, and u, and wherein n of (X)n represent the number of
      bases, which is an integer of 1 to 15.

<400> SEQUENCE: 302
aaggcuaguc cgn                                                   13

<210> SEQ ID NO 303
<211> LENGTH: 11
<212> TYPE: RNA
<213> ORGANISM: Artificial sequence
<220> FEATURE:
```

-continued

<223> OTHER INFORMATION: an example of a proximal domain

<400> SEQUENCE: 303
aaagaguuug c                                                            11

<210> SEQ ID NO 304
<211> LENGTH: 12
<212> TYPE: RNA
<213> ORGANISM: Artificial sequence
<220> FEATURE:
<223> OTHER INFORMATION: an example of a proximal domain
<220> FEATURE:
<221> NAME/KEY: misc_feature
<222> LOCATION: (12)..(12)
<223> OTHER INFORMATION: n is (X)n, wherein each of the X is selected
      from a, c, g, and u, and wherein n of (X)n represent the number of
      bases, which is an integer of 1 to 40.

<400> SEQUENCE: 304
aaagaguuug cn                                                           12

<210> SEQ ID NO 305
<211> LENGTH: 34
<212> TYPE: RNA
<213> ORGANISM: Artificial sequence
<220> FEATURE:
<223> OTHER INFORMATION: an example of tail domain

<400> SEQUENCE: 305
uuaucaacuu gaaaaagugg caccgagucg gugc                                   34

<210> SEQ ID NO 306
<211> LENGTH: 35
<212> TYPE: RNA
<213> ORGANISM: Artificial sequence
<220> FEATURE:
<223> OTHER INFORMATION: an example of tail domain
<220> FEATURE:
<221> NAME/KEY: misc_feature
<222> LOCATION: (35)..(35)
<223> OTHER INFORMATION: n is (X)n, wherein each of the X is selected
      from a, c, g, and u, and wherein n of (X)n represent the number of
      bases, which is an integer of 1 to 15.

<400> SEQUENCE: 306
uuaucaacuu gaaaaagugg caccgagucg gugcn                                  35

<210> SEQ ID NO 307
<211> LENGTH: 38
<212> TYPE: RNA
<213> ORGANISM: Artificial sequence
<220> FEATURE:
<223> OTHER INFORMATION: an example of tail domain

<400> SEQUENCE: 307
gggacucugc gggguuacaa uccccuaaaa ccgcuuuu                               38

<210> SEQ ID NO 308
<211> LENGTH: 39
<212> TYPE: RNA
<213> ORGANISM: Artificial sequence
<220> FEATURE:
<223> OTHER INFORMATION: an example of tail domain
<220> FEATURE:
<221> NAME/KEY: misc_feature
<222> LOCATION: (39)..(39)
<223> OTHER INFORMATION: n is (X)n, wherein each of the X is selected
      from a, c, g, and u, and wherein n of (X)n represent the number of
      bases, which is an integer of 1 to 15.

-continued

```
<400> SEQUENCE: 308
gggacucugc gggguuacaa uccccuaaaa ccgcuuuun                              39

<210> SEQ ID NO 309
<211> LENGTH: 22
<212> TYPE: RNA
<213> ORGANISM: Artificial sequence
<220> FEATURE:
<223> OTHER INFORMATION: an example of a first complementary domain

<400> SEQUENCE: 309
guuuuagagc uguguuguuu cg                                               22

<210> SEQ ID NO 310
<211> LENGTH: 24
<212> TYPE: RNA
<213> ORGANISM: Artificial sequence
<220> FEATURE:
<223> OTHER INFORMATION: an example of a second complementary domain

<400> SEQUENCE: 310
cgaaacaaca cagcgaguua aaau                                             24

<210> SEQ ID NO 311
<211> LENGTH: 13
<212> TYPE: RNA
<213> ORGANISM: Artificial sequence
<220> FEATURE:
<223> OTHER INFORMATION: an example of proximal domain

<400> SEQUENCE: 311
aaggcuuagu ccg                                                         13

<210> SEQ ID NO 312
<211> LENGTH: 38
<212> TYPE: RNA
<213> ORGANISM: Artificial sequence
<220> FEATURE:
<223> OTHER INFORMATION: an example of tail domain

<400> SEQUENCE: 312
uacucaacuu gaaaaggugg caccgauucg guguuuuu                              38

<210> SEQ ID NO 313
<211> LENGTH: 7
<212> TYPE: PRT
<213> ORGANISM: Artificial sequence
<220> FEATURE:
<223> OTHER INFORMATION: an example of a nuclear localization sequence
      or signal

<400> SEQUENCE: 313

Pro Lys Lys Lys Arg Lys Val
1               5

<210> SEQ ID NO 314
<211> LENGTH: 16
<212> TYPE: PRT
<213> ORGANISM: Artificial sequence
<220> FEATURE:
<223> OTHER INFORMATION: an example of a nuclear localization sequence
      or signal

<400> SEQUENCE: 314

Lys Arg Pro Ala Ala Thr Lys Lys Ala Gly Gln Ala Lys Lys Lys Lys
```

```
<210> SEQ ID NO 315
<211> LENGTH: 9
<212> TYPE: PRT
<213> ORGANISM: Artificial sequence
<220> FEATURE:
<223> OTHER INFORMATION: an example of a nuclear localization sequence
      or signal

<400> SEQUENCE: 315

Pro Ala Ala Lys Arg Val Lys Leu Asp
1               5

<210> SEQ ID NO 316
<211> LENGTH: 11
<212> TYPE: PRT
<213> ORGANISM: Artificial sequence
<220> FEATURE:
<223> OTHER INFORMATION: an example of a nuclear localization sequence
      or signal

<400> SEQUENCE: 316

Arg Gln Arg Arg Asn Glu Leu Lys Arg Ser Pro
1               5                   10

<210> SEQ ID NO 317
<211> LENGTH: 38
<212> TYPE: PRT
<213> ORGANISM: Artificial sequence
<220> FEATURE:
<223> OTHER INFORMATION: an example of a nuclear localization sequence
      or signal

<400> SEQUENCE: 317

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 318
<211> LENGTH: 42
<212> TYPE: PRT
<213> ORGANISM: Artificial sequence
<220> FEATURE:
<223> OTHER INFORMATION: an example of a nuclear localization sequence
      or signal

<400> SEQUENCE: 318

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 319
<211> LENGTH: 8
<212> TYPE: PRT
<213> ORGANISM: Artificial sequence
<220> FEATURE:
<223> OTHER INFORMATION: an example of a nuclear localization sequence
      or signal
```

-continued

```
<400> SEQUENCE: 319

Val Ser Arg Lys Arg Pro Arg Pro
1               5

<210> SEQ ID NO 320
<211> LENGTH: 8
<212> TYPE: PRT
<213> ORGANISM: Artificial sequence
<220> FEATURE:
<223> OTHER INFORMATION: an example of a nuclear localization sequence
      or signal

<400> SEQUENCE: 320

Pro Pro Lys Lys Ala Arg Glu Asp
1               5

<210> SEQ ID NO 321
<211> LENGTH: 8
<212> TYPE: PRT
<213> ORGANISM: Artificial sequence
<220> FEATURE:
<223> OTHER INFORMATION: an example of a nuclear localization sequence
      or signal

<400> SEQUENCE: 321

Pro Gln Pro Lys Lys Lys Pro Leu
1               5

<210> SEQ ID NO 322
<211> LENGTH: 12
<212> TYPE: PRT
<213> ORGANISM: Artificial sequence
<220> FEATURE:
<223> OTHER INFORMATION: an example of a nuclear localization sequence
      or signal

<400> SEQUENCE: 322

Ser Ala Leu Ile Lys Lys Lys Lys Lys Met Ala Pro
1               5                   10

<210> SEQ ID NO 323
<211> LENGTH: 5
<212> TYPE: PRT
<213> ORGANISM: Artificial sequence
<220> FEATURE:
<223> OTHER INFORMATION: an example of a nuclear localization sequence
      or signal

<400> SEQUENCE: 323

Asp Arg Leu Arg Arg
1               5

<210> SEQ ID NO 324
<211> LENGTH: 7
<212> TYPE: PRT
<213> ORGANISM: Artificial sequence
<220> FEATURE:
<223> OTHER INFORMATION: an example of a nuclear localization sequence
      or signal

<400> SEQUENCE: 324

Pro Lys Gln Lys Lys Arg Lys
1               5

<210> SEQ ID NO 325
<211> LENGTH: 10
<212> TYPE: PRT
```

```
<213> ORGANISM: Artificial sequence
<220> FEATURE:
<223> OTHER INFORMATION: an example of a nuclear localization sequence
      or signal

<400> SEQUENCE: 325

Arg Lys Leu Lys Lys Lys Ile Lys Lys Leu
1               5                   10

<210> SEQ ID NO 326
<211> LENGTH: 10
<212> TYPE: PRT
<213> ORGANISM: Artificial sequence
<220> FEATURE:
<223> OTHER INFORMATION: an example of a nuclear localization sequence
      or signal

<400> SEQUENCE: 326

Arg Glu Lys Lys Lys Phe Leu Lys Arg Arg
1               5                   10

<210> SEQ ID NO 327
<211> LENGTH: 20
<212> TYPE: PRT
<213> ORGANISM: Artificial sequence
<220> FEATURE:
<223> OTHER INFORMATION: an example of a nuclear localization sequence
      or signal

<400> SEQUENCE: 327

Lys Arg Lys Gly Asp Glu Val Asp Gly Val Asp Glu Val Ala Lys Lys
1               5                   10                  15

Lys Ser Lys Lys
            20

<210> SEQ ID NO 328
<211> LENGTH: 17
<212> TYPE: PRT
<213> ORGANISM: Artificial sequence
<220> FEATURE:
<223> OTHER INFORMATION: an example of a nuclear localization sequence
      or signal

<400> SEQUENCE: 328

Arg Lys Cys Leu Gln Ala Gly Met Asn Leu Glu Ala Arg Lys Thr Lys
1               5                   10                  15

Lys

<210> SEQ ID NO 329
<211> LENGTH: 99
<212> TYPE: RNA
<213> ORGANISM: Artificial sequence
<220> FEATURE:
<223> OTHER INFORMATION: an example of a sgRNA
<220> FEATURE:
<221> NAME/KEY: misc_feature
<222> LOCATION: (1)..(3)
<223> OTHER INFORMATION: nnn is 2'OMe(C(ps)U(ps)C(ps)), wherein the 2OMe
      means 2-methly RNA and ps means phosphorothioate)
<220> FEATURE:
<221> NAME/KEY: misc_feature
<222> LOCATION: (97)..(99)
<223> OTHER INFORMATION: nnn is 2'OMe(U(ps)U(ps)U(ps)U), wherein the
      2OMe means 2-methly RNA and ps means phosphorothioate)

<400> SEQUENCE: 329
nnnucaagcu gagugggucc guuuuagagc uagaaauagc aaguuaaaau aaggcuaguc    60
```

```
cguuaucaac uugaaaaagu ggcaccgagu cggugcnnn                              99

<210> SEQ ID NO 330
<211> LENGTH: 104
<212> TYPE: RNA
<213> ORGANISM: Artificial sequence
<220> FEATURE:
<223> OTHER INFORMATION: an example of a sgRNA

<400> SEQUENCE: 330
gcuuguggcg cugaaaacga aguuuuagag cuagaaauag caaguuaaaa uaaggcuagu       60
ccguuaucaa cuugaaaaag uggcaccgag ucggugcuuu uuuu                       104

<210> SEQ ID NO 331
<211> LENGTH: 20
<212> TYPE: DNA
<213> ORGANISM: Artificial sequence
<220> FEATURE:
<223> OTHER INFORMATION: An example of target sequence

<400> SEQUENCE: 331
ctctcaagct gagtgggtcc                                                  20

<210> SEQ ID NO 332
<211> LENGTH: 20
<212> TYPE: DNA
<213> ORGANISM: Artificial sequence
<220> FEATURE:
<223> OTHER INFORMATION: An example of target sequence

<400> SEQUENCE: 332
acgagcactc accagcatcc                                                  20
```

What is claimed is:

1. A composition for the production of an artificially engineered immune cell comprising any one or more of an artificially engineered Dgkα gene and an artificially engineered Dgkζ gene,
   wherein the composition comprises:
   (i) a Cas9 protein derived from *Streptococcus pyogenes*, or a nucleic acid encoding the Cas9 protein derived from *S. pyogenes*; and
   (ii) a guide RNA or a nucleic acid encoding the guide RNA, wherein the guide RNA is at least one selected from a first guide RNA and a second guide RNA,
   wherein the first guide RNA comprises a first guide sequence which consists of the $1^{st}$ to $20^{th}$ nucleotides of SEQ ID NO: 23, in which each thymine of the first guide sequence are changed to uracil,
   wherein the second guide RNA comprises a second guide sequence which consists of the $1^{st}$ to $20^{th}$ nucleotides of SEQ ID NO: 113, in which each thymine of the second guide sequence are changed to uracil, and
   wherein the first guide RNA and the Cas9 protein are capable of forming a first RNA-protein complex which is capable of manipulating the Dgkα gene, and wherein the second guide RNA and the Cas9 protein are capable of forming a second RNA-protein complex which is capable of manipulating the Dgkζ gene.

2. The composition of claim 1, wherein the composition comprises:
   (i) the first guide RNA or the nucleic acid encoding the first guide RNA; and
   (ii) the Cas9 protein or the nucleic acid encoding the Cas9 protein.

3. The composition of claim 1, wherein the composition comprises:
   (i) the second guide RNA or the nucleic acid encoding the second guide RNA; and
   (ii) the Cas9 protein or the nucleic acid encoding the Cas9 protein.

4. The composition of claim 1, wherein the composition comprises:
   (i) the first guide RNA or the nucleic acid encoding the first guide RNA and the second guide RNA or the nucleic acid encoding the second guide RNA; and
   (ii) the Cas9 protein or the nucleic acid encoding the Cas9 protein.

* * * * *